United States Patent
Nakamura et al.

(10) Patent No.: US 9,616,101 B2
(45) Date of Patent: Apr. 11, 2017

(54) DIFFERENTIATION MARKER AND DIFFERENTIATION CONTROL OF EYE CELL

(71) Applicants: Kyoto Prefectural Public University Corporation, Kamigyo-ku, Kyoto-shi, Kyoto (JP); The Doshisha, Kamigyo-ku, Kyoto-shi, Kyoto (JP); Senju Pharmaceutical Co., Ltd., Osaka-shi, Osaka (JP)

(72) Inventors: Takahiro Nakamura, Kyotanabe (JP); Noriko Koizumi, Kyotanabe (JP); Naoki Okumura, Kyotanabe (JP); Shigeru Kinoshita, Kyoto (JP); Kana Tominaga, Kyoto (JP); Satoshi Kawasaki, Kyoto (JP)

(73) Assignees: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/413,066

(22) PCT Filed: Jul. 3, 2013

(86) PCT No.: PCT/JP2013/068802
§ 371 (c)(1),
(2) Date: Jan. 6, 2015

(87) PCT Pub. No.: WO2014/007402
PCT Pub. Date: Jan. 9, 2014

(65) Prior Publication Data
US 2015/0202256 A1    Jul. 23, 2015

(30) Foreign Application Priority Data

Jul. 6, 2012 (JP) .................................. 2012-152960
Jan. 31, 2013 (JP) .................................. 2013-016848

(51) Int. Cl.
| | | |
|---|---|---|
| A61K 38/00 | (2006.01) | |
| A61K 38/22 | (2006.01) | |
| A61K 39/00 | (2006.01) | |
| C07K 14/47 | (2006.01) | |
| C07K 14/785 | (2006.01) | |
| C07K 14/005 | (2006.01) | |
| A61K 38/17 | (2006.01) | |
| A61K 48/00 | (2006.01) | |
| C07K 14/705 | (2006.01) | |
| A61K 35/30 | (2015.01) | |
| G01N 33/569 | (2006.01) | |

(Continued)

(52) U.S. Cl.
CPC .......... *A61K 38/1709* (2013.01); *A61K 35/30* (2013.01); *A61K 48/00* (2013.01); *C07K 14/705* (2013.01); *C12N 5/0621* (2013.01); *C12Q 1/6881* (2013.01); *G01N 33/56966* (2013.01); *A61K 38/00* (2013.01); *C12N 2501/40* (2013.01); *C12N 2501/415* (2013.01); *C12Q 2600/158* (2013.01); *G01N 2333/726* (2013.01); *G01N 2800/16* (2013.01)

(58) Field of Classification Search
None
See application file for complete search history.

(56) References Cited

U.S. PATENT DOCUMENTS

| | | |
|---|---|---|
| 2009/0232772 A1 | 9/2009 | Amano et al. |
| 2010/0209402 A1 | 8/2010 | Koizumi et al. |
| 2011/0223660 A1 | 9/2011 | Park |

(Continued)

FOREIGN PATENT DOCUMENTS

| | | |
|---|---|---|
| EP | 1835023 | 9/2007 |
| EP | 1835023 A1 | 9/2007 |

(Continued)

OTHER PUBLICATIONS

Puliafito et al., "Collective and single cell behavior in epithelial contact inhibition," available online at http://arxiv.org/pdf/1112.0465.pdf, 20 pages (2011).*
Wim BM De Lau et al., "The R-spondin protein family" Genome Biology, vol. 13, No. 3, Jan. 1, 2012, p. 242, ISSN: 1465-6906, DOI: 10.1038/embor.2011.175.
Supplementary Partial European Search Report issued Mar. 8, 2016 in connection with EP 13812481.
International Search Report dated Oct. 22, 2013, which issued during prosecution of International Application No. PCT/JP2013/068802, which corresponds to the present application.
Jurian Schuijers and Hans Clevers, "Adult mammalian stem cells: the role of Wnt, Lgr5 and R-spondins", The EMBO Journal (2012) 31, 2685-2696.

(Continued)

*Primary Examiner* — Hasan Ahmed
*Assistant Examiner* — Thea D'Ambrosio
(74) *Attorney, Agent, or Firm* — Clark Sullivan

(57) ABSTRACT

The present invention relates to a differentiation marker and a differentiation controlling technique for an eye cell. More particularly, the present invention has attained an object of providing a differentiation marker for an eye cell among the aforementioned problems, by providing a marker for identifying a cell having a high proliferation ability among corneal endothelial cells and/or the differentiation ability of a corneal endothelial cell, the marker comprising GPR49/LGR5, as well as a detection agent or detection method for identifying a cell having a high proliferation ability among corneal endothelial cells and/or the differentiation ability of a corneal endothelial cell, comprising a substance binding to GPR49/LGR5. In addition, the present invention has attained an object of providing a differentiation controlling technique for an eye cell, by providing an agent for suppressing differentiation and/or promoting proliferation of an eye cell, comprising R-spondins.

13 Claims, 34 Drawing Sheets
(24 of 34 Drawing Sheet(s) Filed in Color)

(51) Int. Cl.
    C12N 5/079    (2010.01)
    C12Q 1/68     (2006.01)

(56)           References Cited

U.S. PATENT DOCUMENTS

2012/0028355  A1    2/2012  Sato
2014/0243227  A1*   8/2014  Clevers .............. C12N 5/067
                                                          506/9
2014/0370007  A1*  12/2014  McCabe ............... A61K 35/30
                                                        424/133.1

FOREIGN PATENT DOCUMENTS

EP        2718422         4/2014
EP        2718422 A1      4/2014
JP        2006-187281 A   7/2006
JP        2009-268433 A  11/2009
WO        2009/028631 A1  3/2009
WO        2012168930     12/2012

OTHER PUBLICATIONS

Joanna Brzeszczynska et al., "Molecular profile of organ culture-stored corneal epithelium: Lgr5 is a potential new phenotypic marker of residual human corneal limbal epithelial stem cells", International Journal of Molecular Medicine, 2012, vol. 29, No. 5, p. 871-876.
Krulova, Magdalena et al., A Rapid Separation of Two Distinct Populations of Mouse Corneal Epithelial Cells with Limbal Stem Cell Characteristics by Centrifugation on Percoll Gradient, Invest. Opthalmol. Vis. Sci., vol. 49, No. 9, 2008, p. 3903-3908.
Akifumi Ootani et al., "Sustained in vitro intestinal epithelial culture within a Wnt-dependent stem cell nichel", Nature Medicine, Jun. 2009, vol. 15, No. 6, p. 701-706.
Noriko Koizumi et al., "Development of new therapeutic modalities for corneal endothelial disease focused on the proliferation of corneal endothelial cells using animal models", Experimental Eye Research, vol. 95, No. 1, Feb. 2012, p. 60-67.
Shin Hato, Kazuo TsuBota, "Saisei Igaku Series [44] Kakumaku Saisei no Genjo to Kadai", Organ Biology, vol. 17, No. 1, pp. 51-60. (English abstract provided).
Kana Hirata-Tominaga et al., Corneal endothelial cell fate is maintained by LGR5 through the regulation of hedgehog and Wnt pathway, Stem Cell, Jul. 2013, vol. 31, No. 7, p. 1396-1407.
Jeong Kyo Yoon, Jin-Seon Lee, "Cellular Signalling and biological functions of R-spondins", SciVerse ScienceDirect: Elsevier 24 (2012) 369-377.
A. Glinka et al., "LGR4 and LGR5 act a R-spondin receptors mediating Wnt/B-Catenin and Wnt/PCP signalling", European Molecular Biology Organization 2011; doe: 10.1038/embor.2011.175; EMBO Rep. Sep. 30, 2011;12(10):1055-1061.
Wim de Lau et al,. "Lgr5 homologues associate with Wnt receptors and mediate R-spondin signalling", 2011 Macmillian Publishers Limited, doe:10.1038/nature 10337; Nature. Jul. 4, 2011;476(7360):293-297.

Viljar Jaks et al., "Lgr5 marks cycling, yet long-lived, hair follicle stem cells", Nature Genetics. 2008, 40, 1291-1299: Nature Publishing Group.
Keiji Tanese et al., "G-Protein-Coupled Receptor GPR49 is Up-regulated in Basal Cell Carcinoma and Promotes Cell Proliferation and Tumor Formation", The American Journal of Pathology, vol. 173, No. 3, Sep. 2008, 835-843.
Terrill McClanahan et al., "Identification of Overexpression of Orphan G Protein-Coupled Receptor GPR49 in Human Colon and Ovarian Primary Tumors", Cancer Biology & Therapy 5:4, 419-426 Apr. 2006, Landes Bioscience.
Yamamoto et al., "Overexpression of Orphan G-Protein-Coupled Receptor, Gpr49, in Human Hepatocellular Carcinomas with B-Catenin Mutations", Hepatology, vol. 37, No. 3, 2003, 528-533.
Sara L. McGowan et al., "Stem cell markers in the human posterior limbus and corneal endothelium of unwounded and wounded corneas", Molecular Vision, 2007; 13:1984-2000.
Yokoo et al., "Human Corneal Endothelial Cell Precursors Isolated by Sphere-Forming Assay", Investigative Ophthalmology & Visual Science, May 2005, vol. 46, No. 5, 1626-1631.
David R. Whikehart et al., "Evidence suggesting the existence of stem cells for the human corneal endothelium" Molecular Vision, 2005; 11:816-24.
B.H. Schimmelpfennig, "Direct and Indirect Determination of Non-uniform Cell Density Distribution in Human Corneal Endothelium" Investigative Ophthalmology & Visual Science/Feb. 1984 vol. 25, pp. 223-229.
Kendra S. Carmon et al., "R-spondins function as ligands of the orphan receptors LGR4 and LGr5 to regulate Wnt/B-catenin signaling" PNAS Jul. 12, 2011; 108(28), 11452-11457.
Noriko Koizumi et al., "Progress in the Development of Tissue Engineering of the Cornea in Japan", Journal of Japanese Ophthalmological Society, 2007, vol. 111, No. 7, 493-503 (English abstract provided).
Barker N., et al., "Identification of stem cells in small intestine and colon by marker gene Lgr5" Nature 449: 1003-1007, 2007.
Yamagami S., et al., "Distribution of Precursors in Human Corneal Stromal Cells and Endothelial Cells" Ophthalmology, 114, 433-439, 2007.
Hsu Sy., et al., "Characterization of Two LGR Genes Homologous to Gonadotropin and Thyrotropin Receptors with Extracellular Leucine-Rich Repeats and a G Protein-Coupled, Seven-Transmembrane Region" J. Mol. Endocrinol. 12, 1830-1845, 1998.
Barker N., et al., "Tissue-Resident Adult Stem Cell Populations of Rapidly Self-Renewing Organs" Cell Stem Cell. 7, 656-670, 2010.
V Holan, "The presence of cells with stem cell markers and characteristics in the central cornea of the mouse", Acta Ophthalmologica, vol. 88, Issue Supplement s246, (/doi/10.1111/j.1755-3768.2010.issue-s246/issuetoc) p. 0, Sep. 2010.
Extended European Search Report issued in corresponding European Application No. 13812481.3 on Jul. 8, 2016.
Wim BM De Lau et al: "The R-spondin protein family", Genome Biology, vol. 13, No. 3, Jan. 1, 2012 (Jan. 1, 2012), p. 242.

* cited by examiner

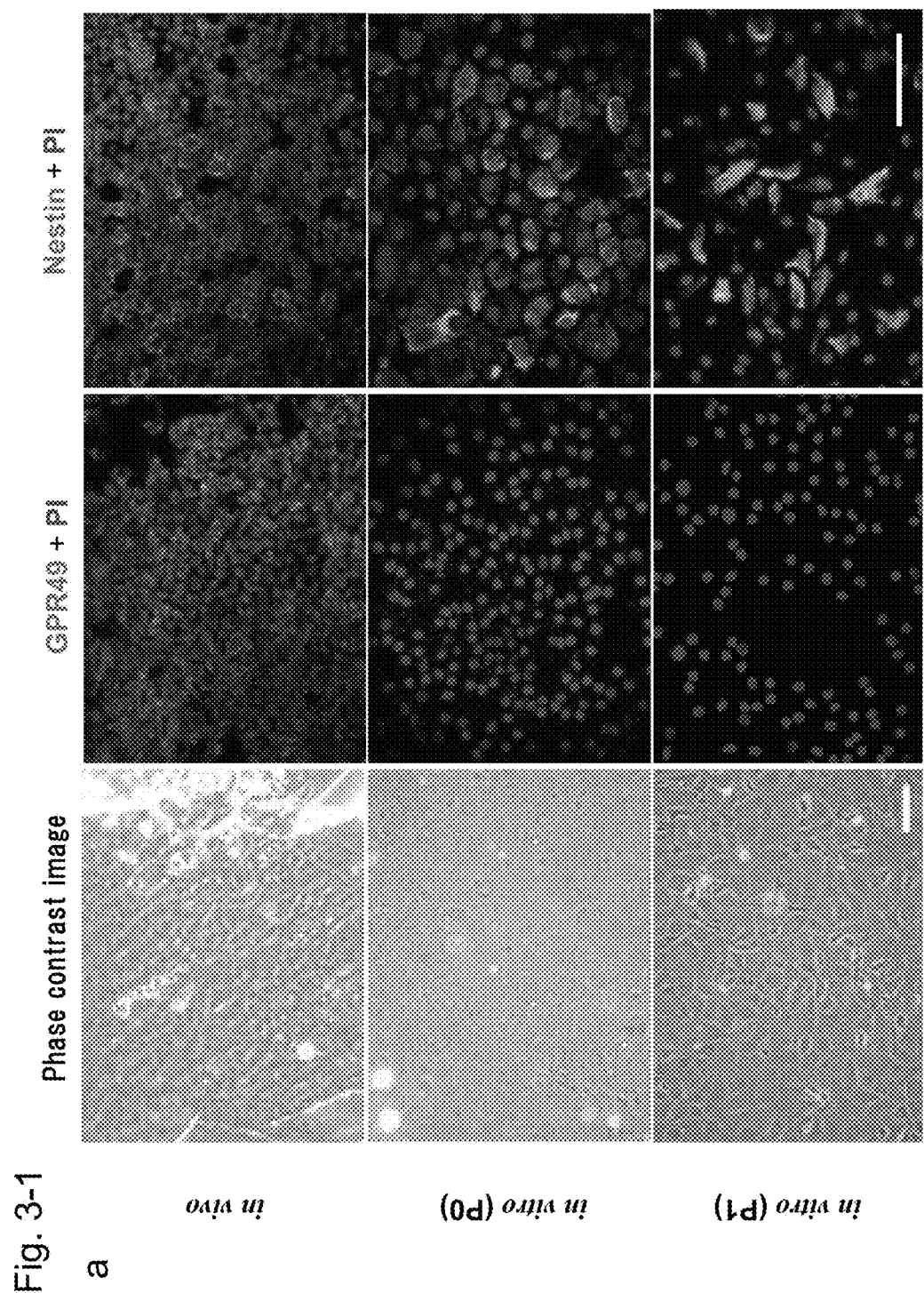

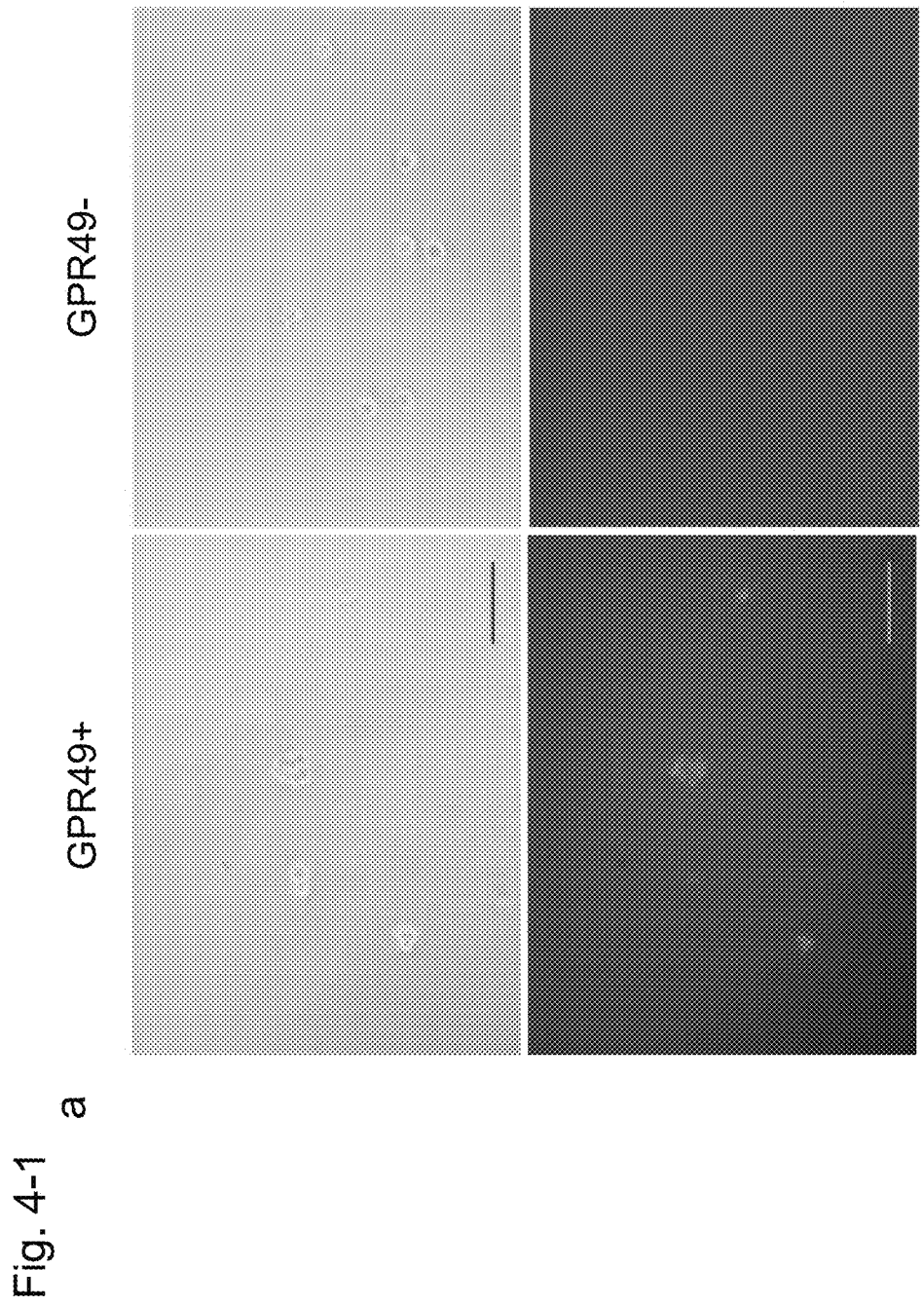

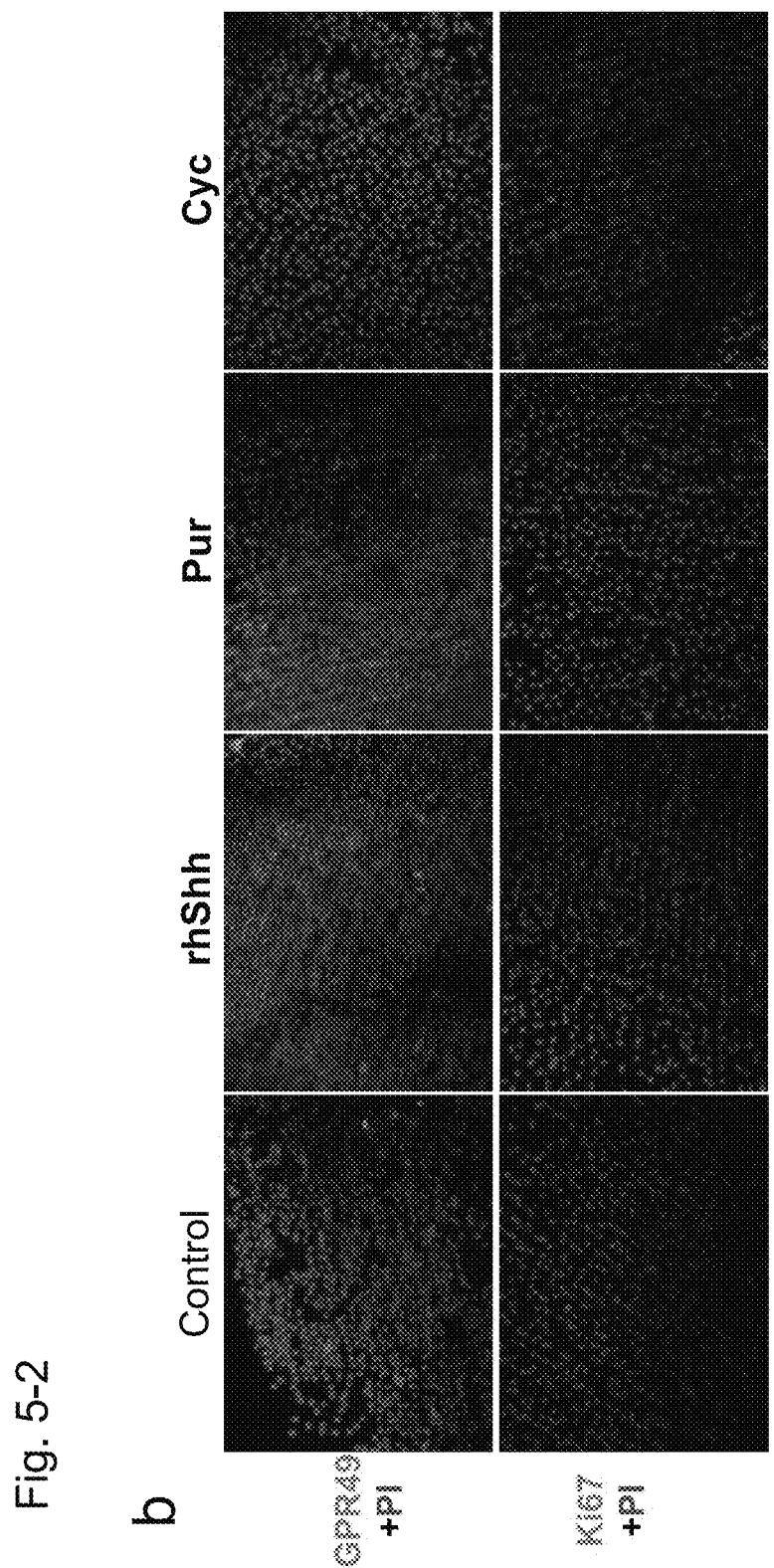

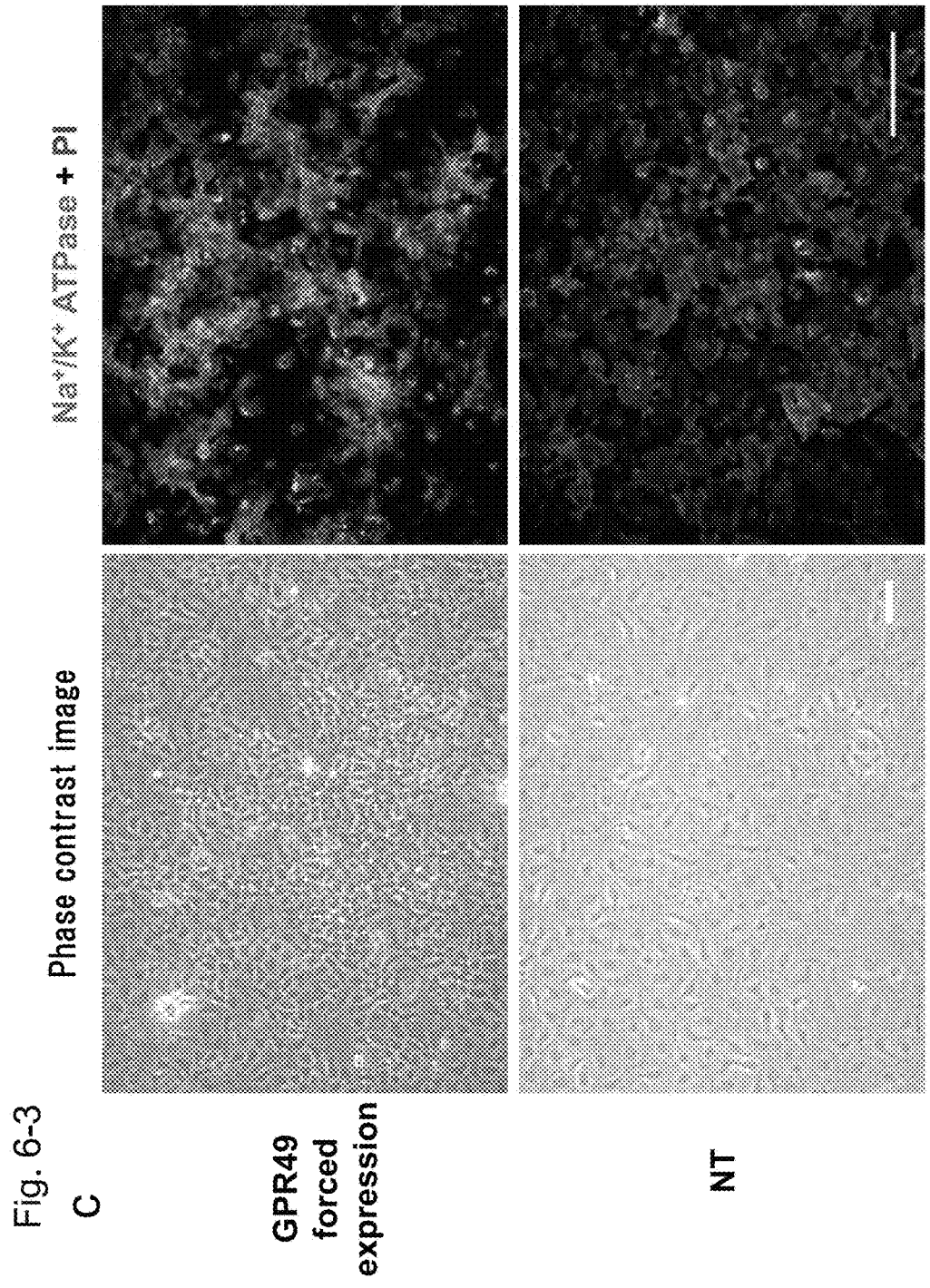

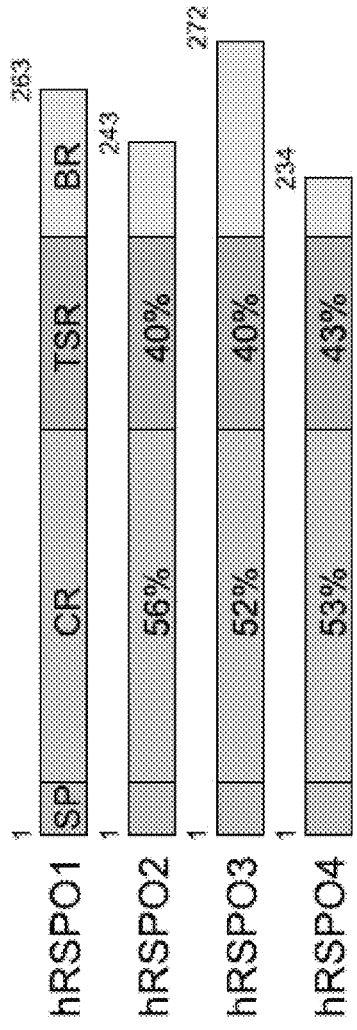

Fig. 7

RSPO1 Mutation; palmoplantar hyperkeratosis, predisposition of skin flat epithelial cancer, sex differentiation, generation of ovary RSPO2 Mutation; Dupuytren's contracture
(Mouse) high lethality after birth, abnormality in crania, pharynx, trachea, and limb, sterility due to polycystic ovarian disease, FGF signal transmission RSPO3 Mutation; (Frog) ventral edema, morphological abnormality in blood vessel and chondrocranium, development of placenta RSPO4 Mutation; anonychosis (RSPO2)

RSPO4/generation of nail through β-catenin

| Addition of R-spondin to medium | Non (left) | 10 ng/m (center) | 50 ng/m (right) |
|---|---|---|---|
| Cell density (Cells/mm²) | 2212 | 2959 | 3030 |

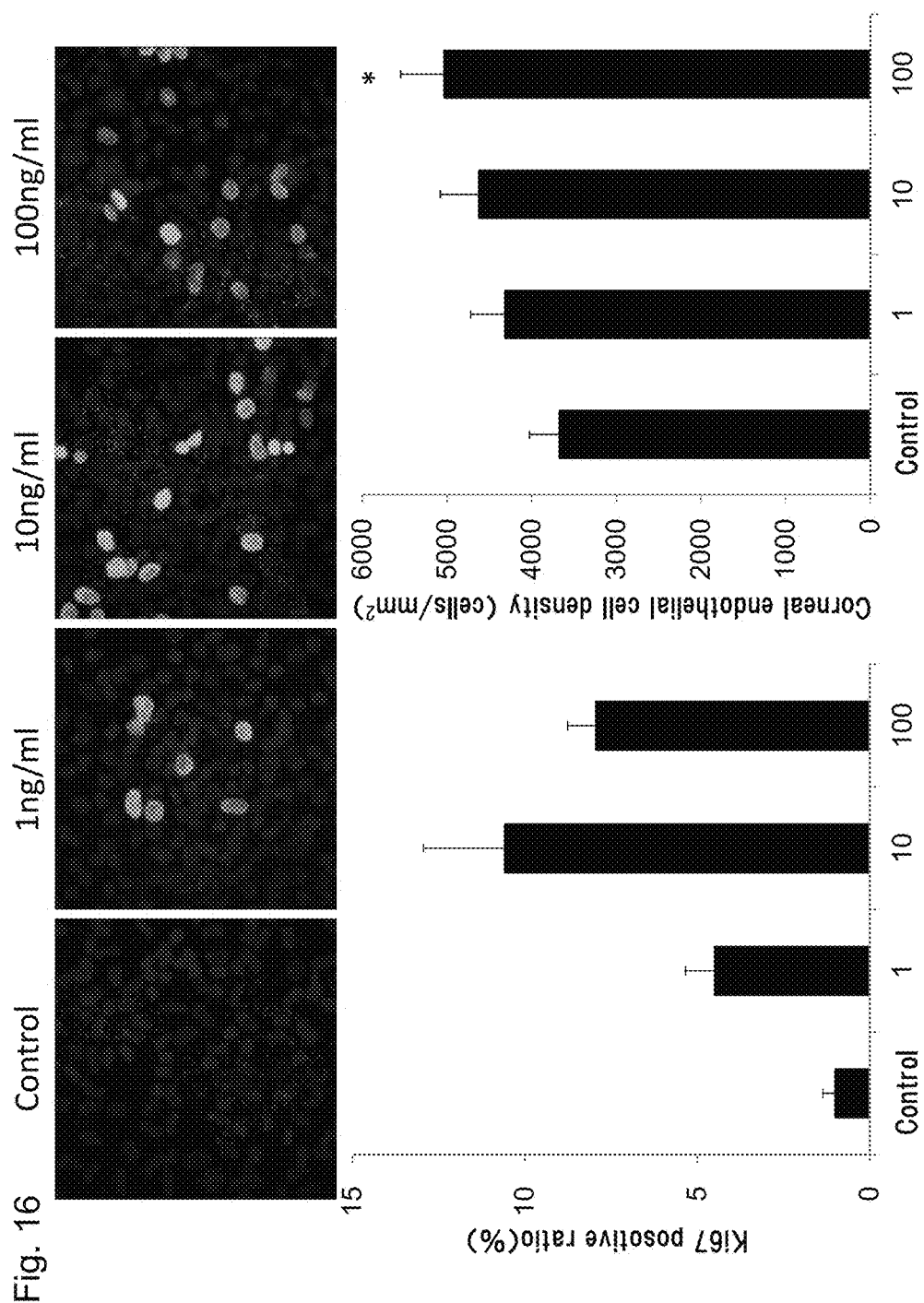

DIFFERENTIATION MARKER AND DIFFERENTIATION CONTROL OF EYE CELL

CROSS REFERENCE TO RELATED APPLICATIONS

This application is a U.S. National Phase Application under 35 U.S.C. §371 of International Patent Application PCT/JP2013/068802 filed Jul. 3, 2013 which claims priority to Japanese Patent Application No. 2012-152960 filed Jul. 6, 2012 and Japanese Patent Application No. 2013-016848 filed Jan. 31, 2013. The International Application was published on Jan. 9, 2014, as International Publication No. WO 2014/007402 A1. The entire contents of these applications are hereby incorporated by reference.

SEQUENCE LISTING

The instant application contains a Sequence Listing which has been submitted in ASCII format via EFS-Web and is hereby incorporated by references in its entirety. Said ASCII copy created on Jan. 6, 2015, is named DS2002PCT.txt and is 272,542 bytes in size.

TECHNICAL FIELD

The present invention relates to a cell, particularly, a marker in a differentiated state in the ophthalmological region, a technique and a method for suppressing differentiation and/or stimulating proliferation of an eye cell (particularly, corneal endothelial cell which is difficult in differentiation control), as well as an agent and a culture medium therefor.

BACKGROUND ART

Visual information is recognized in such a manner that light transmitted into the cornea, which is a transparent tissue at the forefront of an eyeball, reaches the retina to excite the nerve cell of the retina, and an electric signal generated is transferred through the optic nerve to the visual cortex of the cerebrum. In order to obtain good visual acuity, it is necessary that the cornea is transparent. The transparency of the cornea is maintained by retaining a constant moisture content with the pumping function and barrier function of a corneal endothelial cell.

The cornea is a transparent tissue which is positioned in front of the eyeball and the structure of cornea is mainly composed of three-layers known as corneal epithelial cell layer, corneal stromal layer and corneal endothelial cell layer. The corneal endothelial cell layer is a single cell layer existing in a corneal deep part, has the barrier function and the pumping function, and plays a role in maintaining the transparency of the cornea by retaining a constant corneal moisture amount. In addition, it is known that even if the corneal endothelial cells are damaged, they do not proliferate in a living body, and also it is known that a serious visual disorder is generated by damaging corneal endothelial cells with trauma, a disease or the like to decrease their number.

Human corneal endothelial cells exist at a density of about 3000 cells per 1 square millimeter at birth, but once the corneal endothelial cells are damaged, they have no ability to regenerate themselves. In endothelial corneal dystrophy or bullous keratopathy which is generated by dysfunction of the corneal endothelium due to a variety of causes, the cornea becomes opaque due to edema, which leads to remarkable reduction in the visible acuity. Currently, penetrating keratoplasty for transplanting the whole three-layered structure of epithelium, stroma and endothelium of the cornea is performed for bullous keratopathy. However, donation of the cornea in Japan is insufficient, and the number of waiting patients for corneal transplantation is about 2600, but the number of corneal transplantation performed by using the cornea from a donor in Japan per year is about 1700.

In recent years, for the purpose of reducing the risk of immunological rejection or the risk of postoperative complications and obtaining better visual function, the idea of "parts transplantation" for transplanting a damaged tissue alone has been drawing the attention. Among the cornea transplantations, deep layer and superficial layer corneal transplantations in which the stromal tissue is transplanted, Descemet's Stripping Automated Endothelial Keratoplasty in which the corneal endothelial tissue is transplanted, and the like have been performed. In addition, cultured mucosal epithelial transplantation in which the corneal epithelium or the oral mucosa which has been cultured in vitro is transplanted in place of the corneal epithelium has been already applied clinically, and a method for transplanting the corneal endothelium which has been cultured in vitro similarly has been also studied.

It is known that a corneal endothelial cell is differentiated when cultured, and morphology changes to a fibroblast cell-like form. In addition, it is known that GPR49/LGR5 is expressed in a small intestine epithelial stem cell in a limited manner, and plays an important role. As a ligand of GPR49/LGR5, R-spondins are reported (Non-Patent Documents 1 to 4).

Non-Patent Document 5 describes that a stem cell-like cell exists in a corneal limbal epithelial cell, and GPR49/LGR5 can be a phenotype marker of a remaining human corneal limbal epithelial stem cell.

In Non-Patent Document 6, GPR49/LGR5 is exemplified as a stem cell marker. Non-Patent Document 6 describes that, in two cell populations of mouse corneal epithelial cells, GPR49/LGR5 and ABCG2 are highly expressed.

Non-Patent Document 7 describes GPR49/LGR5 as a stem cell marker.

Non-Patent Document 8 discloses that intestinal tract epithelial stem cell culturing is established.

Non-Patent Document 9 discloses a method of small intestinal culture and a large intestinal culture in a stable manner and for a long term. Non-Patent Document 9 describes that culture growth is markedly stimulated by a fusion protein (RSpol-Fc) between R-spondin 1 and immunoglobulin Fe.

Previously, it has been considered that corneal endothelial cells do not proliferate in vivo, but by molecular biological or cellular biological study in recent years, it has been reported that a cell group very rich in proliferation ability also exists in the corneal endothelial cell layer. Schimmelpfenning et al. revealed that the endothelial cell density is increased more at a peripheral part of the human cornea than at a central part, and proposed a possibility that the proliferation of cells at a corneal peripheral part supplies cells to a corneal central part (Non-Patent Document 10).

In addition, using the rabbit cornea, Whikehart et al. confirmed that telomerase, which is observed to be highly expressed in a stem cell or a precursor cell, is highly expressed in an endothelial cell at a corneal peripheral part. Further, by an evaluation method of using BrdU as a cell proliferation marker, it is shown that a fast response is observed when an endothelial cell at a corneal peripheral part is damaged (Non-Patent Document 11). In addition, Yokoo et al. succeeded in collection of a precursor cell of a corneal endothelial cell from the adult human cornea using a sphere method which is a method for collecting a mesenchymal stem cell (Non-Patent Document 12). This cell expresses an undifferentiated cell marker, and when the ability to form a sphere was compared between corneal endothelial cells at a central part and a peripheral part, it was confirmed that the ability is high in a peripheral endothelial cell (Non-Patent Document 13). Furthermore, McGowan et al. reported that a large number of cells expressing an undifferentiated cell marker exist at a corneal peripheral part, and these cells are activated by being damaged (Non-Patent Document 14).

G protein-coupled receptor 49 (also referred to as "GPR49/LGR5" as used herein) is one kind of seven-transmembrane receptors similar to thyroid-stimulating hormone, follicle-stimulating hormone (FSH), or leuteinizing hormone (LH), and has a unique structure associated with an extracellular N-terminal domain including a leucine rich repeat (FIG. 1, Non-Patent Document 15). It has been reported that since GPR49/LGR5 is a target gene of Wnt-signaling pathway and Hedgehog-signaling pathway involved in oncogenesis, expression of GPR49/LGR5 is elevated by abnormality of these signaling pathways (Non-Patent Document 16, Non-Patent Document 17 and Non-Patent Document 18). Furthermore, since it was confirmed that specific expression of GPR49/LGR5 is seen in an intestinal tract epithelial stem cell (Non-Patent Document 8), GPR49/LGR5 has been drawing attention as a novel protein which is expressed in a stem cell-specific manner. Thereafter, it has been confirmed that expression of GPR49/LGR5 is elevated in a stem cell-specific manner also in a tissue such as hair follicle (Non-Patent Document 19) or stomach epithelium (Non-Patent Document 20), and a possibility that GPR49/LGR5 is involved in construction of stem cell niche and tissue formation has been also reported.

PRIOR ART DOCUMENT

Patent Documents

Non-Patent Document 1: Carmon K S. et al., Proc Natl Acad Sci USA. 2011 Jul. 12; 108(28): 11452-11457
Non-Patent Document 2: de Lau W. et al., Nature. 2011 Jul. 4; 476(7360):293-297
Non-Patent Document 3: Glinka A. et al., EMBO Rep. 2011 Sep. 30; 12(10):1055-1061
Non-Patent Document 4: J. Yoon, J. Lee, Cellular Signalling 24 (2012) 369-377
Non-Patent Document 5: Brzeszczynska J, et al., Int J Mol Med. 2012 May; 29(5):871-876
Non-Patent Document 6: Krulova M, et al., Invest Ophthalmol Vis Sci. 2008 September; 49(9):3903-3908
Non-Patent Document 7: HOLAN V., Ophthalmologica Volume 88, Issue Supplements 246, page 0, September 2010
Non-Patent Document 8: Barker N., et al., Nature 449: 1003-1007, 2007
Non-Patent Document 9: Ootani A., Li X. et al., Nat Med. 2009 June; 15(6):701-706
Non-Patent Document 10: Schimmelpfennig B., et al., IOVS, Vol. 25, pp. 223-229. 1984
Non-Patent Document 11: Whikehart D R., et al., Mol. Vis., 11, pp. 816-824, 2005
Non-Patent Document 12: Yokoo S. et al, IOVS. 46, 1626-1631, 2005
Non-Patent Document 13: Yamagami S., et al., Ophthalmology, 114, 433-439, 2007
Non-Patent Document 14: McGowan S L., et al., Mol. Vis., 13:1984-2000. 2007
Non-Patent Document 15: Hsu S Y., et al., J. Mol. Endocrinol. 12, 1830-1845, 1998
Non-Patent Document 16: Yamamoto Y., et al., Hepatology. 37, 528-533, 2003
Non-Patent Document 17: McClanahan T., et al., Cancer Biol Ther. 5, 419-426, 2006
Non-Patent Document 18: Tanese K., et al., Am J Pathol. 173, 835-843, 2008
Non-Patent Document 19: Jaks V., et al., Nature Genetics. 40, 1291-1299, 2008
Non-Patent Document 20: Barker N., et al., Cell Stem Cell. 7, 656-670, 2010

SUMMARY OF THE INVENTION

Solutions to the Problems

The present invention provides a technique for using GPR49/LGR5 as a marker of proliferation/differentiation. The present inventors have found that GPR49/LGR5 is strongly expressed in a cornea endothelial cell (particularly, peripheral part) in a human corneal tissue; found that the expression amount of GPR49/LGR5 is significantly reduced in a cultured cell of a human cornea endothelial cell; and also found that a GPR49/LGR5-positive cell group has a small cell size, and has a high proliferation ability. Based on these findings, the present inventors have applied the above findings to a technique for using GPR49/LGR5 as a marker of proliferation/differentiation.

The present invention also provides use of R-spondins as an agent for suppressing differentiation or promoting proliferation.

The present inventors have found a tendency such that the differentiation of a human cultured corneal endothelial cell is suppressed, and the proliferation of the cell is promoted by R-spondins, particularly R-spondin 1. The present inventors have applied the above finding to a technique for using R-spondins as applications such as a liquid for corneal preservation, a liquid for culturing corneal endothelial cell, a therapeutic agent for corneal endothelial cell disorder (eye drops, cell infusion) and an agent for preventing progression of corneal endothelial cell disorder.

In the previous studies, there is no report on clear presentation of the presence of a corneal endothelial stem cell. In addition, the proliferation ability of a corneal endothelial cell and the mechanism of controlling undifferentiation in a living body have not been elucidated. The present inventors have found that there is GPR49/LGR5 as a protein which is specifically expressed in a precursor cell of a corneal endothelial cell, and have verified the in vivo and in vitro functional role, resulting in an application as a marker.

In one aspect, the present invention provides an agent for suppressing differentiation and/or promoting proliferation of a cell, comprising at least one kind selected from the group consisting of R-spondins and a functional equivalent thereof.

In one embodiment, the present invention provides an agent for suppressing differentiation and/or promoting proliferation of a cell selected from an eye cell, a nerve cell including a cell derived from a neural crest cell (including corneal endothelial cell), and epithelial cells such as a conjunctival epithelial cell, an amniotic epithelial cell, an oral mucosal epithelial cell, a nasal mucosal epithelial cell, and a corneal epithelial cell, comprising at least one kind selected from the group consisting of R-spondins and a functional equivalent thereof.

In another embodiment, the present invention provides an agent for suppressing differentiation and/or promoting proliferation of an eye cell, comprising at least one kind selected from the group consisting of R-spondins and a functional equivalent thereof.

In another embodiment, the R-spondins in the present invention include at least one selected from R-spondin 1, R-spondin 2, R-spondin 3 and R-spondin 4.

In a specific embodiment, the R-spondins include R-spondin 1.

In another embodiment, the eye cell is a cell which does not proliferate in the stationary state.

In a specific embodiment, the eye cell includes at least one kind cell selected from a retinal cell, a vitreous body cell, a corneal epithelial cell, a corneal parenchymal cell and a corneal endothelial cell.

In a specific embodiment, the eye cell includes a corneal endothelial cell.

In a specific embodiment, the eye cell includes a corneal endothelial cell of a primate.

In a specific embodiment, the eye cell includes a human corneal endothelial cell.

In a specific embodiment, the eye cell is in the confluent state.

In one aspect, the present invention provides an agent for suppressing differentiation and/or promoting proliferation of a cell, comprising at least one kind selected from the group consisting of SHH, an agonist of SHH (e.g., agonist of Frizzled family such as purmorphamine) and a functional equivalent thereof.

In one embodiment, the present invention provides an agent for suppressing differentiation and/or promoting proliferation of a cell selected from an eye cell, a nerve cell including a cell derived from an neural crest cell (including corneal endothelial cell), and epithelial cells such as a conjunctival epithelial cell, an amniotic epithelial cell, an oral mucosal epithelial cell, a nasal mucosal epithelial cell, and a corneal epithelial cell, comprising at least one kind selected from the group consisting of SHH, purmorphamine and a functional equivalent thereof.

In another embodiment, the present invention provides an agent for suppressing differentiation and/or promoting proliferation of an eye cell, comprising at least one kind selected from the group consisting of SHH, an agonist of SHH (e.g., agonist of Frizzled family such as purmorphamine) and a functional equivalent thereof.

In another embodiment, the eye cell is a cell which does not proliferate in the stationary state.

In a specific embodiment, the eye cell includes at least one kind cell selected from a retinal cell, a vitreous body cell, a corneal epithelial cell, a corneal parenchymal cell and a corneal endothelial cell.

In a specific embodiment, the eye cell includes a corneal endothelial cell.

In a specific embodiment, the eye cell includes a corneal endothelial cell of a primate.

In a specific embodiment, the eye cell includes a human corneal endothelial cell.

In a specific embodiment, the eye cell is in the confluent state.

In one aspect, the present invention provides an agent for suppressing differentiation and/or promoting proliferation of a cell, comprising an agent suppressing GPR49/LGR5.

In one embodiment, the present invention provides an agent for suppressing differentiation and/or promoting proliferation of a cell selected from an eye cell, a nerve cell including a cell derived from an neural crest cell (including corneal endothelial cell), and an epithelial cell such as a conjunctival epithelial cell, an amniotic epithelial cell, an oral mucosal epithelial cell, a nasal mucosal epithelial cell, and a corneal epithelial cell, comprising an agent suppressing GPR49/LGR5.

In another embodiment, the present invention provides an agent for suppressing differentiation and/or promoting proliferation of an eye cell, comprising an agent suppressing GPR49/LGR5.

In another embodiment, the agent suppressing GPR49/LGR5 is a nucleic acid, an antibody or an antibody fragment, or a functional equivalent thereof.

In another embodiment, the eye cell is a cell which does not proliferate in the stationary state.

In a specific embodiment, the eye cell includes at least one kind cell selected from a retinal cell, a vitreous body cell, a corneal epithelial cell, a corneal parenchymal cell and a corneal endothelial cell.

In a specific embodiment, the eye cell includes a corneal endothelial cell.

In a specific embodiment, the eye cell includes a corneal endothelial cell of a primate.

In a specific embodiment, the eye cell includes a human corneal endothelial cell.

In a specific embodiment, the eye cell is in the confluent state.

In a specific embodiment, the eye cell is provided in the form of a corneal tissue.

In a further aspect, the present invention provides a composition for preserving the cornea or culturing a corneal endothelial cell, comprising the agent for suppressing differentiation and/or promoting proliferation of the present invention.

In a further aspect, the present invention provides a pharmaceutical composition for treating a corneal endothelial cell disorder or preventing the progression of a corneal endothelial cell disorder, comprising the agent for suppressing differentiation and/or promoting proliferation of the present invention.

In a further aspect, the present invention provides a therapeutic agent or a progression preventive agent for a corneal endothelial cell disorder, comprising a corneal endothelial cell which is cultured using the agent for suppressing differentiation and/or promoting proliferation described in the present invention.

In one embodiment, the cell exists as a population having cell density higher than that of a normal corneal endothelial cell and/or containing undifferentiated cells in a larger amount.

In a further another aspect, the present invention provides a marker for identifying a cell having a high proliferation ability among corneal endothelial cells and/or the differentiation ability of a corneal endothelial cell, comprising GPR49/LGR5.

In one embodiment of the marker of the present invention, the cell having a high proliferation ability is an undifferentiated cell.

In another embodiment of the marker of the present invention, the cell having a high proliferation ability is a stem cell.

In another embodiment of the marker of the present invention, the corneal endothelial cell is a human cell.

In another embodiment of the marker of the present invention, the proliferation ability of the corneal endothelial cell is identified by a characteristic selected from the group consisting of colony forming ability, Ki-67 positivity and BrdU positivity.

In another aspect, the present invention provides a culture which is a corneal endothelial culture, in which the corneal endothelium exits at density higher than the cell density in the confluent state. The corneal endothelial culture in this case usually refers to a culture existing in a state which is different from the state existing in a living body.

In one embodiment, the cell density is about 570 cells/$mm^2$ or more.

In another embodiment, the cell density is about 700 cells/$mm^2$ or more.

In another embodiment, the cell density is about 800 cells/$mm^2$ or more.

In another embodiment, the cell density is about 1000 cells/$mm^2$ or more.

In another aspect, the present invention provides a corneal tissue comprising a corneal endothelial cell, wherein a Ki67-positive cell in the tissue exists at a ratio higher than the ratio in a living body, and/or the density of the corneal endothelial cell is higher than the density in a living body.

In one embodiment, the Ki67-positive cell exists at a ratio of about 4% or more.

In another embodiment, the Ki67-positive cell exists at a ratio of about 7% or more.

In another embodiment, the Ki67-positive cell exists at a ratio of about 10% or more.

In another embodiment, the density of the corneal endothelial cell is about 4000 cells/$mm^2$ or more.

In another embodiment, the density of the corneal endothelial cell is about 4500 cells/$mm^2$ or more.

In another embodiment, the density of the corneal endothelial cell is about 5000 cells/$mm^2$ or more.

In another aspect, the present invention provides a method for using GPR49/LGR5 as an index for identifying a cell having a high proliferation ability among corneal endothelial cells and/or the differentiation ability of a corneal endothelial cell.

In one embodiment in the method for using GPR49/LGR5 as an index of the present invention, the cell having a high proliferation ability is an undifferentiated cell.

In another embodiment in the method for using GPR49/LGR5 as an index of the present invention, the cell having a high proliferation ability is a stem cell.

In another embodiment in the method for using GPR49/LGR5 as an index of the present invention, the corneal endothelial cell is a human cell.

In another embodiment in the method for using GPR49/LGR5 as an index of the present invention, the proliferation ability of the corneal endothelial cell is identified by a characteristic selected from the group consisting of colony forming ability, Ki-67 positivity and BrdU positivity.

In a further another aspect, the present invention provides a detection agent for identifying a cell having a high proliferation ability among corneal endothelial cells and/or the differentiation ability of a corneal endothelial cell, comprising a substance binding to GPR49/LGR5.

In one embodiment of the detection agent of the present invention, the direction agent is an antibody or a fragment or functional equivalent thereof, or a nucleic acid primer or a probe.

In another embodiment of the detection agent of the present invention, the detection agent is labeled.

In another embodiment of the detection agent of the present invention, the cell having a high proliferation ability is a stem cell.

In another embodiment of the detection agent of the present invention, the corneal endothelial cell is a human cell.

In another embodiment of the detection agent of the present invention, the proliferation ability of the corneal endothelial cell is identified by a characteristic selected from the group consisting of colony forming ability, Ki-67 positivity and BrdU positivity.

In a further another aspect, the present invention provides a marker for identifying a cell having a high proliferation ability among corneal endothelial cells and/or the differentiation ability of a corneal endothelial cell, comprising SHH.

In one embodiment of the marker of the present invention, the cell having a high proliferation ability is an undifferentiated cell.

In another embodiment of the marker of the present invention, the cell having a high proliferation ability is a stem cell.

In another embodiment of the marker of the present invention, the corneal endothelial cell is a human cell.

In another embodiment of the marker of the present invention, the proliferation ability of the corneal endothelial cell is identified by a characteristic selected from the group consisting of colony forming ability, Ki-67 positivity and BrdU positivity.

In another aspect, the present invention provides a method for using SHH as an index for identifying a cell having a high proliferation ability among corneal endothelial cells and/or the differentiation ability of a corneal endothelial cell.

In one embodiment in the method for using SHH as an index of the present invention, the cell having a high proliferation ability is an undifferentiated cell.

In another embodiment in the method for using SHH as an index of the present invention, the cell having a high proliferation ability is a stem cell.

In another embodiment in the method for using SHH as an index of the present invention, the corneal endothelial cell is a human cell.

In another embodiment in the method for using SHH as an index of the present invention, the proliferation ability of the corneal endothelial cell is identified by a characteristic selected from the group consisting of colony forming ability, Ki-67 positivity and BrdU positivity.

In a further another aspect, the present invention provides a detection agent for identifying a cell having a high proliferation ability among corneal endothelial cells and/or the differentiation ability of a corneal endothelial cell, comprising a substance binding to SHH.

In one embodiment of the detection agent of the present invention, the detection agent is an antibody or a fragment or functional equivalent thereof, or a nucleic acid primer or a probe.

In another embodiment of the detection agent of the present invention, the detection agent is labeled.

In another embodiment of the detection agent of the present invention, the cell having a high proliferation ability is a stem cell.

In another embodiment of the detection agent of the present invention, the corneal endothelial cell is a human cell.

In another embodiment of the detection agent of the present invention, the proliferation ability of the corneal endothelial cell is identified by a characteristic selected from the group consisting of colony forming ability, Ki-67 positivity and BrdU positivity.

In a further another aspect, the present invention provides a marker for identifying a cell having a high proliferation ability among corneal endothelial cells and/or the differentiation ability of a corneal endothelial cell, comprising a factor of the Hedgehog pathway.

In one embodiment of the marker of the present invention, the cell having a high proliferation ability is an undifferentiated cell.

In another embodiment of the marker of the present invention, the cell having a high proliferation ability is a stem cell.

In another embodiment of the marker of the present invention, the corneal endothelial cell is a human cell.

In another embodiment of the marker of the present invention, the proliferation ability of the corneal endothelial cell is identified by at least one characteristic selected from the group consisting of colony forming ability, Ki-67 positivity and BrdU positivity.

In another embodiment of the marker of the present invention, the factor of the Hedgehog pathway is selected from the group consisting of SHH, PTCT1, GLI1 and GLI2.

In a further another aspect, the present invention provides a method for using a factor of the Hedgehog pathway as an index for identifying a cell having a high proliferation ability among corneal endothelial cells and/or the differentiation ability of a corneal endothelial cell.

In one embodiment of the method of the present invention, the cell having a high proliferation ability is an undifferentiated cell.

In another embodiment of the method of the present invention, the cell having a high proliferation ability is a stem cell.

In another embodiment of the method of the present invention, the corneal endothelial cell is a human cell.

In another embodiment of the present invention, the proliferation ability of the corneal endothelial cell is identified by at least one characteristic selected from the group consisting of colony forming ability, Ki-67 positivity and BrdU positivity.

In another embodiment of the present invention, the factor of the Hedgehog pathway is selected from the group consisting of SHH, PTCH1, GLI1 and GLI2.

In another aspect, the present invention provides a detection agent for identifying a cell having a high proliferation ability among corneal endothelial cells and/or the differentiation ability of a corneal endothelial cell, comprising a substance binding to a factor of the Hedgehog pathway.

In one embodiment of the detection agent of the present invention, the detection agent is an antibody or a fragment or functional equivalent thereof, or a nucleic acid primer or a probe.

In another embodiment of the detection agent of the present invention, the detection agent is labeled.

In another embodiment of the detection agent of the present invention, the cell having a high proliferation ability is a stem cell.

In another embodiment of the detection agent of the present invention, the corneal endothelial cell is a human cell.

In another embodiment of the detection agent of the present invention, the proliferation ability of the corneal endothelial cell is identified by at least one characteristic selected from the group consisting of colony forming ability, Ki-67 positivity and BrdU positivity.

In another embodiment of the detection agent of the present invention, the factor of the Hedgehog pathway is selected from the group consisting of SHH, PTCH1, GLI1 and GLI2.

In another aspect, the present invention provides a marker for identifying a cell having a high proliferation ability among corneal endothelial cells and/or the differentiation ability of a corneal endothelial cell, comprising a factor of the Wnt pathway.

In one embodiment of the marker of the present invention, the cell having a high proliferation ability is an undifferentiated cell.

In another embodiment of the marker of the present invention, the cell having a high proliferation ability is a stem cell.

In another embodiment of the marker of the present invention, the corneal endothelial cell is a human cell.

In another embodiment of the marker of the present invention, the proliferation ability of the corneal endothelial cell is identified by at least one characteristic selected from the group consisting of colony forming ability, Ki-67 positivity and BrdU positivity.

In another embodiment of the marker of the present invention, the factor of the Wnt pathway is selected from the group consisting of LRP6 and β-catenin.

In another aspect, the present invention provides a method for using a factor of the Wnt pathway as an index for identifying a cell having a high proliferation ability among corneal endothelial cells and/or the differentiation ability of a corneal endothelial cell.

In one embodiment of the method of the present invention, the cell having a high proliferation ability is an undifferentiated cell.

In another embodiment of the method of the present invention, the cell having a high proliferation ability is a stem cell.

In another embodiment of the method of the present invention, the corneal endothelial cell is a human cell.

In another embodiment of the method of the present invention, the proliferation ability of the corneal endothelial cell is identified by a characteristic selected from the group consisting of colony forming ability, Ki-67 positivity and BrdU positivity.

In another embodiment of the method of the present invention, the factor of the Wnt pathway is selected from the group consisting of LRP6 and β-catenin.

In another aspect, the present invention provides a detection agent for identifying a cell having a high proliferation ability among corneal endothelial cells and/or the differentiation ability of a corneal endothelial cell, comprising a substance binding to a factor of the Wnt pathway.

In one embodiment of the detection agent of the present invention, the detection agent is an antibody or a fragment or functional equivalent thereof, or a nucleic acid primer or a probe.

In another embodiment of the detection agent of the present invention, the detection agent is labeled.

In another embodiment of the detection agent of the present invention, the cell having a high proliferation ability is a stem cell.

In another embodiment of the detection agent of the present invention, the corneal endothelial cell is a human cell.

In another embodiment of the detection agent of the present invention, the proliferation ability of the corneal endothelial cell is identified by a characteristic selected from the group consisting of colony forming ability, Ki-67 positivity and BrdU positivity.

In another embodiment of the detection agent of the present invention, the factor of the Wnt pathway is selected from the group consisting of LRP6 and β-catenin.

In a further another aspect, the present invention provides a diagnostic, a detection kit, a diagnostic kit, a detection system, a diagnostic system or the like using the detection agent, marker or the like of the present invention.

In a further another aspect, the present invention provides a treatment method, a prevention method, use or the like using the pharmaceutical composition, therapeutic agent or progression preventive agent of the present invention.

It is understood that the aforementioned characteristics can be used in further combining one or more of the aforementioned characteristics therewith.

A person skilled in the art recognizes still further embodiments and advantages of the present invention by reading and understanding the following detailed description, if necessary.

Advantages of the Invention

The present invention can identify the differentiation ability of a cell existing in corneal endothelial cells and can identify a cell having a high proliferation ability, and as a result, it has become possible to effectively identify and collect an undifferentiated cell which exists in the corneal endothelium at a small amount. In addition, the corneal endothelium can proliferate by using R-spondins, and a disease or disorder of the corneal endothelium, which has previously been impossible or difficult to treat or prevent, can be treated or prevented.

BRIEF DESCRIPTION OF THE DRAWINGS

The patent or application file contains drawings executed in color. Copies of this patent or patent application publication with color drawings will be provided by the Office upon request and payment of the necessary fee.

FIG. 2 shows expression of GPR49/LGR5 in the human cornea. c. shows a whole mount of immunostaining of GPR49/LGR5. Center shows a central portion, and Periphery shows a peripheral portion. d. shows an enlarged view of the central region vs. peripheral portion region of the human cornea. Center shows a central portion, and Periphery shows a peripheral portion. e. shows the real time PCR of GPR49/LGR5 at a central portion (Center) and a peripheral portion (Periphery) of the human cornea. The vertical axis shows the relative level of mRNA, when the level of corneal endothelium is set to be 1. N=3. The error bar shows S.E. *In Student's t-test, p<0.05.

FIG. 3 shows expression of GPR49/LGR5 in a cultured corneal endothelial cell. b. shows, from the left side, expressions in cHCEC of GPR49/LGR5 and a nestin mRNA. The vertical axis shows the relative level of mRNA, when the level of primary culturing (P0) is set to be 1. In vivo, and primary culturing (P0) are shown. N=4. An error bar shows S.E. *In Student's t-test, p<0.05. ND=not detected.

FIG. 3 shows expression of GPR49/LGR5 in a cultured corneal endothelium cell. c. shows the immunostain of GPR49/LGR5 in a cultured monkey corneal endothelial cell (cMCEC). From the left side, a phase contrast image and a GPR49 PI image are shown. From the upper side, in vivo, primary culturing (P0), and passage first generation (P1) are shown. The scale bar shows 100 μm.

FIG. 3 shows expression of GPR49/LGR5 in a cultured corneal endothelium cell. d. shows expression in cMCEC of GPR49/LGR5 mRNA. The vertical axis shows the relative level of mRNA, when the level of primary culturing (P0) is set to be 1. In vivo, primary culturing (P0), passage first generation (P1) and passage second generation (P2) are shown. N=3. An error bar shows S.E. *In Student's t-test, p<0.05.

FIG. 4 shows the characterization of a GPR49/LGR5-positive cell. b. shows the surface area of each cell. The average cell size of GPR49$^+$ is 184.6±45.8 μm$^2$, and the average cell size of GPR49$^-$ is 326.78±78.8 N=35. An error bar shows S.E. *In Student's t-test, p<0.01. c. shows the Ki-67 positivity ratio of GPR49$^+$ and GPR49$^-$. N=4. An error bar shows S.E. *In Student's t-test, p<0.05.

FIG. 4 shows the characterization of a GPR49/LGR5-positive cell. d. shows the cell sorting of the cell proliferation of GPR49$^+$ by double staining (vertical axis: Cy3-Ki67 and transverse axis: FITC-GPR49): GPR49$^+$/Ki-67$^+$; 3.4%, GPR49$^+$/Ki-67$^-$; 3.8%, GPR49$^-$/Ki-67$^-$; 0%, GPR49$^-$/Ki-67$^-$; 92.8%.

FIG. 5 shows the Hedgehog signal transmission pathway in cHCEC. b. shows, from the left side, the immunostaining of a control, GPR49/LGR5 and Ki-67 in HCEC treated with 100 ng/ml rhShh (second from the left side), 10 μM purmorphamine (Pur) (third from the left side) and 10 μM cyclopamide (Cyc) (the rightmost). The upper row shows GPR49 staining, and the lower row shows Ki67 staining. The control is 0.1% DMSO. The scale bar shows 100 μm.

FIG. 5 shows the Hedgehog signal transmission pathway in cHCEC. c. shows, in the upper row and from the left side, the real time PCR of GPR49/LGR5 and Ptch1, and in the lower row and from the left side, the real time PCR of Gli1 and Gli2. Control means a control, and the vertical axis shows the relative level of mRNA, when the result from the control is set to be 1. rhShh shows treatment with rhShh, Pur shows treatment with purmorphamine, and Cyc shows treatment with cyclopamide. N=4. An error bar shows S.E. *In Student's t-test, p<0.05. **In Student's T-test, p<0.01.

FIG. 5 shows the Hedgehog signal transmission pathway in cHCEC. d. shows expression (relative mRNA level) of GPR49/LGR5 in cHCEC treated with rhSHH. e. shows the immunostaining of GPR49/LGR5 in cHCEC treated with rhSHH. The scale bar shows 100 µm.

FIG. 5 shows the Hedgehog signal transmission pathway in cHCEC. f. shows, from the left side, the immunostaining of a control, Ki-67 in cHCEC treated with 100 ng/ml rhSHH, 2 µM Pur and 2 µM Cyc. The upper row shows GRP49 staining. The lower row shows Ki67 staining. The control is 0.01% DMSO. The scale bar shows 100 µm.

FIG. 5 shows the Hedgehog signal transmission pathway in cHCEC. g. shows, from the light side, the Ki-67 positivity ratio of a control, cHCEC treated with, 100 ng/ml rhShh, 2 µM purmorphamine (Pur) and 2 µM cyclophosphamide (Cyc). N=5. An error bar shows S.E. *In Student's t-test, p<0.01.

FIG. 6 shows the function of GPR49/LGR5 in a corneal endothelial cell. b. shows expressions of Ptch1, Gli1 and Gli2 (from the left side) treated with shRNA (589). NT: non-target. N=5. An error bar shows S.E. ND=not detected.

FIG. 6 shows the function of GPR49/LGR5 in a corneal endothelial cell. c. shows the effect of overexpression of GPR49/LGR5 on cHCEC. The left side shows a phase contrast image, and the right side shows $Na^+/K^+$ ATPase PI staining. The upper row shows GPR49 expression, and the lower row shows NT (control).

FIG. 6 shows the function of GPR49/LGR5 in a corneal endothelial cell. d. shows, in the upper row and from the left side, expressions of GPR49/LGR5 and Ptch1, and in the lower row and from the left side, expressions of Gli1 and Gli2 mRNA. NT shows a control, and ExpGPR49 shows a GPR49/LGR5 expression product. N=3. An error bar shows S.E. *In Student's t-test, *p<0.01.

FIG. 6B(A) is partially overlapped with FIG. 6-3 (phase contrast image, NaKATP), but for comparison, both of them are shown side by side. (B) shows the cell density of CEC in the presence or absence of RSPO1. Average±SEM. P<0.01. N=5. (C) shows the cell density of NT and LGR5-transfected cell. Average±SEM. P<0.01. N=5. (D) shows real time PCR concerning EMT-associated genes (Snail (the leftmost), Slug (second from the left side), Twist (second from the right side) and collagen 1 (the rightmost)) in NT and a LGR5-transfected cell. Average±SEM. **P<0.01. N=3. (E) shows a phase contrast microscope image of human CEC in the presence (RSPO1(+), right) or absence (RSPO1(−), left) of RSPO1 (50 ng/ml). The scale bar=100 µm. (F) shows the western blotting of activated β-catenin (the uppermost row), pLRP6 (second from the upper side), tLRP6 (second from the lower side) and β-actin (the lowermost row) in NT and a LGR5-transfected cell in the presence or absence of RSPO1 (50 ng/ml).

FIG. 7 shows an outline of R-spondins 1 to 4.

FIG. 16 shows the results concerning organ culturing using a rabbit sclerocornea slice, which are obtained by culturing the organ in an incubator at 37° C. for one week in DMEM (INVITROGEN, catalog number: 12320)+10% fetal bovine serum (FBS) (BIOWEST, catalog number: S1820-500) in the presence (from the right side, 100 ng/ml, 10 ng/ml, 1 ng/ml) or absence (the leftmost, control) of R-spondin 1; immunostaining a corneal endothelial cell using Ki67 (Sigma-Aldrich Co., catalog number: P6834) as a marker of cell proliferation; and observing the resultant with a fluorescent microscope. Nuclear staining was performed with DAPI, a Ki67-positive cell rate was calculated, and the results are shown in the left lower panel. In addition, immunostaining was performed with ZO-1, and the cell density was calculated, and results are shown in the right lower panel.

MODE FOR CARRYING OUT THE INVENTION

Figure 1:
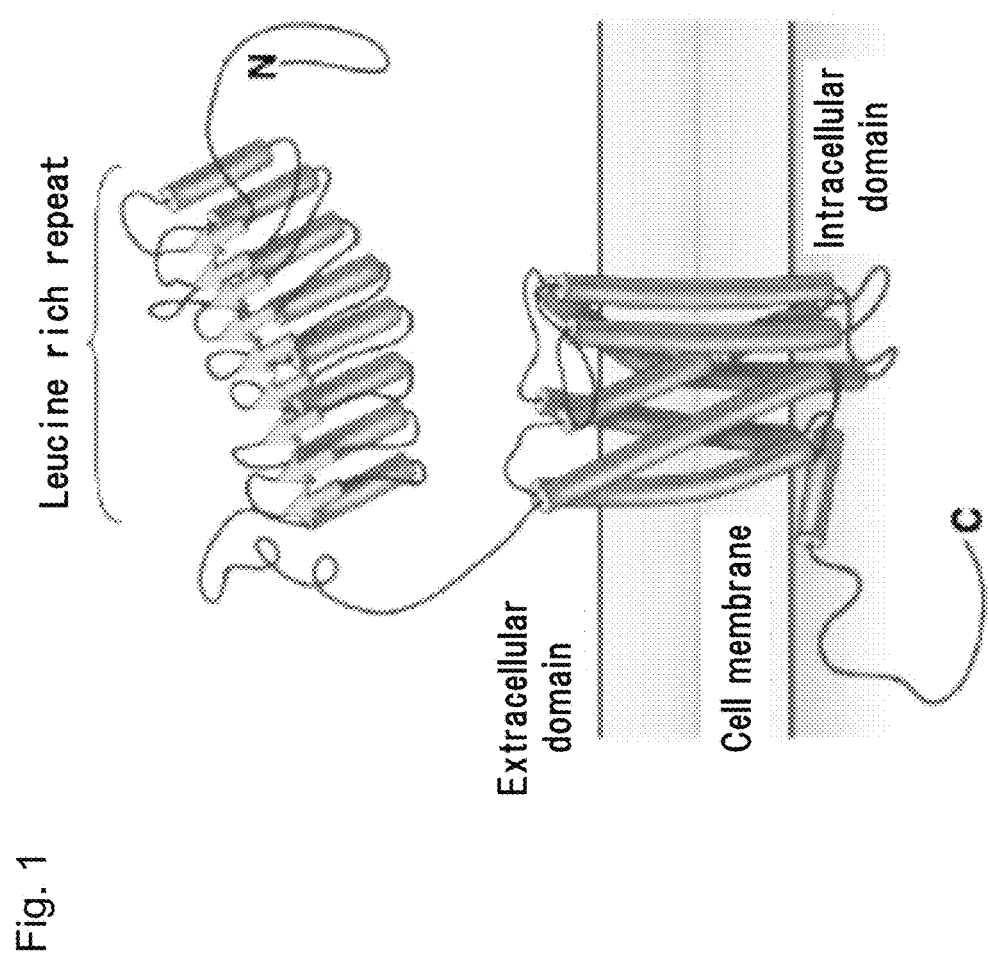
FIG. 1 shows the structure of GRP49/LGR5 (see Barker N. et al., Gastroenterology, 2010 May; 138 (5): 1681-96).

The present invention will be described below. It should be understood that expression in a singular form also includes the conception of its plural form, unless specifically defined, throughout the present description. Therefore, it should be understood that an article in a singular form (e.g., "a", "an", and "the" in English) also includes the conception of its plural form, unless specifically mentioned. In addition, it should be understood that terms used herein are used in a sense which is usually used in the art, unless specifically mentioned. Therefore, unless defined otherwise, all technical terminology and scientific and technical terminology used herein have the same meanings as those generally understood by a person skilled in the art to which the present invention belongs. In the case of confliction, the present description (including definition) prevails.

As used herein, "GPR49/LGR5" is a seven-transmembrane protein which is a member of LGR family. GPR49/LGR5 is named based on a leucine rich repeat-containing G protein-coupled receptor-5, which is an abnormal G protein-coupled receptor (GPCR), that is characterized by a large N-terminal extracellular domain containing leucine rich repeats that in some cases have been shown to be important for interaction with glycoprotein ligands, and recently, the frequency of such a name is increased, and both names are described together herein. This is also known as FEX HG38, GPR67. An amino acid sequence of human GPR49/LGR5 and a gene sequence encoding this are disclosed in NCBI registration number NP 003658.1 (SEQ ID No.: 2) and NM_003667.2 (SEQ ID No.: 1), respectively. In the art, they are also called by a single name such as GPR49 or LGR5. As used herein, "GPR49/LGR5" is described, but it is understood that any expression shows the same meaning. GPR49/LGR5 can be identified by the accession number of OMIM: 606667. It is understood when used for the purpose of the present description, "GPR49/LGR5" means not only a protein having an amino acid sequence described in a specific sequence number or an accession number (or nucleic acid encoding the same), but also a functionally active derivative thereof, a functionally active fragment thereof, or a homolog thereof, or a mutant encoded by a nucleic acid which hybridizes with a nucleic acid encoding this protein under a high stringency condition or a low stringency condition.

In addition, the same shall apply to all other proteins listed in the present invention. Therefore, the already defined name of a protein or a nucleic acid refers to not only a protein or a nucleic acid as shown in Sequence Listing, but also a functionally active derivative, or a functionally active fragment thereof, or a homolog thereof, or a mutant encoded by a nucleic acid which hybridizes with a nucleic acid encoding the protein under a high stringency condition or a low stringency condition, preferably under the aforementioned condition. Preferably, a "derivative" or an "analog of a constituent protein" or a "mutant" used herein, does not intend limitation, but includes a molecule containing a region substantially homologous to a constituent protein. In various embodiments, such a molecule is at least 30%, 40%, 50%, 60%, 70%, 80%, 90%, 95% or 99% identical with the comparative lengths of amino acid sequences, or in comparison with sequences which are aligned by a computer homology program known in the art, or a nucleic acid encoding such a molecule can hybridize with a sequence encoding a constituent protein under a stringent condition, under a moderately stringent condition, or under not stringent condition. This is an outcome of modification of a naturally-occurring protein by amino acid substitution, deletion and addition, respectively, and means a protein such that a derivative thereof still exhibits the biological function of a naturally-occurring protein to a degree that may not be necessarily the same. For example, it is also possible to investigate the biological function of such a protein by an appropriately utilizable in vitro assay which is described herein or known in the art. In the present invention, human GPR49/LGR5 is mainly discussed, but since it is known that many mammals other than human, such as chimpanzee (*Pan troglodytes*) (ENSPTRG00000005223 (XR_021586.1)), rhesus monkey (*Macaca mulatta*) (ENSMMUG00000020942), mouse (*Mus musculus*) (ENSMUSG00000020140), rat (*Rattus norvegicus*) (ENSRNOG00000004221 (LOC687868)), guinea pig (*Cavia porcellus*) (ENSCPOG00000009492), dog (*Canis familiaris*) (ENSCAFG00000000451), cat (*Felis catus*) (ENSFCAG00000008064), and chicken (*Gallus gallus*) (ENSGALG00000010163), express a GPR49/LGR5 protein, it is understood that these mammals are within the scope of the present invention.

It has been found that GPR49/LGR5 forms a part of different protein complexes, which is involved in abnormal processing of APP with gamma secretase, in an Alzheimer's disease. Since it has been found that GPR49/LGR5 is a part of an Aphla complex, a Fe65L2 complex, an APP-C99 complex and a BACE1 complex, GPR49/LGR5 can be also detected by detecting these complexes. These complexes are named after respective important protein compounds, which are used as TAP technical entry points.

The "functionally active" as used herein refers to the polypeptide of the present invention, that is, a polypeptide having the structural function, controlling function, or biochemical function, such as a biological activity, of a protein, which is a fragment or a derivative, in accordance with an aspect associated with a fragment or a derivative, as used herein.

In the present invention, the fragment of GPR49/LGR5 is a polypeptide comprising an arbitrary region of GPR49/LGR5, and may not have the biological function of natural GPR49/LGR5. Examples of the fragment include fragments comprising an extracellular region of GPR49/LGR5. The extracellular region of GPR49/LGR5 corresponds to 1-556$^{th}$, 615-637$^{th}$, 704-722$^{nd}$, and 792-800$^{th}$ in the amino acid sequence of SEQ ID No.: 2. A transmembrane region corresponds to 557-579$^{th}$, 592-614$^{th}$, 638-660$^{th}$, 681-703$^{rd}$, 723-745$^{th}$, 769-791$^{st}$ and 801-823$^{rd}$ in the amino acid sequence of SEQ ID No.: 2.

A representative nucleotide sequence of GPR49/LGR5 can be:
(a) a polynucleotide having a nucleotide sequence of SEQ ID No.: 1 or a fragment sequence thereof;
(b) a polynucleotide encoding a polypeptide consisting of an amino acid sequence of SEQ ID No.: 2 or a fragment thereof;
(c) a polynucleotide encoding a variant polypeptide in which one or more amino acids have one mutation selected from the group consisting of substitution, addition and deletion in an amino acid sequence of SEQ ID No.: 2, or a fragment thereof, the variant polypeptide having a biological activity;
(d) a polynucleotide which is a splicing mutant or an allele mutant of a nucleotide sequence of SEQ ID No.: 1 or a fragment thereof;
(e) a polynucleotide encoding a species homolog of a polypeptide consisting of an amino acid sequence of SEQ ID No.: 2 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of GPR49/LGR5.

An amino acid sequence of GPR49/LGR5 can be:
(a) a polypeptide consisting of an amino acid sequence of SEQ ID No.: 2 or a fragment thereof;
(b) a polypeptide in which one or more amino acids have one mutation selected from the group consisting of substitution, addition and deletion in an amino acid sequence of SEQ ID No.: 2, and the polypeptide has a biological activity;
(c) a polypeptide encoded by a splicing mutant or an allele mutant of a nucleotide sequence of SEQ ID No.: 1;
(d) a polypeptide which is a species homolog of an amino acid sequence of SEQ ID No.: 2; or
(e) a polypeptide having an amino acid sequence in which the identity to the polypeptide of any one of (a) to (d) is at least 70%, and having a biological activity.
Herein, the biological activity representatively refers to an activity of GPR49/LGR5.

In a context with the present invention, the "substance binding to GPR49/LGR5" or the "GPR49/LGR5 interaction molecule" is a molecule or a substance which binds to GPR49/LGR5 at least temporarily, and preferably, can indicate that it has bound thereto (e.g., in the state where it is labeled or can be labeled). The substance binding to GPR49/LGR5 may be an inhibitor of GPR49/LGR5, and examples thereof may include an antibody, an antisense-oligonucleotide, siRNA, a low molecular weight (LMW) molecule, a binding peptide, an aptamer, a ribozyme and a peptidomimetic, and for example, a binding protein or a binding peptide directed to GPR49/LGR5, particularly, directed to an active site of GPR49/LGR5, as well as a nucleic acid directed to a GPR49/LGR5 gene are also included. A nucleic acid to GPR49/LGR5 refers to, for example, double-stranded or single-stranded DNA or RNA which inhibits expression of a GPR49/LGR5 gene or the activity of GPR49/LGR5, or a modified product or derivative thereof, and includes, without limitation, an antisense nucleic acid, an aptamer, siRNA (low-molecular interference RNA) and a ribozyme. As used herein, concerning GPR49/LGR5, the "binding protein" or the "binding peptide" refers to a kind of a protein or a peptide which binds to GPR49/LGR5, and includes, but is not limited to, a polyclonal antibody or a monoclonal antibody, an antibody fragment and a protein skeleton directed to GPR49/LGR5.

As used herein, "R-spondin(s)" refers to a gene group having the same structure and function as those of R-spondin 1 and the like, and is explained in Non-Patent Document 4 (J. Yoon, J. Lee, Cellular Signalling 24 (2012) 369-377). For example, it is known, as a structure, that R-spondin(s) has a domain of SP, CR, TSR and BR from the N-terminal. In addition, as a function, it is known that R-spondin(s) is a ligand for GPR49. Therefore, R-spondins can be identified using such a structure and function as an index. For example, in human, R-spondin 1 (RSPO1 OMIM: 609595; nucleic acid sequence (gene sequence): SEQ ID No.: 3, 35, 37 or 39; amino acid sequence: SEQ ID No.: 4, 36, 38 or 40), R-spondin 2 (RSPO2 OMIM: 610575, SEQ ID Nos.: 5 and 6), R-spondin 3 (RSPO3 OMIM: 610574, SEQ ID Nos.: 7 and 8), R-spondin 4 (RSPO4 OMIM: 610573: nucleic acid sequence (gene sequence): SEQ ID Nos.: 9 and 41; amino acid sequence: SEQ ID No.: 10 or 42) are known. From the information of Non-Patent Document 4, respective R-spondins are summarized as in FIG. 7.

A representative nucleotide sequence of R-spondin 1 can be:
 (a) a polynucleotide having a nucleotide sequence of SEQ ID No.: 3, 35, 37 or 39, or a fragment sequence thereof;
 (b) a polynucleotide encoding a polypeptide consisting of an amino acid sequence of SEQ ID No.: 4, 36, 38 or 40, or a fragment thereof;
 (c) a polynucleotide encoding a variant polypeptide in which one or more amino acids have one mutation selected from the group consisting of substitution, addition and deletion in an amino acid sequence of SEQ ID No.: 4, 36, 38 or 40, or a fragment thereof, the variant polypeptide having a biological activity;
 (d) a polypeptide which is a splicing mutant or an allele mutant of a nucleotide sequence of SEQ ID NO.: 3, 35, 37 or 39, or a fragment thereof;
 (e) a polynucleotide encoding a species homolog of a polypeptide consisting of an amino acid sequence of SEQ ID No.: 4, 36, 38 or 40, or a fragment thereof;
 (f) a polynucleotide encoding a polypeptide wherein the polynucleotidehybridizes with the polynucleotide of any one of (a) to (e) under a stringent condition, and the polypeptide has a biological activity; or
 (g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity.
Herein, the biological activity representatively refers to an activity of R-spondin 1.
An amino acid sequence of R-spondin 1 can be:
 (a) a polypeptide consisting of an amino acid sequence of SEQ ID No.: 4, 36, 38 or 40, or a fragment thereof;
 (b) a polypeptide in which one or more amino acids have one mutation selected from the group consisting of substitution, addition and deletion in an amino acid sequence of SEQ ID No.: 4, 36, 38 or 40, and the polypeptide has a biological activity;
 (c) a polypeptide encoded by a splicing mutant or an allele mutant of a nucleotide sequence of SEQ ID No.: 3, 35, 37 or 39;
 (d) a polypeptide which is a species homolog of an amino acid sequence of SEQ ID No.: 4, 36, 38 or 40; or
 (e) a polypeptide having an amino acid sequence in which the identity to the polypeptide of any one of (a) to (d) is at least 70%, and having a biological activity.
Herein, the biological activity representatively refers an activity of R-spondin 1.

A representative nucleotide sequence of R-spondin 2 can be:
 (a) a polynucleotide having a nucleotide sequence of SEQ ID No.: 5 or a fragment sequence thereof;
 (b) a polynucleotide encoding a polypeptide consisting of an amino acid sequence of SEQ ID No.: 6 or a fragment thereof;
 (c) a polynucleotide encoding a variant polypeptide in which one or more amino acids have one mutation selected from the group consisting of substitution, addition and deletion in an amino acid sequence of SEQ ID No: 6, or a fragment thereof, the variant polypeptide having a biological activity;
 (d) a polynucleotide which is a splicing mutant or an allele mutant of a nucleotide sequence of SEQ ID No.: 5 or a fragment thereof;
 (e) a polynucleotide encoding a species homolog of a polypeptide consisting of an amino acid sequence of SEQ ID No.: 6 or a fragment thereof;
 (f) a polynucleotide encoding a polypeptide wherein the polynucleotide hybridizes with the polynucleotide of any one of (a) to (e) under a stringent condition, and the polypeptide has a biological activity; or
 (g) a polynucleotide encoding a polypeptide which consists of a nucleotide sequence in which the identity to the polynucleotide of any one of (a) to (e) or a complementary sequence thereof is at least 70%, and the polypeptide has a biological activity.
Herein, the biological activity representatively refers to an activity of R-spondin 2.
An amino acid sequence of R-spondin 2 can be:
 (a) a polypeptide consisting of an amino acid sequence of SEQ ID No.: 6 or a fragment thereof;
 (b) a polypeptide in which one or more amino acids have one mutation selected from the group consisting of substitution, addition and deletion in an amino acid sequence of SEQ ID No.: 6, and the polypeptide has a biological activity;
 (c) a polypeptide encoded by a splicing mutant or an allele mutant of a nucleotide sequence of SEQ ID No.: 5;
 (d) a polypeptide which is a species homolog of an amino acid sequence of SEQ ID No.: 6; or
 (e) a polypeptide having an amino acid sequence in which the identity to the polypeptide of any one of (a) to (d) is at least 70%, and having a biological activity.
Herein, the biological activity representatively refers to an activity of R-spondin 2.

A representative nucleotide sequence of R-spondin 3 can be:
 (a) a polynucleotide having a nucleotide sequence of SEQ ID No.: 7 or a fragment sequence thereof;
 (b) a polynucleotide encoding a polypeptide consisting of an amino acid sequence of SEQ ID No.: 8 or a fragment thereof;
 (c) a polynucleotide encoding a variant polypeptide in which one or more amino acids have one mutation selected from the group consisting of substitution, addition and deletion in an amino acid sequence of SEQ ID No.: 8, or a fragment thereof, the variant polypeptide having a biological activity;

(d) a polynucleotide which is a splicing mutant or an allele mutant of a nucleotide sequence of SEQ ID No.: 7 or a fragment thereof;
(e) a polynucleotide encoding a species homolog of a polypeptide consisting of an amino acid sequence of SEQ ID No.: 8 or a fragment thereof;
(f) a polynucleotide encoding a polypeptide which hybridizes with the polynucleotide of any one of (a) to (e) under a stringent condition, and the polynucleotide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of R-spondin 3.

An amino acid sequence of R-spondin 3 can be:
(a) a polypeptide consisting of an amino acid sequence of SEQ ID No.: 8 or a fragment thereof;
(b) a polypeptide in which one or more amino acids have one mutation selected from the group consisting of substitution, addition and deletion in an amino acid sequence of SEQ ID No.: 8, and the polypeptide has a biological activity;
(c) a polypeptide encoded by a splicing mutant or an allele mutant of a nucleotide sequence of SEQ ID No.: 7;
(d) a polypeptide which is a species homolog of an amino acid sequence of SEQ ID No.: 8; or
(e) a polypeptide having an amino acid sequence in which the identity to the polypeptide of any one of (a) to (d) is at least 70%, and having a biological activity.
Herein, the biological activity representatively refers to an activity of R-spondin 3.

A representative nucleotide sequence of R-spondin 4 can be:
(a) a polynucleotide having a nucleotide sequence of SEQ ID No.: 9 or 41, or a fragment sequence thereof;
(b) a polynucleotide encoding a polypeptide consisting of an amino acid sequence of SEQ ID No.: 10 or 42, or a fragment thereof;
(c) a polynucleotide encoding a variant polypeptide in which one or more amino acids have one mutation selected from the group consisting of substitution, addition and deletion in an amino acid sequence of SEQ ID No.: 10 or 42, or a fragment thereof, the variant polypeptide having a physiological activity;
(d) a polynucleotide which is a splicing mutant or an allele mutant of a nucleotide sequence of SEQ ID No.: 9 or 41, or a fragment thereof;
(e) a polynucleotide encoding a species homolog of a polypeptide consisting of an amino acid sequence of SEQ ID No.: 10 or 42, or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of R-spondin 4.

An amino acid sequence of R-spondin 4 can be:
(a) a polypeptide consisting of an amino acid sequence of SEQ ID No.: 10 or 42, or a fragment thereof;
(b) a polypeptide in which one or more amino acids have one mutation selected from the group consisting of substitution, addition and deletion in an amino acid sequence of SEQ ID No.: 10 or: 42, and the polypeptide has a biological activity;
(c) a polypeptide encoded by a splicing mutant or an allele mutant of a nucleotide sequence of SEQ ID No.: 9 or 41;
(d) a polypeptide which is a species homolog of an amino acid sequence of SEQ ID No.: 10 or 42; or
(e) a polypeptide having an amino acid sequence in which the identity to the polypeptide of any one of (a) to (d) is at least 70%, and having a biological activity.
Herein, the biological activity representatively refers to an activity of R-spondin 4.

As used herein, "SONIC HEDGEHOG (SHH)" is one of five kinds of proteins belonging to Hedgehog (HH) family, and a gene encoding this is shown by shh. SHH has a role in patterning many organs such as limbs and midline structures in the brain, as the most important morphogen in development. It is known that, in mutation of a human sonic hedgehog gene, deletion of ventral midline occurs to cause holoprosencephaly (HPE), and additionally, hyperdactyly is generated due to a cause of change in a cis regulating element. As other proteins of this family, there are Desert Hedgehog (DHH) and Indian Hedgehog (IHH) in a mammal. For example, SHH (SHH OMIM 600725; human: NM_000193 (SEQ ID Nos.: 11 and 12); mouse: NM_009170) is known as a protein of human.

A representative nucleotide sequence of shh can be:
(a) a polynucleotide having a nucleotide sequence of SEQ ID No.: 11 or a fragment thereof;
(b) a polynucleotide encoding a polypeptide consisting of an amino acid sequence of SEQ ID No.: 12 or a fragment thereof;
(c) a polynucleotide encoding a variant polypeptide in which one or more amino acids have one mutation selected from the group consisting of substitution, addition and deletion in an amino acid sequence of SEQ ID No.: 12, or a fragment thereof, the variant polypeptide having a biological activity;
(d) a polynucleotide which is a splicing mutant or an allele mutant of a nucleotide sequence of SEQ ID No.: 11 or a fragment thereof;
(e) a polynucleotide encoding a species homolog of a polypeptide consisting of an amino acid sequence of SEQ ID No.: 12 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of SHH.

An amino acid sequence of SHH can be:
(a) a polypeptide consisting of an amino acid sequence of SEQ ID No.: 12 or a fragment thereof;
(b) a polypeptide in which one or more amino acids have one mutation selected from the group consisting of substitution, addition and deletion in an amino acid sequence of SEQ ID No.: 12, and the polypeptide has a biological activity;

(c) a polypeptide encoded by a splicing mutant or an allele mutant of a nucleotide sequence of SEQ ID No.: 11;
(d) a polypeptide which is a species homolog of an amino acid sequence of SEQ ID No.: 12; or
(e) a polypeptide having an amino acid sequence in which the identity to the polypeptide of any one of (a) to (d) is at least 70%, and having a biological activity.

Herein, the biological activity representatively refers to an activity of SHH.

Examples of the factors of the Hedgehog pathway include SHH, PTCH1, GLI1 and GLI2.

As used herein, "PTCH1" is one of the factors of the Hedgehog pathway, is a receptor called Patched-1, and is a receptor to which SHH binds. A gene encoding this factor is shown by ptch1. It is stated that, by binding between SHH and PTCH1, suppression of Smoothened (SMO) which is also a component of a SHH receptor complex is cancelled, a signal is transmitted into a cell, and finally, transcription of a variety of target genes is activated through a Gli transcription factor to exert a physiological function. It is stated that the gamete mutation of PTCH1 causes a hereditary disease of nevoid basal cell carcinoma syndrome (NBCCS) (also called Gorlin syndrome) characterized by minor anomaly and high oncogenesis. PTCH1 is also a cancer suppressing gene. This gene is also known as PTC; BCNS; HPE7; PTC1; PTCH; NBCCS; or PTCH11. For example, the factor in human is NC_000009.11 (NCBI Reference Sequence), and NC_000009 (Accession No.) and NM_001083602.1 (Accession No.) (SEQ ID Nos.: 43 and 44) are known.

A representative nucleotide sequence of ptch1 can be:
(a) a polynucleotide having a nucleotide sequence of SEQ ID No.: 43 <NM_001083602.1> or a fragment sequence thereof;
(b) a polynucleotide encoding a polypeptide consisting of an amino acid sequence of SEQ ID No.: 44 or a fragment thereof;
(c) a polynucleotide encoding a variant polypeptide in which one or more amino acids have one mutation selected from the group consisting of substitution, addition and deletion in an amino acid sequence of SEQ ID No.: 44, or a fragment thereof, the variant polypeptide having a biological activity;
(d) a polynucleotide which is a splicing mutant or an allele mutant of a nucleotide sequence of SEQ ID No.: 43 or a fragment thereof;
(e) a polynucleotide encoding a species homolog of a polypeptide consisting of an amino acid sequence of SEQ ID No.: 44 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of PTCH1.

An amino acid sequence of PTCH1 can be:
(a) a polypeptide consisting of an amino acid sequence of SEQ ID No.: 44 or a fragment thereof;
(b) a polypeptide in which one or more amino acids have one mutation selected from the group consisting of substitution, addition and deletion in an amino acid sequence of SEQ ID No.: 44, and the polypeptide has a biological activity;
(c) a polypeptide encoded by a splicing mutant or an allele mutant of a nucleotide sequence of SEQ ID No.: 43;
(d) a polypeptide which is a species homolog of an amino acid sequence of SEQ ID No.: 44; or
(e) a polypeptide having an amino acid sequence in which the identity to the polypeptide of any one of (a) to (d) is at least 70%, and having a biological activity.

Herein, the biological activity representatively refers to an activity of PTCH1.

As used herein, "GLI1" is a factor of the Hedgehog (HH) pathway, and one of transcription factor Gli family members (GLI1, GLI2, GLI3 etc.). A gene encoding GLI1 is shown by gli1. It is stated that GLI1 is located downstream from PTCH1, and a signal is transmitted to GPR49/LGR5 from this point. It is stated that, by binding between SHH and PTCH1, suppression of Smoothened (SMO) which is also a component of a SHH receptor complex is cancelled, a signal is transmitted into a cell, and finally, transcription of a variety of target genes is activated through a GLI transcription factor to exert a physiological function. For example, as the factors in human, NM_005269.2 (NCBI Reference Sequence), NM_005269 (Genbank Accession) for variant 1; NM_001160045.1 (NCBI Reference Sequence), NM_001160045 (Genbank Accession) for variant 2; NM_001167609.1 (NCBI Reference Sequence), NM_001167609 (Genbank Accession) (SEQ ID Nos.: 45 and 46) for variant 3 are known.

A representative nucleotide sequence of gli1 can be:
(a) a polynucleotide having a nucleotide sequence of SEQ ID No.: 45 <NM_001167609.1> or a fragment sequence thereof;
(b) a polynucleotide encoding a polypeptide consisting of an amino acid sequence of SEQ ID No.: 46 or a fragment thereof;
(c) a polynucleotide encoding a variant polypeptide in which one or more amino acids have one mutation selected from the group consisting of substitution, addition and deletion in an amino acid sequence of SEQ ID No.: 46, or a fragment thereof, the variant polypeptide having a biological activity;
(d) a polynucleotide which is a splicing mutant or an allele mutant of a nucleotide sequence of SEQ ID No.: 45 or a fragment thereof;
(e) a polynucleotide encoding a species homolog of a polypeptide consisting of an amino acid sequence of SEQ ID No.: 46 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of GLI1.

An amino acid sequence of GLI1 can be:
(a) a polypeptide consisting of an amino acid sequence of SEQ ID No.: 46 or a fragment thereof;
(b) a polypeptide in which one or more amino acids have one mutation selected from the group consisting of substitution, addition and deletion in an amino acid sequence of SEQ ID No.: 46, and the polypeptide has a biological activity;
(c) a polypeptide encoded by a splicing mutant or an allele mutant of a nucleotide sequence of SEQ ID No.: 45;

(d) a polypeptide which is a species homolog of an amino acid sequence of SEQ ID No.: 46; or (e) a polypeptide having an amino acid sequence in which the identity to the polypeptide of any one of (a) to (d) is at least 70%, and having a biological activity.

Herein, the biological activity representatively refers to an activity of GLI1.

As used herein, "GLI2" is a factor of the Hedgehog (HH) pathway, and one of transcription factor GLI family members (GLI1, GLI2, GLI3 etc.). A gene encoding GLI2 is shown by gli2. It is stated that GLI2 is located downstream from PTCH1, and a signal is transmitted to GPR49/LGR5 from this point. It is stated that, by binding between Shh and PTCH1, suppression of Smoothened (SMO) which is also a component of a Shh receptor complex is cancelled, a signal is transmitted into a cell, and finally, transcription of a variety of target genes is activated through a Gli transcription factor to exert a physiological function. For example, NM_005270.4 (NCBI Reference Sequence), NM_005270 (Genbank Accession) (SEQ ID Nos.: 47 and 48) are known as the factors in human.

A representative nucleotide sequence of gli2 can be:
(a) a polynucleotide having a nucleotide sequence of SEQ ID No.: 47 <NM_005270.4> or a fragment thereof;
(b) a polynucleotide encoding a polypeptide consisting of an amino acid sequence of SEQ ID No.: 48 or a fragment thereof;
(c) a polynucleotide encoding a variant polypeptide in which one or more amino acids have one mutation selected from the group consisting of substitution, addition and deletion in an amino acid sequence of SEQ ID No.: 48, or a fragment thereof, the variant polypeptide having a biological activity;
(d) a polynucleotide which is a splicing mutant or an allele mutant of a nucleotide sequence of SEQ ID No.: 47 or a fragment thereof;
(e) a polynucleotide encoding a species homolog of a polypeptide consisting of an amino acid sequence of SEQ ID No.: 48 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity.

Herein, the biological activity representatively refers to an activity of GLI2.

An amino acid sequence of GLI2 can be:
(a) a polypeptide consisting of an amino acid sequence of SEQ ID No.: 48 or a fragment thereof;
(b) a polypeptide in which one or more amino acids have one mutation selected from the group consisting of substitution, addition and deletion in an amino acid sequence of SEQ ID No.: 48, and the polypeptide has a biological activity;
(c) a polypeptide encoded by a splicing mutant or an allele mutant of a nucleotide sequence of SEQ ID No.: 47;
(d) a polypeptide which is a species homolog of an amino acid sequence of SEQ ID No.: 48; or
(e) a polypeptide having an amino acid sequence in which the identity to the polypeptide of any one of (a) to (d) is at least 70%, and having a biological activity.

Herein, the biological activity representatively refers to an activity of GLI2.

Examples of the factors of the Wnt pathway include LRP6 and β-catenin.

As used herein, "LRP6" is one of the factors of the Wnt pathway, and is abbreviation of low-density lipoprotein receptor-related protein 6. A gene encoding this is expressed by lrp6. Gβγ which is G protein activates GSK3, and promotes the transcription activity of β-catenin through LRP6. For example, as the factors in human, NM_002336.2 (NCBI Reference Sequence), NM_002336 (Genbank Accession) LRP6, NM_002336.2 (SEQ ID Nos.: 49 and 50) are known.

A representative nucleotide sequence of lrp6 can be:
(a) a polynucleotide having a nucleotide sequence of SEQ ID No.: 49 <NM_002336.2> or a fragment thereof;
(b) a polynucleotide encoding a polypeptide consisting of an amino acid sequence of SEQ ID No.: 50 or a fragment thereof;
(c) a polynucleotide encoding a variant polypeptide in which one or more amino acids have one mutation selected from the group consisting of substitution, addition and deletion in an amino acid sequence of SEQ ID No.: 50, or a fragment thereof, the variant polypeptide having a biological activity;
(d) a polynucleotide which is a splicing mutant or an allele mutant of a nucleotide sequence of SEQ ID No.: 49 or a fragment thereof;
(e) a polynucleotide encoding a species homolog of a polypeptide consisting of an amino acid sequence of SEQ ID No.: 50 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity.

Herein, the biological activity representatively refers to an activity of LRP6.

An amino acid sequence of LRP6 can be:
(a) a polypeptide consisting of an amino acid sequence of SEQ ID No.: 50 or a fragment thereof;
(b) a polypeptide in which one or more amino acids have one mutation selected from the group consisting of substitution, addition and deletion in an amino acid sequence of SEQ ID No.: 50, and the polypeptide has a biological activity;
(c) a polypeptide encoded by a splicing mutant or an allele mutant of a nucleotide sequence of SEQ ID No.: 49;
(d) a polypeptide which is a species homolog of an amino acid sequence of SEQ ID No.: 50; or
(e) a polypeptide having an amino acid sequence in which the identity to the polypeptide of any one of (a) to (d) is at least 70%, and having a biological activity.

Herein, the biological activity representatively refers to an activity of LRP6.

As used herein, "β-catenin" is one of the factors of the Wnt pathway, and a gene encoding this is shown by beta-catenin/CTNNB1. The Wnt/β-catenin pathway regulates the determination of the destiny of a cell in development in a vertebrate and an invertebrate. A Wnt-ligand is a secreted glycoprotein, and binds to a Frizzled receptor. This binding initiates a cascade such that GSK-3β as a multifunctional kinase is eliminated from an APC/Axin/GSK-4 complex. It is stated that, when there is no Wnt-signal, β-catenin, which is a coupling factor of transcription, and at the same time, which is embedded in a cell membrane and exists as an adaptor protein in adhesion between cells, are degraded by an APC/Axin/GSK-3β complex. It is stated that, when β-catenin undergoes proper phosphorylation by the cooperative action of CK1 and GSK-3β, it leads to ubiquitination and degradation with a proteasome through a β-TrCP/SKP complex. When Wnt binds thereto, Dishevelled (Dvl) undergoes phosphorylation and polyubiquitination to be activated, and this activation in turn keeps GSK-3β away from the degradation complex. This causes Rac-1-dependent nuclear translocation to guide to a LEF/TCF DNA-binding factor for stabilizing β-catenin, where it is stated to act as a transcription activation factor by substitution with a Groucho-HDAC co-repressor. It is stated that the Wnt/β-catenin pathway integrates signals from many other pathways such as retinoic acid, FGF, TGF-β, and BMP, in many different types of cells and tissues. For example, as the factors in human, NM_001904.3 (NCBI Reference Sequence), NM_001904, XM_942045, XM_945648, XM_945650, XM_945651, XM_945652, XM_945653, XM_945654, XM_945655, XM_945657 (Genbank Accession) for variant 1; NM_001098209.1 (NCBI Reference Sequence), NM_001098209, XM_001133660, XM_001133664, XM_001133673, XM_001133675 (Genbank Accession) for variant 2; and NM_001098210.1 (NCBI Reference Sequence), NM_001098210 (Genbank Accession), NM_131059.2 (CTNNB, Accession No.) (SEQ ID Nos.: 51 and 52) for variant 3 are known.

A representative nucleotide sequence of β-catenin can be:
(a) a polynucleotide having a nucleotide sequence of SEQ ID No.: 51 <NM_131059.2> or a fragment thereof;
(b) a polynucleotide encoding a polypeptide consisting of an amino acid sequence of SEQ ID No.: 52 or a fragment thereof;
(c) a polynucleotide encoding a variant polypeptide in which one or more amino acids have one mutation selected from the group consisting of substitution, addition and deletion in an amino acid sequence of SEQ ID No.: 52, or a fragment thereof, the variant polypeptide having a biological activity;
(d) a polynucleotide which is a splicing mutant or an allele mutant of a nucleotide sequence of SEQ ID No.: 51 or a fragment thereof;
(e) a polynucleotide encoding a species homolog of a polypeptide consisting of an amino acid sequence of SEQ ID No.: 52 or a fragment thereof;
(f) a polynucleotide encoding a polypeptide wherein the polynucleotide hybridizes with the polynucleotide of any one of (a) to (e) under a stringent condition, and the polypeptide has a biological activity; or
(g) a polynucleotide encoding a polypeptide wherein the polynucleotide consists of a nucleotide sequence in which the identity to the polynucleotide of any one of (a) to (e) or a complementary sequence thereof is at least 70%, and the polypeptide has a biological activity. Herein, the biological activity representatively refers to an activity of β-catenin.

An amino acid sequence of β-catenin can be:
(a) a polypeptide consisting of an amino acid of SEQ ID No.: 52 or a fragment thereof;
(b) a polypeptide in which one or more amino acids have one mutation selected from the group consisting of substitution, addition and deletion in an amino acid sequence of SEQ ID No.: 52, and the polypeptide has a biological activity;
(c) a polypeptide encoded by a splicing mutant or an allele mutant of a nucleotide sequence of SEQ ID No.: 51;
(d) a polypeptide which is a species homolog of an amino acid sequence of SEQ ID No.: 52; or
(e) a polypeptide having an amino acid sequence in which the identity to the polypeptide of any one of (a) to (d) is at least 70%, and having a biological activity.
Herein, the biological activity representatively refers to an activity of β-catenin.

As used herein, purmorphamine is another name of N-(4-morpholinophenyl)-2-(1-naphthyloxy)-9-cyclohexyl-9H-purine-6-amine, and is a known compound having a CAS number of 483367-10-8. It is known as an agonist of a Frizzled family (membrane protein responsible for Hedgehog signal transmission route) of a seven-transmembrane protein called Smoothened. Therefore, in the present invention, it can be used as an agonist of SHH, for example, as an agonist of a Frizzled family such as purmorphamine.

As used herein, a "protein", a "polypeptide", an "oligopeptide" and a "peptide" are herein used in the same meaning, and refer to a polymer of amino acids having any length. This polymer may be straight or branched, or cyclic. An amino acid may be natural or non-natural, or may be an altered amino acid. This term can also encompass an assembly of a complex of a plurality of polypeptide chains. This term also encompasses a natural or artificially altered amino acid polymer. Examples of such alterations include disulfide bond formation, glycosylation, lipidation, acetylation, phosphorylation and any other manipulation or alteration (e.g., binding with a label component). This definition also encompasses a polypeptide containing one, two or more analogs of amino acids (e.g., including non-natural amino acid), a peptide-like compound (e.g., peptoid) and other alterations known in the art.

As used herein, an "amino acid" may be natural or non-natural, as far as the object of the present invention is satisfied.

As used herein, a "polynucleotide", an "oligonucleotide", and a "nucleic acid" are herein used in the same meaning, and refer to a polymer of nucleotides having any length. This term also encompasses an "oligonucleotide derivative" and a "polynucleotide derivative". The "oligonucleotide derivative" or the "polynucleotide derivative" includes a derivative of a nucleotide, or refers to an oligonucleotide or a polynucleotide in which a bond between nucleotides is different from the normal bond, and the terms are used interchangeably. Specific examples of such an oligonucleotide include 2'-O-methyl-ribonucleotide, an oligonucleotide derivative in which a phosphodiester bond in an oligonucleotide is converted into a phosphorothioate bond, an oligonucleotide derivative in which a phosphodiester bond in an oligonucleotide is converted into an N3'-P5' phosphoramidate bond, an oligonucleotide derivative in which ribose and a phosphodiester bond in an oligonucleotide are converted into a peptide nucleic acid bond, an oligonucleotide derivative in which uracil in an oligonucleotide is substituted with C-5 propynyluracil, an oligonucleotide derivative in which uracil in an oligonucleotide is substituted with C-5 thiazoleuracil, an oligonucleotide derivative in which cytosine in an oligonucleotide is substituted with C-5 propynylcytosine, an oligonucleotide derivative in which cytosine in an oligonucleotide is substituted with phenoxazine-modified cytosine, an oligonucleotide derivative in which ribose in DNA is substituted with 2'-O-propylribose, and an oligonucleotide derivative in which ribose in an oligonucleotide is substituted with 2'-methoxyethoxyribose. Unless otherwise indicated, it is intended that a specified nucleic acid sequence also includes a preservatively altered variant (e.g., degenerate codon substitution) and a complementary sequence thereof, like an explicitly shown sequence. Specifically, a degenerate codon substitution is attained by making a sequence in which a third position of one or more selected (or all) codons is substituted with a mixed base and/or a deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). As used herein, a "nucleic acid" is used interchangeably with a gene, cDNA, mRNA, an oligonucleotide, and a polynucleotide. As used herein, a "nucleotide" may be natural or non-natural.

As used herein, a "gene" refers to an agent defining a genetic trait. Genes are usually arranged on a chromosome in a certain order. A gene defining a primary structure of a protein, is referred to as a structural gene, and a gene influencing on the expression thereof is referred to as a regulator gene. As used herein, a "gene" may refer to a "polynucleotide", an "oligonucleotide" and a "nucleic acid".

As used herein, "homology" between genes refers to a degree of identity of two or more gene sequences to each other, and having "homology" generally refers to a high degree of identity or similarity. Therefore, as the homology between certain two genes is higher, identity or similarity between those sequences is higher. Whether two kinds of genes have homology or not can be examined by direct comparison of sequences, or in the case of a nucleic acid, by a hybridization method under a stringent condition. In the case where two gene sequences are directly compared, those genes have homology when DNA sequences of the gene sequences are representatively at least 50% identical between the gene sequences, preferably when the DNA sequences are at least 70% identical, more preferably when the DNA sequences are at least 80%, 90%, 95%, 96%, 97%, 98% or 99% identical. Therefore, as used herein, a "homolog" or a "homologous gene product" means a protein in another species, preferably a mammal, which exerts the same biological function as that of a protein constituent of a complex which will be further described herein. Such a homolog may also be named as an "ortholog gene product". The algorithm for detecting an ortholog gene pair from human, a mammal or other species uses the whole genome of these organisms. First, a pairing best hit is recovered using expected complete Smith-Waterman Alignment of proteins. In order to further improve reliability, a cluster of these pairs may be formed using a pairing best hit including *Drosophila melanogaster* and *C. elegans* proteins. Such analysis is provided, for example, in Nature, 2001, 409: B60-921. Based on sequence homology on genes of other species of genes encoding proteins provided. As used herein, homologs of the proteins described herein can be isolated by applying a conventional technique to clone respective genes, and expressing proteins from such genes, or by isolating similar complexes according to the method provided herein, or according to another appropriate method well-known in the art.

An amino acid may be referred herein to by any of the generally known three letter symbol, or one letter symbol recommended by the IUPAC-IUB Biochemical Nomenclature Commission. A nucleotide may be similarly referred to by the generally recognized one letter code. As used herein, comparison of similarity, identity and homology of amino acid sequences and nucleotide sequences can be made based on the calculation by using default parameters employing BLAST which is a tool for analyzing sequences. Retrieval of identity can be performed, for example, using BLAST 2.2.9 of NCBI (published on May 12, 2004). A value of identity as used herein usually refers to a value obtained by alignment under the default condition using the BLAST, however, in the case where a higher value is obtained by change in the parameters, the highest value is adopted as the value of identity. In the case where identity is evaluated in a plurality of regions, among the obtained values, the highest value is adopted as the value of identity. Similarity is a numerical value obtained by also considering similar amino acids, in addition to identity.

As used herein, a polynucleotide which "hybridizes under a stringent condition" refers to a well-known condition which is conventionally used in the art. Such a polynucleotide can be obtained by performing a colony hybridization method, a plaque hybridization method or a Southern blot hybridization method using a polynucleotide selected from the polynucleotides of the present invention as a probe. Specifically, such a polynucleotide means a polynucleotide which can be identified by performing hybridization at 65° C. in the presence of 0.7 to 1.0 M NaCl using a filter on which DNA derived from a colony or a plaque is immobilized, and washing the filter under a condition of 65° C. using a SSC (saline-sodium citrate) solution having a 0.1 to 2-fold concentration (the composition of the SSC solution having a 1-fold concentration is 150 mM sodium chloride and 15 mM sodium citrate). Hybridization can be performed in accordance with the methods described in experimental texts such as Molecular Cloning 2nd ed., Current Protocols in Molecular Biology, Supplement 1-38, DNA Cloning 1: Core Techniques, A Practical Approach, Second Edition, Oxford University Press (1995). Herein, a sequence containing only an A sequence or only a T sequence is preferably eliminated from sequences which hybridize under a stringent condition. Therefore, a polypeptide used in the present invention (e.g., transthyretin) also includes a polypeptide encoded by a nucleic acid molecule which hybridizes with a nucleic acid molecule encoding a polypeptide particularly described in the present invention under a stringent condition. These low stringency conditions include hybridization at 40° C. for 18 to 20 hours in a buffer containing 35% formamide, 5×SSC, 50 mM Tris-HCl (pH 7.5), 5 mM EDTA, 0.02% PVP, 0.02% BSA, 100 μg/ml denatured salmon sperm DNA, and 10% (weight/volume) dextran sulfate, washing the resultant at 55° C. for 1 to 5 hours in a buffer consisting of 2×SSC, mM Tris-HCl (pH 7.4), 5 mM EDTA, and 0.1% SDS, and washing the resultant at 60° C. for 1.5 hours in a buffer consisting of 2×SSC, 25 mM Tris-HCl (pH 7.4), 5 mM EDTA, and 0.1% SDS.

As used herein, a "purified" substance or biological an agent (e.g., nucleic acid or protein) refers to a substance or a biological an agent from which at least a part of an agent naturally associated with the biological agent has been removed. Therefore, usually, the purity of a biological agent in a purified biological agent is higher than that in the state where the biological agent usually exists (that is, concentrated). The term "purified" used herein means that preferably at least 75% by weight, more preferably at least 85% by weight, further preferably at least 95% by weight, and most preferably at least 98% by weight of the same type of a biological agent exists. A substance used in the present invention is preferably a "purified" substance.

As used herein, a "corresponding" amino acid or nucleic acid refers to an amino acid or a nucleotide which has or is expected to have, in a certain polypeptide molecule or polynucleotide molecule, an action similar to that of a predetermined amino acid or nucleotide in a polypeptide or a polynucleotide as a standard of comparison, and particularly, in the case of an enzyme molecule, refers to an amino acid which exists at a similar position in an active site and makes a similar contribution to the catalytic activity. For example, in the case of an antisense molecule, it can be a similar part in an ortholog corresponding to a specified part of the antisense molecule. A corresponding amino acid can be a specified amino acid which is subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Therefore, in such a case, as used herein, it is named as a "corresponding" region or domain.

As used herein, a "corresponding" gene (e.g., polynucleotide sequence or molecule) refers to a gene (e.g., polynucleotide sequence or molecule) of a certain species which has or is expected to have an action similar to that of a predetermined gene in a species being a standard of comparison, and when there is a plurality of genes having such an action, the corresponding gene refers to a gene having evolutionarily the same origin. Therefore, a gene corresponding to a certain gene can be an ortholog of the gene. Therefore, regarding RPG49 and R-spondins of a mouse or a rat, corresponding RPG49 and R-spondins can be found, respectively, in human. Such a corresponding gene can be identified using a technique well-known in the art. Therefore, for example, a corresponding gene in a certain animal (e.g., mouse), or a gene being a standard of a corresponding gene (e.g., RPG49, R-spondins, or shh) can be found by retrieval from sequence database of the animal (e.g., human or rat) using sequences such as SEQ ID Nos.: 1, 3, 5, 7, 9, and 11 as a query sequence.

As used herein, a "fragment" refers to a polypeptide or a polynucleotide having a sequence length of 1 to n−1, relative to a full length polypeptide or polynucleotide (length: n). The length of the fragment can be appropriately changed depending on the purpose thereof. Examples of the lower limit of the length, in the case of a polypeptide, include 3, 4, 5, 6, 7, 8, 9, 10, 15, 20, 25, 30, 40, 50 and more amino acids, and a length which is represented by an integer not specifically listed herein (e.g., 11) can also be proper as the lower limit. In addition, in the case of a polynucleotide, examples of the lower limit include 5, 6, 7, 8, 9, 10, 15, 20, 25, 30, 40, 50, 75, 100 and more nucleotides, and a length represented by an integer not specifically listed herein (e.g., 11) can also be proper as the lower limit. As used herein, concerning such a fragment, it is understood that, for example, when a full length polypeptide or polynucleotide functions as a marker, the fragment itself is also within the scope of the present invention, as far as it has a function as a marker.

According to the present invention, the term "activity" as used herein refers to the function of a molecule in a broadest sense. The activity is not intended to be particularly limited, but generally includes a biological function, a biochemical function, a physical function or a chemical function of a molecule. The activity includes, for example, an enzyme activity, an ability to interact with other molecules, an ability to activate, promote, stabilize, inhibit, suppress, or destabilize the function of other molecules, the stability, and an ability to be localized at a specified position in a cell. When applicable, this term also relates to the function of a protein complex in a broadest sense.

As used herein, the "biological function" used when referring to a certain gene or a nucleic acid molecule or a polypeptide relating thereto, refers to a specified function which can be possessed by the gene, the nucleic acid molecule or the polypeptide in a living body. This function includes, but is not limited to, production of a specific antibody, the enzyme activity, and impartation of resistance. In the present invention, this function includes, but is not limited to, a function of GPR49/LGR5 or the like of recognizing an R-spondin. As used herein, the biological function can be exerted by the "biological activity". As used herein, the "biological activity" refers to the activity which can be possessed by a certain agent (e.g., polynucleotide or protein) in a living body, includes an activity of exerting a variety of functions (e.g., transcription promoting activity), and for example, includes an activity of activating or inactivating another molecule by interaction with a certain molecule. When two agents interact, the biological activity is binding between two molecules and biological change caused by the binding, for example, when one molecule is settled using an antibody, the other molecule is also settled, and the two molecules are thought to be bound together. Therefore, observation of such coprecipitation is one determination procedure. For example, when a certain agent is an enzyme, the biological activity includes the enzyme activity. In another example, when a certain agent is a ligand, the biological activity includes binding of the ligand to a corresponding receptor. Such a biological activity can be measured by a technique well-known in the art. Therefore, the "activity" refers to a variety of measurable indices which show or reveal a bond (either direct or indirect); and influence on a response (that is, having a measurable influence in response to some exposure or stimulation), and examples thereof include affinity of a compound which directly binds to the polypeptide or the polynucleotide of the present invention, the amount of proteins upstream or downstream after some stimulations or events, or the measure of other similar functions.

As used herein, "expression" of a gene, a polynucleotide, a polypeptide or the like refers to that the gene or the like receives a certain action in vivo to be converted into another form. Preferably, the expression refers to that a gene, a polynucleotide or the like is transcribed and translated into the form of a polypeptide, and transcription to make mRNA can also be one aspect of the expression. More preferably, such a form of a polypeptide can be a form which has undergone processing after translation (derivative referred to herein). For example, the expression level of GPR49/LGR5 can be determined by any method. Specifically, by evaluating the amount of mRNA of GPR49/LGR5, the amount of a GPR49/LGR5 protein, and the biological activity of a GPR49/LGR5 protein, the expression level of GPR49/LGR5 can be known. The amount of mRNA or a protein of GPR49/LGR5 can be determined by the method described herein.

As used herein, a "functional equivalent" refers to any matter having the same objective function but a different structure relative to the original entity as a subject. Therefore, when referring to "R-sporadins or a functional equivalent thereof" or "the group consisting of R-spondins and a functional equivalent thereof", it is understood that a functional equivalent includes, in addition to R-spondins themselves, a mutant or a variant of R-spondins (e.g., amino acid sequence variant) which has an action of controlling differentiation and/or promoting proliferation of an eye cell or the like, as well as one which can be changed into R-spondins themselves, or a mutant or a variant of the R-spondins (e.g., including nucleic acids encoding R-spondins themselves or a mutant or a variant of R-spondins, and a vector, a cell or the like comprising the nucleic acid) at the time point of the action. In the present invention, it is understood that a functional equivalent of an R-spondin can be used similarly to an R-spondin, unless particularly referred to.

In addition, when referring to "GPR49/LGR5 or a functional equivalent thereof" or "the group consisting of GPR49/LGR5 and a functional equivalent thereof", it is understood that they include, in addition to GPR49/LGR5 itself, a mutant or a variant (e.g., amino acid sequence variant) of GPR49/LGR5 which has an action of controlling differentiation and/or promoting proliferation of an eye cell or the like, or has a function as the marker described herein, as well as one which can be changed to GPR49/LGR5 itself or a mutant or a variant of GPR49/LGR5 (e.g., including a nucleic acid encoding GPR49/LGR5 itself or a mutant or a variant of GPR49/LGR5, and a vector, a cell or the like comprising the nucleic acid) at the time point of the action. In the present invention, it is understood that a functional equivalent of GPR49/LGR5 can be used similarly to GPR49/LGR5, unless particularly referred to.

In addition, when referring to "SONIC HEDGEHOG (SHH) or a functional equivalent thereof" or "the group consisting of SONIC HEDGEHOG (SHH) and a functional equivalent thereof", it is understood that they include, in addition to SHH itself, a mutant or a variant (e.g., amino acid sequence variant) of SHH which has an action of controlling differentiation and/or promoting proliferation of an eye cell or the like, or has a function as the marker described herein, as well as one which can be changed to SHH itself or a mutant or a variant of SHH (e.g., including a nucleic acid encoding SHH itself or a mutant or a variant of SHH, and a vector, a cell or the like comprising the nucleic acid) at the time point of the action. In the present invention, it is understood that a functional equivalent of SHH can be used similarly to SHH, unless particularly referred to.

When referring to "an agent suppressing GPR49/LGR5 or a functional equivalent thereof" or "the group consisting of an agent suppressing GPR49/LGR5 and a functional equivalent thereof", it is understood that they include, in addition to an agent suppressing GPR49/LGR5 itself, a mutant or a variant (e.g., synthetic variant) of an agent suppressing GPR49/LGR5 which is changed so as to have an action of controlling differentiation and/or promoting proliferation of an eye cell or the like (can be changed to an agent suppressing GPR49/LGR5 (e.g., a precursor or a prodrug such as an ester)) at the time point of the action. In the present invention, it is understood that a functional equivalent of the agent suppressing GPR49/LGR5 can be used similarly to the agent suppressing GPR49/LGR5, unless particularly referred to.

In addition, when referring to "an agonist of SHH (e.g., agonist of Frizzled family such as purmorphamine) or a functional equivalent thereof" or "the group consisting of an agonist of SHH (e.g., agonist of Frizzled family such as purmorphamine) and a functional equivalent thereof", it is understood that they include, in addition to an agonist of SHH (e.g., agonist of Frizzled family such as purmorphamine), a mutant or a variant (e.g., synthetic variant) of an agonist of SHH (e.g., agonist of Frizzled family such as purmorphamine) which is changed so as to have an action of controlling differentiation and/or promoting proliferation of an eye cell or the like (and is changed to an agonist of SHH (e.g., agonist of Frizzled family such as purmorphamine) itself or a mutant or a variant of an agonist of SHH (e.g., agonist of Frizzled family such as purmorphamine) (e.g., a precursor or a prodrug such as an ester)) at the time point of the action. In the present invention, it is understood that a functional equivalent of an agonist of SHH (e.g., agonist of Frizzled family such as purmorphamine) can be used similarly to the agonist of SHH (e.g., agonist of Frizzled family such as purmorphamine), unless particularly referred to.

As used herein, an "agonist" refers to a substance which makes an entity as a subject (e.g., receptor) expresses the biological action of the receptor. Examples thereof include a synthesized agonist and an altered agonist, in addition to a natural agonist (also named as a ligand).

As used herein, an "antagonist" refers to a substance which, relative to an entity (e.g., receptor) as a subject, inhibits the biological action of the receptor. There are an antagonist which inhibits the action non-competitively with an agonist (or a ligand), in addition to an antagonist which inhibits the action competitively with an agonist (or a ligand). An antagonist can also be obtained by altering an agonist. Since an antagonist inhibits a physiological phenomenon, it can be included in the concept of an inhibitor or a suppressing (suppressing) agent.

As used herein, an "agent inhibiting (GPR49/LGR5 etc.)" refers to an agent which can reduce or eliminate the function of GPR49/LGR5 or the like as a subject temporarily or permanently. Examples of such an agent include, but are not limited to, an antibody, an antigen-binding fragment thereof, a derivative thereof, and agents in the form of a nucleic acid such as antisense and RNAi agent such as siRNA.

A functional equivalent of GPR49/LGR5 and R-spondins used in the present invention can be found by retrieval from database and the like. As used herein, "retrieval" refers to finding out other nucleic acid nucleotide sequences a having specified function and/or nature utilizing a certain nucleic acid nucleotide sequence electronically or by a biological or other method. Examples of electronic retrieval include, but are not limited to BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), and Needleman and Wunsch method (Needleman and Wunsch, J. Mol. Biol. 48: 443-453 (1970)). Examples of biological retrieval include, but are not limited to stringent hybridization, a microarray in which genome DNA is stuck on a nylon membrane or the like, or a microarray stuck to a glass plate (microarray assay), PCR and in situ hybridization. As used herein, it is intended that a gene used in the present invention should include a corresponding gene identified by such electronic retrieval or biological retrieval.

As the functional equivalent of the present invention, a functional equivalent in which, in an amino acid sequence, one or a plurality of amino acids are inserted, substituted or deleted, or added to one or both ends thereof can be used. As used herein, "in an amino acid sequence, one or a plurality of amino acids are inserted, substituted or deleted, or added to one or both ends thereof" means that the alteration has been performed by a well-known technical method such as site-specific metagenesis, or by substitution of a plurality of amino acids by natural mutation to the extent that they are generated naturally.

An altered amino acid sequence of GPR49/LGR5, R-spondins, the factors of the Hedgehog pathway such as SHH, PTCH1, GLI1, and GLI2, the factors of the Wnt pathway such as LRP6 and β-catenin, and the like can be the one in which, for example, insertion, substitution, or deletion, or addition to one or both ends of 1 to 30, preferably 1 to 20, more preferably 1 to 9, further preferably 1 to 5, particularly preferably 1 to 2 amino acids is performed. An altered amino acid sequence is preferably a sequence in which an amino acid sequence thereof may be an amino acid sequence in which an amino acid sequence of GPR49/LGR5, R-spondins, the factors of the Hedgehog pathway such as SHH, PTCH1, GLI1, and GLI2, the factors of the Wnt pathway such as LRP6 and β-catenin, or the like has 1 or a plurality of (preferably, 1 or a few, or 1, 2, 3 or 4) preservative substitutions. Herein, the "preservative substitution" means that 1 or a plurality of amino acid residues are substituted with another chemically similar amino acid residue so that the function of a protein is not substantially altered. For example, there are the case where a certain hydrophobic residue is substituted with another hydrophobic residue, the case where a certain polar residue is substituted with another polar residue having the same charge, and the like. A functionally similar amino acid which can be subjected to such substitution is known in the art for every amino acid. Specific examples thereof include, as a nonpolar (hydrophobic) amino acid, alanine, valine, isoleucine, leucine, proline, tryptophan, phenylalanine, and methionine. Examples of a polar (neutral) amino acid include glycine, serine, threonine, tyrosine, glutamine, asparagine, and cysteine. Examples of a (basic) amino acid having positive charge include arginine, histidine, and lysine. In addition, examples of an (acidic) amino acid having negative charge include aspartic acid and glutamic acid.

As used herein, a "marker (substance or gene)" refers to a substance which serves as a criterion for pursuing whether a subject is in a certain state (e.g., the level, or the presence or absence of a disease state, a disorder state, a proliferation ability, or a differentiated state) or not, or whether there is such a risk or not. Examples of such a marker include a gene, a gene product, a metabolite, and an enzyme. In the present invention, detection, diagnosis, preliminary detection, prediction or advance diagnosis concerning the certain state (e.g., a disease such as differentiation disorder) can be realized using a pharmaceutical, a drug, an agent, a factor or means specific for a marker associated with the state, or a composition, a kit, a system of the like comprising them. As used herein, a "gene product" refers to a protein encoded by a gene or mRNA. As used herein, it was found that a gene product for which association with an eye cell has not been shown (i.e. GPR49/LGR5, etc.) can be used as an index of differentiation of an eye cell.

As used herein, a "nerve cell" is used in a broad sense, and means any cell included in an organ of a nervous system. Particularly, it is understood that a cell derived from a neural crest cell (e.g., corneal endothelial cell) is also included.

As used herein, an "eye cell" is used in a broad sense, and means any cell existing in an eye. The eye cell includes any cell existing in eyelid, sclera, cornea, uvea, crystalline lens, vitreous body, retina, and optic nerve.

As used herein, a "corneal endothelial cell" is used in the ordinary meaning used in the art. The cornea is one of lamellar tissues constituting an eye, is transparent, and is positioned at a part closest to the outside world. In human, the cornea is stated to be composed of five layers from the external side (body surface) in order, and is composed of corneal epithelium, Bowman's membrane (external boundary line), Lamina propria, Descemet's membrane (internal boundary line), and corneal endothelium from the external side. Unless specified, parts other than epithelium and endothelium may be collectively named as "corneal stroma", and are named so used herein.

As used herein, a "corneal tissue" is used in an ordinary sense, and refers to a tissue itself constituting the cornea. When referring to a corneal tissue, it may include all of corneal epithelium, Bowman's membrane (external boundary line), Lamina propria, Descemet's membrane (internal boundary line), and corneal endothelium (in the case of human; in the case of other animals, all of the above as appropriate depending on the classification corresponding thereto), or may lack a part, or may include another tissue (sclera) in addition to the cornea. In such a case, it may be particularly called sclerocornea. Therefore, it is possible to state that the sclerocornea or a sclerocornea slice is one embodiment of a corneal tissue.

As used herein, a "proliferation ability" refers to an ability of a cell to proliferate. As used herein, unless particularly referred to, the state of proliferation shows a possibility of proliferation in a stationary state. Herein, the "stationary state" refers to a state where homeostasis of a living body is maintained under the normal condition of the living body. Such a state can be easily determined by a person skilled in the art. For example, such a state can be confirmed by analysis of the cell density based on that the cell density is approximately constant and does not change, or that expression of a cell proliferation marker is not recognized.

As used herein, a "high proliferation ability" refers to that a cell has the proliferation ability in the stationary state.

As used herein, "proliferation promotion" refers to that the proliferation state of a certain cell is promoted. In the case where a subject cell has not proliferated, when proliferation is initiated if only a little, this corresponds to proliferation promotion, and in the case of a cell which has been proliferating already, when the proliferation level is maintained or enhanced, preferably, enhanced, this corresponds to proliferation promotion.

As used herein, a "differentiation ability" refers to the ability of a cell to differentiate. It can be said that a cell having the differentiation ability is "undifferentiated" in that sense. Since a stem cell (embryonic stem cell, reproduction cell, iPS cell, tissue stem cell, etc.) can be further differentiated, it can be said as having the differentiation ability.

As used herein, an "undifferentiated cell" refers to any cell having the differentiation ability. Therefore, the undifferentiated cell includes a cell which has differentiated to a certain extent, but can still differentiate, in addition to a stem cell.

As used herein, "differentiation suppression" refers to suppression of differentiation. It is understood that both of the case where the differentiation level is unchanged if a cell is not differentiated, and the case where the differentiation level is advancing toward an undifferentiation direction are included in the "differentiation suppression".

As used herein, an "agent for suppressing differentiation and/or promoting proliferation", when referring to a substance or an agent, refers to an agent which can suppress differentiation of the cell as a subject and/or promote proliferation of the cell. As used herein, particularly, the "agent for suppressing differentiation and/or promoting proliferation" includes at least one kind selected from the group consisting of R-spondins, SHH, an agonist of SHH (e.g., agonist of Frizzled family such as purmorphamine), an agent suppressing GPR49/LGR5 (antagonist) and a functional equivalent thereof.

As used herein, a "stem cell" refers to a cell having both of the ability to differentiate into cells of a plurality of lineages (pluripotency), and the ability to maintain pluripotency even after cell division (ability to self-renew). The stem cell includes an embryonic stem cell, a reproduction cell, an IPS cell, and a tissue stem cell.

As used herein, a "specimen" refers to a subject which is to be subjected to diagnosis or detection in the present invention (e.g., an organism such as human or an organ (eye) or a cell which has been taken out from an organism).

As used herein, a "sample" refers to any substance obtained from a specimen or the like, and includes, for example, a cell of an eye. A person skilled in the art can appropriately select a preferable sample based on the descriptions described herein.

As used herein, a "colony forming ability", when referring to that of a cell, refers to an ability to form a colony. As used herein, the colony forming ability can be determined using, for example, a colony formation test of a cell under culturing conditions known in the art, as a standard test method.

As used herein, "Ki-67" is a cell proliferation marker, and is representatively a cell cycle-associated nucleoprotein represented by the accession number P46013. In a cell during proliferation, Ki-67 is expressed in the $G_1$ phase, the S phase, the $G_2$ phase and the M phase, but Ki-67 does not exist in the $G_0$ phase in which proliferation pauses, and therefore, it is used as a marker of cell proliferation and cell cycle. In addition, since a positive correlation is observed between the Ki-67 expression quantity and malignancy of a tumor, Ki-67 is also useful as a marker for detecting a proliferating cell in a tumor tissue.

As used herein, "Ki-67 positivity" refers to that Ki-67 being a cell marker is expressed in a target cell.

As used herein, "BrdU" is abbreviation of brominated deoxyuridine. Since BrdU is taken as an analog of dTTP during DNA synthesis, DNA (cell nucleus) which has taken BrdU can be detected with an antibody specific for BrdU which has been taken into DNA.

As used herein, "BrdU positivity" refers to that BrdU being a cell marker is expressed in a target cell.

As used herein, an "agent" is used in a broad sense, and may be any substance or other elements (e.g., energy such as light, radioactivity, heat, and electricity), as far as an intended object can be attained. Examples of such a substance include, but are not limited to a protein, a polypeptide, an oligopeptide, a peptide, a polynucleotide, an oligonucleotide, a nucleotide, a nucleic acid (e.g., including DNA such as cDNA and genome DNA, and RNAs such as mRNA), a polysaccharide, an oligosaccharide, a fat, an organic low molecule (e.g., a hormone, a ligand, an information transmitting substance, an organic low molecule, a molecule synthesized by combinatorial chemistry, and a low molecule which can be utilized as a medicine (e.g., a low-molecular weight ligand)), and a composite molecule thereof. Representative examples of an agent specific for a polynucleotide include, but are not limited to a polynucleotide having complementarity by certain sequence homology (e.g., 70% or more sequence identity) relative to a sequence of the polynucleotide, and a polypeptide such as a transcription factor binding to a promoter region. Representative examples of an agent specific for a polypeptide include, but are not limited to an antibody specifically directed to the polypeptide or a derivative thereof or an analog thereof (e.g., single-stranded antibody), a specific ligand or receptor when the polypeptide is a receptor or a ligand, and, when the polypeptide is an enzyme, a substrate.

As used herein, a "detection agent" in a broad sense refers to any drug by which an objective subject can be detected.

As used herein, a "diagnostic agent (or diagnostic)" in a broad sense refers to any agent by which an objective condition (e.g., a disease) can be diagnosed.

As used herein, a "therapeutic agent (or therapeutic)" in a broad sense refers to any agent by which an objective condition (e.g., a disease) can be treated.

As used herein, a "preventive agent (or preventive)" in a broad sense refers to any agent by which an objective condition (e.g., a disease) can be prevented. As used herein, a "progression preventive agent (progression preventive)", regarding a certain disease or the like, refers to any agent by which progression of the condition can be prevented.

As used herein, "in vivo" refers to the inside of a living body. In a specific context, "inside a living body" refers to a position at which an objective substance should be arranged.

As used herein, "in vitro" refers to a state where a part of a living body is isolated or liberated "outside a living body" (e.g., into a test tube) for a variety of research objectives. This is a term in contrast to in vivo.

As used herein, "ex vivo" refers to a series of motions, in the case where certain treatment is performed outside a body, and thereafter, a part of the body is intended to be returned to the inside of the body. Also in the present invention, it is possible to simulate an embodiment in which a cell in a living body is treated with an agent of the present invention, and is returned to a patient again.

(Preferable Embodiments)

Preferable embodiments of the present invention will be illustrated below. Embodiments provided below are provided for better understanding of the present invention, and it is understood that the scope of the present invention should not be limited to the following descriptions. Therefore, it is clear that a person skilled in the art can appropriately perform the alteration within the scope of the present invention, in view of the descriptions described herein.

(Differentiation Suppression and/or Proliferation Promotion)

In one aspect, the present invention provides an agent for suppressing differentiation and/or promoting proliferation of a cell, comprising at least one kind selected from the group consisting of R-spondins, SHE, an agonist of SHH (e.g., agonist of Frizzled family such as purmorphamine), an agent suppressing GPR49/LGR5 and a functional equivalent thereof. Examples of the cell which is a subject of the present invention may include, but are not particularly limited to, an eye cell, a nerve cell including a cell derived from a neural crest cell (including a corneal endothelial cell), and epithelial cells such as a conjunctival epithelial cell, an amniotic epithelial cell, an oral mucosa epithelial cell, a nose mucosa epithelial cell, and a corneal epithelial cell. In a preferable embodiment, a cell which is a subject of the present invention is an eye cell. The eye cell which is a subject of the present invention can include, but is not limited to a retinal cell, a vitreous body cell, a corneal epithelial cell, a corneal parenchymal cell and a corneal endothelial cell. A functional equivalent of R-spondins includes a mutant or a variant of R-spondins (e.g., amino acid sequence variant) which has an action of controlling differentiation and/or promoting proliferation of an eye cell or the like, and as well as one which can be changed to R-spondins themselves or a mutant or a variant of R-spondins (e.g., including a nucleic acid encoding R-spondins themselves or a mutant or a variant of R-spondins, and a vector, a cell or the like comprising the nucleic acid) at the time point of the action. A functional equivalent of SHH includes a mutant or a variant of SHH (e.g., amino acid sequence variant) which has an action of controlling differentiation and/or promoting proliferation of an eye cell or the like, or has a function as the marker described herein, as well as one which can be changed to SHE itself or a mutant or a variant of SHH (e.g., including a nucleic acid encoding SHH itself or a mutant or a variant of SHH, and a vector, a cell or the like comprising the nucleic acid) at the time point of the action. A functional equivalent of an agonist of SHH (e.g., agonist of Frizzled family such as purmorphamine) includes a mutant or a variant (e.g., synthetic variant) of an agonist of SHH (e.g., agonist of Frizzled family such as purmorphamine) which has an action of controlling differentiation and/or promoting proliferation of an eye cell or the like, or has a function as the marker herein described as well as one which can be changed into an agonist of SHH (e.g., agonist of Frizzled family such as purmorphamine) itself or a mutant or a variant of this agonist of SHH (e.g., agonist of Frizzled family such as purmorphamine) (e.g., a precursor or a prodrug such as an ester) at the time point of the action. A functional equivalent of an agent suppressing GPR49/LGR5 includes a mutant or a variant (e.g., synthetic variant) of an agent suppressing GPR49/LGR5 which is changed so as to have an action of controlling differentiation and/or promoting proliferation of an eye cell or the like (can be changed into an agent suppressing GPR49/LGR5 (e.g., a precursor or a prodrug such as an ester)) at the time point of the action.

In one embodiment, R-spondins used in the present invention include at least one selected from R-spondin 1, R-spondin 2, R-spondin 3 and R-spondin 4.

In a preferable embodiment, R-sporadins used in the present invention include R-spondin 1.

In one embodiment, an eye cell which is a subject of the present invention is a cell which does not proliferate in the stationary state. Not wishing to be bound by any theory, the present invention exerts an effect which has not been obtained previously in a point that even a cell which does not proliferate in the stationary state can be proliferated by the present invention.

In another embodiment, an eye cell which is a subject of the present invention includes at least one kind of cell selected from a retinal cell, a vitreous body cell, a corneal epithelial cell, a corneal parenchymal cell and a corneal endothelial cell. Particularly, a corneal endothelial cell is a cell which proliferates little in the stationary state, and a point that this cell can be proliferated has an extremely important meaning from the viewpoint of treatment or prevention of an ophthalmological disease. Therefore, in one preferable embodiment, an eye cell which is a subject of the present invention includes a corneal endothelial cell. In addition, even in other cells, for example, in a corneal epithelial cell, a small fraction of basal cells proliferate, and a majority of cells do not proliferate. Therefore, it is possible to state that even a retinal cell, a vitreous body cell, a corneal epithelial cell, and a corneal parenchymal cell other than a corneal endothelial cell have an extremely important meaning from the viewpoint of treatment or prevention of an ophthalmological disease.

In a further preferable embodiment, an eye cell which is a subject of the present invention includes a corneal endothelial cell of a primate. In a further more preferable embodiment, an eye cell which is a subject of the present invention includes a human corneal endothelial cell.

In another embodiment, a cell which is a subject of the present invention (e.g., eye cell) is in a confluent state. No technique in which a cell can proliferate in such a confluent state has previously been reported as far as the present inventors know. Therefore, such a technique has extremely high usefulness in a point that a cell in an unprecedented category can be proliferated, from the viewpoint of treatment or prevention of a disease or a disorder.

In a preferable embodiment, the present invention can utilize a corneal endothelial cell in the confluent state. In the confluent state, in ordinary culturing, it is observed that the form of a cell becomes fibroblast-like. It is one important characteristic of the present invention that even a corneal endothelial cell in the confluent state can further proliferate and differentiation can be further suppressed, and this means that a cell having a high corneal endothelium density which is an important prognosis determination factor after transplantation can be transplanted, toward clinical application of cultured corneal endothelium transplantation. A preferable concentration in that case is not limited, but when R-spondin 1 is used, it can be about 1 ng/ml to about 100 ng/ml, preferably about 10 ng/ml to about 100 ng/ml, further preferably about 10 ng/ml. No technique in which a cell can proliferate in such a confluent state has previously been reported as far as the present inventors know. Therefore, such a technique has extremely high usefulness in a point that a cell in an unprecedented category can be proliferated, from the viewpoint of treatment or prevention of a disease or a disorder. For example, the cell density can be preferably about 570 cells/mm$^2$ or more, about 700 cells/mm$^2$ or more, about 800 cells/mm$^2$ or more, or about 1000 cells/mm$^2$ or more.

As used herein, a "culture" refers to what is produced by culturing a cell such as a corneal endothelial cell. Therefore, a "corneal endothelium culture" refers to a culture of the corneal endothelium, and usually refers to a culture which exists in a state different from that of a cell existing in a living body. As a corneal endothelium culture obtained by a previous culturing method, at best, only a confluent culture of about 500 cells/mm$^2$ was obtained, as shown in Examples. Therefore, from the viewpoint of a culture, it is possible to state that such a cell density was not attained concerning a culture obtained by culturing or subculturing for a long term. That is, a corneal endothelial cell is easily reduced in the density by culturing. The corneal endothelium density is clinically one of the most important indices of degree of health. For this reason, it is important to culture a cell to the high density from the viewpoint of regeneration therapy. In addition, after the endothelium density is increased in advance, the cell can be administered to a living body, and this can be an extremely important therapeutic agent. In this sense, it is important that the reduced density was increased again by an ordinary culturing method. A normal value of the human corneal endothelium in a living body is around 2500 to 3000 cells/mm$^2$, and the present invention is meaningful in a point that it provides a technique of bringing the cell density of a culture close to the range, or making the density exceed the range.

In another embodiment, a cell which is a subject of the present invention (e.g., eye cell) can be a corneal tissue itself. Such a corneal tissue itself can be a sclerocornea slice.

Therefore, in another aspect, the present invention provides a corneal endothelium culture, wherein the corneal endothelium exists at a higher density than the cell density in the confluent state.

Preferably, the Ki67-positive cell exits at a percentage of about 4% or more, more preferably at a percentage of about 7% or more, further preferably at a percentage of about 10% or more. Since the ordinary existence percentage is around 1%, a corneal tissue containing such a Ki67-positive cell, that is, a proliferating cell was not present previously, and the corneal tissue is found to be also valuable as a novel graft for treatment.

The density of the corneal endothelial cell is preferably about 4000 cells/mm$^2$ or more, more preferably about 4500 cells/mm² or more, further preferably about 5000 cells/mm² or more. An ordinary value of the human corneal endothelium in a living body is around 2500 to 3000 cells/mm², and it is understood that a novel tissue in which the ratio of a proliferating cell or an undifferentiated cell, or a corneal endothelial cell is increased to an unprecedented extent is provided by applying an agent for suppressing differentiation and/or promoting proliferation of the present invention to a tissue directly. It is understood that such a tissue is utilized for improving, treating or preventing a disease, a disorder or a condition of the cornea.

(Preservation or Culturing of Cell)

In another aspect, the present invention provides a composition for preserving a cell or culturing a cell, comprising the agent for suppressing differentiation and/or promoting proliferation of the present invention. The agent for suppressing differentiation and/or promoting proliferation used in the present invention may be any agent for suppressing differentiation and/or promoting proliferation described in the item of (Differentiation suppression and/or proliferation promotion) and other items. In addition, a cell which is a subject of the present invention is intended for preserving a cell or culturing a cell, and it is understood that the cell may be any cell embodiment described in the item of (Differentiation suppression and/or proliferation promotion) and other items. That is, a cell which is a subject of the present invention is not particularly limited, but is intended for preserving a cell or culturing a cell, and includes an eye cell, a nerve cell including a cell derived from a neural crest cell (including a corneal endothelial cell), and an epithelial cell such as a conjunctival epithelial cell, an amniotic epithelial cell, an oral mucosa epithelial cell, a nose mucosa epithelial cell, and a corneal epithelial cell. In a preferable embodiment, a cell which is a subject of the present invention is an eye cell. An eye cell which is a subject of the present invention is intended for preserving a cell or culturing a cell, and includes, but is not limited to a retinal cell, a vitreous body cell, a corneal epithelial cell, a corneal parenchymal cell and a corneal endothelial cell.

In one embodiment of a composition for preserving a cell or culturing a cell of the present invention, an eye cell which is a subject of the present invention is a cell which does not proliferate in the stationary state. Not wishing to be bound by any theory, the present invention exerts an unprecedented effect from the viewpoint of cell preservation or cell culturing in a point that even a cell which does not proliferate in the stationary state can be proliferated by the present invention.

In another embodiment of the composition for preserving a cell or culturing a cell of the present invention, an eye cell which is a subject of the present invention includes at least one kind of cell selected from a retinal cell, a vitreous body cell, a corneal epithelial cell, a corneal parenchymal cell and a corneal endothelial cell. Particularly, a corneal endothelial cell is a cell which proliferates little in the stationary state, and a point that this cell can be proliferated has an extremely important meaning from the viewpoint of cell preservation or cell culturing, and as a result, from the viewpoint of treatment or prevention of an ophthalmological disease using a cell to be used. Therefore, in one preferable embodiment, an eye cell which is a subject of the present invention includes a corneal endothelial cell. In addition, even in other cells, for example, in a corneal epithelial cell, a small fraction of basal cells proliferate, and a majority of cells do not proliferate. Therefore, it is possible to state that even a retinal cell, a vitreous body cell, a corneal epithelial cell, and a corneal parenchymal cell other than a corneal endothelial cell have an extremely important meaning from the viewpoint of cell preservation or cell culturing, and as a result, from the viewpoint of treatment or prevention of an ophthalmological disease by cell treatment or the like to be used.

In a further preferable embodiment of the composition for preserving a cell or culturing a cell of the present invention, an eye cell which is a subject of the present invention includes a corneal endothelial cell of a primate. In a further more preferable embodiment, an eye cell which is a subject of the present invention includes a human corneal endothelial cell.

In another embodiment of the composition for preserving a cell or culturing a cell of the present invention, a cell which is a subject of the present invention (e.g., eye cell) is in the confluent state. A technique in which a cell can proliferate in such a confluent state is extremely meaningful also from the viewpoint of cell preservation or cell culturing. Therefore, such a technique has extremely high usefulness in a point that a cell in an unprecedented category can be proliferated, and also from the viewpoint of treatment or prevention of a disease or a disorder using a cell which is obtained as a result of cell preservation or cell culturing.

Therefore, in a preferable embodiment, the present invention provides a composition for preserving the cornea or culturing a corneal endothelial cell, comprising the agent for suppressing differentiation and/or promoting proliferation of the present invention. Such a composition may utilize at least one kind of R-sporadins, SHH, an agonist of SHH (e.g., agonist of Frizzled family such as purmorphamine), an agent suppressing GPR49/LGR5 or a functional equivalent thereof which are an active ingredient of the agent for suppressing differentiation and/or promoting proliferation of the present invention, as it is, or can be prepared by addition of other ingredients. Alternatively, the present invention provides a method for preserving or culturing a cell, using the agent for suppressing differentiation and/or promoting proliferation of the present invention. In one embodiment, the present invention provides a method for preserving the cornea or culturing a corneal endothelial cell, comprising the step of using the agent for suppressing differentiation and/or promoting proliferation of the present invention. It should be understood that the agent for suppressing differentiation and/or promoting proliferation contained in the composition for preserving the cornea or culturing a corneal endothelial cell of the present invention can adopt any embodiment described in (Differentiation suppression and/or proliferation promotion).

In addition, whether a corneal endothelial cell is normally cultured or not can be determined herein by confirming if a corneal endothelial cell maintains at least one characteristic such as its inherent function (as used herein, also referred to as "normal function"). Examples of such a function include ZO-1 and Na$^+$/K$^+$-ATPase, adaptive capacity to corneal transplantation (Matsubara M, Tanishima T: Wound-healing of the corneal endothelium in the monkey: a morphometric study, Jpn J Ophthalmol 1982, 26: 264-273; Matsubara M, Tanishima T: Wound-healing of corneal endothelium in monkey: an autoradiographic study, Jpn J Ophthalmol 1983, 27: 444-450; Van Horn D L, Hyndiuk R A: Endothelial wound repair in primate cornea, Exp Eye Res 1975, 21: 113-124 and VanHorn D L, Sendele D D, Seideman S, Buco P J: Regenerative capacity of the corneal endothelium in rabbit and cat, Invest Ophthalmol Vis Sci 1977, 16: 597-613), but are not limited thereto. That is, it is understood that the "normal function" may be an index showing a function necessary for realizing corneal transplantation, or sufficiency for realizing corneal transplantation. For example, a method for determining normalization can be performed by observing a change in expression thereof using a functional protein in a corneal endothelial cell such as ZO-1 and Na$^+$/K$^+$-ATPase as an index, or investigating whether the cell is engrafted and functions or not, by transplantation into a monkey or the like. A determination method by transplantation can be performed as follows. That is, the corneal endothelium is cultured on type I collagen to make a cultured corneal endothelium sheet. Under general anesthesia, limbus corneae of a cynomolgus monkey is incised 1.5 mm, an operation tool made of silicon is inserted into an anterior chamber, and a corneal endothelial cell is mechanically curetted to make a bullous keratopathy model. Subsequently, limbus corneae is incised 5 to 6 mm, the cultured corneal endothelium sheet is inserted into the anterior chamber, and the anterior chamber is replaced with the air, thereby, the sheet is adhered to the corneal endothelium surface. The effect of treating bullous keratopathy by transplantation of the cultured corneal endothelium sheet can be obtained by evaluating cornea transparency with a slit lamp microscope.

(Treatment or Prevention of Cell Disorder)

In another aspect, the present invention provides a pharmaceutical composition for treating a disorder of a cell or preventing progression of the disorder of the cell, comprising the agent for suppressing differentiation and/or promoting proliferation of the present invention. The agent for suppressing differentiation and/or promoting proliferation used in the present invention may be any agent for suppressing differentiation and/or promoting proliferation described in the item of (Differentiation suppression and/or proliferation promotion) and other items. In addition, it is understood that a cell which is a subject of the present invention may be any cell embodiment described in the item of (Differentiation suppression and/or proliferation promotion) and other items, as far as it is intended for treating a disorder of a cell or preventing progression of the disorder of the cell. That is, a cell which is a subject of the present invention is not particularly limited, and includes an eye cell, a nerve cell including a cell derived from a neural crest cell (including a corneal endothelial cell), and an epithelial cell such as a conjunctival epithelial cell, an amniotic epithelial cell, an oral mucosa epithelial cell, a nose mucosa epithelial cell, and a corneal epithelial cell, as far as the cell is intended for treating a disorder of a cell or preventing progression of the disorder of the cell. In a preferable embodiment, a cell which is a subject of the present invention is an eye cell. An eye cell which is a subject of the present invention includes a retinal cell, a vitreous body cell, a corneal epithelial cell, a corneal parenchymal cell and a corneal endothelial cell, but is not limited to them.

In one embodiment of the pharmaceutical composition of the present invention, an eye cell which is a subject of the present invention is a cell which does not proliferate in the stationary state. Not wishing to be bound by any theory, in a point that even a cell which does not proliferate in the stationary state can be proliferated by the present invention, the present invention exerts a meaningful effect in a point that treatment of a disorder of a cell or prevention of progression of the disorder of the cell can be performed.

In another embodiment of the pharmaceutical composition of the present invention, an eye cell which is a subject of the present invention includes at least one kind of cell selected from a retinal cell, a vitreous body cell, a corneal epithelial cell, a corneal parenchymal cell and a corneal endothelial cell. Particularly, a corneal endothelial cell is a cell which proliferates little in the stationary state, and a point that this cell can be proliferated has an extremely important meaning from the viewpoint of treatment of a disorder of a cell or prevention of progression of the disorder of the cell, and from the viewpoint of treatment or prevention of an ophthalmologial disease. Therefore, in one preferable embodiment, an eye cell which is a subject of the present invention includes a corneal endothelial cell. In addition, even in other cells, for example, in a corneal epithelial cell, a small fraction of basal cells proliferate, and a majority of cells do not proliferate. Therefore, it is possible to state that even a retinal cell, a vitreous body cell, a corneal epithelial cell, and a corneal parenchymal cell other than a corneal endothelial cell have an extremely important meaning from the viewpoint of treatment or prevention of an ophthalmological disease, in light of a viewpoint of treatment of a disorder of a cell or prevention of progression of the disorder of the cell.

In a further preferable embodiment of the pharmaceutical composition of the present invention, an eye cell which is a subject of the present invention includes a corneal endothelial cell of a primate. In a further more preferable embodiment, an eye cell which is a subject of the present invention includes a human corneal endothelial cell.

In another embodiment of the pharmaceutical composition of the present invention, a cell which is a subject of the present invention (e.g., eye cell) is in the confluent state. A technique in which a cell can proliferate in such a confluent state is meaningful also from the viewpoint of treatment of a disorder of a cell or prevention of progression of the disorder of the cell. Therefore, such a technique has extremely high usefulness in a point that a cell of an unprecedented category can be proliferated, from the viewpoint of treatment of a disorder of a cell or prevention of progression of the disorder of the cell.

In a preferable embodiment, the present invention provides a pharmaceutical composition for treating a corneal endothelial cell disorder or preventing progression of a corneal endothelial cell disorder, comprising the agent for suppressing differentiation and/or promoting proliferation of the present invention. It should be understood that the agent for suppressing differentiation and/or promoting proliferation contained in the pharmaceutical composition of the present invention can adopt any embodiment described in (Differentiation suppression and/or proliferation promotion).

As used herein, "treatment", concerning a certain disease or disorder (e.g., corneal disease), refers to that, when such a condition occurs, worsening of such a disease or disorder is prevented, preferably the current condition is maintained, more preferably the disease or the disorder is alleviated, further preferably it is eliminated.

As used herein, "prevention", concerning a certain disease or disorder, refers to avoid such a condition before it occurs. The agent of the present invention can be used to perform diagnosis, and if necessary, the agent of the present invention can be used to, for example, prevent a corneal disease or the like, or take a precaution.

When the effect of the therapeutic agent of the present invention is confirmed, determination can be conducted by observing adaptive capacity to corneal transplantation. Concerning adaptive capacity to corneal transplantation, generally a transplantation test of a cultured cell can be performed by mechanically curetting the corneal endothelium, as a bullous keratopathy model, in an experimental animal such as a rabbit. However, since a corneal endothelial cell of a rabbit proliferates in a living body, a possibility of spontaneous recovery due to proliferation of a corneal endothelial cell of a host cannot be denied (Matsubara M, et al., Jpn J Ophthalmol 1982, 26: 264-273; Matsubara M, et al., Jpn J Ophthalmol 1983, 27: 444-450; Van Horn D L, et al., Exp Eye Res 1975, 21: 113-124 and Van Horn D L, et al., Invest Ophthalmol Vis Sci 1977, 16: 597-613). Therefore, in order to evaluate the adaptive capacity to transplantation more accurately, it is preferable to evaluate engraftment in a primate. When adaptive capacity to transplantation in human is evaluated, adaptability is evaluated after at least 1 month, preferably at least 2 months, more preferably at least 3 months, further preferably at least 6 months, further more preferably at least 12 months in a cynomolgus monkey or the like which is a primate. It is particularly important in application to human to confirm the adaptive capacity to transplantation in a primate such as a monkey.

When the present invention is administered as a pharmaceutical, a variety of delivery systems are known, and the therapeutic agent of the present invention can be administered using such a system. Examples of such a system include encapsulation into a liposome, a microparticle, and a microcapsule; use of a recombinant cell which can express a therapeutic agent (e.g., polypeptide), use of endocytosis mediated with a receptor; and construction of a therapeutic nucleic acid as a part of a retrovirus vector or another vector. Examples of the administration method include, but are not limited to, intradermal, intramuscular, intraperitoneal, intravenous, subcutaneous, intranasal, extradural and oral routes. It is also possible to administer a pharmaceutical by any of preferable routes, for example, by infusion, by bolus injection, by inhalation through an epithelium or skin mucosal lining (e.g., oral cavity, rectum, and intestinal mucosa), and, if necessary, an inhaler or a sprayer can be employed using an aerosol agent, and the pharmaceutical can also be administered together with other biologically active agents. Administration can be systemic or local. Further, when the present invention is used in the ophthalmological field, the pharmaceutical can be administered by any of appropriate routes, such as direct infusion into an eye.

In the case of treatment of the cornea or the like, a conventional technique such as ocular instillation, eye ointment application, subconjunctival injection, and vitreous body injection can be used.

In a specific aspect in which a therapeutic agent is a nucleic acid encoding a protein, expression of an encoded protein can be promoted by constructing the nucleic acid as a part of an appropriate nucleic acid expression vector, and administering the nucleic acid so as to exist in a cell for in vivo application. This can be performed, for example, by use of a retrovirus vector, by direct injection, by use of a microparticle gun, by coating a nucleic acid with a lipid, a cell surface receptor or a transfection agent, or by administering a nucleic acid connected to a tag sequence which is known to enter a nucleus. Alternatively, the nucleic acid therapeutic agent can be introduced into a cell, and, for expression, can be taken into a host cell DNA by homologous recombination.

Generally, the pharmaceutical, the therapeutic agent, the preventive agent or the like of the present invention comprises a therapeutically effective amount of a therapeutic agent or active ingredient, and a pharmaceutically acceptable carrier. As used herein, "pharmaceutically acceptable" means that the pharmaceutical, agent or the like is approved by a governmental regulatory authority, or listed in pharmacopoeia or other generally accepted pharmacopoeias, for use in an animal, more particularly, human. A "carrier" as used herein refers to a diluent, an adjuvant, an excipient, or a vehicle which is administered together with a therapeutic agent. Such a carrier can be a sterile liquid, for example, water and an oil, includes carries derived from a petroleum, an animal, a plant or a synthetic origin, and includes a peanut oil, a soybean oil, a mineral oil, and a sesame oil without limitation. When the pharmaceutical is orally administered, water is a preferable carrier. When the pharmaceutical composition is administered intravenously, physiological saline and aqueous dextrose are preferable carriers. Preferably, a physiological saline solution, as well as aqueous dextrose and a glycerol solution are used for a liquid carrier of an injectable solution. An appropriate excipient includes light silicic anhydride, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropylcellulose, hydroxypropylmethylcellulose, polyvinyl acetal diethyl aminoacetate, polyvinylpyrrolidone, gelatin, medium chain fatty acid tryglyceride, polyoxyethylene hydrogenated castor oil 60, white sugar, carboxymethylcellulose, corn starch, and an inorganic salt. The composition, when desirable, can contain a small amount of a wetting agent or emulsifying agent, or a pH buffer. These compositions can take the form of a solution, a suspension, an emulsion, a tablet, a pill, a capsule, a powder, a sustained-release formulation or the like. Using a traditional binder and a carrier, for example, triglyceride, the composition can also be formulated as a suppository. An oral formulation can also contain a standard carrier such as pharmaceutical grade mannitol, lactose, starch, magnesium stearate, saccharin sodium, cellulose, and magnesium carbonate. Examples of an appropriate carrier are described in E. W. Martin, Remington's Pharmaceutical Sciences (Mark Publishing Company, Easton, U.S.A.). Such a composition contains a therapeutically effective amount of a therapeutic agent, preferably, a purified type of a therapeutic agent together with an appropriate amount of a carrier so as to provide an adequate dosage form to a patient. A formulation must be suitable for an administration mode. In addition, for example, a surfactant, an excipient, a coloring agent, a flavoring agent, a preservative, a stabilizer, a buffer, a suspending agent, a tonicity agent, a binder, a disintegrating agent, a lubricant, a flow promoter, and a taste masking agent may be contained.

In a preferable embodiment, a composition can be formulated as a pharmaceutical composition adapted to injection administration to human according to a known method. Representatively, a composition for injection administration is a solution in a sterile isotonic aqueous buffer. If necessary, the composition can also contain a solubilizer and a local anesthetic such as lidocaine which mitigates a pain at an injection site. Generally, ingredients can be supplied as a lyophilized powder or a water-free concentrate by supplying the ingredients separately, or by mixing them together in a unit dosage form in a sealed container such as an ampoule or a sachet indicating the amount of an active agent. When the composition is to be administered by infusion, the composition can also be dispensed using an infusion bottle containing a sterile pharmaceutical grade water or physiological saline. When the composition is to be administered by injection, an ampoule of sterile water or physiological saline for injection can be provided so that the ingredients can be mixed prior to administration.

The pharmaceutical, the therapeutic agent, or the preventive agent of the present invention can also be formulated with another prodrug (e.g., ester) of a neutral type or a salt type. A pharmaceutically acceptable salt includes salts formed with a free carboxyl group derived from hydrochloric acid, phosphoric acid, acetic acid, oxalic acid and tartaric acid, salts formed with a free amine group derived from isopropylamine, triethylamine, 2-ehtylaminoethanol, histidine, and procaine, as well as salts derived, from sodium, potassium, ammonium, calcium, and ferric hydroxide.

The amount of the therapeutic agent of the present invention effective for treating a specific disorder or condition can vary depending on the nature of the disorder or the condition, but a person skilled in the art can determine the amount by a standard clinical technique based on the descriptions described herein. Further, depending on the situation, it is also possible to assist identification of an optimal dose range using an in vitro assay. Since the precise dose to be used in a formulation can also vary depending on an administration route, and severity of a disease or a disorder, the dose should be determined according to the judgment of an attending physician and the situation of each patient. However, a dose range suitable for direct administration to the cornea is generally about 1 to 500 micrograms of an active ingredient per kilogram weight, but is not limited to this, and can be smaller or larger than this range. An effective dose can be presumed from a dose-response curve obtained from an in vitro or animal model test system.

The pharmaceutical composition, the therapeutic agent or the preventive agent of the present invention can be provided as a kit.

As used herein, a "kit" refers to a unit which is usually divided into two or more sections, and which provides a part to be provided (e.g., therapeutic agent, antibody, label, and direction). For the purpose of providing a composition which should not be provided in the form of a mixture but is preferably used by mixing immediately before use, this form of kit is preferable. It is advantageous that such a kit is preferably provided with a part to be provided (e.g., instruction or direction describing how to use the therapeutic agent, or how to treat the reagent). As used herein, when the kit is used as a reagent kit, the kit usually includes an instruction describing how to use an antibody.

As used herein, an "instruction" has a description explaining how to use the present invention to a doctor or other users. This instruction describes wording instructing the reader on the detection method of the present invention, how to use a diagnostic, or administration of a pharmaceutical or the like. In addition, the instruction may describe wording instructing the reader on administration to a skeletal muscle (e.g., by injection) as an administration site. This instruction is written according to the format defined by a regulatory authority of a country where the present invention is implemented (e.g., Ministry of Health, Labour and Welfare in Japan and Food and Drug Administration (FDA) in the U.S.), and explicitly describes that the pharmaceutical was approved by the regulatory authority. The instruction is the so-called package insert, and is usually provided in a paper medium, but is not limited thereto. For example, the instruction can be provided in the form such as an electronic medium (e.g., homepage provided on the internet and electronic mail).

In a specific embodiment, the present invention provides a pharmaceutical pack or kit, comprising one or more containers filled with one or more ingredients of the pharmaceutical composition of the present invention. Depending on the situation, it is possible to indicate on such a container information showing approval by a governmental organization which regulates manufacture, use or sales of a pharmaceutical or a biological product in relation to manufacture, use or sales for administration to human, in a form defined by the governmental organization.

The kit of the present invention can also contain an expression vector encoding a protein used as the therapeutic agent, the preventive agent or the agent of the present invention, and this protein can also be reconstituted in order to form a biologically active complex after expression. Such a kit preferably also contains a necessary buffer and a necessary reagent. Depending on the situation, it is possible to indicate on such a container a direction for the use of the kit and/or information showing approval by a governmental organization which regulates manufacture, use or sales of a pharmaceutical or a biological product in relation to manufacture, use or sales for administration to human, in a form defined by the governmental organization.

In a specific embodiment, the pharmaceutical composition comprising a nucleic acid of the present invention can be administered by means of a liposome, a microparticle, or a microcapsule. In various aspects of the present invention, it may be useful to attain sustained release of a nucleic acid using such a composition.

In another aspect, treatment of the present invention can be implemented using a corneal tissue itself prepared using the present invention, for example, a sclerocornea slice. Preferably, the Ki67-positive cell exits at a ratio of about 4% or more, more preferably at a ratio of about 7% or more, further preferably at a ratio of about 10% or more. Since the ordinary existence ratio is around 1%, a corneal tissue containing such a Ki67-positive cell, that is, a proliferating cell was not present previously, and a therapeutic effect better than that of a corneal tissue which is directly transplanted from a living body, as a graft for novel treatment, is expected.

The density of the corneal endothelial cell is preferably about 4000 cells/mm$^2$ or more, more preferably about 4500 cells/mm$^2$ or more, further preferably about 5000 cells/mm$^2$ or more. A normal value of the human corneal endothelium in a living body is around 2500 to 3000 cells/mm$^2$. It is understood that a novel tissue in which the ratio of a proliferating cell or an undifferentiated cell, or a corneal endothelial cell is increased to an unprecedented extent is provided by directly applying the agent for suppressing differentiation and/or promoting proliferation of the present invention to a tissue. It is understood that such a tissue is utilized for improving, treating or preventing a disease, a disorder or a condition of the cornea for the purpose of exerting a therapeutic effect better than that of a corneal tissue which is directly transplanted from a living body.

(Cell Treatment)

In another aspect, the present invention provides a therapeutic agent or a progression preventive agent for a disorder of a cell, or a disease or a disorder due to the cell disorder, comprising a cell which is cultured using the agent for suppressing differentiation and/or promoting proliferation of the present invention. The agent for suppressing differentiation and/or promoting proliferation used in the present invention may be any agent for suppressing differentiation and/or promoting proliferation described in the item of (Differentiation suppression and/or proliferation promotion) and other items. In addition, it is understood that a cell which is a subject of the present invention may be any cell embodiment described in the item of (Differentiation suppression and/or proliferation promotion) and other items. That is, examples of the cell which is a subject of the present invention may include, but are not particularly limited to, an eye cell, a nerve cell including a cell derived from a neural crest cell (including a corneal endothelial cell), and epithelial cells such as a conjunctival epithelial cell, an amniotic epithelial cell, an oral mucosa epithelial cell, a nose mucosa epithelial cell, and a corneal epithelial cell. In a preferable embodiment, a cell which is a subject of the present invention is an eye cell. An eye cell which is a subject of the present invention can include a retinal cell, a vitreous body cell, a corneal epithelial cell, a corneal parenchymal cell and a corneal endothelial cell, but is not limited to them.

In one embodiment of the therapeutic agent or the progression preventive agent of the present invention, an eye cell which is a subject of the present invention is a cell which does not proliferate in the stationary state. Not wishing to be bound by any theory, the present invention exerts an unprecedented effect in a point that even a cell which does not proliferate in the stationary state can be proliferated by the present invention.

In another embodiment of the therapeutic agent or the progression preventive agent of the present invention, an eye cell which is a subject of the present invention includes at least one kind of cell selected from a retinal cell, a vitreous body cell, a corneal epithelial cell, a corneal parenchymal cell and a corneal endothelial cell. Particularly, a corneal endothelial cell is a cell which proliferates little in the stationary state, and a point that this cell can be proliferated has an extremely important meaning from the viewpoint of treatment or prevention of an ophthalmological disease. Therefore, in one preferable embodiment, an eye cell which is a subject of the present invention includes a corneal endothelial cell. In addition, even in other cells, for example, in a corneal epithelial cell, a small fraction of basal cells proliferate, and a majority of cells do not proliferate. Therefore, it is possible to state that even a retinal cell, a vitreous body cell, a corneal epithelial cell and a corneal parenchymal cell other than a corneal endothelial cell have an extremely important meaning from the viewpoint of treatment or prevention of an ophthalmological disease.

In a further preferable embodiment of the therapeutic agent or the progression preventive agent of the present invention, an eye cell which is a subject of the present invention includes a corneal endothelial cell of a primate. In a further more preferable embodiment, an eye cell which is a subject of the present invention includes a human corneal endothelial cell.

In another embodiment of the therapeutic agent or the progression preventive agent of the present invention, a cell which is a subject of the present invention (e.g., eye cell) is in the confluent state. No technique in which a cell can proliferate in such a confluent state has previously been reported as far as the present inventors know. Therefore, such a technique has extremely high usefulness in a point that a cell in an unprecedented category can be proliferated, from the viewpoint of treatment or prevention of a disease or a disorder.

In one embodiment, the present invention provides a therapeutic agent or a progression preventive agent for a corneal endothelial cell disorder, comprising a corneal endothelial cell which was cultured using the agent for suppressing differentiation and/or promoting proliferation of the present invention. It should be understood that the agent for suppressing differentiation and/or promoting proliferation contained in the therapeutic agent or the progression preventive agent of the present invention can adopt any embodiment described in (Differentiation suppression and/or proliferation promotion), (Treatment or prevention of cell disorder), (Preservation or culturing of cell) and the like.

In one embodiment, particularly, in the case of a corneal endothelial cell, a cell contained in the therapeutic agent or the progression preventive agent of the present invention exists as a population including more cells which have a higher cell density than that of normal cells which exist in a natural state and/or are undifferentiated. Since a therapeutic agent or a progression preventive agent containing such a cell was unable to be produced before, the present invention has high clinical usefulness in that a disease or a disorder which was unable to be treated or prevented, or difficult to treat or prevent before (e.g., including corneal endothelial diseases such as bullous keratopathy and Fuchs endothelial corneal dystrophy without being limited to them) can be treated.

The therapeutic agent or the preventive agent of the present invention can be produced by culturing a cell such as a corneal endothelial cell using the agent for suppressing differentiation and/or promoting proliferation of the present invention. In such a case, the proliferation ability or the differentiation level can be determined using, as an index, GPR49/LGR5, and/or the factors of the Hedgehog pathway such as SHH, PTCH1, GLI1, and GLI2, the factors of the Wnt pathway such as LRP6 and β-catenin, or known differentiation markers such as Ki-67 and BrdU described in another aspect of the present invention. Determination of the proliferation ability or the differentiation level is explained in detail separately described herein.

The present invention provides a process for producing a therapeutic agent or a progression preventive agent comprising the following steps: (A) a step of providing a cell such as a corneal endothelial cell; (B) a step of contacting the agent for suppressing differentiation and/or promoting proliferation of the present invention with the cell; and (C) a step of culturing the cell which was brought into contact in the step (B). Further, if necessary, the process may include a step of determining the proliferation ability or the differentiation level using, as an index, GPR49/LGR5, and/or the factors of the Hedgehog pathway such as SHH, PTCH1, GLI1, and GLI2, the factors of the Wnt pathway such as LRP6 and β-catenin, or known differentiation markers such as Ki-67 and BrdU described in another aspect of the present invention, and selecting a cell having a high differentiation ability and a high proliferation ability.

According to the present invention, a method for treating or preventing a corneal endothelial disease, disorder, or condition, comprising a step of administering the agent for suppressing differentiation and/or promoting proliferation of the present invention to a subject in need of treatment, or a step of administering the therapeutic agent or the progression preventive agent of the present invention to a subject in need of treatment. Since the step of administering the therapeutic agent or the progression preventive agent of the present invention to a subject in need of treatment is an act of administering a pharmaceutical containing a cell, it may be called transplantation.

According to the method of treatment or the method of prevention of the present invention, a corneal endothelial disease, disorder or condition can be prevented and/or treated, since an administered or transplanted cell cures or restores damage of the corneal endothelium.

In implementation of the method of treatment in accordance with the present invention, a cell which can contain a corneal endothelial cell can be obtained from a mammal including human, preferably, an individual itself undergoing transplantation or an aborted fetus.

(Marker for Identifying Differentiation Ability and Proliferation of GPR49/LGR5, and/or Factors of Hedgehog Pathway such as SHH, PTCH1, GLI1, and GLI2, and Factors of Wnt Pathway such as LRP6 and β-Catenin)

In one aspect, the present invention provides a marker for identifying a cell having a high proliferation ability among corneal endothelial cells and/or the differentiation ability of a corneal endothelial cell, comprising GPR49/LGR5, and/or the factors of the Hedgehog pathway such as SHH, PTCH1, GLI1, and GLI2, and/or the factors of the Wnt pathway such as LRP6 and β-catenin. GPR49/LGR5, the factors of the Hedgehog pathway such as SHH, PTCH1, GLI1, and GLI2 and the factors of the Wnt pathway such as LRP6 and β-catenin exist in a living body, and it was found in the present invention that they can be used as an index marker of a cell having a high proliferation ability and/or the differentiation ability.

In one embodiment, a cell having a high proliferation ability which is a subject of the present invention is an undifferentiated cell.

In another embodiment, a cell having a high proliferation ability which is a subject of the present invention is a stem cell.

In another embodiment, a corneal endothelial cell which is a subject of the present invention is a human cell.

In still another embodiment, the proliferation ability of a corneal endothelial cell which is a subject of the present invention is identified by a characteristic selected from the group consisting of colony forming ability, Ki-67 positivity and BrdU positivity.

Expression of GPR49/LGR5, and/or the factors of the Hedgehog route such as SHH (gene), PTCH1, GLI1, and GLI2 serves as an index of a cell having a high proliferation ability among corneal endothelial cells and/or the differentiation ability of a corneal endothelial cell. Therefore, according to the present invention, by defecting expression of GPR49/LGR5 and/or SHH, a cell having a high proliferation ability (an undifferentiated cell, a precursor cell or a stem cell) among corneal endothelial cells and/or the differentiation ability of a corneal endothelial cell can be detected or selected. On the other hand, expression of the factors of the Wnt pathway such as LRP6 and β-catenin serves as an index of a cell having a low proliferation ability among corneal endothelial cells and/or the differentiation ability of a corneal endothelial cell. Therefore, according to the present invention, by detecting expression of the factors of the Wnt pathway such as LRP6 and β-catenin, a cell having a low proliferation ability (a relatively differentiated cell, which is not an undifferentiated cell, a precursor cell or a stem cell) among corneal endothelial cells and/or a low differentiation ability of a corneal endothelial cell can be detected or selected. Alternatively, when suppression or disappearance of expression of the factors of the Wnt pathway such as LRP6 and β-catenin has been detected, a cell having a high proliferation ability (an undifferentiated cell, a precursor cell or a stem cell) among corneal endothelial cells and/or the differentiation ability of a corneal endothelial cell can be detected or selected.

In another aspect, the present invention provides a detection agent or a diagnostic agent for identifying a cell having a high proliferation ability among corneal endothelial cells and/or the differentiation ability of a corneal endothelial cell, comprising a substance which binds to, or interacts with GPR49/LGR5, and/or the factors of the Hedgehog pathway such as Sonic hedgehog (SHH), PTCH1, GLI1, and GLI2, and/or the factors of the Wnt pathway such as LRP6 and β-catenin. For such detection or diagnosis, it is preferable that binding of the substance is specific.

As such a detection agent or diagnostic, any substance may be utilized as far as it can bind to, or interact with GPR49/LGR5, and/or the factors of the Hedgehog pathway such as Sonic hedgehog (SHH), PTCH1, GLI1, and GLI2, and/or the factors of the Wnt pathway such as LRP6 and β-catenin Representative examples thereof include an antibody of these factors or a fragment or functional equivalent thereof, or a nucleic acid primer or a probe concerning a nucleic acid encoding these factors, but are not limited to them.

The detection agent or the diagnostic agent of the present invention can be utilized as a detection kit or a diagnosis kit.

In one embodiment, a cell having a high proliferation ability which is a subject of detection or diagnosis of the present invention is an undifferentiated cell.

In another embodiment, a cell having a high proliferation ability which is a subject of detection or diagnosis of the present invention is a stem cell.

In another embodiment, a corneal endothelial cell which is a subject of detection or diagnosis of the present invention is a human cell.

In still another embodiment, the proliferation ability of a corneal endothelial cell which is a subject of detection or diagnosis of the present invention is identified by a characteristic selected from the group consisting of colony forming ability, Ki-67 positivity and BrdU positivity.

The detection agent of the present invention may be a complex or a composite molecule in which another substance (e.g., label) is bound to a portion which allows for detection (e.g., antibody). As used herein, a "complex" or a "composite molecule" means any constituent comprising two or more parts. For example, when one of the parts is a polypeptide, the other part may be a polypeptide, or may be another substance (e.g., a sugar, a lipid, a nucleic acid, or a different hydrocarbon). As used herein, two or more parts constituting the complex may be bound with a covalent bond, or may be bound with another bond (e.g., a hydrogen bond, an ionic bond, hydrophobic interaction, or Van der Waals force). When two or more parts are each a polypeptide, this can also be named as a chimeric polypeptide. Therefore, as used herein, a "complex" includes a molecule obtained by connecting a plurality of kinds of molecules such as a polypeptide, a polynucleotide, a lipid, a sugar, and a low molecule.

As used herein, "interaction", when referring to two substances, refers to that a force (e.g., intermolecular force (Van der Waals force), a hydrogen bond, or hydrophobic interaction) is exerted between one substance and the other substance. Usually, the two substances which have interacted with each other are in an associated or bonded state.

The term "bond", as used herein, means physical interaction or chemical interaction between two substances, or between combinations thereof. The bond includes an ionic bond, a non-ionic bond, a hydrogen bond, a Van der Waals bond, and hydrophobic interaction. Physical interaction (bond) can be direct or indirect, and indirect interaction arises through or due to the effect of another protein or compound. A direct bond does not occur through or due to the effect of another protein or compound, and refers to interaction accompanying no other substantial chemical intermediate.

Therefore, as used herein, an "agent" (or a factor, a detection agent or the like) which "specifically" interacts with (or binds to) a biological agent such as a polynucleotide or a polypeptide includes an agent whose affinity for a biological agent such as a polynucleotide or a polypeptide is representatively equal to or higher than, preferably significantly (e.g., statistically significantly) higher than the affinity for other irrelevant (particularly, identity is less than 30%) polynucleotide or polypeptide. Such affinity can be measured, for example, by a hybridization assay, a binding assay or the like.

As used herein, that a first substance or agent "specifically" interacts with (or binds to) a second substance or agent refers to that a first substance or agent interacts with (or binds to) a second substance or agent with higher affinity than that for a substance or agent other than the second substance or agent (particularly, a different substance or agent existing in a sample containing the second substance or agent). Examples of interaction (or bond) specific for a substance or a agent include, but are not limited to a ligand-receptor reaction, hybridization in nucleic acids, an antigen-antibody reaction in proteins, and an enzyme-substrate reaction, and when both of a nucleic acid and a protein are involved, a reaction between a transcription agent and a binding site of the transcription factor, protein-lipid interaction, and nucleic acid-lipid interaction. Therefore, when both of the substances or agents are nucleic acids, a first substance or agent "specifically interacts" with a second substance or agent including that a first substance or agent has complementarity to at least a part of a second substance or agent. In addition, for example, when both of the substances or agents are proteins, that a first substance or agent "specifically" interacts with (or binds to) a second substance or agent includes, for example, interaction by an antigen-antibody reaction, interaction by a receptor-ligand reaction, and enzyme-substrate interaction, but is not limited thereto. When two kinds of substances or agents include a protein and a nucleic acid, that a first substance or agent "specifically" interacts with (or binds to) a second substance or agent includes interaction (or bond) between a transcription factor and a binding region of a nucleic acid molecule which is a subject of the transcription factor.

As used herein, "detection" or "quantitation" of polynucleotide or polypeptide expression can be attained, for example, using an appropriate method including mRNA measurement and an immunological measuring method, that includes binding or interaction with a marker detection agent. Examples of the molecular biological measuring method include a Northern blotting method, a dot blotting method and a PCR method. Examples of the immunological measuring method include, as a method, an ELISA method using a microtiter plate, an RIA method, a fluorescent antibody method, a luminescence immunoassay (LIA), an immunoprecipitation method (IP), a single radical immunodiffusion method (SRID), turbidimetric immunoassay (TIA), a Western blotting method, and an immunohistological staining method. In addition, as a quantitation method, an ELISA method or an RIA method can be mentioned. Detection or quantitation can also be performed by a genetic analysis method using an array (e.g., DNA array or protein array). The DNA array is widely reviewed in (Cell Technology, separate volume, "DNA Microarray and Advanced PCR method", edited by Shujunsha Co., Ltd.). The protein array is described in detail in Nat Genet. 2002 December; 32 Suppl: 526-532. Examples of a method for analyzing gene expression include, but are not limited to RT-PCR, a RACE method, a SSCP method, an immunoprecipitation method, a two-hybrid system, and in vitro translation, in addition to the aforementioned methods. Such additional analysis methods are described, for example, in Genome Analysis Experimental Method, Nakamura Yusuke Lab. Manual, edited by Yusuke Nakamura, Yodosha Co., Ltd. (2002), the entirety of descriptions in the document are incorporated herein by reference.

As used herein, an "expression amount" refers to an amount of expression of a polypeptide or mRNA in an objective cell, tissue or the like. Examples of such an expression amount include an expression amount at the protein level of the present polypeptide evaluated by any appropriate method including an ELISA method, an RIA method, a fluorescent antibody method, a Western blotting method, or an immunological measuring method such as an immunohistological staining method using the antibody of the present invention, and an expression amount at the mRNA level of a polypeptide used in the present invention which is evaluated by any appropriate method including a molecular biological measuring method such as a Northern blotting method, a dot blotting method, and a PCR method. "Change in an expression amount" means that an expression amount at the protein level or the mRNA level of a polypeptide used in the present invention, which is evaluated by any appropriate method including the immunological measuring method and the molecular biological measuring method, is increased or decreased. By measuring an expression amount of a certain marker, a variety of detections or diagnoses based on the marker can be performed.

As used herein, "decrease" or "suppression" or a synonym thereof of the activity or an expression product (e.g., a protein or a transcription product (such as RNA)) refers to decrease in an amount, nature or the effect of a specific activity, transcription product or protein, or an activity that decreases them.

As used herein, "increase" or "activation" or a synonym thereof of the activity or an expression product (e.g., a protein or a transcription product (such as RNA)) refers to an increase in an amount, nature or the effect of a specific activity, transcription product or protein, or an activity that increases them.

Therefore, it is understood that an agent which performs differentiation modulation of an eye cell can be detected or screened using the modulation ability such as decrease, suppression, increase or activation of the marker of the present invention as an index.

As used herein, an "antibody" includes, in a broad sense, a polyclonal antibody, a monoclonal antibody, a multispecific antibody, a chimeric antibody, and an anti-idiotype antibody, as well as a fragment thereof, for example, a Fv fragment, a Fab' fragment, F(ab')$_2$ and Fab fragments, as well as other conjugates or functional equivalents produced by recombination (e.g., chimeric antibody, humanized antibody, multifunctional antibody, bispecific or oligospecific antibody, single chain antibody, scFV, diabody, sc(Fv)$_2$ (single chain (Fv)$_2$), and scFv-Fc). Furthermore, such an antibody may be covalently bound, or recombinantly fused with an enzyme, for example, alkaline phosphatase, horseradish peroxidase, or a galactosidase. An anti-GPR49/LGR5 antibody and a Sonic hedgehog (SHH) antibody used in the present invention may be bound to GPR49/LGR5 and Sonic hedgehog (SHH) proteins, respectively, regardless of the origin, kind, shape or the like thereof. Specifically, known antibodies such as a non-human animal antibody (e.g., a mouse antibody, a rat antibody, or a camel antibody), a human antibody, a chimeric antibody, and a humanized antibody can be used. In the present invention, a monoclonal or polyclonal antibody can be utilized as an antibody, and preferred is a monoclonal antibody. It is preferable that binding of an antibody to each protein of GPR49/LGR5, the factors of the Hedgehog pathway such as Sonic hedgehog (SHH), PTCH1, GLI1, and GLI2, and the factors of the Wnt pathway such as LRP6 and β-catenin is specific binding.

As used herein, an "antigen" refers to any substrate which can be specifically bound with an antibody molecule. As used herein, an "immunogen" refers to an antigen which can initiate lymphocyte activation that produces an antigen-specific immunological response. As used herein, an "epitope" or an "antigen determinant" refers to a site in an antigen molecule to which an antibody or a lymphocyte receptor binds. A method for determining an epitope is well-known in the art. When a primary sequence of a nucleic acid or an amino acid is provided, such an epitope can be determined by a person skilled in the art using the well-known conventional technique.

As used herein, "means" refers to any matter which can serve as any tool for attaining a certain object (e.g., detection, diagnosis, or treatment). Particularly, as used herein, "means which selectively recognizes" refers to means which can recognize a certain subject differently from others.

It is understood that, as an antibody used herein, an antibody of any specificity may be used as far as pseudo-positivity is decreased. Therefore, an antibody used in the present invention may be a polyclonal antibody, or may be a monoclonal antibody. As used herein, a "ligand" refers to a substance specifically binding to a certain protein. Examples of the ligand include lectin, an antigen, an antibody, a hormone, and a neurotransmitter which specifically bind to a variety of receptor protein molecules existing on a cell membrane.

The detection agent or the diagnostic agent or other pharmaceuticals or drugs of the present invention can take a form of a probe and a primer. The probe and the primer of the present invention can specifically hybridize with GPR49/LGR5, R-spondins, the factors of the Hedgehog pathway such as Sonic hedgehog (SHH), PTCH1, GLI1, and GLI2, and/or the factors of the Wnt pathway such as LRP6 and β-catenin. As used herein, expression of GPR49/LGR5, the factors of the Hedgehog pathway such as Sonic hedgehog (SHH), PTCH1, GLI1, and GLI2, and/or the factors of the Wnt pathway such as LRP6 and β-catenin is an index of the proliferation ability in a corneal endothelial cell, and is also useful as an index of the differentiated state. Therefore, the probe and the primer in accordance with the present invention can be used for identifying a cell having a high proliferation ability among corneal endothelial cells and/or the differentiation ability of a corneal endothelial cell. The probe and the primer of the present invention, in one embodiment, may detect expression of GPR49/LGR5, the factors of the Hedgehog pathway such as Sonic hedgehog (SHH), PTCH1, GLI1, and GLI2, and/or the factors of the Wnt pathway such as LRP6 and β-catenin, and refer to a polymer formed of a plurality of nucleotides or nucleotide pairs such as deoxyribonucleic acids (DNAs) or ribonucleic acids (RNAs). It is known that a double-stranded cDNA can also be utilized in tissue in situ hybridization, and the probe and the primer of the present invention also include such a double-stranded cDNA. Examples of the probe and the primer particularly preferable in detection of RNA in a tissue include an RNA probe (riboprobe).

As used herein, a "(nucleic acid) primer" refers to a substance necessary for initiation of a reaction of a polymer compound to be synthesized, in a polymer synthesizing enzyme reaction. In a reaction of synthesizing a nucleic acid molecule, a nucleic acid molecule (e.g., DNA or RNA) complementary to a part of a sequence of a polymer compound to be synthesized can be used. As used herein, a primer can be used as a marker detection means.

Examples of a nucleic acid molecule which is usually used as a primer include molecules having a nucleic acid sequence having a length of at least 8 consecutive nucleotides, which is complementary to a nucleic acid sequence of an objective gene. Such a nucleic acid sequence can be preferably a nucleic acid sequence of a length of at least 9 consecutive nucleotides, more preferably a length of at least 10 consecutive nucleotides, further preferably a length of at least 11 consecutive nucleotides, a length of at least 12 consecutive nucleotides, a length of at least 13 consecutive nucleotides, a length of at least 14 consecutive nucleotides, a length of at least 15 consecutive nucleotides, a length of at least 16 consecutive nucleotides, a length of at least 17 consecutive nucleotides, a length of at least 18 consecutive nucleotides, a length of at least 19 consecutive nucleotides, a length of at least 20 consecutive nucleotides, a length of at least 25 consecutive nucleotides, a length of at least 30 consecutive nucleotides, a length of at least 40 consecutive nucleotides, or a length of at least 50 consecutive nucleotides. A nucleic acid sequence used as a probe includes a nucleic acid sequence which is at least 70% homologous, more preferably at least 80% homologous, further preferably at least 90% homologous, or at least 95% homologous to the aforementioned sequences. A sequence appropriate as a primer can vary depending on the nature of a sequence which is intended to be synthesized (amplified), and a person skilled in the art can appropriately design a primer depending on the intended sequence. Design of such a primer is well-known in the art, and may be performed manually, or may be performed using a computer program (e.g., LASERGENE, PrimerSelect, or DNAStar).

The primer in accordance with the present invention can also be used as a primer set consisting of two or more of the primers.

The primer and the primer set in accordance with the present invention can be utilized as a primer and a primer set according to a conventional method, in a known method for detecting an objective gene utilizing a nucleic acid amplification method such as a PCR method, an RT-PCR method, a real time PCR method, an in situ PCR method, or a LAMP method.

The primer set in accordance with the present invention can be selected so that a nucleotide sequence of an objective protein such as GPR49/LGR5, R-spondins, the factors of the Hedgehog pathway such as Sonic hedgehog (SHH), PTCH1, GLI1, and GLI2, and/or the factors of the Wnt pathway such as LRP6 and β-catenin can be amplified by a nucleic acid amplification method such as a PCR method. The nucleic acid amplification method is well-known, and selection of a primer pair in the nucleic acid amplification method is obvious to a person skilled in the art. For example, in a PCR method, primers can be selected so that one of the two primers (primer pair) pairs with a plus chain of double-stranded DNA of an objective protein such as GPR49/LGR5, R-spondins, the factors of the Hedgehog pathway such as SHH, PTCH1, GLI1, and GLI2, and/or the factors of the Wnt pathway such as LRP6 and β-catenin, the other primer pairs with a minus chain of the double-stranded DNA, and the latter primer pairs with an extended chain which is extended by the former primer. In addition, in a LAMP method (WO 00/28082), three regions of F3c, F2c and F1c from the 3' terminal side, and three regions of B1, B2 and B3 from the 5' terminal side are defined, respectively, for a target gene, and these six regions can be used to design four kinds of primers. The primer of the present invention can be chemically synthesized based on nucleotide sequences disclosed herein. Preparation of the primer is well-known, and can be performed according to, for example, "Molecular Cloning, A Laboratory Manual $2^{nd}$ ed." (Cold Spring Harbor Press (1989)), "Current Protocols in Molecular Biology" (John Wiley & Sons (1987-1997)).

As used herein, a "probe" refers to a substance being means for retrieval, which is used in a biological experiment such as in vitro and/or in vivo screening. Examples thereof include, but are not limited to a nucleic acid molecule comprising a specified nucleotide sequence or a peptide comprising a specified amino acid sequence, a specific antibody or a fragment thereof. As used herein, the probe can also be used as a marker detection means.

Examples of a nucleic acid molecule which is usually used as a probe include a nucleic acid molecule having a nucleic acid sequence of a length of at least 8 consecutive nucleotides, which is homologous or complementary to a nucleic acid sequence of an objective gene. Such a nucleic acid sequence can be preferably a nucleic acid sequence of a length of at least 9 consecutive nucleotides, more preferably a length of at least 10 consecutive nucleotides, further preferably a length of at least 11 consecutive nucleotides, a length of at least 12 consecutive nucleotides, a length of at least 13 consecutive nucleotides, a length of at least 14 consecutive nucleotides, a length of at least 15 consecutive nucleotides, a length of at least 20 consecutive nucleotides, a length of at least 25 consecutive nucleotides, a length of at least 30 consecutive nucleotides, a length of at least 40 consecutive nucleotides, or a length of at least 50 consecutive nucleotides. A nucleic acid sequence used as a probe includes a nucleic acid sequence which is at least 70% homologous, more preferably at least 80% homologous, further preferably at least 90% homologous, or at least 95% homologous to the aforementioned sequences.

In one embodiment, the detection agent of the present invention can be labeled. Alternatively, the detection agent of the present invention may be an agent bound to a tag.

As used herein, a "label" refers to an entity (e.g., substance, energy, or electromagnetic wave) for identifying an objective molecule or substance from others. Examples of such a labeling method include an RI (radioisotope) method, a fluorescence method, a biotin method, and a chemiluminescence method. When a plurality of markers of the present invention, or agents or means for capturing them is labeled by a fluorescence method, labeling is performed with fluorescent substances having different fluorescence maximum wavelengths. A difference in the fluorescence maximum wavelength is preferably 10 nm or more. When a ligand is labeled, any label can be used as far as it does not influence on the function, and as a fluorescent substance, Alexa™ Fluor is desirable. Alexa™ Fluor is a water-soluble fluorescent dye obtained by modifying coumarin, rhodamine, fluorescein, cyanine or the like, is a series in response to a wide range of fluorescent wavelengths, and is very stable, bright, and low in pH sensitivity as compared with other fluorescent dyes of the corresponding wavelengths. Examples of a combination of fluorescent dyes having a fluorescent maximum wavelength of 10 nm or longer include a combination of Alexa™ 555 and Alexa™ 633 and a combination of Alexa™ 488 and Alexa™ 555. When a nucleic acid is labeled, any label can be used as far as it can bind to a base portion thereof, and it is preferable that a cyanine dye (e.g., Cy3 and Cy5 of CyDye™ series), a rhodamine 6G reagent, 2-acetylaminofluorene (AAF), AAIF (iodine derivative of AAF) or the like is used. Examples of the fluorescent substances having a difference in the fluorescence maximum wavelength of 10 nm or more include a combination of Cy5 and a rhodamine 6G reagent, a combination of Cy3 and fluorescein, and a combination of a rhodamine 6G reagent and fluorescein. In the present invention, such a label can be utilized to alter an objective subject so that it can be detected with a detection means to be used. Such an alteration is known in the art, and a person skilled in the art can appropriately carry out such a method in accordance with a label and an objective subject.

As used herein, a "tag" refers to a substance for selecting a molecule by a specific recognizing mechanism such as receptor-ligand, more specifically, a substance which plays a role of a binding partner for binding to a specified substance (e.g., a substance having a relationship such as biotin-avidin or biotin-streptavidin), and can be included in the category of "label". Hence, for example, a specified substance with a tag bound thereto can be selected by contacting the substance with a substrate with a binding partner of a tag sequence bound thereto. Such a tag or label is well-known in the art. Representative tag sequences include a myc tag, a His tag, HA, and an Avi, but are not limited to them. The marker or the marker detection agent of the present invention may be bound to such a tag.

In one aspect, the present invention provides a method for using GPR49/LGR5, and/or the factors of the Hedgehog pathway such as Sonic hedgehog (SHH), PTCH1, GLI1, and GLI2, and/or the factors of the Wnt pathway such as LRP6 and β-catenin as an index for identifying a cell having a high proliferation ability among corneal endothelial cells and/or the differentiation ability of a corneal endothelial cell, or a method for detecting or diagnosing a cell having a high proliferation ability among corneal endothelial cells and/or the differentiation ability of a corneal endothelial cell.

The method of the present invention can be implemented by performing, for example, a step of detecting GPR49/LGR5, and/or the factors of the Hedgehog pathway such as SHH, PTCH1, GLI1, and GLI2, and/or the factors of the Wnt pathway such as LRP6 and β-catenin, or genes of these factors in a living body, for using GPR49/LGR5, and/or the factors of the Hedgehog pathway such as SHH, PTCH1, GLI1, and GLI2, and/or the factors of the Wnt pathway such as LRP6 and β-catenin as an index for identifying a cell having a high proliferation ability among corneal endothelial cells and/or the differentiation ability of a corneal endothelial cell. For example, in such a case, a detection agent comprising a substance binding to GPR49/LGR5, and/or the factors of the Hedgehog pathway such as Sonic hedgehog (SHH), PTCH1, GLI1, and GLI2, and/or the factors of the Wnt pathway such as LRP6 and β-catenin, or genes of these factors can be used. Such a detection agent is described herein, and it is understood that a person skilled in the art can implement the method of the present invention based on the description.

In the method of the present invention, the detection agent or the diagnostic agent of the present invention is contacted with an objective sample, and whether there are GPR49/LGR5, and/or the factors of the Hedgehog pathway such as Sonic hedgehog (SHH), PTCH1, GLI1, and GLI2, and/or the factors of the Wnt pathway such as LRP6 and β-catenin, or genes of these factors, being an objective subject, in the sample is determined, or the level or amount thereof is measured.

"Contact (contacted)", as used herein, means that a substance is made to physically approach a polypeptide or a polynucleotide which can function as the marker, the detection agent, the diagnostic, the ligand or the like of the present invention, either directly or indirectly. The polypeptide or the polynucleotide can be made to exist in many buffers, salts, solutions or the like. Contact includes placing a compound on, for example, a beaker, a microtiter plate, a cell culturing flask or a microarray (e.g., gene chip), containing a polypeptide encoding a nucleic acid molecule or a fragment thereof.

In one embodiment, a cell having a high proliferation ability which is a subject in the method of the present invention is an undifferentiated cell.

In another embodiment, a cell having a high proliferation ability which is a subject in the method of the present invention is a stem cell.

In another aspect, a corneal endothelial cell which is a subject in the method of the present invention is a human cell.

In still another embodiment, the proliferation ability of a corneal endothelial cell which is a subject in the method of the present invention is identified by a characteristic selected from the group consisting of colony forming ability, Ki-67 positivity and BrdU positivity.

In one embodiment of the present invention, diagnosis regarding the differentiated state can be performed, based on the method which is an index of the present invention.

A specific method for detecting expression of GPR49/LGR5, and/or the factors of the Hedgehog pathway such as SHH, PTCH1, GLI1, and GLI2, and/or the factors of the Wnt pathway such as LRP6 and β-catenin, or genes of these factors is not particularly limited, as far as it is a method which can detect expression of GPR49/LGR5, and/or the factors of the Hedgehog pathway such as SHH, PTCH1, GLI1, and GLI2, and/or the factors of the Wnt pathway such as LRP6 and β-catenin, or genes of these factors, in a test sample (e.g., cell), and includes a hybridization method, a nucleic acid amplification method, and an antigen-antibody reaction method.

Herein, a "test sample" may be a sample that is a corneal endothelial cell or an objective cell, or a substance derived therefrom, which is thought to contain a matter that enables gene expression. For example, a cell which is directly isolated from the corneal endothelium can be used. A cell of the corneal endothelium can be obtained by a known method (Koizumi N, Okumura N, Kinoshita S., Experimental Eye Research. 2012; 95: 60-7.). Preferably, a cell obtained from a donor of the corneal endothelium, a corneal endothelial cell or the like can be used as a test cell sample. Alternatively, a cultured cell containing a corneal endothelial cell which was differentiation-induced in vitro can be used as a sample. In vitro differentiation induction into a corneal endothelial cell can be implemented by performing differentiation treatment using a known cell such as an ES cell, an iPS cell, and a bone marrow parenchymal cell as a starting material by a known method, for example, an AMED method <see Ueno M, Matsumura M, Watanabe K, Nakamura T, Osakada F, Takahashi M, Kawasaki H, Kinoshita S, Sasai Y; Proc Natl Acad Sci USA. 103 (25): 9554-9559, 2006.>.

According to one embodiment of detection in accordance with the present invention, expression of GPR49/LGR5 in a cell sample can be detected by hybridizing the probe in accordance with the present invention with a nucleic acid sample (mRNA or a transcription product thereof), and directly or indirectly detecting a hybridization complex, that is, a double-stranded nucleotide. Regarding a detailed procedure of a hybridization method, see "Molecular Cloning, A Laboratory Manual $2^{nd}$ ed." (Cold Spring Harbor Press (1989), particularly Section 9.47-9.58), "Current Protocols in Molecular Biology" (John Wiley & Sons (1987-1997), particularly Section 6.3-6.4), and "DNA Cloning 1: Core Techniques, A Practical Approach $2^{nd}$ ed." (Oxford University (1995), regarding the condition, see particularly section 2.10).

Detection of expression of GPR49/LGR5, and/or the factors of the Hedgehog pathway such as SHH, PTCH1, GLI1, and GLI2, and/or the factors of the Wnt pathway such as LRP6 and β-catenin, or genes of these factors utilizing a hybridization method can be implemented by, for example, (a) a step of contacting a polynucleotide derived from a test sample with the probe in accordance with the present invention; and (b) a step of detecting a hybridization complex. In the step (a), mRNA prepared from an objective test sample or complementary DNA (cDNA) transcribed from the mRNA as a polynucleotide derived from a test cell sample can be contacted with the probe. In a detection method using a probe, the probe can be labeled before use. Examples of the label include labels utilizing radioactivity (e.g., $^{32}P$, $^{14}C$, and $^{35}S$), fluorescence (e.g., FITC and europium), or an enzyme reaction such as chemiluminescence (e.g., peroxidase and alkaline phosphatase). Detection of a hybridization product can be performed using a well-known method such as Northern hybridization, Southern hybridization, or colony hybridization. Since a cell from which a hybridization complex was detected is a cell expressing GPR49/LGR5, and/or the factors of the Hedgehog pathway such as SHH, PTCH1, GLI1, and GLI2, and/or the factors of the Wnt pathway such as LRP6 and β-catenin, the cell can be determined to have a high proliferation ability (an undifferentiated cell, a precursor cell or a stem cell) and/or a high differentiation ability.

According to another embodiment of detection in accordance with the present invention, expression of GPR49/LGR5, and/or the factors of the Hedgehog pathway such as SHE, PTCH1, GLI1, and GLI2, and/or the factors of the Wnt pathway such as LRP6 and β-catenin, or genes of these factors in a sample can be detected by amplifying a nucleic acid sample (mRNA or a transcription product thereof) by a nucleic acid amplification method using the primer or the primer set in accordance with the present invention, and detecting the amplification product.

Detection of expression of GPR49/LGR5, and/or the factors of the Hedgehog pathway such as SHH, PTCH1, GLI1, and GLI2, and/or the factors of the Wnt pathway such as LRP6 and β-catenin, or genes of these factors utilizing a nucleic acid amplification method can be implemented, for example, by (i) a step of implementing a nucleic acid amplification method using the primer or the primer set in accordance with the present invention and employing a polynucleotide derived from a test sample as a template; and (ii) a step of detecting the formed amplification product.

In the step (i), mRNA prepared from an objective test sample or complementary DNA (cDNA) transcribed from the mRNA can be used as a template. Detection of an amplification product can be implemented using a nucleic acid amplification method such as a PCR method, an RT-PCR method, a real time PCR method, or a LAMP method. Since a cell from which an amplification product is detected is a cell expressing GPR49/LGR5, the cell can be determined to have a high proliferation ability (an undifferentiated cell, a precursor cell or a stem cell) and/or a high differentiation ability.

According to another embodiment of detection in accordance with the present invention, expression of GPR49/LGR5, and/or the factors of the Hedgehog pathway such as SHH, PTCH1, GLI1, and GLI2, and/or the factors of the Wnt pathway such as LRP6 and β-catenin in a sample can be detected by contacting the antibody in accordance with the present invention with a sample, and detecting an antigen-antibody reaction.

Detection of expression of GPR49/LGR5, and/or the factors of the Hedgehog pathway such as SHH, PTCH1, GLI1, and GLI2, and/or the factors of the Wnt pathway such as LRP6 and β-catenin utilizing an antigen-antibody reaction can be implemented, for example, by the following steps: (I) a step of contacting a protein derived from a test cell sample with the antibody in accordance with the present invention; and (II) a step of measuring an antigen-antibody complex. A method for detecting an antigen-antibody reaction is well-known to a person skilled in the art, and for example, GPR49/LGR5 protein, and/or the factors of the Hedgehog pathway such as SHH, PTCH1, GLI1, and GLI2, and/or the factors of the Wnt pathway such as LRP6 and β-catenin in a test cell sample which is thought to contain a corneal endothelial cell can be detected by an immunological method. As the immunological method, concerning a sample obtained by, if necessary, subjecting a cell sample to an appropriate treatment, for example, separation of a cell or an extraction operation, a known method such as an immunohistological staining method, an enzyme immunometric assay, a Western blotting method, an agglutination method, a competition method, or a sandwich method can be applied. The immunohistological staining method can be performed, for example, by a direct method using a labeled antibody, an indirect method using a labeled antibody to the above antibody, or the like. As a labeling agent, a known labeling substance such as a fluorescent substance, a radioactive substance, an enzyme, a metal, or a dye can be used.

Since a cell from which an antigen-antibody complex is detected is a cell expressing GPR49/LGR5, and/or the factors of the Hedgehog pathway such as SHH, PTCH1, GLI1, and GLI2, and/or the factors of the Wnt pathway such as LRP6 and β-catenin, the cell can be determined to have a high proliferation ability (an undifferentiated cell, a precursor cell or a stem cell) and/or a high differentiation ability. For use in treatment of a disease requiring transplantation of the corneal endothelium, for example, bullous keratopathy, corneal edema, leukoma corneae, particularly, corneal dystrophy, and a corneal endothelial disorder caused by trauma or internal eye operation, or other specified corneal endothelial diseases (Fuchs endothelial corneal dystrophy, back polymorphic endothelial corneal dystrophy etc.), it is desirable that a cell having a high proliferation ability (an undifferentiated cell, a precursor cell or a stem cell) has a high purity.

By performing the above-mentioned respective detection steps not only once, but also by repeating or combining the same steps, the precision of detection or selection of a cell having a high proliferation ability/differentiation ability can be enhanced. Therefore, when such an embodiment is adopted, according to the detection method in accordance with the present invention, a cell having a high proliferation ability/differentiation ability can be detected or selected more precisely, by performing the above-mentioned steps two or more times.

In addition, the precision of detection or selection of a cell having a high proliferation ability/differentiation ability can be enhanced by concurrently using another marker gene, preferably, a proliferation marker gene (e.g., Ki-67 and BrdU) other than genes encoding GPR49/LGR5, and/or the factors of the Hedgehog pathway such as SHH, PTCH1, GLI1, and GLI2, and/or the factors of the Wnt pathway such as LRP6 and β-catenin, or these factors.

As used herein, "diagnosis" refers to determination of the current status or the future of a disease, a disorder or a condition in a subject by identifying a variety of parameters associated with such a disease, disorder or condition. By using the method, the apparatus or the system of the present invention, the state in a body can be examined, and such information can be used to select a variety of parameters such as a disease, a disorder, or a condition in a subject, and a formulation or a method for treatment or prevention to be administered. As used herein, in a narrow sense, the "diagnosis" refers to diagnosis of the current status, and in a broad sense, it includes "early diagnosis", "presumptive diagnosis", and "advance diagnosis". Since the diagnosis method of the present invention, in principle, can utilize what has moved out of a body, and can be implemented independently of healthcare professionals such as a doctor, it is industrially useful. As used herein, in order to make clear that the diagnosis method can be implemented independently of healthcare professionals such as a doctor, particularly, "presumptive diagnosis, advance diagnosis or diagnosis" may be named as "assistance".

A procedure of formulating a diagnostic agent or the like of the present invention as a pharmaceutical or the like is known in the art, and is described, for example, in Japanese Pharmacopoeia, U.S. Pharmacopoeia, and other countries' Pharmacopoeias. Therefore, a person skilled in the art can determine the amount of the diagnostic agent to be used with the descriptions described herein without performing undue experiments.

An antibody used in the present invention can be produced as follows.

An antibody used in the present invention (e.g., anti-GPR49/LGR5 antibody, an antibody to the factors of the Hedgehog pathway such as SHH, PTCH1, GLI1, and GLI2, and an antibody to the factors of the Wnt pathway such as LRP6 and β-catenin) can be obtained as a polyclonal or monoclonal antibody using known means. As an antibody used in the present invention, particularly, a monoclonal antibody derived from a mammal is preferable. Monoclonal antibodies derived from a mammal include a monoclonal antibody produced by a hybridoma, and a monoclonal antibody produced by a host transformed with an expression vector comprising an antibody gene by a genetic engineering procedure.

As one example, a method for preparing a monoclonal antibody will be described below. The monoclonal antibody can be prepared by preparing a hybridoma by cell fusion between an antibody producing cell obtained from an animal immunized with an antigen and a myeloma cell, and selecting a clone producing an antibody which specifically inhibits the activity of GPR49/LGR5, R-spondins, the factors of the Hedgehog pathway such as SHH, PTCH1, GLI1, and GLI2, and/or the factors of the Wnt pathway such as LRP6 and β-catenin from the resulting hybridoma.

The whole of an amino acid sequence of a protein such as a mature protein, such as GPR49/LGR5, R-spondins, the factors of the Hedgehog pathway such as SHH, PTCH1, GLI1, and GLI2, and/or the factors of the Wnt pathway such as LRP6 and β-catenin used as an antigen in immunization of an animal, or a fragment thereof having immunogenicity can be used as an immunogen. In addition, it is preferable to use a peptide consisting of any 10 or more in an amino acid sequence of a protein of the marker of the present invention as an antigen, as a monoclonal antibody for specifically detecting a protein existing on a cell surface. Concerning any of the other factors of the present invention (e.g., GPR49/LGR5, R-spondins, the factors of the Hedgehog pathway such as SHH, PTCH1, GLI1, and GLI2, and/or the factors of the Wnt pathway such as LRP6 and β-catenin as well as proteins corresponding to them), an antigen can be designed similarly.

After binding to the resulting GPR49/LGR5, R-spondins, the factors of the Hedgehog pathway such as SHH, PTCH1, GLI1, and GLI2, and/or the factors of the Wnt pathway such as LRP6 and β-catenin for an antigen, an adjuvant is added. The adjuvant includes a Freund complete adjuvant and a Freund incomplete adjuvant, and any of them may be mixed.

The antigen obtained as described above is administered to a mammal, for example, a mouse, a rat, a horse, a monkey, a rabbit, a goat, or sheep. Any method can be used for immunization as far as it is an existing method, and immunization is mainly performed by intravenous injection, subcutaneous injection, intraperitoneal injection or the like. In addition, an interval of immunization is not particularly limited, and immunization is performed at an interval of a few days to a few weeks, preferably at an interval of 4 to 21 days.

After 2 to 3 days from the day of last immunization, an antibody producing cell is collected. Examples of the antibody producing cell include a spleen cell, a lymph node cell, and a peripheral blood cell, and a spleen cell is generally used. As the immunization amount of an antigen, for example, 100 μg of an antigen is used once per mouse.

A monoclonal antibody producing hybridoma can be basically produced as follows using a known technique. First, an objective protein (e.g., a protein such as GPR49/LGR5, the factors of the Hedgehog pathway such as SHH, PTCH1, GLI1, and GLI2, and/or the factors of the Wnt pathway such as LRP6 and β-catenin) as a sensitizing antigen is immunized according to a normal immunization method. An immune cell obtained from an immunized animal is fused with a known parent cell by a normal cell fusion method to obtain a hybridoma. Further, by screening a cell producing an objective antibody from this hybridoma by a normal screening method, a hybridoma producing an objective antibody can be selected.

Specifically, production of the monoclonal antibody is performed, for example, as shown below. First, by expressing an objective gene (a GPR49/LGR5 gene, the factors of the Hedgehog pathway such as SHH, PTCH1, GLI1, and GLI2, and/or the factors of the Wnt pathway such as LRP6 and β-catenin), an objective protein used as a sensitizing antigen for obtaining an antibody can be obtained. A nucleotide sequence of the objective gene is described in other places of the present description (e.g., disclosed in NCBI registration number NM_003667.2 (SEQ ID No.: 1) and NM_000193 (SEQ ID No.: 11)). That is, after a gene sequence encoding the objective gene is inserted into a known expression vector to transform an appropriate host cell, an objective protein can be purified from the host cell or the culture supernatant by a known method. Alternatively, a purified natural protein can also be used similarly. Alternatively, as used in the present invention, a fusion protein obtained by fusing a desired partial polypeptide of an objective protein with a different polypeptide can also be utilized as an immunogen. In order to produce the fusion protein as an immunogen, for example, a Fc fragment of an antibody or a peptide tag can be utilized. A vector expressing the fusion protein can be produced by fusing genes encoding desired two or more kinds of polypeptide fragments in frame, and inserting the fused gene in an expression vector. A method of producing the fusion protein is described in Molecular Cloning 2nd ed. (Sambrook, J et al., Molecular Cloning 2nd ed., 9.47-9.58, Cold Spring Harbor Lab. press, 1989).

The thus purified objective protein (e.g., a protein such as GPR49/LGR5, the factors of the Hedgehog pathway such as SHH, PTCH1, GLI1, and GLI2, and/or the factors of the Wnt pathway such as LRP6 and β-catenin) can be used as a sensitizing antigen used in immunization of a mammal. A partial peptide of an objective protein can also be used as a sensitizing antigen. For example, the following peptides can be used as a sensitizing antigen: a peptide obtained by chemical synthesis based on an amino acid sequence of an objective protein (a protein such as human GPR49/LGR5, the factors of the Hedgehog pathway such as SHH, PTCH1, GLI1, and GLI2, and/or the factors of the Wnt pathway such as LRP6 and β-catenin); a peptide obtained by incorporating a part of an objective gene (a gene encoding human GPR49/LGR5, the factors of the Hedgehog pathway such as SHH, PTCH1, GLI1, and GLI2, and/or the factors of the Wnt pathway such as LRP6 and β-catenin) into an expression vector to express the gene; and a peptide obtained by degrading an objective protein (a protein such as human GPR49/LGR5, the factors of the Hedgehog pathway such as SHH, PTCH1, GLI1, and GLT2, and/or the factors of the Wnt pathway such as LRP6 and β-catenin) with a protease.

The region and size of a protein used as a partial peptide are not limited. As an example of the region, in the case of GPR49/LGR5, a region can be selected from an amino acid sequence constituting an extracellular domain of GPR49/LGR5 ($1$-$556^{th}$, $615$-$637^{th}$, $704$-$722^{nd}$, and $792$-$800^{th}$ amino acids in an amino acid sequence of SEQ ID No.: 2). It is preferable that the number of amino acids constituting a peptide used as a sensitizing antigen is at least 3, for example, 5 or more, or 6 or more. More specifically, a peptide of 8 to 50, preferably 10 to 30 residues can be used as a sensitizing antigen. Also in the case of the factors of the Hedgehog pathway such as SHH, PTCH1, GLI1, and GLI2, and/or the factors of the Wnt pathway such as LRP6 and β-catenin, an appropriate peptide can be used as a sensitizing antigen similarly based on information such as sequences described herein, for example, SEQ ID Nos.: 12, 44, 46, 48, 50, and 52.

A mammal to be immunized with the sensitizing antigen is not particularly limited. In order to obtain the monoclonal antibody by a cell fusion method, it is preferable to select an immune animal in view of compatibility with a parent cell to be used in cell fusion. Generally, rodent animals are preferable as an immune animal. Specifically, a mouse, a rat, a hamster or a rabbit can be used as an immune animal. In addition, a monkey and the like can also be used as an immune animal.

The animals can be immunized with a sensitizing antigen according to a known method. For example, as a general method, a mammal can be immunized by injecting a sensitizing antigen intraperitoneally or subcutaneously. Specifically, the sensitizing antigen is administered to a mammal several times every 4 to 21 days. The sensitizing antigen is diluted with PBS (Phosphate-Buffered Saline) or physiological saline at an appropriate dilution rate, and is used in immunization. Furthermore, the sensitizing antigen can be administered together with an adjuvant. For example, the sensitizing antigen can be mixed with a Freund complete adjuvant, and emulsified to obtain a sensitizing antigen. In addition, in immunization with the sensitizing antigen, an appropriate carrier can be used. Particularly, when a partial peptide having a small molecular weight is used as the sensitizing antigen, it is desirable to bind the sensitizing antigen peptide with a carrier protein such as albumin or keyhole limpet hemocyanin to perform immunization.

In addition, the monoclonal antibody can also be obtained by DNA immunization. DNA immunization is a method for imparting immune stimulation by administering vector DNA constructed in such a form that a gene encoding an antigenic protein can be expressed in an immune animal to the immune animal, and expressing an immunizing antigen in a living body of the immune animal. In order to obtain the monoclonal antibody of the present invention by DNA immunization, first, DNA expressing an objective protein (e.g., GPR49/LGR5, and/or the factors of the Hedgehog pathway such as SHH, PTCH1, GLI1, and GLI2, and/or the factors of the Wnt pathway such as LRP6 and β-catenin) is administered to the immune animal. DNA encoding an objective protein (e.g., GPR49/LGR5, the factors of the Hedgehog pathway such as SHH, PTCH1, GLI1, and GLI2, and/or the factors of the Wnt pathway such as LRP6 and β-catenin) can be synthesized by a known method such as PCR. The resulting DNA is inserted into an appropriate expression vector, and is administered to the immune animal. As the expression vector, for example, a commercially available expression vector such as pcDNA3.1 can be utilized. As a method of administering the vector to a living body, a generally used method can be utilized. For example, by shooting gold particles with an expression vector adsorbed thereon into a cell with a gene gun, DNA immunization can be performed.

After a mammal is immunized in this way, and an increase in the amount of the desired antibody in serum is confirmed, an immune cell is collected from the mammal, and is subjected to cell fusion. As a preferable immune cell, particularly, a spleen cell can be used.

As a cell to be fused with the immune cell, a myeloma cell of a mammal is used. It is preferable that the myeloma cell has an appropriate selection marker for screening. The selection marker refers to a character that a cell can survive (or cannot survive) under specified culturing conditions. As the selection marker, hypoxanthine-guanine-phosphoribosyl transferase deficiency (hereinafter, abbreviated as HGPRT deficiency) or thymidine kinase deficiency (hereinafter, abbreviated as TK deficiency) is known. A cell having deficiency of HGPRT or TK has hypoxanthine-aminopterin-thymidine sensitivity (hereinafter, abbreviated as HAT sensitivity). A HAT-sensitive cell cannot synthesize DNA in a HAT selective medium, and dies. However, when the cell is fused with a normal cell, it comes to be able to proliferate even in the HAT selective medium since the cell can continue synthesis of DNA utilizing a salvage circuit of a normal cell.

A HGPRT-deficient or TK-deficient cell can be selected in a medium containing 6-thioguanine, 8-azaguanine (hereinafter, abbreviated as 8AG), or 5'-bromodeoxyuridine. Since a normal cell takes these pyrimidine analogs into DNA, it dies. However, a cell deficient in these enzymes cannot take in these pyrimidine analogs, it can survive in a selective medium. In addition, a selection marker called G418 resistance imparts resistance to a 2-deoxystreptamine antibiotic (gentamycin analog) by a neomycin resistance gene. A variety of myeloma cells suitable for cell fusion are known. Basically, cell fusion between an immune cell and a myeloma cell is performed in accordance with a known method, for example, Koehler C. and Milstein C., Methods Enzymol. (1981) 73, 3-46. More specifically, for example, cell fusion can be carried out in a normal nutrient culture solution in the presence of a cell fusion promoter. As the fusion promoter, for example, polyethylene glycol (PEG) or a sendaivirus (HVJ) can be employed. Further, in order to enhance the fusion efficiency, an assistant such as dimethyl sulfoxide can be optionally added. The use ratio between an immune cell and a myeloma cell can be arbitrarily set. For example, it is preferable that 1 to times of the immune cells are used relative to the myeloma cells. As a culture solution used in cell fusion, for example, an RPMI1640 culture, solution suitable for proliferation of a myeloma cell strain, an MEM culture solution, and a normal culture solution used in this kind of cell culturing can be utilized. Further, a serum replenisher solution such as fetal calf serum (FCS) can be utilized.

In cell fusion, by mixing predetermined amounts of the immune cell and the myeloma cell in a culture solution well, and mixing a PEG solution which has been warmed to around 37° C. in advance, an objective fused cell (hybridoma) is formed. In a cell fusion method, for example, PEG having an average molecular weight of around 1000 to 6000 can be added usually in a concentration of 30% (w/v) to 60% (w/v). Subsequently, by repeating an operation of sequentially adding suitable culture solutions listed above, and centrifuging the resultant to remove the supernatant, a cell fusion agent and the like which are not preferable for the growth of a hybridoma are removed.

The thus obtained hybridoma can be selected by utilizing a selection culture solution appropriate for a selection marker possessed by a myeloma used in cell fusion. For example, a cell having deficiency of HGPRT or TK can be selected by culturing in a HAT culture solution (a culture solution containing hypoxanthine, aminopterin and thymidine). That is, when a HAT-sensitive myeloma cell is used in cell fusion, a cell succeeded in fusion with a normal cell can be selectively proliferated in a HAT culture solution. Culturing using the HAT culture solution is continued for a period sufficient for a cell other than an objective hybridoma (non-fused cell) to die. Specifically, generally, the objective hybridoma can be selected by culturing for a few days to a few weeks. Then, by performing a normal limiting dilution method, screening and single cloning of a hybridoma producing an objective antibody can be performed. Alternatively, an antibody recognizing an objective protein (e.g., GPR49/LGR5, the factors of the Hedgehog pathway such as SHH, PTCH1, GLI1, and GLI2, and/or the factors of the Wnt pathway such as LRP6 and β-catenin) can be produced by the method described in International Publication WO 03/104453.

Screening and single cloning of an objective antibody can be appropriately performed by a screening method based on a known antigen-antibody reaction. For example, an antigen is bound to a carrier such as beads made of polystyrene or the like, or a commercially available 96-well microtiter plate, and the resultant is reacted with the culture supernatant of a hybridoma. Then, after the carrier is washed, the carrier is reacted with a secondary antibody or the like labeled with an enzyme. When an objective antibody reacting with a sensitizing antigen is contained in the culture supernatant, the secondary antibody binds to the carrier via this antibody. By finally detecting the secondary antibody binding to the carrier, whether the objective antibody exists in the culture supernatant or not can be determined. It becomes possible to clone a hybridoma producing a desired antibody having an ability to bind to an antigen by a limiting dilution method or the like. In this case, as an antigen, a protein such as GPR49/LGR5, the factors of the Hedgehog pathway such as SHH, PTCH1, GLI1, and GLI2, and/or the factors of the Wnt pathway such as LRP6 and β-catenin, which is substantially of the same nature, including those used in immunization can be preferably used. For example, a cell strain expressing an objective protein (e.g., GPR49/LGR5, the factors of the Hedgehog pathway such as SHH, PTCH1, GLI1, and GLI2, and/or the factors of the Wnt pathway such as LRP6 and β-catenin), an extracellular domain of an objective protein (e.g., GPR49/LGR5, the factors of the Hedgehog pathway such as SHH, PTCH1, GLI1, and GLI2, and/or the factors of the Wnt pathway such as LRP6 and β-catenin), or an oligopeptide consisting of a partial amino acid sequence constituting the region can be utilized as an antigen.

In addition, an objective antibody can also be obtained by antigen-sensitizing a human lymphocyte, in addition to a method of obtaining the hybridoma by immunizing an animal other than human with an antigen. Specifically, first, a human lymphocyte is in vitro sensitized with a protein such as GPR49/LGR5, the factors of the Hedgehog pathway such as SHH, PTCH1, GLI1, and GLI2, and/or the factors of the Wnt pathway such as LRP6 and β-catenin. Then, an immunized lymphocyte is fused with an appropriate fusion partner. As the fusion partner, for example, a myeloma cell which is derived from human and has a permanent division potential can be utilized (see JP-H01-59878 B (Kokoku)). An anti-GPR49/LGR5 antibody obtained by this method is a human antibody having an activity of binding to a GPR49/LGR5 protein. This also applies to the factors of the Hedgehog pathway such as SHH, Ptch1, Gli1, and Gli2, and/or the factors of the Wnt pathway such as LRP6 and β-catenin.

Further, by administering an objective protein (e.g., a protein such as GPR49/LGR5, the factors of the Hedgehog pathway such as SHH, PTCH1, GLI1, and GLI2, and/or the factors of the Wnt pathway such as LRP6 and (β-catenin) which is to be an antigen to a transgenic animal having the whole repertory of a human antibody gene, or immunizing the animal with DNA which was constructed so as to express an objective protein (e.g., GPR49/LGR5) in the animal, a human antibody to an objective protein (e.g., GPR49/LGR5, the factors of the Hedgehog pathway such as SHH, PTCH1, GLI1, and GLI2, and/or the factors of the Wnt pathway such as LRP6 and β-catenin) can be obtained. An antibody producing cell of an immune animal can be immortalized by cell fusion with an appropriate fusion partner or treatment such as infection with an Epstein-Barr virus. From the thus obtained immortalized cell, a human antibody to an objective protein (e.g., GPR49/LGR5, the factors of the Hedgehog pathway such as SHH, PTCH1, GLI1, and/or the factors of the Wnt pathway such as LRP6 and β-catenin) can be isolated (see International Publications WO 94/25585, WO 93/12227, WO 92/03918, and WO 94/02602). Further, by cloning the immortalized cell, a cell producing an antibody having objective reaction specificity can be cloned. When a transgenic animal is an immune animal, an immune system of the animal recognizes an object human protein (e.g., human GPR49/LGR5) as a foreign substance. Therefore, a human antibody to an objective human protein (e.g., human GPR49/LGR5, the factors of the Hedgehog pathway such as SHH, PTCH1, GLI1, and GLI2, and/or the factors of the Wnt pathway such as LRP6 and β-catenin) can be easily obtained.

The thus produced hybridoma producing a monoclonal antibody can be subcultured in a normal culture solution. Alternatively, the hybridoma can also be preserved in liquid nitrogen over a long term. The hybridoma is cultured according to a normal method, and from the culture supernatant, an objective monoclonal antibody can be obtained. Alternatively, a monoclonal antibody can also be obtained as ascites by administering the hybridoma to a mammal having compatibility therewith and proliferating the hybridoma. The former method is suitable for obtaining an antibody having high purity.

In the present invention, an antibody encoded by an antibody gene which was cloned from an antibody producing cell can also be utilized. By incorporating the cloned antibody gene into an appropriate vector and introducing it into a host, the gene can be expressed as an antibody. Isolation of the antibody gene, introduction into the vector, and a method for transforming a host cell have already been established (e.g., see Vandamme, A. M., et al., Eur. J. Biochem. (1990) 192, 767-775).

For example, for the purpose of obtaining an antibody to an objective protein (e.g., GPR49/LGR5, the factors of the Hedgehog pathway such as SHH, PTCH1, GLI1, and GLI2, and/or the factors of the Wnt pathway such as LRP6 and β-catenin), it is further preferable that binding of an antibody to an objective protein (e.g., GPR49/LGR5, the factors of the Hedgehog pathway such as SHH, PTCH1, GLI1, and GLI2, and/or the factors of the Wnt pathway such as LRP6 and β-catenin) is specific. An antibody binding to an objective protein (e.g., GPR49/LGR5, the factors of the Hedgehog pathway such as SHH, PTCH1, GLI1, and GLI2, and/or the factors of the Wnt pathway such as LRP6 and β-catenin) can be screened, for example, by a method comprising (1) a step of contacting an antibody comprising a V region encoded by the resulting cDNA with the objective protein (e.g., GPR49/LGR5, the factors of the Hedgehog pathway such as SHH, PTCH1, GLI1, and GLI2, and/or the factors of the Wnt pathway such as LRP6 and (β-catenin); (2) a step of detecting binding between the objective protein (e.g., GPR49/LGR5, the factors of the Hedgehog pathway such as SHH, PTCH1, GLI1, and GLI2, and/or the factors of the Wnt pathway such as LRP6 and (β-catenin) and an antibody, and (3) a step of selecting an antibody binding to the objective protein (e.g., GPR49/LGR5, the factors of the Hedgehog pathway such as SHH, PTCH1, GLI1, and GLI2, and/or the factors of the Wnt pathway such as LRP6 and β-catenin).

A method for detecting binding between an antibody and the objective protein (e.g., GPR49/LGR5, the factors of the Hedgehog pathway such as SHH, PTCH1, GLI1, and GLI2, and/or the factors of the Wnt pathway such as LRP6 and β-catenin) is known. Specifically, a test antibody is reacted with the objective protein (e.g., GPR49/LGR5, the factors of the Hedgehog pathway such as SHH, PTCH1, GLI1, and GLI2, and/or the factors of the Wnt pathway such as LRP6 and (β-catenin) immobilized on a carrier and, then, the resultant is reacted with a labeled antibody recognizing an antibody. When a labeled antibody is detected on a carrier after washing, binding of the test antibody to the objective protein (e.g., GPR49/LGR5, the factors of the Hedgehog pathway such as SHH, PTCH1, GLI1, and GLI2, and/or the factors of the Wnt pathway such as LRP6 and β-catenin) can be demonstrated. For labeling, an enzymatically active protein such as peroxidase and β-glactosidase, or a fluorescent substance such as FITC can be utilized. For evaluating the binding activity of an antibody, a fixed specimen of a cell expressing the objective protein (e.g., GPR49/LGR5, the factors of the Hedgehog pathway such as SHH, PTCH1, GLI1, and GLI2, and/or the factors of the Wnt pathway such as LRP6 and β-catenin) can also be utilized.

As a method for screening an antibody using the binding activity as an index, a panning method utilizing a phage vector can also be used. When an antibody gene is obtained as a library of a subclass of a heavy chain and a light chain as described above, a screening method utilizing a phage vector is advantageous. Genes encoding variable regions of a heavy chain and a light chain can be prepared into a single chain Fv(scFv) by linking with an appropriate linker sequence. When a gene encoding scFv is inserted into a phage vector, a phage expressing scFv on a surface can be obtained. When this phage is contacted with an objective antigen, and a phage bound to the antigen is recovered, DNA encoding scFv having the objective binding activity can be recovered. By repeating this operation, if necessary, scFv having the objective binding activity can be concentrated.

In the present invention, a polynucleotide encoding an antibody may encode the full length of an antibody, or may encode a part of an antibody. A part of an antibody refers to any part of an antibody molecule. Hereinafter, as used herein, an antibody fragment may be used in implementation of the present invention. A preferable antibody fragment in the present invention comprises a complementarity determination region (CDR) of an antibody. Further preferably, the antibody fragment of the present invention comprises all of three CDRs constituting a variable region.

In one embodiment, the antibody of the present invention includes not only a divalent antibody, a representative of which is IgG, but also a monovalent antibody, and a polyvalent antibody, a representative of which is IgM, as far as it binds to the objective protein (e.g., GPR49/LGR5, the factors of the Hedgehog pathway such as SHH, PTCH1, GLI1, and GLI2, and/or the factors of the Wnt pathway such as LRP6 and β-catenin). The polyvalent antibody of the present invention includes a polyvalent antibody all having the same antigen-binding site, and a polyvalent antibody having a partially or entirely different antigen-binding site. The antibody of the present invention is not limited to a full length molecule of an antibody, and may be a low-molecular antibody or a modification product thereof, as far as it binds to the objective protein (e.g., GPR49/LGR5, the factors of the Hedgehog pathway such as SHH, PTCH1, GLI1, and GLI2, and/or the factors of the Wnt pathway such as LRP6 and β-catenin).

In order to confirm the immune response level of an immunized animal, and select an objective hybridoma from a cell after cell fusion treatment, the antibody titer in the blood of an immunized animal, or the antibody titer in the culture supernatant of an antibody producing cell is measured. Examples of a method for detecting an antibody include a known technique, for example, EIA (enzyme immunoassay), RIA (radioimmunoassay), and ELISA (enzyme linked immunosorbent assay).

According to the immunoassay, even when a sample contains a large amount of contaminating substance, the concentration of a marker can be accurately measured. Examples of the immunoassay include a classical method such as a precipitation reaction of directly or indirectly measuring an antigen-antibody bound product, an agglutination reaction, and a hemolytic reaction, enzyme immunoassay (EIA) whose detection sensitivity has been enhanced by combining a labeling method therewith, radioimmunoassay (RIA), and fluorescent immunoassay (FIA). In addition, an antibody specific for a marker used in these immunoassays may be monoclonal or polyclonal.

As a method for ionization when the concentration of a marker is measured by mass spectrometry, either of matrix-assisted laser desorption/ionization (MALDI) and electrospray ionization (ESI) can be applied, and MALDI producing little polyvalent ions is preferable. Particularly, according to MALDI-TOF-MS which is a combination with a time-of-flight mass spectrometer (TOF), the concentration of a marker can be measured more accurately. Further, according to MS/MS using two mass spectrometers, the concentration of a marker can be measured more accurately.

When the concentration of a marker is measured by electrophoresis, for example, a test material is subjected to SDS-polyacrylamide gel electrophoresis (SDS-PAGE) to separate an objective marker, the gel is stained with an appropriate dye or fluorescent substance, and the concentration or fluorescent intensity of a band corresponding to an objective marker may be measured. When separation of the marker is insufficient only by SDS-PAGE, two-dimensional electrophoresis which is a combination with isoelectric electrofocusing (IEF) can also be used. Further, not by direct detection from a gel, but by performing Western blotting, the amount of the marker on a membrane can be measured.

When the concentration of the marker is measured by chromatography, for example, a method by high performance liquid chromatography (HPLC) can be used. That is, by subjecting a sample to HPLC to separate an objective marker, and measuring the peak area of the chromatogram, the concentration of the marker in a sample can be measured.

As a myeloma cell to be fused with an antibody producing cell, an established cell which is derived from a variety of animals such as a mouse, a rat, or human, and is generally available to a person skilled in the art is used. As a cell strain to be used, a cell strain which has drug resistance, and has such a nature that it cannot survive in a selective medium (e.g., HAT medium) in an unfused state, and can survive only in a fused state is used. Generally, an 8-azaguanine-resistant strain is used, and this cell strain is deficient in hypoxanthine-guanine-phosphoribosyltransferase, and cannot be grown in a hypoxanthine-aminopterin-thymidine (HAT) medium.

As the myeloma cell, already known various cell strains, for example, P3 (P3x63Ag8.653) (J. Immunol. (1979) 123: 1548-1550), P3x63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies D. H. et al., Cell (1976) 8: 405-415), SP2/0 (Shulman M. et al., Nature (1978) 276: 269-270), FO (Lazekas de St. Groth, S. and Scheidegger, D., J. Immunol. Methods (1980) 35: 1-21), 5194 (Trowbridge, I. S., J. Exp. Med. (1978) 148: 313-323), and R210 (Galfre G. et al., Nature (1979) 277: 131-133) are preferably employed.

An antibody producing cell is obtained from a spleen cell, a lymph node cell or the like. That is, a spleen, a lymph node or the like is isolated or collected from the animals, and these tissues are crushed. The resulting crushed product is suspended in a medium or a buffer such as PBS, DMEM, and RPMI1640, and the suspension is filtered with a stainless mesh or the like, and centrifuged, thereby, an objective antibody producing cell is prepared.

Then, the myeloma cell and the antibody producing cell are fused. Cell fusion is performed by contacting the myeloma cell with the antibody producing cell at a mixing ratio of 1:1 to 1:10 at 30 to 37° C. for 1 to 15 minutes in a medium for culturing an animal cell such as MEM, DMEM, and RPME-1640 media in the presence of a fusion promoter. In order to promote cell fusion, a fusion promoter or a fusion virus such as polyethylene glycol having an average molecular weight of 1,000 to 6,000, polyvinyl alcohol or a sendaivirus can be used. Alternatively, the antibody producing cell can be fused with the myeloma cell using a commercially available cell fusion apparatus utilizing electric stimulation (e.g., electroporation).

From the cells after cell fusion treatment, an objective hybridoma is selected. Examples of a method for selection include a method that employs selective proliferation of a cell in a selective medium. That is, a cell suspension is diluted with an appropriate medium, and seeded on a microtiter plate, a selective medium (HAT medium etc.) is added to each well, and thereafter, the selective medium is appropriately exchanged to perform culturing. As a result, a growing cell can be obtained as a hybridoma.

Screening of the hybridoma is performed by a limiting dilution method, a fluorescence excitation cell sorter method or the like, and finally, a monoclonal antibody-producing hybridoma is obtained. Examples of a method for collecting a monoclonal antibody from the obtained hybridoma include a normal cell culturing method and an ascites forming method. In the cell culturing method, the hybridoma is cultured in an animal cell culturing medium such as an RPMI-1640 medium containing 10 to 20% fetal calf serum, a MEM medium, or a serum-free medium for 2 to 14 days under normal culturing conditions (e.g., 37° C., 5% $CO_2$ concentration), and an antibody is obtained from the culture supernatant. In the ascites forming method, the hybridoma is administered into the abdominal cavity of an animal of the same species as a mammal from which the myeloma cell is derived, and the hybridoma is proliferated in a large amount. Then, after 1 to 4 weeks, ascites or serum is collected.

In the method for collecting an antibody, when purification of an antibody is required, the antibody is purified by appropriately selecting a known method such as an ammonium sulfate salting-out method, ion exchange chromatography, and affinity chromatography, or combining them.

Therefore, a substance contained as an antigen in antibody production may be a partial sequence, as far as it comprises at least one epitope which can induce immunization, although the full length of a marker as a subject is preferable. An epitope can be used even if the precise position and the precise structure thereof have not been necessarily found, but if necessary, identification of an epitope in a predetermined protein can be easily attained using a technique well-known in the art. For example, Geysen et al. (1984) Proc. Natl. Acad. Sci. USA 81: 3998; U.S. Pat. No. 4,708,871; and Geysen et al. (1986) Molecular Immunology 23: 709 can be referred to. Antibodies recognizing the same epitope can be identified by a simple immunoassay. In this way, a method for determining an epitope including a peptide is well-known in the art, and such an epitope, when a primary sequence of a nucleic acid or an amino acid is provided, can be determined by a person skilled in the art using such a well-known conventional technique.

Therefore, for use as an epitope including a peptide, a sequence of a length of at least 3 amino acids is necessary, and preferably, a sequence of a length of at least 4 amino acids, more preferably at least 5 amino acids, at least 6 amino acids, at least 7 amino acids, at least 8 amino acids, at least 9 amino acids, at least 10 amino acids, at least 15 amino acids, at least 20 amino acids, or at least 25 amino acids may be required. The epitope may be straight, or may be in a conformation form.

In one aspect, according to the present invention, there is provided a detection kit for implementing the detection method in accordance with the present invention.

In one embodiment, the detection kit in accordance with the present invention includes a detection kit for implementing detection of an embodiment in accordance with the present invention, specifically, a kit for detecting expression of GPR49/LGR5, and/or the factors of the Hedgehog pathway such as SHE, PTCH1, GLI1, and GLI2, and/or the factors of the Wnt pathway such as LRP6 and β-catenin, comprising at least the probe in accordance with the present invention. This probe may be labeled. This kit for detection detects expression of GPR49/LGR5, and/or the factors of the Hedgehog pathway such as SHE, PTCH1, GLI1, and GLI2, and/or the factors of the Wnt pathway such as LRP6 and β-catenin by a hybrid forming method. Therefore, a detection method of a first aspect can optionally further comprise a variety of reagents for carrying out the hybrid forming method, for example, a substrate compound used in detection of a label, a hybridization buffer, a direction, and/or an instrument.

The detection kit of this embodiment in accordance with the present invention may further comprise a probe, a primer, a primer set, or an antibody which can detect expression of a differentiation marker gene (e.g., Ki-67, or BrdU) other than GPR49/LGR5, and/or the factors of the Hedgehog pathway such as SHH, PTCH1, GLI1, and GLI2, and/or the factors of the Wnt pathway such as LRP6 and β-catenin, in order to perform detection precisely. These probe, primer, primer set and antibody may be labeled. This kit for detection further detects expression of a differentiation marker gene other than GPR49/LGR5, and/or the factors of the Hedgehog pathway such as SHH, PTCH1, GLI1, and GLI2, and/or the factors of the Wnt pathway such as LRP6 and β-catenin, by any of a hybrid forming method, a nucleic acid amplification method, and an antigen-antibody reaction method.

In another embodiment, the kit for detection in accordance with the present invention includes a detection kit for carrying out detection of another embodiment in accordance with the present invention, specifically, a kit for detecting expression of GPR49/LGR5, and/or the factors of the Hedgehog pathway such as SHH, PTCH1, GLI1, and GLI2, and/or the factors of the Wnt pathway such as LRP6 and β-catenin, comprising at least the primer in accordance with the present invention or the primer set in accordance with the present invention. This kit for detection detects expression of GPR49/LGR5, and/or the factors of the Hedgehog pathway such as SHH, PTCH1, GLI1, and GLI2, and/or the factors of the Wnt pathway such as LRP6 and β-catenin, by a nucleic acid amplification method. Therefore, a detection method of a second aspect may optionally further comprise a variety of reagents for carrying out a nucleic acid amplification method, for example, a buffer, an internal standard which can indicate that PCR can normally progress, a direction, and/or an instrument.

The detection kit of this embodiment in accordance with the present invention may further comprise a probe, a primer, a primer set, or an antibody which can detect expression of a differentiation marker gene other than GPR49/LGR5, and/or the factors of the Hedgehog pathway such as SHH, PTCH1, GLI1, and GLI2, and/or the factors of the Wnt pathway such as LRP6 and β-catenin, in order to perform detection precisely. These probe, primer, primer set, and antibody may be labeled. This kit for detection further detects expression of a differentiation marker other than GPR49/LGR5, and/or the factors of the Hedgehog pathway such as SHH, PTCH1, GLI1, and GLI2, and/or the factors of the Wnt pathway such as LRP6 and β-catenin, by any of a hybrid forming method, a nucleic acid amplification method, and an antigen-antibody reaction method.

In a further embodiment, the detection kit in accordance with the present invention includes a detection kit for carrying out detection of a further embodiment in accordance with the present invention, specifically, a kit for detecting a protein of GPR49/LGR5, and/or the factors of the Hedgehog pathway such as SHH, PTCH1, GLI1, and GLI2, and/or the factors of the Wnt pathway such as LRP6 and β-catenin, comprising at least the antibody in accordance with the present invention. This antibody may be labeled. This kit for detection detects expression of GPR49/LGR5, and/or the factors of the Hedgehog pathway such as SHE, PTCH1, GLI1, and GLI2, and/or the factors of the Wnt pathway such as LRP6 and β-catenin, by detecting an antigen-antibody reaction. The detection method of this embodiment may optionally further comprise a variety of reagents for carrying out an antigen-antibody reaction, for example, a secondary antibody, a coloring reagent, a buffer, a direction, and/or an instrument used in an ELISA method or the like.

In this embodiment, the detection kit in accordance with the present invention may further comprise a probe, a primer, a primer set, or an antibody which can detect expression of a differentiation marker other than GPR49/LGR5, and/or the factors of the Hedgehog pathway such as SHH, PTCH1, GLI1, and GLI2, and/or the factors of the Wnt pathway such as LRP6 and β-catenin, in order to perform detection precisely. These probe, primer, primer set, and antibody may be labeled. This kit for detection further detects expression of a differentiation marker other than GPR49/LGR5, and/or the factors of the Hedgehog pathway such as SHH, Ptch1, Gli1, and Gli2, and/or the factors of the Wnt pathway such as LRP6 and β-catenin, by any of a hybrid forming method, a nucleic acid amplification method, and an antigen-antibody reaction method.

It can be understood that, in these kit, composition or system, a marker in a sample derived from any subject, the factors specifically interacting with the marker, or means selectively recognizing the marker can be used, as far as the marker of the present invention (e.g., GPR49/LGR5, and/or the factors of the Hedgehog pathway such as SHH, PTCH1, GLI1, and GLI2, and/or the factors of the Wnt pathway such as LRP6 and β-catenin) can be identified. Therefore, it is understood that not only a factor or means specifically described herein, but also any equivalent factor or means known in the art can be used.

In one embodiment, the factor used in the present invention is selected from the group consisting of a nucleic acid molecule, a polypeptide, a fat, a sugar chain, an organic low molecule and a complex molecule thereof, and preferably, the factor is a protein or a complex molecule (e.g., a glycoprotein or a lipoprotein). Preferably, the factor is an antibody (e.g., a polyclonal antibody or a monoclonal antibody). It is preferable that such a factor is labeled, or can be labeled. This is because diagnosis becomes easy.

In a preferable embodiment of the present invention, means to be used is selected from the group consisting of a mass spectrometry apparatus, a nuclear magnetic resonance measuring apparatus, an X-ray analysis apparatus, SPR, chromatography (e.g., HPLC, thin layer chromatography, or gas chromatography), an immunological means (e.g., Western blotting, EIA (enzyme immunoassay), RIA (radioimmunoassy), or ELISA (enzyme linked immunosorbent assay)), a biochemical means (e.g., pI electrophoresis, Southern blotting, or two-dimensional electrophoresis), an electrophoresis instrument, a chemical analytical instrument, a fluorescent two-dimensional differential electrophoresis method (2DE-DIGE), an isotope-coded affinity tag (ICAT), a tandem affinity purification method (TAP method), a physical means, laser microdissection and a combination thereof.

In a preferable embodiment of the present invention, the system or the kit of the present invention further comprises a standard of a marker. It is preferable that such a standard is used in order to confirm whether means for detecting a marker (a factor specifically interacting with the marker, or means selectively recognizing the marker) normally functions or not.

In a preferable embodiment, the present invention can further comprise means for purifying a sample as a subject. Examples of such a purification means include chromatography. Since the precision of diagnosis can be enhanced by purification, the purification means can be used in a preferable embodiment, but it is not essential.

In one embodiment, the factor or the means used in the present invention has an ability to quantitate the marker of the present invention. Such quantitation may be performed by such means or factor that enables a proper calibration curve to be drawn when a standard curve is drawn. Preferable examples thereof include an antibody, mass spectrometry, and chromatography analysis. Therefore, in a certain embodiment, the system of the present invention further comprises a quantitation means for quantitating a marker.

In one embodiment, a quantitation means comprises a determination means for determining whether the marker is within the range of a normal value or not, by comparing the standard curve with the measured result. Such a determination means can be realized using a computer.

In one embodiment, the kit or the system of the present invention comprises a composition comprising a marker or the factor specifically interacting with a marker.

In one aspect, the present invention provides use of a marker in a sample derived from a subject, a factor specifically interacting with the marker, or means selectively recognizing the marker, in production of a pharmaceutical for presumptively diagnosing, pre-diagnosing or advancingly diagonsing, predicting, detecting or diagnosing the level of the proliferation ability or the differentiated state, or a disease, a disorder or a condition associated therewith. Herein, a sample may be obtained by any means. Usually, when a person in charge other than a doctor is engaged in measurement, the sample may be one that was obtained by a doctor in some way. Determination of the level of the proliferation ability or the differentiated state, or whether there is a possibility of a disease, a disorder or a condition associated therewith or not, from the measurement result, can be implemented by determining whether the result is abnormal or not as compared with each marker, or as compared with a normal value. In the method of the present invention, it is understood that a marker to be used or the like may have any one or a plurality of characteristics described in other places of the present description, as far as they are not contradictory. In the detection or the diagnosis of present invention, as a method for measuring the concentration of a marker, a method which is generally used for quantitating a protein can be used as it is, as far as it is a method which can specifically measure the concentration of the marker. For example, various immunoassays, mass spectrometry (MS), chromatography, and electrophoresis can be used.

One preferable embodiment in the detection or the diagnosis of the present invention is to trap a marker on a carrier, and measure the concentration of the trapped marker. That is, a substance having affinity for the marker is immobilized on a carrier, and the marker is trapped on the carrier via the substance having affinity. According to the present embodiment, influence of a contaminating substance contained in a sample can be reduced, and the concentration of the marker can be measured precisely at higher sensitivity.

In one embodiment, when an immunoassay is used in a method for measuring a marker, it is preferable to use a carrier on which an antibody is immobilized. Such use enables easy construction of a system of an immunoassay using an antibody immobilized on a carrier as a primary antibody. For example, a system of sandwich EIA can be constructed by preparing two kinds of antibodies which are specific for the marker and are different in the epitope, immobilizing one of them on a carrier as a primary antibody, and labeling the other as a secondary antibody with an enzyme. In addition, a system of an immunoassay by a binding inhibition method or a competition method can also be constructed. Further, when a substrate is used as a carrier, an immunoassay by an antibody chip is possible. With the antibody chip, the concentrations of a plurality of markers can be measured simultaneously, and rapid measurement is possible.

On the other hand, in one embodiment, when mass spectrometry is used in a method for measuring a marker, the marker can be trapped on a carrier by an ionic bond or hydrophobic interaction, in addition to an antibody. An ionic bond or hydrophobic interaction has no higher specificity than that of bioaffinity such as that between an antigen and antibody, and a substance other than the marker is trapped, but they have no problem since mass spectrometry performs quantitation by a mass spectrometer spectrum reflecting the molecular weight. Particularly, when surface-enhanced laser desorption/ionization-time-of-flight mass spectrometry (referred to as "SELDI-TOF-MS" as used herein) is performed using a protein chip employing a substrate as a carrier, the concentration of the marker can be measured more precisely. As the kind of substrate which can be used, a cation exchange substrate, an anion exchange substrate, a normal phase substrate, a reverse phase substrate, a metal ion substrate, an antibody substrate and the like can be used, and a cation exchange substrate, particularly, a weak cation exchange substrate and a metal ion substrate are preferably used.

When the marker is trapped on a carrier by an ionic bond, an ion exchanger is immobilized on a carrier. In this case, as an ion exchanger, either of an anion exchanger and a cation exchanger can be used, and further, any of a strong anion exchanger, a weak anion exchanger, a strong cation exchanger, and a weak cation exchanger can be used. Examples of the weak anion exchanger include exchangers having a weak anion exchange group such as dimethylaminoethyl (DE) and diethylaminoethyl (DEAE). In addition, examples of the strong anion exchanger include exchangers having a strong anion exchange group such as quaternary ammonium (trimethylaminomethyl) (QA), quaternary aminoethyl (diethyl, mono-2-hydroxybutylaminoethyl) (QAE), and quaternary ammonium (trimethylammonium) (QMA). In addition, examples of the weak cation exchanger include exchangers having a weak cation exchange group such as carboxymethyl (CM). Further, examples of the strong cation exchanger include exchangers having a strong cation exchange group such as sulfopropyl (SP). On the other hand, when the marker is trapped on a carrier by hydrophobic interaction, a substance having a hydrophobic group is immobilized on a carrier. Examples of the hydrophobic group include a C4-C20 alkyl group and a phenyl group. Further, the marker can be trapped on a carrier on which a metal ion such as $Cu^{2+}$, $Zn^{2+}$, $Ni^{2+}$, $Ca^{2+}$, $Co^{2+}$, or $Mg^{2+}$ is immobilized.

In one embodiment, as an example of a carrier to be used, known carriers such as beads, a microtiter plate, and a resin can be employed. Particularly, beads and a microtiter plate have previously been used in an immunoassay, and construction of a measuring system is easy. On the other hand, a carrier having a flat part such as a substrate can also be used. In this case, it is preferable to immobilize a substance having affinity for the marker on a part of the flat part. As an example, there can be mentioned a carrier including a chip as a substrate, and an antibody specific for the marker is immobilized on a plurality of places on the chip in a spot-like manner.

Since a cell which was selected by using, as an index, the detection agent or the diagnostic agent such as a probe, a primer, or an antibody in accordance with the present invention is an undifferentiated cell or a precursor cell having a proliferation ability (e.g., an undifferentiated cell or a precursor cell existing in a corneal endothelial cell), it is preferable for treating or preventing a corneal endothelial disease, disorder or condition such as bullous keratopathy or corneal endotheliitis or other ophthalmological diseases, from the viewpoint of safety, the survival rate, and the network forming ability, as compared with the previous miscellaneous cell populations or a precursor cell in which a foreign gene is introduced. Since a cell which can be selected is an undifferentiated cell or a precursor cell before division arrest, that is, during proliferation, and has a possibility that it is differentiated and matured at an optimal place in a brain, and there is a possibility that an undifferentiated cell or a precursor cell further proliferates in vivo, a therapeutic effect for a longer term can be expected. Therefore, it is possible to state that the present invention paves the way for practical application of effective treatment or prevention of a corneal endothelial disease, disorder or condition such as bullous keratopathy or corneal endotheliitis or other ophthalmological diseases.

(Screening)

The detection method in accordance with the present invention can be applied to screening of a substance effective in inducing differentiation into a cell having a high proliferation ability and/or an undifferentiated cell existing in corneal endothelial cells. That is, by determining whether or not a cell was differentiation-induced into a cell having a high proliferation ability and/or an undifferentiated cell existing in corneal endothelial cells by addition of a test substance using, as an index, expression of GPR49/LGR5, and/or the factors of the Hedgehog pathway such as SHH, PTCH1, GLI1, and GLI2, and/or the factors of the Wnt pathway such as LRP6 and β-catenin, a substance effective in inducing differentiation into a cell having a high proliferation ability and/or an undifferentiated cell existing in corneal endothelial cells can be screened.

Therefore, according to the present invention, a method for screening a substance effective in inducing differentiation into a cell having a high proliferation ability and/or an undifferentiated cell existing in corneal endothelial cells is provided, and this method includes (i) a step of contacting a test substance with a cell (e.g., an ES cell or an iPS cell) which can differentiate into a cell having a high proliferation ability and/or an undifferentiated cell existing in corneal endothelial cells; and (ii) a step of detecting expression of GPR49/LGR5, and/or the factors of the Hedgehog pathway such as SHH, PTCH1, GLI1, and GLI2, and/or the factors of the Wnt pathway such as LRP6 and β-catenin in the cell after contact with the test substance. In the step (i), the cell which can differentiate into a cell having a high proliferation ability and/or an undifferentiated cell existing in corneal endothelial cells can be preferably collected from a cultured cell containing an iPS cell and an ES cell, or a neural precursor cell or a neural crest cell which was differentiation-induced from these cells.

In the step (i), "contacting a test substance" can be performed by adding a test substance to a cultured cell containing a cell which can differentiate into a cell having a high proliferation ability and/or an undifferentiated cell existing in corneal endothelial cells.

Examples of the usable "test substance" include, but are not limited to a synthetic low-molecular weight compound, a protein, a synthetic peptide, a purified or partially purified polypeptide, an antibody, a bacterium-releasing substance (including a bacterial metabolite), and a nucleic acid (antisense, ribozyme, RNAi, etc.), preferably, a compound or a salt thereof or a solvate thereof (e.g., a hydrate). The "test substance" may be a novel substance, or may be a known substance.

In the step (ii), according to the detection method of the present invention, expression of GPR49/LGR5, and/or the factors of the Hedgehog pathway such as SHH, PTCH1, GLI1, and GLI2, and/or the factors of the Wnt pathway such as LRP6 and β-catenin can be detected.

As a specific embodiment, by appropriately implementing detection utilizing a hybridization method, detection utilizing a nucleic acid amplification method, and detection utilizing an antigen-antibody reaction described herein, expression of GPR49/LGR5, and/or the factors of the Hedgehog pathway such as SHH, PTCH1, GLI1, and GLI2, and/or the factors of the Wnt pathway such as LRP6 and β-catenin can be detected.

In the step (ii), when the test substance is contacted with the cell, and expression of GPR49/LGR5, and/or the factors of the Hedgehog pathway such as SHH, PTCH1, and GLI2 is detected in a cell sample, it can be determined that the substance is a substance effective in inducing differentiation into a cell having a high proliferation ability and/or an undifferentiated cell existing in corneal endothelial cells. When suppression or disappearance of expression of the factors of the Wnt pathway such as LRP6 and β-catenin is detected, it can be determined that the substance is a substance effective in inducing differentiation into a cell having a high proliferation ability and/or an undifferentiated cell existing in corneal endothelial cells.

A substance specified by the screening method in accordance with the present invention can be used as a substance effective in inducing differentiation into a cell having a high proliferation ability and/or an undifferentiated cell existing in corneal endothelial cells. According to the present invention, a method for screening a substance effective in inducing differentiation into a cell having a high proliferation ability and/or an undifferentiated cell existing in corneal endothelial cells is provided, and this method may further comprise (iii) a step of detecting expression of a differentiation marker gene other than GPR49/LGR5, and/or the factors of the Hedgehog pathway such as SHH, PTCH1, GLI1, and GLI2, and/or the factors of the Wnt pathway such as LRP6 and β-catenin, in the cell after contact with the test substance. When expression of GPR49/LGR5, and/or the factors of the Hedgehog pathway such as SHH, PTCH1, GLI1, and GLI2, and/or the factors of the Wnt pathway such as LRP6 and β-catenin is detected in the step (ii), and expression of a differentiation marker gene (e.g., Ki-67 or BrdU) other than GPR49/LGR5, and/or the factors of the Hedgehog pathway such as SHH, PTCH1, GLI1, and GLI2, and/or the factors of the Wnt pathway such as LRP6 and β-catenin is detected in the step (iii), the substance can be precisely determined to be a substance effective in induction into a cell having a high proliferation ability and/or an undifferentiated cell existing in corneal endothelial cells. In addition, the step (iii) has only to be performed after the step (i), and may be performed before or after the step (ii).

(General Technique)

A molecular biological procedure, a biochemical procedure and a microbiological procedure as used herein are well-known and conventionally used in the art, and are described, for example, in Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, and Experimental Medicine, separate volume, "Gene Introduction & Expression Analysis Experimental Method" Yodosha Co., Ltd., 1997, the relevant part (which can be the whole) of them is incorporated herein by reference.

A DNA synthesis technique for producing an artificially synthesized gene and nucleic acid chemistry are described, for example, in Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; and Hermanson, G. T. (1996). Bioconjugate Techniques, Academic Press, the relevant part of them is incorporated herein by reference.

For example, as used herein, the oligonucleotide of the present invention can also be synthesized using, for example, an automated DNA synthesizer (e.g., a synthesizer commercially available from Biosearch, Applied Biosystems) by a standard method known in the art. For example, a phosphorothioate-oligonucleotide can also be synthesized by the method of Stein et al. (Stein et al., 1988, Nucl. Acids Res. 16: 3209), and a methyl phosphonate-oligonucleotide can also be prepared by using a pore-adjusted glass polymer support (Sarin et al., 1988, Proc. Natl. Acad. Sci. USA 85: 7448-7451).

Reference literatures such as scientific literatures, patents, and patent applications cited herein are incorporated herein by reference to the same extent that the entirety of them is specifically described.

As described above, the present invention has been illustrated by showing preferable embodiments for ease of understanding. The present invention will be illustrated below based on Examples, but the aforementioned illustration and the following Examples are provided only for the purpose of exemplification, and are not provided for the purpose of limiting the present invention. Therefore, the scope of the present invention is not limited to embodiments and Examples specifically described herein, and is limited only by the scope of claims.

EXAMPLES

If necessary, handling of animals used in the following Examples were performed in compliance with a standard defined in Kyoto Prefectural University of Medicine or Doshisha University, and based on Helsinki Declaration. In addition, according to the ARVO Statement for the Use of Animals in Ophthalmic and Vision Research, animals were fed and handled. In addition, as reagents, products specifically described in Examples were used, but equivalent products of other manufacturers (Sigma, Wako Pure Chemical Industries Co., Ltd., Nacalai Tesque, Inc., abcam, Santa Cruz Biotechnology, R & D Systems, Abnova, Assay Pro, Origene, Biobyt, Biorad, Cell Signaling Technology, GE Healthcare, IBL, and the like) can be used as substitutes.
(Experimental Material and Method)
(Material)
(Corneal Tissue)

All human corneal tissues used in the present experiment were tissues imported from SightLife™ (Northwest Lions Foundation) of American Seattle Eye Bank. All monkey corneal tissues used were tissues of a cynomolgus monkey euthanized for other research purposes (Nissei Bilis Co., Ltd., Ohtsu, Japan, or Keari Co., Ltd., Wakayama, Japan). All corneas were preserved at 4° C. in a preservation medium (Optisol; Chiron Vision Corporation, Irvine, Calif.). All experiments were performed according to doctrine of Helsinki Declaration.
(Cell Culture)

In primary culture of a human corneal endothelial cell, a Descemet's membrane containing an endothelial cell layer was peeled from a corneal tissue, and placed into 2 mg/ml Collagenase A (catalog No.: 70164923; Roche Applied Science, Penzberg, Germany) dissolved in OPTIMEM-I, and incubated at 37° C. After 3 hours, the resultant was centrifuged at 1000 rpm for 5 minutes to remove the supernatant, a culture medium was added to a precipitated corneal endothelial cell mass for admixing, and the total amount was seeded on a 12-well plate coated with FNC Coating Mix (catalog No.: 0407; Athena Enzyme Systems, Baltimore, Md., USA). As a culture medium, OPTIMEM-I (catalog No.: 51985; Gibco-Invitrogen, Carlsbad, Calif.), to which 5% fetal bovine serum (catalog No.: 10437-028; fetal bovine serum; FBS; BioWest, France), 50 µg/ml Gentamicin (Invitrogen), and 10 µg/ml Y-27632 (Calbiochem, La Jolla, Calif.) were added, was used.

In primary culture of a monkey corneal endothelial cell, a Descemet's membrane containing an endothelial cell layer was peeled from a corneal tissue, placed in 1.2 U/ml Dispase I [(Sanko Pure Chemical Co., Ltd.) catalog No.: GD81060] dissolved in DMEM (Gibco-Invitrogen), and incubated at 37° C. After 1 hour, a corneal endothelial cell was peeled and recovered from a Descemet's membrane by pipetting, and the resultant was centrifuged at 1000 rpm for 5 minutes to remove the supernatant. A culture medium was added to a precipitated corneal endothelial cell for admixing, and the total amount was seeded on a 6-well plate coated with FNC Coating Mix. As a culture medium, DMEM (catalog No.: 12320; Gibco-Invitrogen), to which 10% FBS, 50 µg/ml Gentamicin (catalog No.: 15710-064; Invitrogen), 10 µg/ml Y-27632 (catalog No.: 6880005; Calbiochem, La Jolla, Calif.), and a 2 ng/ml basic fibroblast growth factor (catalog No.: 13256-029; bFGF; Invitrogen) were added, was used.

As a human cornea, a cornea, in which the period before primary culture was less than 14 days, was used. For culture of human and monkey corneal endothelial cells (CEC), a system previously reported [Tan D T et al., Lancet., 2012; 379: 1749-1761; Koizumi N et al., Exp Eye Res., 2012; 95: 60-67; Koizumi N et al., Invest Ophthalmol Vis Sci. 2007; 48: 4519-4526; Okumura N Et al., Am J Pathol. 2012; 181: 268-277] was used.

A medium was exchanged every 2 days. Subculture was performed at the time point of 50 to 80% confluent. As a subculture method, cells were washed with $Ca^{2+}Mg^{2+}$-not containing (free) PBS (PBS-; Nissui Pharmaceutical Co., Ltd., Tokyo, Japan), TrypLE™ Select (catalog No.: 12563; Invitrogen) was added, and the resultant was incubated at 37° C. for 5 minutes. Cells were peeled and recovered from the plate, and centrifuged at 1000 rpm for 5 minutes, and a culture medium was added to provide a cell suspension. Cells were seeded on a plate coated with FNC Coating Mix at a density of 1:2.
(Immunostain)

Immunohistochemical study was performed according to the method previously described by the present inventors [Nakamura T et al., Stem Cells, 2007; 25: 628-638; Nakamura T et al., Stem Cells, 2008; 26: 1265-1274].

A corneal tissue was embedded with OCT compound (catalog No.: 4583; Sakura Finetek, Tokyo, Japan), and frozen in liquid nitrogen to prepare a frozen corneal tissue section. The frozen block was sliced to 8 µm, applied on a silane-coating slide, and air-dried. For preparing the whole tissue section, a Descemet's membrane containing a corneal endothelial cell was peeled from a corneal tissue, allowed to stand in ice-cooled 100% acetone for 30 seconds, applied on a silane-coating slide, and air-dried. As a cultured corneal endothelial cell, a cell cultured on a LabTek 8-well plastic chamber slide was used. Ice-cooled 100% acetone was added to a corneal tissue and the cultured cell, the resultant was allowed to stand at 4° C. for 15 minutes to fix the cell. After shaking and washing with 0.15% TritonX/PBS-, 1% bovine serum albumin (catalog No.: A4503BSA; Sigma-Aldrich, St. Louis, Mo.) was added, and allowed to stand at room temperature for 30 minutes to perform blocking. A primary antibody was diluted with 1% BSA, and incubated at room temperature for 1 hour. As a primary antibody to be used, anti-rabbit GPR49/LGR5 (catalog No.: GTX71143; 1: 200; GeneTex Inc., San Antonio, Tex.), anti-rabbit Nestin (catalog No.: PRB-570C; 1: 200; COVANCE, Berkeley, Calif.), anti-mouse ABCG2 (catalog No.: NC_236; 1: 2; Kamiya biomedical CO., Seattle, Wash. USA), anti-mouse Ki-67 (catalog No.: 556003; 1: 200 BD Pharmingen™ NJ, USA), anti-rabbit $Na^+/K^+$ ATPase (catalog No.: A132; 1: 100; Zymed), and anti-rabbit ZO1 (Zymed Laboratries Inc., South San Francisco, Calif.) were used. The resultant was washed with 0.15% Triton/PBS- twice, and PBS- once.

A secondary antibody was diluted with a mixed solution of 1% BSA and 0.15% TrironX/PBS-, and incubated at room temperature for 30 minutes. As a secondary antibody to be used, Alexa™ Fluor 488-labeled (conjugated) goat anti-rabbit IgG (catalog No.: A11034; 1: 1500; Molecular Probe-Invitrogen) and Alexa™ Fluor 488-labeled (conjugated) goat anti-mouse IgG (catalog No.: A11029; 1: 1500; Molecular Probe-Invitrogen) were used. The secondary antibody was shaken and washed with 0.15% Triton/PBS- twice, and PBS- once, subjected to nuclear staining with propidium iodide (catalog No.: SP29004-41; PI; Nacalai Tesque, Inc. Kyoto, Japan), and embedded while covered with a cover glass. This was observed with a confocal laser microscope (Olympus Fluoview, Tokyo, Japan), and a photograph was taken.
(Real Time PCR)

A real time PCR experiment was performed according to the method previously described by the present inventors [Nakamura T et al., Stem Cells., 2007; 25: 628-638].

For extracting RNA from a corneal tissue and a cultured cell, RNeasy Mini Kit (catalog No.: 74106; QIAGEN, Valencia, Calif.) was used. Added was 1 µl of OligodT Primer (catalog No.: 18418-020; Invitrogen) per 1 µg of the extracted RNA, and the resultant was incubated at 70° C. for 2 minutes, and immediately ice-cooled. Further, a reaction liquid including 5× First-Strand buffer, 100 mM DTT (catalog No.: 772590; Invitrogen), SuperScript™ II Reverse Transcriptase (catalog No.: 18064-014; Invitrogen), 2.5 mM dNTP (catalog No.: BG7401A; Takara Bio Inc., Otsu, Japan), and 40 unit/µl RNase Inhibitor (catalog No.: SIN-101; Toyobo Co., Ltd., Osaka Japan) was added, and incubated at 42° C. for 45 minutes and 70° C. for 15 minutes to synthesize cDNA. For preparing a primer, BLAST programs (NCBI) were utilized (Table 1). A primer and SYBR (registered trademark) Green PCR Master Mix (catalog No.: 4367659; Applied Biosystems, Foster City, Calif.) were added to 2 of the synthesized cDNA, and the resultant was reacted on ABI Prism 7000 (Applied Biosystems) at 40 cycles of 95° C. for 15 seconds and 60° C. for 1 minute. The resulting data were analyzed by ABI PRISM (registered trademark) 7000 Sequence Detection System. In addition, the amount of expression of each gene was corrected with the amount of a gene expressing β-actin, and was shown as a relative value to a control.

Example> were used, and each was incubated at room temperature for 20 minutes. Using a flow cytometer (FACS Aria II (BD Biosciences, Franklin Lakes, N.J.)), GPR49/LGR5-positive cells and GPR49/LGR5-negative cells were fractionated, and the respective cells were seeded on a S-well chamber slide, and cultured. After 3 days, the cells were immunostained with anti-mouse Ki-67, and the number of Ki-67-positive cells was counted.

For studying the cell proliferation rate in GPR49/LGR5-positive cells, 70% ethanol was added to recovered cells, and the resultant was incubated at −20° C. for 2 hours to fix the cells. After washing with PBS- twice, 1% BSA was added, and incubated at room temperature for 15 minutes to perform blocking. As a primary antibody, anti-rabbit GPR49/LGR5 (1:100) and anti-mouse Ki-67 (1:100) were used, and the resultant was incubated at room temperature for 30 minutes. As a secondary antibody, Alexa™ Fluor 488-conjugated goat anti-rabbit IgG (1:1500) and Alexa™ Fluor 594-conjugated goat anti-mouse IgG (1:1500; Molecular Probe-Invitrogen) were used, and the resultant was incubated at room temperature for 20 minutes. For sorting cells, FACS Aria II (BD Bio-sciences, Franklin

TABLE 1

Primer sequence for real time PCR

| Gene | GenBank Accession Number | Sequence | |
|---|---|---|---|
| Human GPR49 | NM_003667 | Forward 5'-GAGGATCTGGTGAGCCTGAGAA-3' | (SEQ ID NO: 13) |
| | | Reverse 5'-CATAAGTGATGCTGGAGCTGGTAA-3' | (SEQ ID NO: 14) |
| Human Nestin | NM_006617 | Forward 5'-ATGCTCCTCTCTCTCTGCTACCA-3' | (SEQ ID NO: 15) |
| | | Reverse 5'-CTAGTGTCTCATGGGTCTGGTTTTC-3' | (SEQ ID NO: 16) |
| Human ABCG2 | NM_004827.2 | Forward 5'-AGTGGCTTTCTACCTTGTCG-3' | (SEQ ID NO: 17) |
| | | Reverse 5'-ACAGAAACCACACTCTGACC-3' | (SEQ ID NO: 18) |
| Human SHH | NM_000193.2 | Forward 5'-ACGGCCCAGGGCACCATTCT-3' | (SEQ ID NO: 19) |
| | | Reverse 5'-GGACTTGACCGCCATGCCCA-3' | (SEQ ID NO: 20) |
| Human Ptch1 | NM_000264.3 | Forward 5'-TCGCTCTGGAGCAGATTTCCAAGGG-3' | (SEQ ID NO: 21) |
| | | Reverse 5'-GCAGTCTGGATCGGCCGGATTG-3' | (SEQ ID NO: 22) |
| Human Smo | NM_005631.4 | Forward 5'-GTGAGTGGCATTTGTTTTGTGGGC-3' | (SEQ ID NO: 23) |
| | | Reverse 5'-CAGGCATTTCTGCCGGGGCA-3' | (SEQ ID NO: 24) |
| Human Gli1 | NM_005269.2 | Forward 5'-GCCCCCATTGCCCACTTGCT-3' | (SEQ ID NO: 25) |
| | | Reverse 5'-TGCAGGGGACTGCAGCTCC-3' | (SEQ ID NO: 26) |
| Human Gli2 | NM_005270.4 | Forward 5'-GGCCGCCTAGCATCAGCGAG-3' | (SEQ ID NO: 27) |
| | | Reverse 5'-CACCGCCAGGTTGCCCTGAG-3' | (SEQ ID NO: 28) |
| Human beta-actin | NM_001101 | Forward 5'-GGACTTCGAGCAAGAGATGG-3' | (SEQ ID NO: 29) |
| | | Reverse 5'-ATCTGCTGGAAGGTGGACAG-3' | (SEQ ID NO: 30) |

(Flow Cytometry)

A cultured monkey corneal endothelial cell was seeded on a 6-well plate coated with FNC Coating Mix, and cultured under conditions of 37° C. and 5% $CO_2$ for 14 days. Cells were peeled with TrypLE™ Select and recovered. For fractionating GPR49/LGR5-positive cells, 1% BSA was added to recovered cells, and incubated at room temperature for 15 minutes to perform blocking. As a primary antibody, anti-rabbit GPR49/LGR5 and Alexa™ Fluor 488-labeled goat anti-rabbit IgG <concerning both of them, see the above Lakes, N.J.) was used. For analysis of data, an attached software was used.

(Measurement of Cell Area)

Each isolated cell fraction was centrifuged, and re-suspended in a culture medium. Cells (about 100 cells/ml) were placed in a 6-well plate, and photographed under an inverted microscope. The areas of cells were randomly measured using the Scion Image software (200 cells/fraction), and statistically analyzed [Nakamura T et al., Stem Cells., 2007; 25: 628-638].

(Gene Introduction; RNA Interference)

For preparing a lentivirus particle containing GPR49/LGR5 shRNA virus vector, GPR49/LGR5 MISSION (registered trademark) shRNA Plasmid DNA (Sigma-Aldrich) was purchased (Table 2).

TABLE 2

Structure of GPR49 shRNA

| shRNA | Clone ID | Insert sequence (Mspi-Sense-loop-antisense-terminator) |
|---|---|---|
| shGPR49-587 | NM_03667.2-1085s1c1 | CCGGCCGTCTGCAATCAGTTACCTACTCG AGTAGGTAACTGATTGCAGACGGTTTTT (SEQ ID NO: 31) |
| shGPR49-588 | NM_03667.2-2425s1c1 | CCGGCTTACATTTATCAGTCCTGAACTCG AGTTCAGGACTGATAAATGTAAGTTTTT (SEQ ID NO: 32) |
| shGPR49-589 | NM_03667.2-2286s1c1 | CCGGGCTCTACTGCAATTTGGACAACTCG AGTTGTCCAAATTGCAGTAGAGCTTTTT (SEQ ID NO: 33) |
| Non-Target (NT) | none | CCGGCAACAAGATGAAGAGCACCAACTCG AGTTGGTGCTCTTCATCTTGTTGTTTTT (SEQ ID NO: 34) |

In addition, as a GPR49/LGR5 expression vector, a vector assigned from Satoshi Kawasaki, Ophthalmology Department, Kyoto Prefectural University of Medicine was used. A method for preparing this vector is as follows.

That is, for constructing this vector, a lentivirus plasmid vector expressing an objective gene (herein, GPR49/LGR5) was used. As a vector for inserting the objective gene, the present inventors used a commercially available lentivirus vector (pLenti6.3_V5-TOPO; Invitrogen). An amplification reaction was performed using a primer pair including the whole coding sequence of a specified gene and using cDNA as a template, and the resultant was gel-purified, and ligated with a lentivirus plasmid vector.

Upon expression of this lentivirus, for production and infection, a protocol used for shRNA previously reported by a part of the present inventors (Nakatsukasa M. Kawasaki S, Yamasaki K, Fukuoka H, Matsuda A, Tsujikawa M, Tanioka H, Nagata-Takaoka M, Hamuro J, Kinoshita S, Am J Pathol. 2010 September; 177 (3): 1344-55.) was modified for use. In brief, lentivirus plasmid DNA was transfected into HEK 293T cells using ViraPower™ Lentiviral Packaging Mix (Invitrogen) which was a packaging plasmid mixture containing pLP1, pLP2 and pLP/VSVG plasmids, and 14 µl of Fugene HD as a transfection reagent. After 18 hours, a medium was removed by suction, and replaced with a complete medium (DMEM supplemented with 10% FBS; hereinafter, also referred to as "culture medium"), and the quality of lentivirus particles was evaluated.

More particularly, HEK293T cells were seeded on a culture medium obtained by adding 10% FBS to DMEM, at a density of $9.0 \times 10^5$ cells/25 cm$^2$. After culture for 24 hours, OPTIMEM-I, FuGENE (registered trademark) HD Transfection Reagent (Roche Applied Science) and Lentiviral Packaging Mix (Sigma-Aldrich (MISSION Lentiviral Packaging Mix) or Invitrogen) were added, and the resultant was incubated under conditions of 37° C. and 5% $CO_2$. After 18 hours, the medium was exchanged with a culture medium, and cells were cultured under conditions of 37° C. and 5% $CO_2$. After 24 hours, a culture medium containing lentivirus particles was recovered. For measuring the titer of the recovered lentivirus, the HIV-1 p24 Antigen ELISA kit (ZeptoMetrixCorporation, Buffalo, N.Y., USA) was used. In addition, as a control, Non-Target shRNA Control Vector (Sigma-Aldrich) having a random sequence was used. Cultured human and monkey corneal endothelial cells were seeded on a 6-well plate (5000 cells/well; 6-well plate coated with FNC Coating Mix (registered trademark)) or an 8-well chamber slide (500 cells/well), and cultured under conditions of 37° C. and 5% $CO_2$. After 24 hours, lentivirus particles prepared and 4 µg/ml hexadimethrine bromide (Sigma-Aldrich, also referred to as Polybrene) were added, and the cells were transfected under a conditions of 37° C. and 5% $CO_2$. After 24 hours, a medium was exchanged with a culture medium containing 0.4 µg/ml puromycin (Calbiochem), and a puromycin-resistant cell was selected. A puromycin-resistant colony was cultured in the presence of 0.4 µg/ml puromycin, and a medium was exchanged every 2 days.

(Construction of Lentivirus Plasmid Vector for Gene Expression)

For constructing a lentivirus plasmid vector expressing an objective gene, a commercially available lentivirus vector (pLenti6.3_V5-TOPO; Invitrogen) was used. A primer pair surrounding the whole coding sequence of a specified gene was used to amplify cDNA, gel-purified and, then, ligated into a lentivirus plasmid vector.

Production and infection of a lentivirus for expression were performed by a modified version of a protocol by the present inventors, which was used with respect to shRNA [Nakatsukasa M et al., Am J Pathol., 2010; 177: 1344-1355]. In brief, lentivirus plasmid DNA was transfected, together with a plasmid packaging plasmid mixture ViraPower™ Lentiviral Packaging Mix (Invitrogen) containing pLP1, pLP2 and pLP/VSVG plasmids, into HEK293T cells by using FuGENE (registered trademark) HD as a transfection reagent. After 18 hours, the medium was sucked and exchanged with a complete medium, and the amount of lentivirus particles was evaluated.

(Gene Introduction)

The culture supernatant containing virus particles having infection ability were recovered, and transferred to human CEC of 5000 cells/well in a 6-well plate containing FNC Coating Mix (registered trademark). The supernatant was applied on cultured CEC in the presence of 4 µg/ml Polybrene. Upon collection of a puromycin-resistant colony, cells were cultured in the presence of 0.4 µg/ml puromycin, and the medium was exchanged every 2 days.

(Western Blotting)

For Western blotting, the following rabbit polyclonal antibodies: anti-LRP6, p-LRP6 (Cell Signaling Technology, Inc., Beverly, Mass.), as well as the following mouse monoclonal antibodies: β-catenin (BD Biosciences) and β-actin (Sigma-Aldrich, St. Louis, Mo.); were used. As a secondary antibody, HRP-labeled anti-rabbit or mouse IgG (GE Healthcare, Piscataway, N.J.) was used. Recombinant human SHH, purmorphamine, cyclopamine and RSpos were purchased from R&D Systems Inc. (Minneapolis, Minn.).

Cultured human CEC was washed with PBS, and then, rinsed with a lysis buffer containing PBS, 1% TRITON™ X-100, 0.5 M EDTA, phosphatase inhibitor cocktail 2 (Sigma-Aldrich) and phosphatase inhibitor cocktail (Roche). Detection of activated β-catenin (non-membrane-bound type) was implemented according to the protocol previously reported [Aghib D F et al., Exp Cell Res., 1995; 218: 359-369]. In brief, a cell lysate treated with Con A Sepharose™ 4B (GE Healthcare) was incubated at 4° C. for 1 hour. After centrifugation at 4° C. for 10 minutes, the supernatant was transferred into a new tube, Con A Sepharose™ was added to each tube, and the resultant was incubated at 4° C. for 1 hour. Finally, after simple centrifugation, the supernatant was transferred into a new tube, and the protein concentration was determined.

Then, the protein was separated by SDS-PAGE, and transferred to a PVDF membrane. Thereafter, the membrane was blocked with 1% ECL Advance Blocking Reagent (GE Healthcare) in a TBS-T buffer, and incubated at 4° C. overnight together with a primary antibody. After washing in a TBS-T buffer three times, the PVDF membrane was incubated together with an appropriate HRP-labeled anti-rabbit or mouse IgG secondary antibody at room temperature for 1 hour. The membrane was photosensitized with ECL Advance Western Blotting Detection Kit (GE Healthcare), and observed by LAS3000S imaging system. (Fuji Film Co., Ltd., Tokyo).

Each Example and results are shown below.

Example 1

Expression of Stem Cell Marker in Whole Layer Human Corneal Tissue

An in vivo expression pattern of GPR49/LGR5 in human CEC was investigated by an indirect immunostaining method. For comparison, Nestin and ATP binding set subfamily G member 2 (ABCG2) which were markers of an immature cell and a precursor cell were also investigated.

Figures 1, 2:
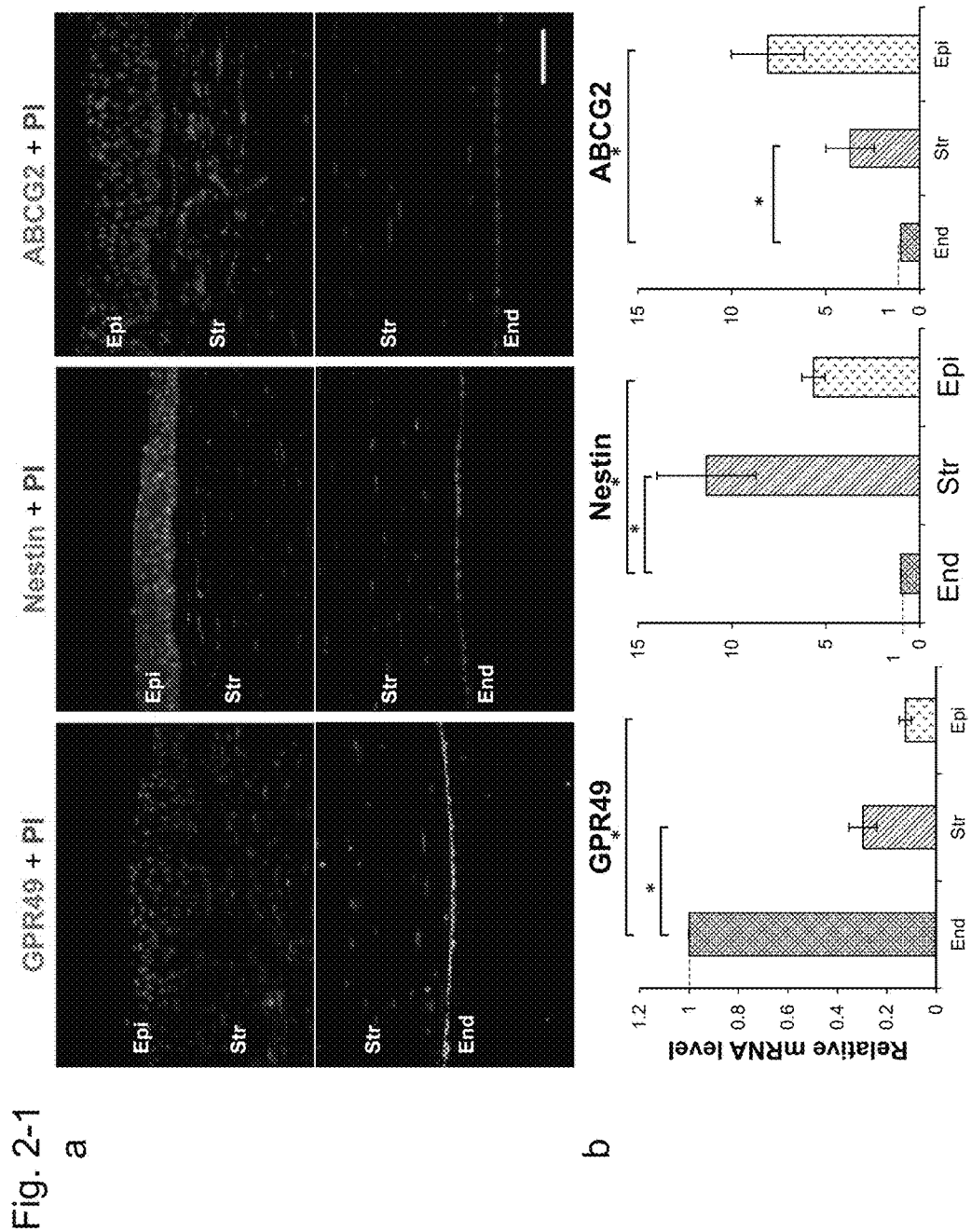
FIG. 2 shows expression of GPR49/LGR5 in the human cornea. a. shows, from the left side, the immunostaining in a human corneal slice of GPR49/LGR5, nestin and ABCG2. The scale bar is 100 μm. In each photograph, from the upper side, parts corresponding to epithelium (Epi), stroma (Str) and endothelium (End) are shown. b. shows, from the left side, the real time PCR of GPR49/LGR5, nestin and ABCG2. The vertical axis shows the relative level of mRNA, when the level of corneal endothelium is set to be 1. N=4. Epi: corneal epithelium; Str: corneal stroma; End: corneal endothelium. The error bar shows S.E. *In Student's t-test, p<0.05.
Figure 2:
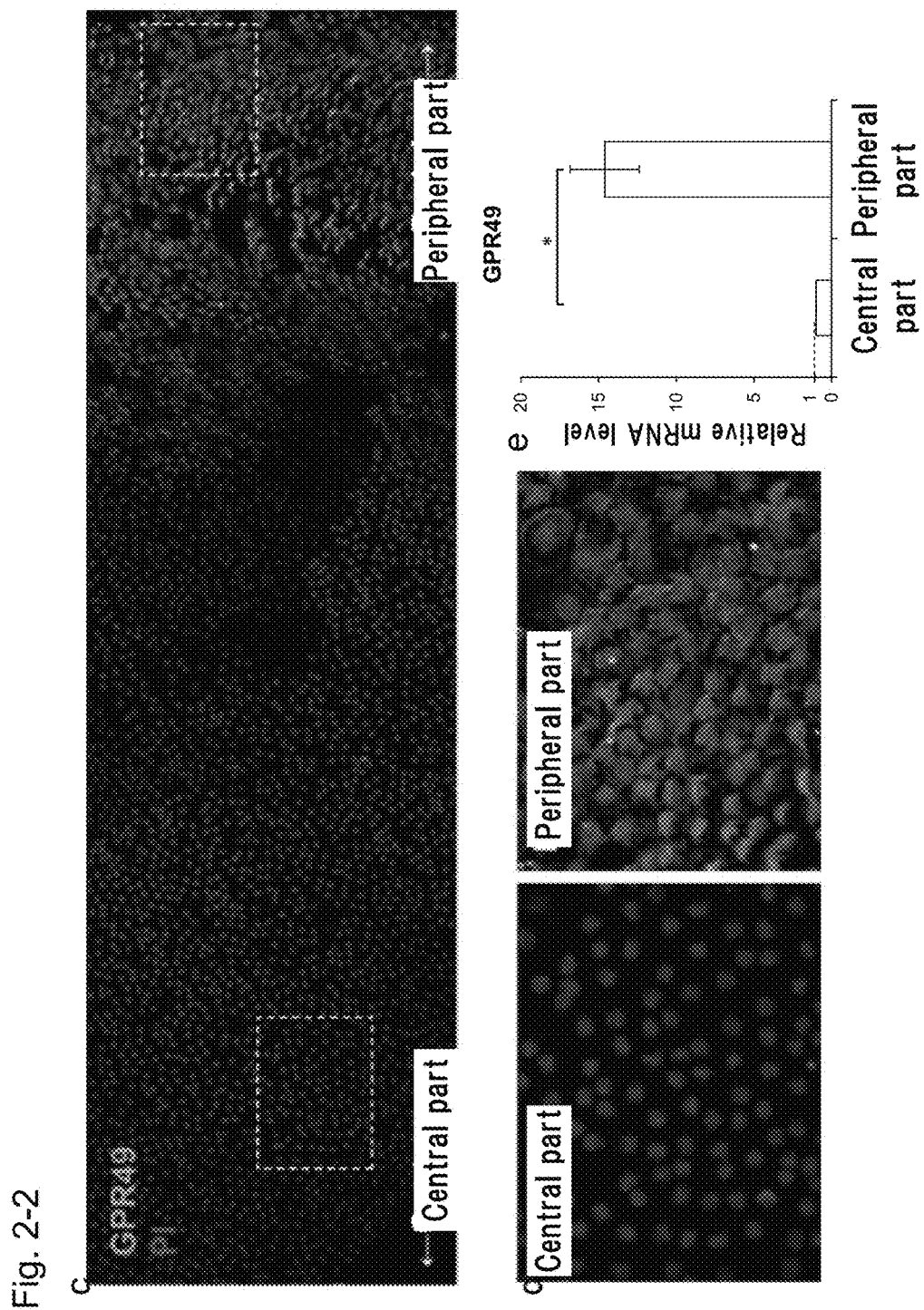

In order to retrieve a protein to be expressed specifically for corneal endothelial cells, immunostaining was comprehensively performed using the already reported stem cell marker (FIG. 2a). As a result, strong expression of GPR49/LGR5 was recognized specifically for corneal endothelial cells. As a comparison subject, Nestin (Lendahl U et al., Cell, 1990) which was an undifferentiated cell marker and ABCG2 (Chen et al., Stem Cells, 2004) which was expressed specifically for limbus corneae basal cells were used.

When CEC of these tissues were investigated in this manner, strong expression of GPR49/LGR5 was observed, particularly, in a peripheral region. However, GPR49/LGR5 was only minimally expressed in a corneal epithelium and a corneal stroma (FIG. 2a). It was found that Nestin is expressed over the whole cornea to a moderate degree, and that ABCG2 is expressed mainly in the basal cell layer of a corneal epithelium, and is weakly expressed in a stroma and an endothelium of a cornea (FIG. 2a).

Strong expression of Nestin was observed in the whole corneal layer. Strong expression of ABCG2 was observed in corneal epithelial basal cells, and expression was also observed in a corneal parenchyma and a corneal endothelium. The amounts of expression of mRNA of GPR49/LGR5, Nestin and ABCG2 were compared by real time PCR (FIG. 2b). The amounts of expression of Nestin mRNA and ABCG2 mRNA were significantly elevated in a corneal epithelium and a corneal parenchyma as compared with a corneal endothelium. On the other hand, the amount of expression of GPR49/LGR5 mRNA was significantly elevated in a corneal endothelium.

In this way, real time PCR showed that the average GPR49/LGR5 mRNA expression was significantly upregulated in CEC as compared with parenchymal cells and epithelial cells of a cornea (*p<0.05) (FIG. 2b). To the contrary, the expression levels of Nestin and ABCG2 in the parenchymal cell and the epithelial cell of a cornea were higher than the expression levels in CEC (FIG. 2b). Therefore, it was found that expression of GPR49/LGR5 is most remarkable in CEC among corneal tissues.

Therefore, GPR49/LGR5 was determined to be one of proteins which were expressed specifically for corneal endothelial cells.

Example 2

Localization of Expression of GPR49/LGR5 in Human Corneal Whole Tissue Section

Then, the present inventors studied a localization pattern of GPR49/LGR5 using the whole mount immunofluorescence method.

In the present Example, in order to investigate localization of expression of GPR49/LGR5 in a corneal endothelial tissue, a Descemet's membrane containing corneal endothelial cells was peeled from a corneal tissue, and the amount of expression was compared and studied by immunostaining and real time PCR (FIG. 2c).

As a result of the immunostaining, as shown in FIGS. 2d to e, strong expression of GPR49/LGR5 was recognized in a cell membrane and a cytoplasm of an endothelial cell in a corneal periphery (FIG. 2d). In addition, the amount of expression of GPR49/LGR5 mRNA was also elevated in a peripheral corneal endothelium as compared with the central portion (FIG. 2e).

It was found that expression of GPR49/LGR5 is increased in a peripheral region, in CEC, and that the expression level thereof is gradually decreased towards the central region of CEC (FIGS. 2c, d). Real time PCR clearly showed that expression of GPR49/LGR5 in a peripheral region is upregulated as compared with the central region (diameter 7 mm) (*p<0.05) (FIG. 2e). These findings show that GPR49/LGR5 is inherently expressed in peripheral CEC, in a corneal tissue.

Example 3

Expression of GPR49/LGR5 in Cultured Human Corneal Endothelial Cell

In the present Example, expression of GPR49/LGR5 in a cultured human corneal endothelial cell was investigated.

A human corneal endothelial cell is poor in the proliferation ability in a living body, and cell culture outside a living body is also extremely difficult. Previously, a variety of culture methods have been studied, but a subculture method in the state where a hexagonal cobblestone cell form is maintained has not been established. Then, the amount of expression of GPR49/LGR5 upon culture of a human corneal endothelial cell was studied by the existing method. As a comparison subject, Nestin was used.

Figures 2, 3:
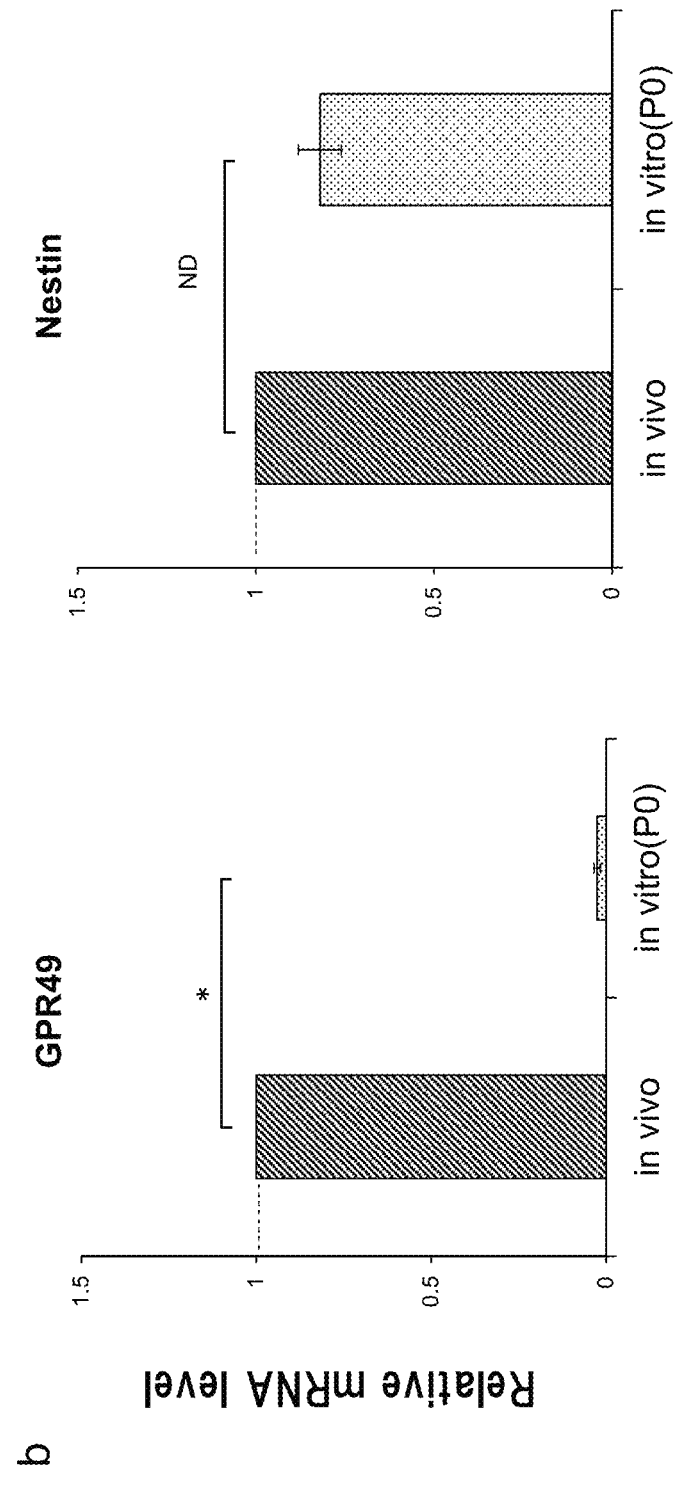
FIG. 3 shows expression of GPR49/LGR5 in a cultured corneal endothelial cell. a. shows the immunostaining of GPR49/LGR5 and nestin in a cultured human corneal endothelial cell (cHCEC). From the left side, a phase contrast image, a GPR49 PI image and a nestin PI image are shown. From the upper side, in vivo, primary culturing (P0), and passage first generation (P1) are shown. The scale bar shows 100 μm.
Figure 3:
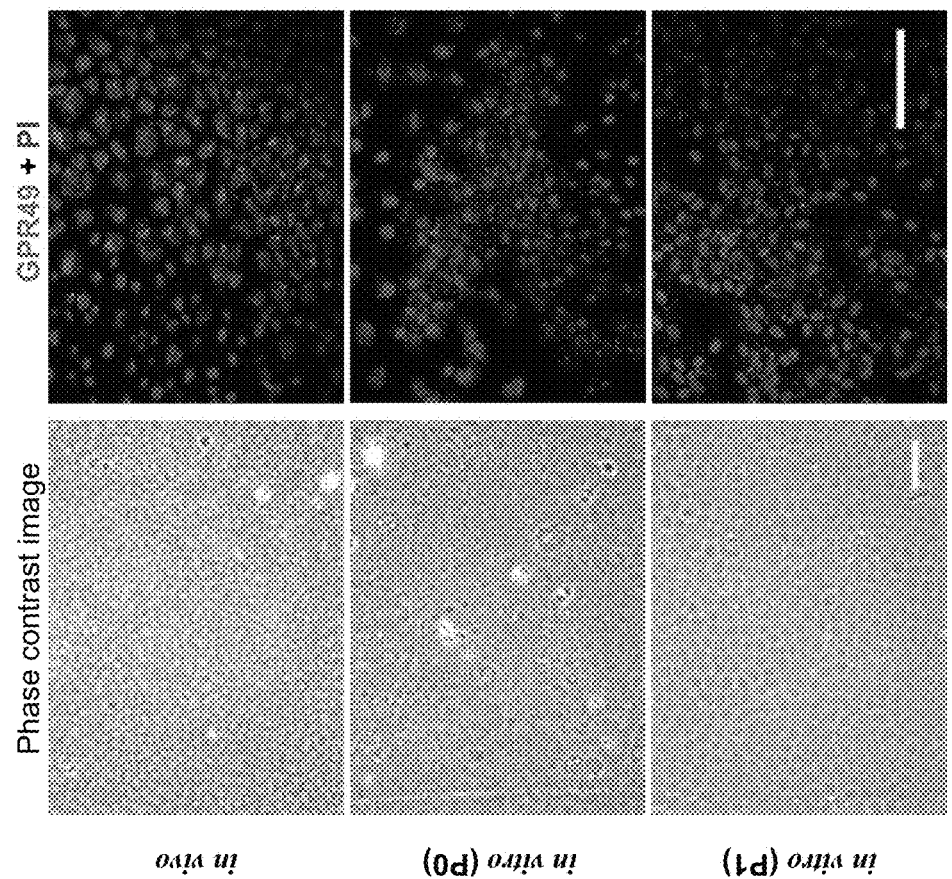

As a result of immunostain, in a corneal tissue (in vivo), very strong expression was observed in both of. GPR49/LGR5 and Nestin (FIG. 3a). In a primary cultured cell, expression of GPR49/LGR5 was not recognized, but expression of Nestin was confirmed. In a subculture cell (in vitro P0), expression of GPR49/LGR5 could not be confirmed, but expression of Nestin was confirmed, although expression was reduced. In addition, in a subculture cell (in vitro P1), cell differentiation was made, and an increase in nucleous was observed. When the amount of each mRNA of a corneal endothelial cell cultured under the same condition was analyzed, the amount of expression of GPR49/LGR5 mRNA was significantly decreased in the culture envelopment, but little decrease in the amount of expression of Nestin mRNA was recognized (FIG. 3b).

In this way, a phase contrast microphotograph of in vivo human CEC revealed that these presented a confluent monolayer of uniform hexagonal cells having a smaller size (FIG. 3a). To the contrary, it was found that cultured CEC (P0, P1) is extended, and is not uniform hexagon (FIG. 3a). Immunostaining showed that GPR49/LGR5 is sufficiently expressed in an in vivo peripheral CEC (FIG. 3a). It is worthy of special mention that, in in vitro cultured CEC (P0, P1), only minimum expression of GPR49/LGR5 was recognized (FIG. 3a). Real time PCR showed that the average GPR49/LGR5 mRNA expression is significantly downregulated in in vitro CEC, as compared with expression in in vivo CEC ($*p<0.05$) (FIG. 3b). To the contrary, the expression revels of Nestin in both of in vivo and in vitro were the same (FIGS. 3a, b).

Example 4

Expression of GPR49/LGR5 in Cultured Monkey Corneal Endothelial Cell

A monkey corneal endothelial cell has a nature that the proliferation ability in a living body is poor like human, but establishment of a stable subculture method has been succeeded (Okumura et al., IOVS 2009, Vol. 50, No. 8, 3680-3687). Then, the amount of expression of GPR49/LGR5 when a monkey corneal endothelial cell was subjected to subculture was evaluated.

As a result of immunostaining, it was found that expression of GPR49/LGR5 can be stably maintained in a corneal endothelial cell subjected to subculture (FIG. 3c). The amount of expression of GPR49/LGR5 mRNA tended to be reduced by subculture as compared with a monkey corneal tissue, but the amount of expression could be maintained (FIG. 3d).

In this way, a phase contrast microphotograph of monkey CEC showed that both of in vivo and in vitro (P0, P1) cells present a confluent monolayer of a uniform hexagonal cell having a smaller size (FIG. 3c). Immunostaining of these cells showed that GPR49/LGR5 is expressed to a moderate degree in both of in vivo and in vitro (FIG. 3c), but the in vitro average GPR49/LGR5 mRNA expression was gradually decreased, as subculture progressed ($*p<0.05$) (FIG. 3d). In view of these findings, it seems that, when cells of human and monkey are used, GPR49/LGR5 can be an important regulating factor for maintaining the undifferentiated state of in vitro CEC.

From the forgoing results, it is understood that GPR49/LGR5 possibly has an important function in in vitro stable culture of a corneal endothelial cell.

Example 5

Study of Cell Biological Characteristic of GPR49/LGR5-Positive Cell

In order to study the cell biological characteristic of a GPR49/LGR5-positive corneal endothelial cell, analysis was performed using FACS. Using a cultured monkey corneal endothelial cell which was confirmed to be able to be subjected to subculture in the state where expression of GPR49/LGR5 was maintained, the cell sizes and the proliferation abilities of a GPR49/LGR5-positive cell (GPR49/LGR5+) and a GPR49/LGR5-negative cell (GPR49/LGR5−) were compared and studied.

Figures 3, 4:
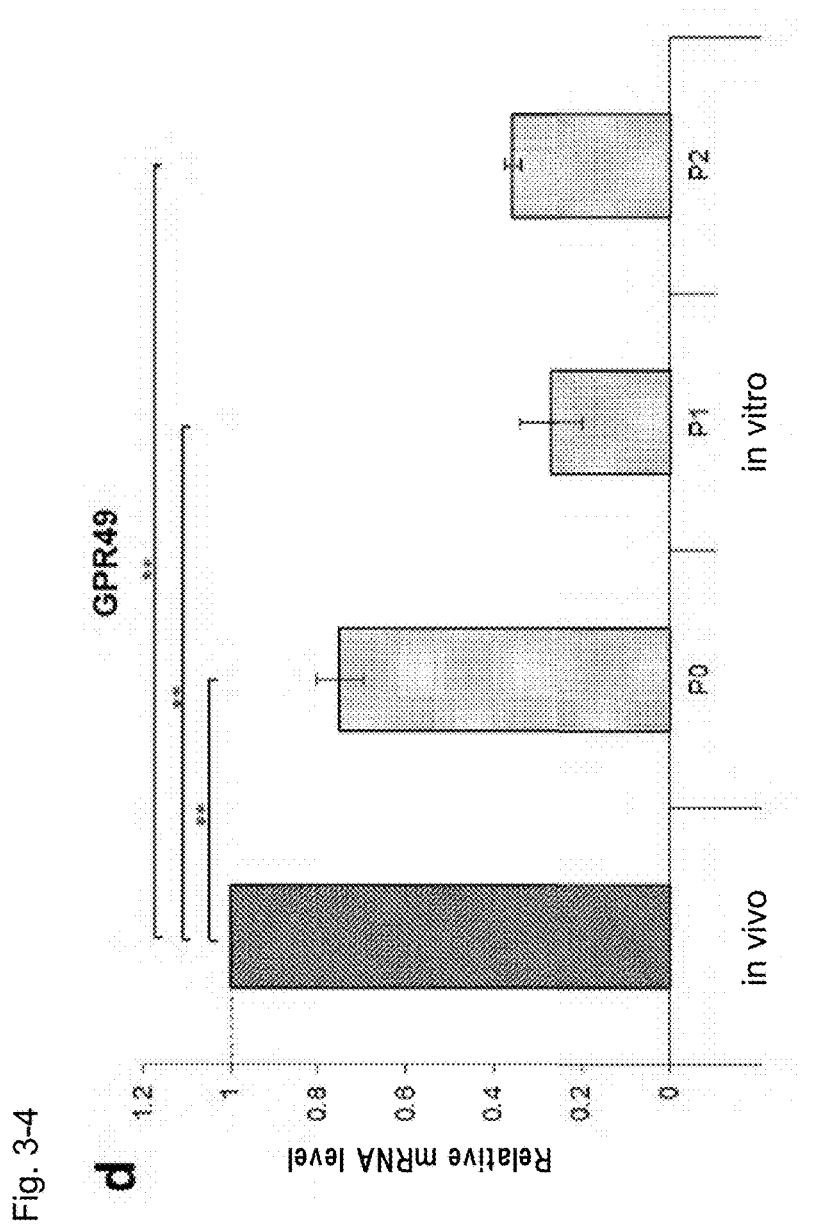
FIG. 4 shows the characterization of a GPR49/LGR5-positive cell. a. shows the phase contrast of a GPR49/LGR5-positive cell (GPR49$^+$) after cell sorting on the left side, and shows the phase contrast of a negative cell (GPR49$^-$) on the right side. The scale bar shows 100 μm.
Figures 2, 4:
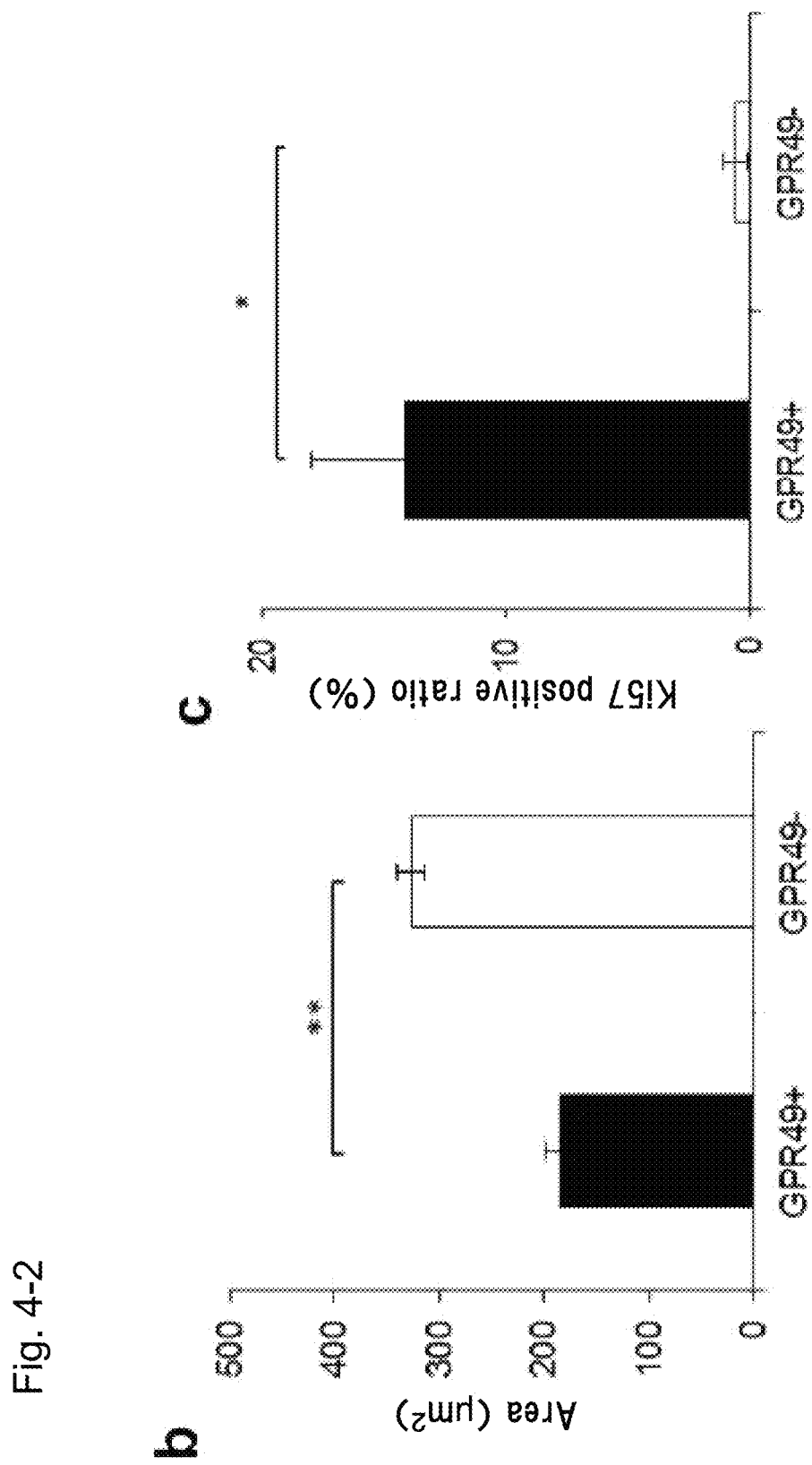
Figures 3, 4:
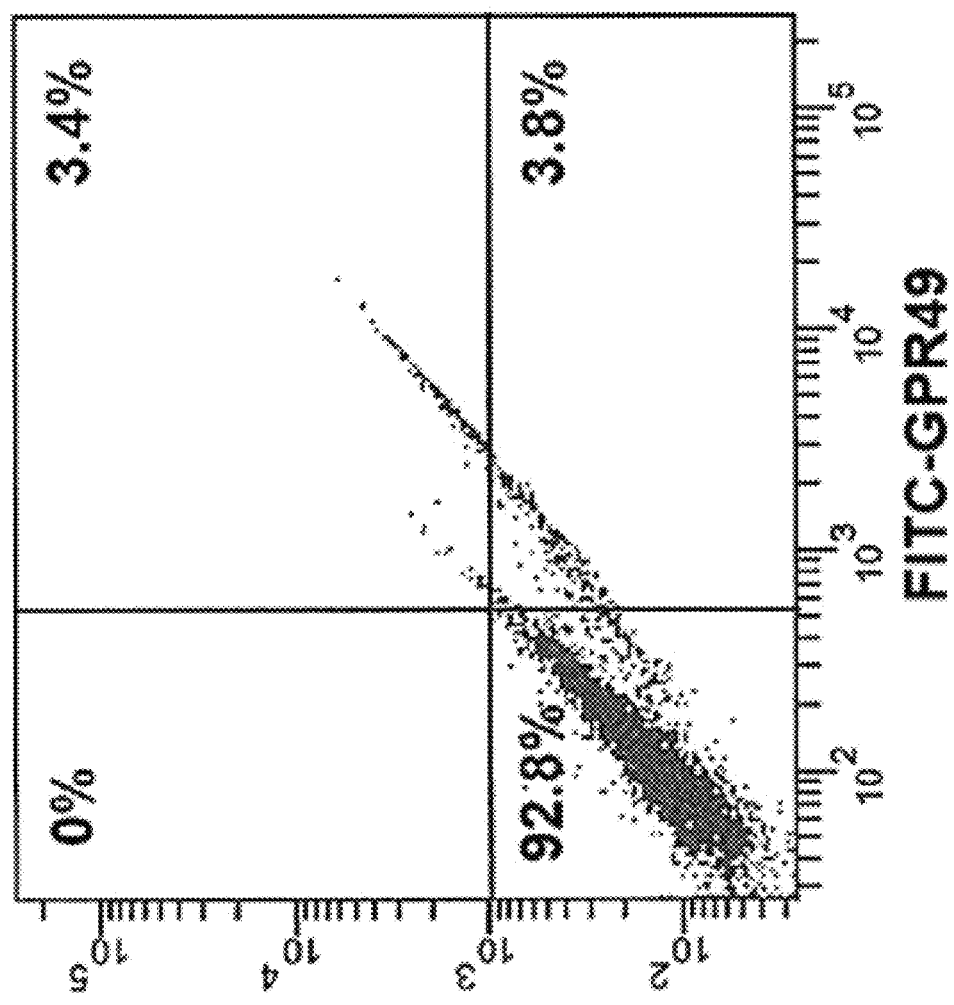

In order to investigate the characteristics of a GPR49/LGR5(+) cell and a GPR49/LGR5(−) cell, a subset of cells was isolated by flow cytometry. In order to inspect a procedure of cell sorting, expression at the protein level was confirmed in a purified fraction by immunofluorescence regarding GPR49/LGR5 (FIG. 4a). Since the highest colony forming ability is found in a minimum keratin-producing cell according to a report [Barrandon Y et al., Proc Natl Acad Sci USA, 1985; 82: 5390-5394], the size of a cell in each of isolated fractions was measured using the Scion Image software.

After cell sorting by FACS, when GPR49/LGR5+ and GPR49/LGR5− were photographed with a fluorescent microscope and the size of each of 35 cells was randomly measured by Image J (Wayne Rasband (NIH) free software), it was found that GPR49/LGR5+ is significantly smaller as compared with GPR49/LGR5− (FIG. 4a, FIG. 4b). Then, it was found that the average size of a GPR49/LGR5(+) cell is significantly smaller than the average size of a GPR49/LGR5(−) cell (184.6±45.8 $\mu m^2$ vs. 326.78±78.8 $\mu m^2$, N=35, $**p<0.01$).

Then, in order to evaluate the state of the cell cycle of each of isolated cell fractions, an isolated cell fraction was cultured on a cell chamber slide. The ratio of a Ki67-labele cell in a GPR49/LGR5(+) cell and that in a GPR49/LGR5(−) cell were 14.2±3.87% and 0.58±0.5%, respectively, and the difference in a Ki67-label index was statistically significant ($*p<0.05$) (FIG. 4c). As a result, it was revealed that the Ki-67-positive cell rate is significantly higher in GPR49/LGR5+ (FIG. 4c). Then, in order to investigate the proliferation ability of each of isolated cell fractions in further detail, FACS was employed concerning double staining of GPR49/LGR5 and Ki67, and in order to make a relationship between GPR49/LGR5 and cell proliferation more clear, a cultured monkey corneal endothelial cell (passage number 3) was double stained with anti-rabbit GPR49/LGR5 and anti-rabbit Ki-67, and analysis by FACS was tried. As a result, among all the cells, GPR49/LGR5+ was 7.2%, and in particular, GPR49/LGR5+/Ki-67+ was 3.4% (FIG. 4d). In addition, a cell of GPR49/LGR5−/Ki-67+ was not observed. FACS analysis showed that while a GPR49/LGR5$^{high}$/Ki67$^{high}$ cell fraction was 3.4%, a GPR49/LGR5$^{high}$/Ki67$^{low}$ cell fraction was 3.8% (FIG. 4d). Most interestingly, all GPR49/LGR5$^{low}$ cell fractions show the low Ki67 level (92.8%), and it is understood that CEC has no proliferation ability without expression of GPR49/LGR5.

Example 6

GPR49/LGR5 as Target Gene of Hedgehog Signal

In the present Example, the function of GPR49/LGR5 in a Hedgehog signal was investigated.

A Hedgehog signal was identified as a signal involved in morphosis at a fetal stage, and thereafter, it was revealed that a Hedgehog signal is also profoundly associated with a stem cell and tumorogenesis of an adult tissue. In addition, it has been reported that HH signaling has an important role in various kinds of biological processes such as differentiation, proliferation and growth of a cell [Barker N et al., Nature, 2007; 449: 1003-1007; Stanton B Z et al., MolBiosyst., 2010; 6: 44-54; Tsuru T et al., Jpn J Ophthalmol., 1984; 28: 105-125]. As a ligand of human, three kinds of proteins of SHH, Indian Hedgehog (Ihh), Desert Hedgehog (Dhh) have been identified. A twelve transmembrane protein Patched1 (Ptch1) which is a receptor suppressively functioning to a signal, in the state where there is no ligand, suppresses cell membrane localization of a seven transmembrane protein Smoothened (Smo), and also inhibits transmission to a downstream signal molecule. Under this situation, a signal is not transmitted to a transcription factor Gli family (Gli1, Gli2, Gli3) located downstream of Smo, and transcription of a target gene does not occur. By binding of a ligand to Ptch1, suppression of Ptch1 on Smo is lost, a signaling pathway from Smo to a transcription factor Gli family is activated, and a target gene such as Cyclin D/E, Myc is transcribed. Both Ptch1 and Gli1 are associated molecules of a signal, a target gene, and an index of activation of a signal.

As described above, GPR49/LGR5 has a high amount of expression in a corneal peripheral part (FIG. 2c, FIG. 2d, FIG. 2e). Then, in order to compare the amounts of expression of mRNA of Hedgehog signal-associated molecules (Shh, Smo, Ptch1, Gli1, Gli2) in a human corneal central endothelial cell and peripheral endothelial cell to define the property of GPR49/LGR5 in CEO at the molecular level, first, expression of a HH signal transmission-associated molecule was investigated.

Figures 1A, 5:
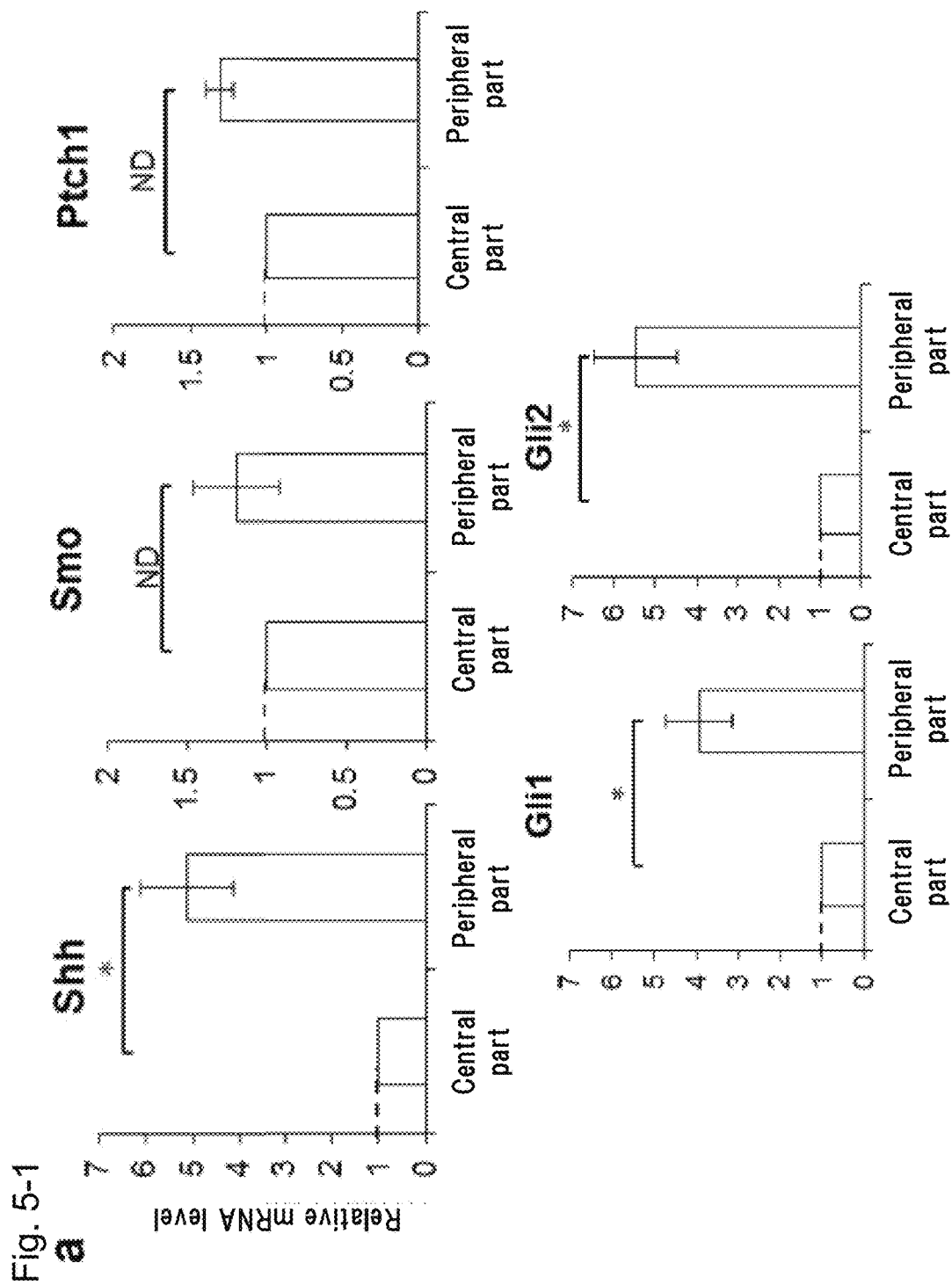
FIG. 5 shows the Hedgehog transmission pathway in cHCEC. a. shows expression of a Hedgehog signal-associated gene (In the upper row and from the left side, Shh, Smo and Ptch1, and in the lower row and from the left side, Gli1 and Gli2). The vertical axis shows the relative level of mRNA, when the level of center is set to be 1.
Figures 3, 5:
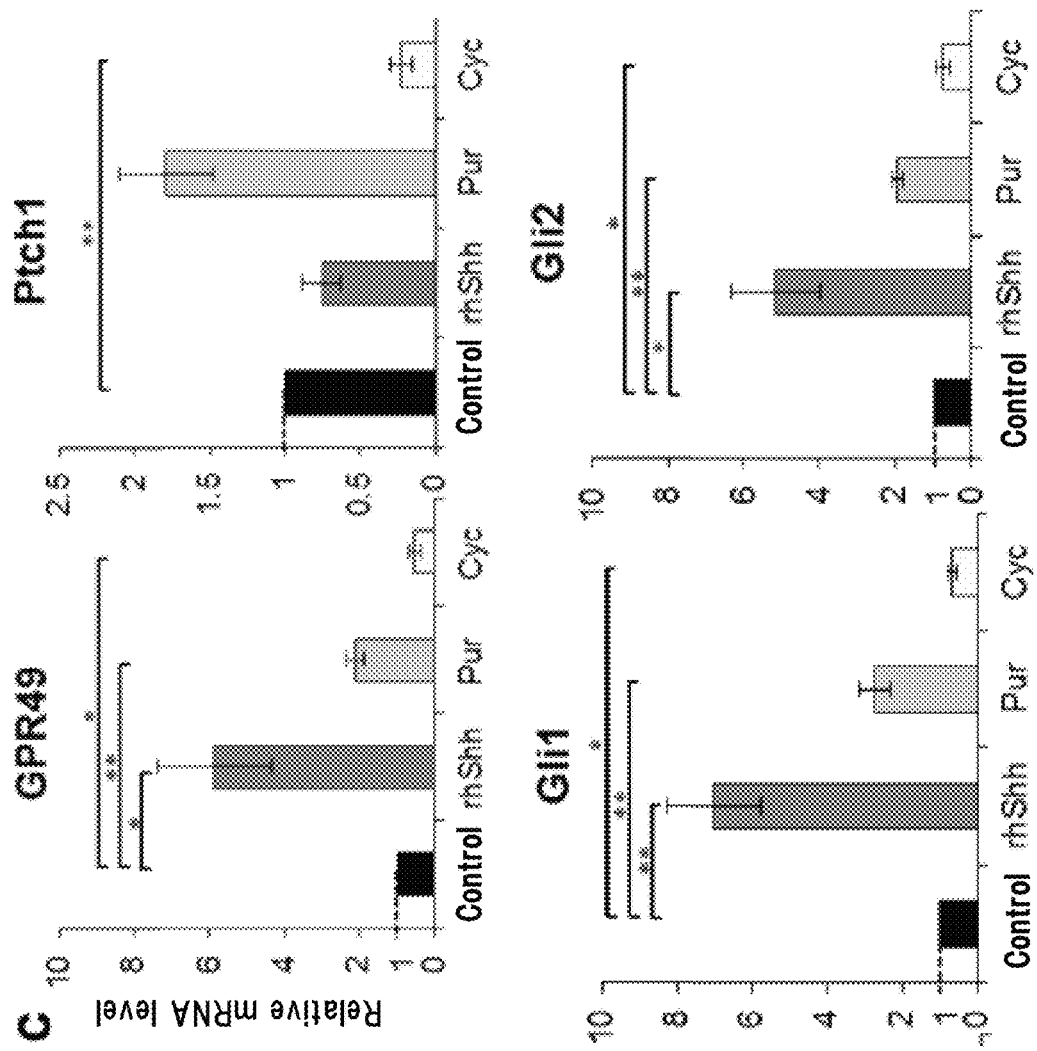
Figures 4, 5:
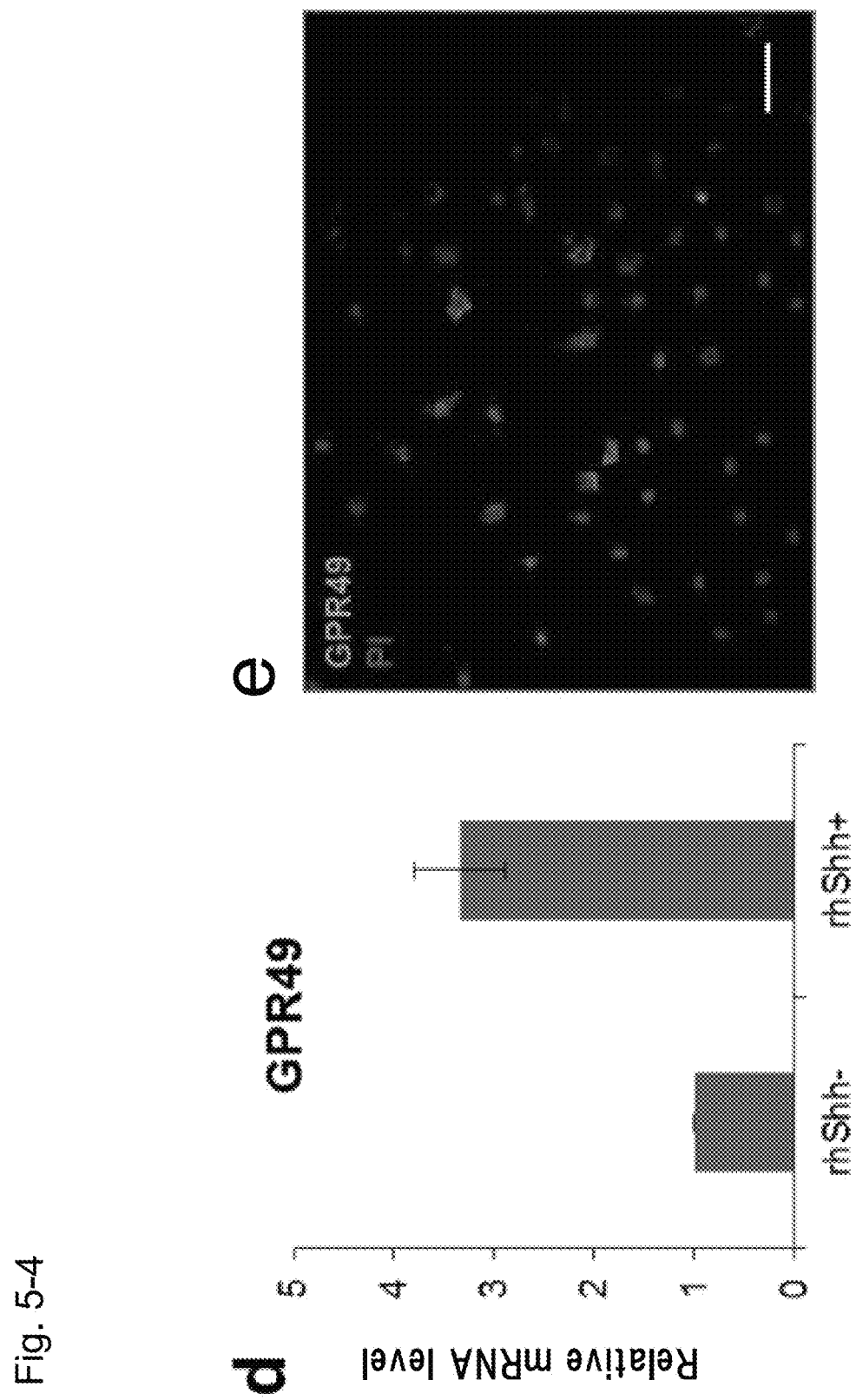
Figure 5:
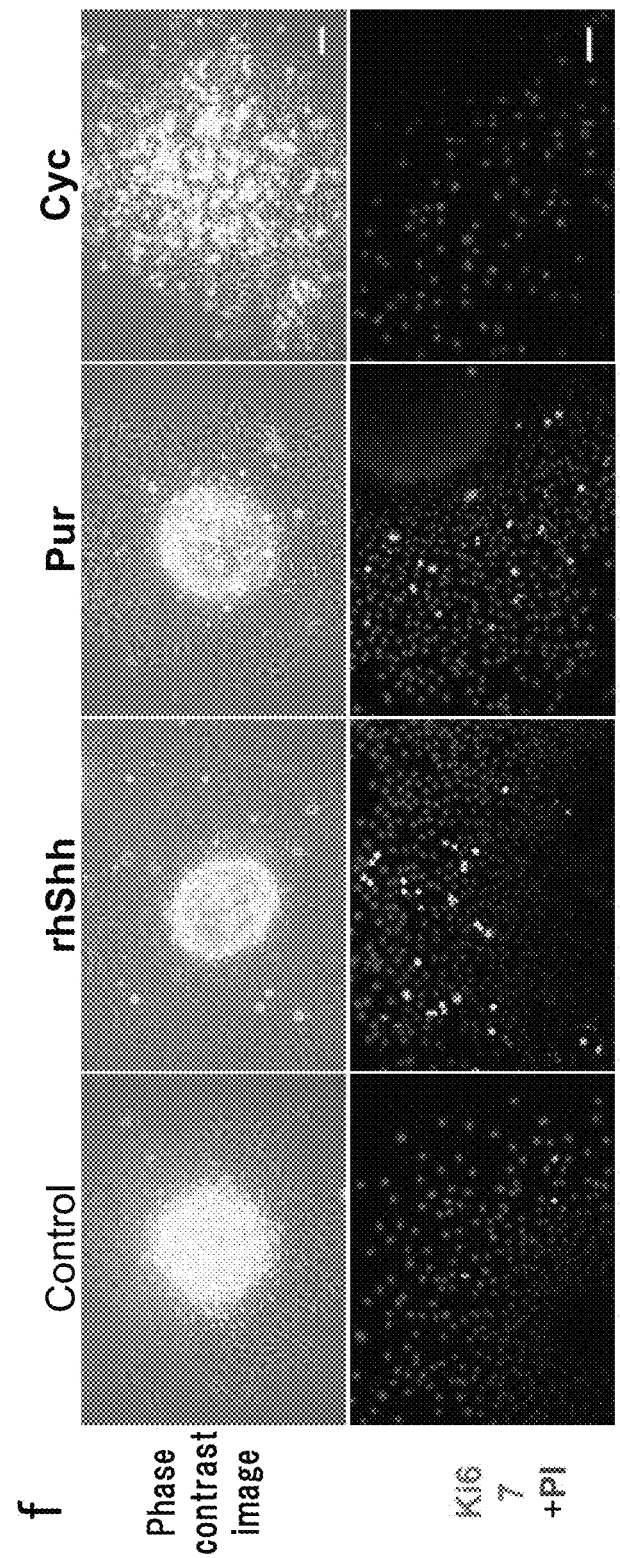
Figures 5, 6:
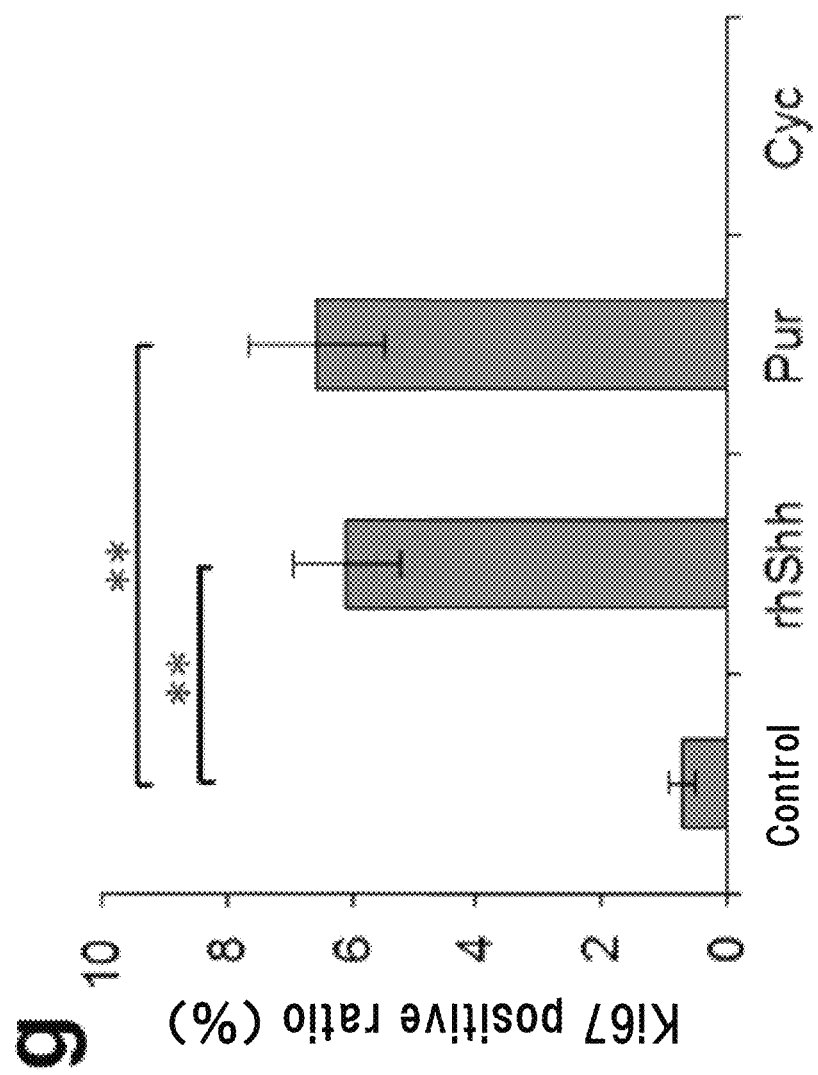
FIG. 6 shows the function of GPR49/LGR5 in a corneal endothelial cell. a. shows the knock down effect of GPR49/LGR5 shRNA. The vertical axis shows the relative level of mRNA, when the level of a control (NT) is set to be 1. From the left side, the effect on GPR49 with NT (control), shGPR49-587, shGPR49-588, and shGPR49-589 is shown.

As a result, it was observed that the amounts (levels of mRNA) of expression of Shh being a ligand, and transcription factors, Gli1 and Gli2, were increased in CEC in a peripheral region, as compared with the amounts of expression in a central region, the amount of expression of a peripheral endothelial cell was elevated, and activation of a signal was recognized (FIG. 5a). On the other hand, the expression levels of Smoothened (Smo) and protein patched homolog 1 (Ptch1) which were each a receptor molecule of the HH pathway were the same, and no difference was seen between such Ptch1 and Smo. Therefore, it was suggested that HH signaling is clearly activated in CEC in a peripheral region and there is variation depending on the place of the HH signaling activity.

In order to investigate a relationship between GPR49/LGR5 and a Hedgehog signal, and determine whether expression of GPR49/LGR5 in CEC was regulated by a HH signaling pathway or not, a relationship between influence of activation or suppression of a Hedgehog signal on GPR49/LGR5 expression, and cell proliferation was studied using recombinant human Sonic hedgehog (rhShh), Purmorphamine being an agonist of Smo (Sinha et al., Nat. Chem. Biol. 2: 29-30, 2006), and Cyclopamine being an antagonist (Chen et al., Genes Dev. 16 (21): 2743-2748, 2002). A human corneal tissue was treated with 100 ng/ml rhShh, 10 µM purmorphamine, and 10 µM cyclopamine, and incubated under conditions of 37° C. and 5% $CO_2$ for 3 days. A Descemet's membrane was peeled from a cornea, and applied to a silane-coating slide, and GPR49/LGR5 and Ki-67 were immunostained. In addition, RNA of a corneal endothelial cell incubated under the same conditions was extracted, and the amount of expression of mRNA was measured by real time PCR.

As a result of immunostaining, in expression of GPR49/LGR5, remarkable increase (upregulation) was observed in both rhShh addition group and purmorphamine addition group, as compared with a control (FIG. 5b). The number of CPR49/LCR5 expressing cells was increased, particularly, in a rhShh addition group, and there was a tendency in a purmorphamine addition group that a GPR49/LGR5-positive cell was strongly expressed. From this, it was presumed that while rhShh functions to activate a signal by binding to Ptch1, purmorphamine is activated by binding to Smo, and thus functions to activate a signal of a GPR49/LGR5 expressing cell. In addition, clear expression suppression was confirmed in cyclopamine. The same result was also confirmed at the mRNA expression level (FIG. 5c). In addition, an expression pattern of Gli1 and Gli2 was the same as that of GPR49/LGR5, but HH activation had no dramatic influence on a HH receptor (Ptch1) (FIG. 5c).

In addition, in order to reveal whether the HH pathway induced CEC proliferation in vivo or not, an immunohistochemical study on Ki67 was performed. Since human CEC is mitotically inactive, and exhibits a weak proliferation ability, or exhibits no proliferation ability in vivo [Joyce N C, Prog Retin Eye Res. 2003; 22: 359-389], a Ki-67-positive cell could not be detected in all groups (FIG. 5b), and therefore, it is considered that promotion of cell proliferation by a Hedgehog signal in a human corneal tissue does not occur, and it is understood that stimulation of only the HH pathway is insufficient for inducing in vivo CEC proliferation.

In order to inspect whether the same result was obtained in a cultured human corneal endothelial cell or not, a primary human corneal endothelial cell was seeded on an 8-well chamber slide, and 100 ng/ml rhShh, 2 µM purmorphamine, and 2 µM cyclopamine were added to a culture medium, and thereafter, the resultant was incubated under conditions of 37° C. and 5% $CO_2$. After 3 days, immunostain of GPR49/LGR5 and Ki-67 was performed. In addition, RNA of a corneal endothelial cell incubated under the same conditions was extracted, and the amount of expression of mRNA was measured by real time PCR.

A cell expressing GPR49/LGR5 was confirmed only in a rhShh addition group (FIG. 5d, FIG. 5e). There was no Ki-67-positive cell in a corneal tissue, but in a cultured corneal endothelial cell, the amount of expression was elevated as compared with a control, with respect to a rhShh addition group and a purmorphamine addition group (FIG. 5f). In a cyclopamine addition group, abnormality of cell morphology and suppression of cell proliferation were recognized.

CEC maintains the ability to proliferate in vitro, according to a report [Engelmann K et al., Invest Ophthalmol Vis Sci., 1988; 29: 1656-1662], and therefore, the present inventors studied whether the HH pathway induced in vitro proliferation of CEC or not, as described above. Expression of Ki67 was found to be upregulated in response to SHH and purmorphamine stimulation, but this was not upregulated in response to cyclopamine (FIG. 5g). These findings show that the HH pathway can induce CEC proliferation under an in vitro situation. The present inventors determined that CEC treated with cyclopamine could not maintain a normal hexagonal form thereof (FIG. 5f). In consideration of these findings, the present inventors first found that GPR49/LGR5 is a target molecule of HH signaling in CEC, and maintenance of CEC is regulated partially by the HH pathway.

Example 7

Suppression of GPR49/LGR5 Gene Expression Using shRNA

In order to make clear a relationship between GPR49/LGR5 and a hedgehog signal, suppression of GPR49/LGR5 expression by shRNA was carried out using a cultured monkey corneal endothelial cell highly expressing GPR49/LGR5.

Figures 1, 6:
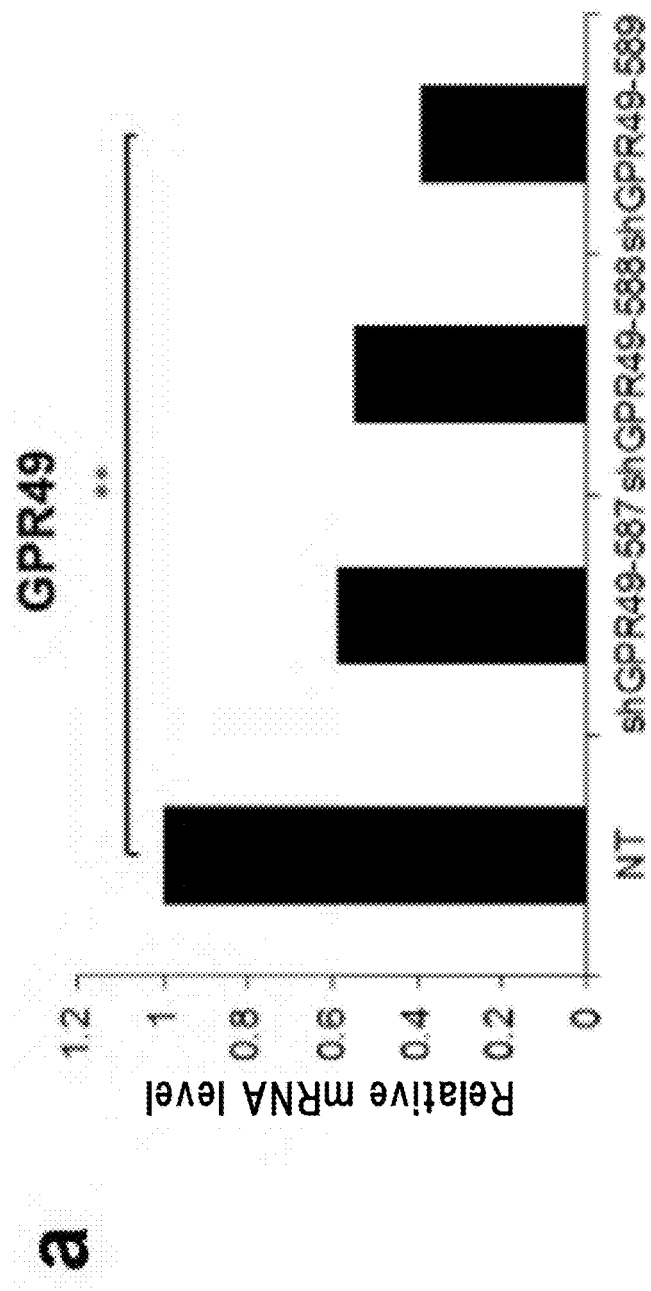
Figures 2, 6:
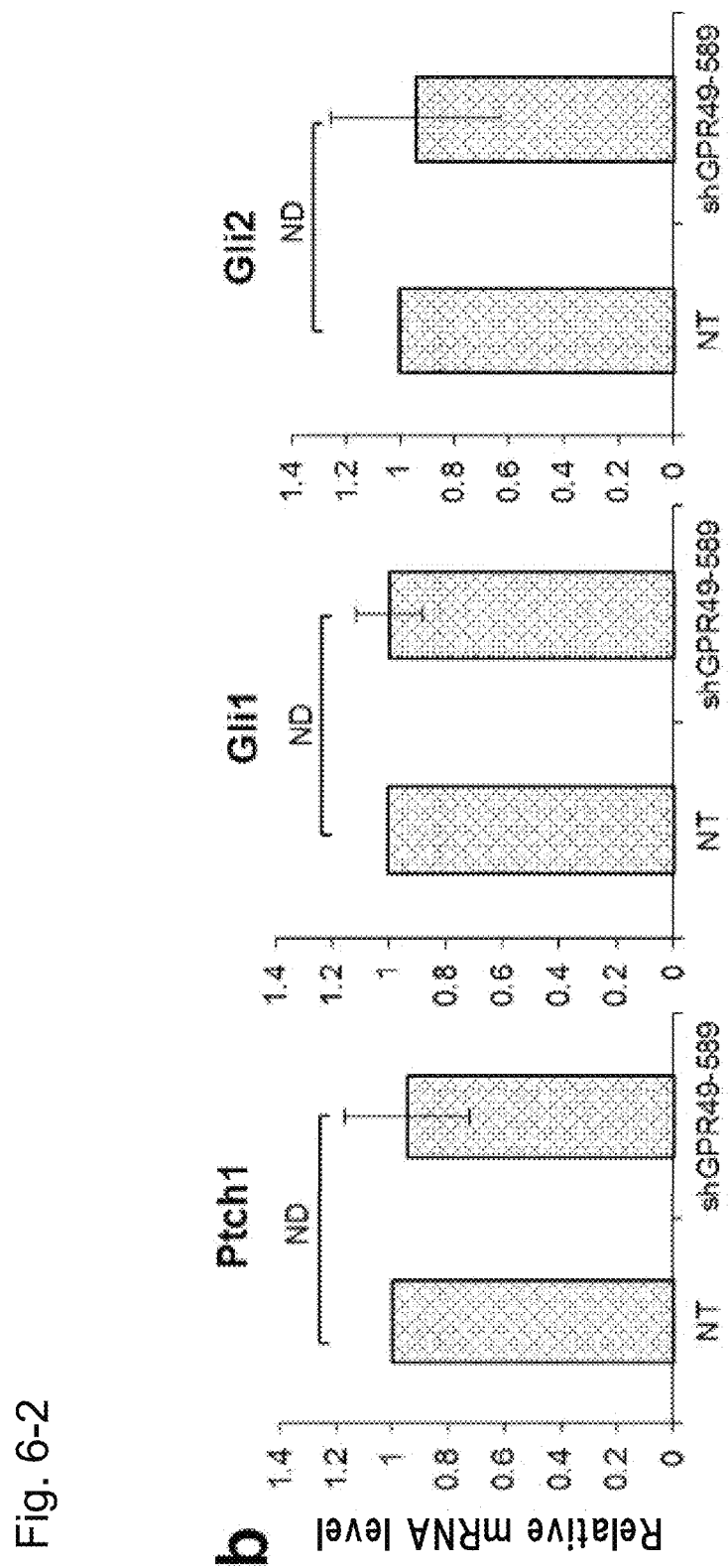
Figures 4, 6:
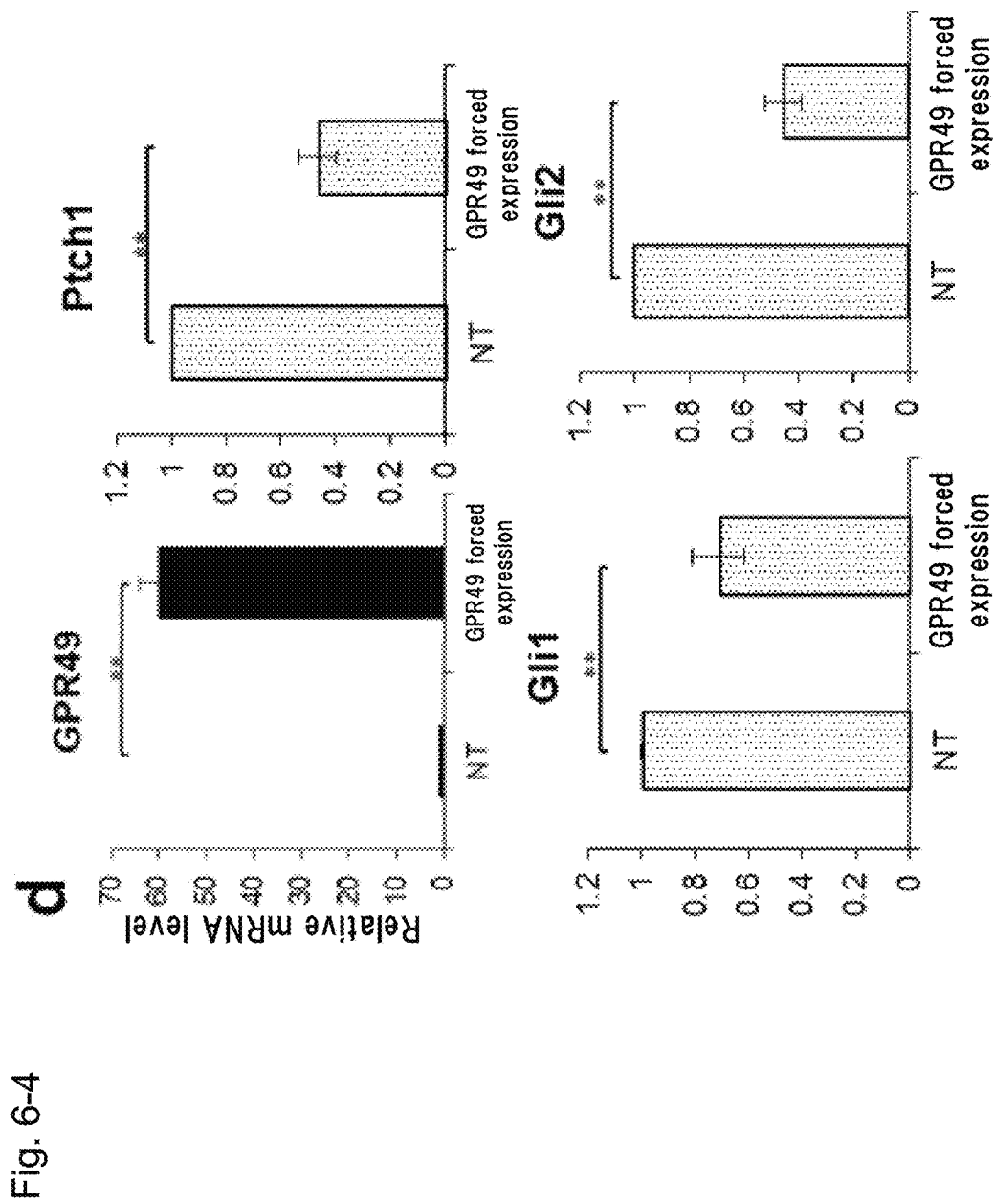
Figure 6A:
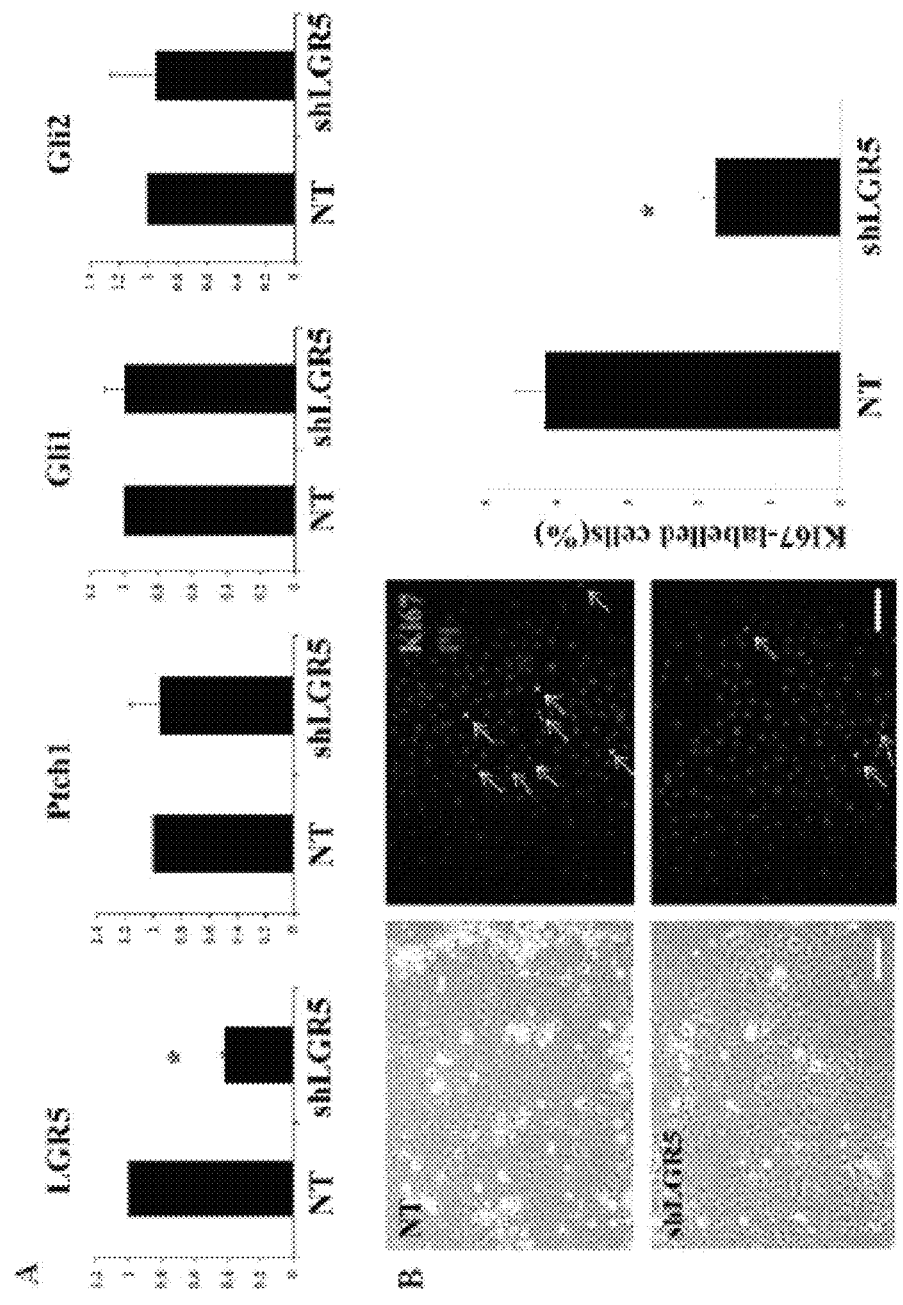
FIG. 6A shows the action of shLGR5 in a human corneal endothelial cell (CDC). (A) shows, from the left side, real time PCR concerning GPR49/LGR5, Ptch1, Gli1 and Gli2 in NT and shLGR-transfected cell. Average±SEM. **P<0.05. N=3. (A) represents the graphs shown in FIG. 6-2 together with GPR49/LGR5, and is partially overlapped. (B) shows a phase contrast microscope image (left column) of Ki67 and the immunostain (light column) of Ki67 in NT (upper row) and shLGR-transfected human CEC (lower row). An arrow shows a Ki67(+) cell. The scale bar is 100 µm. In (B), the right graph shows the results of implementation of immunocytochemistry study concerning percentage of a Ki67 cell in order to demonstrate influence of GPR49/LGR5 gene knock down on CEC proliferation. The left side shows a control (NT), and the right side shows a shLGR5-treated cell (shLGR5).
Figure 6B:
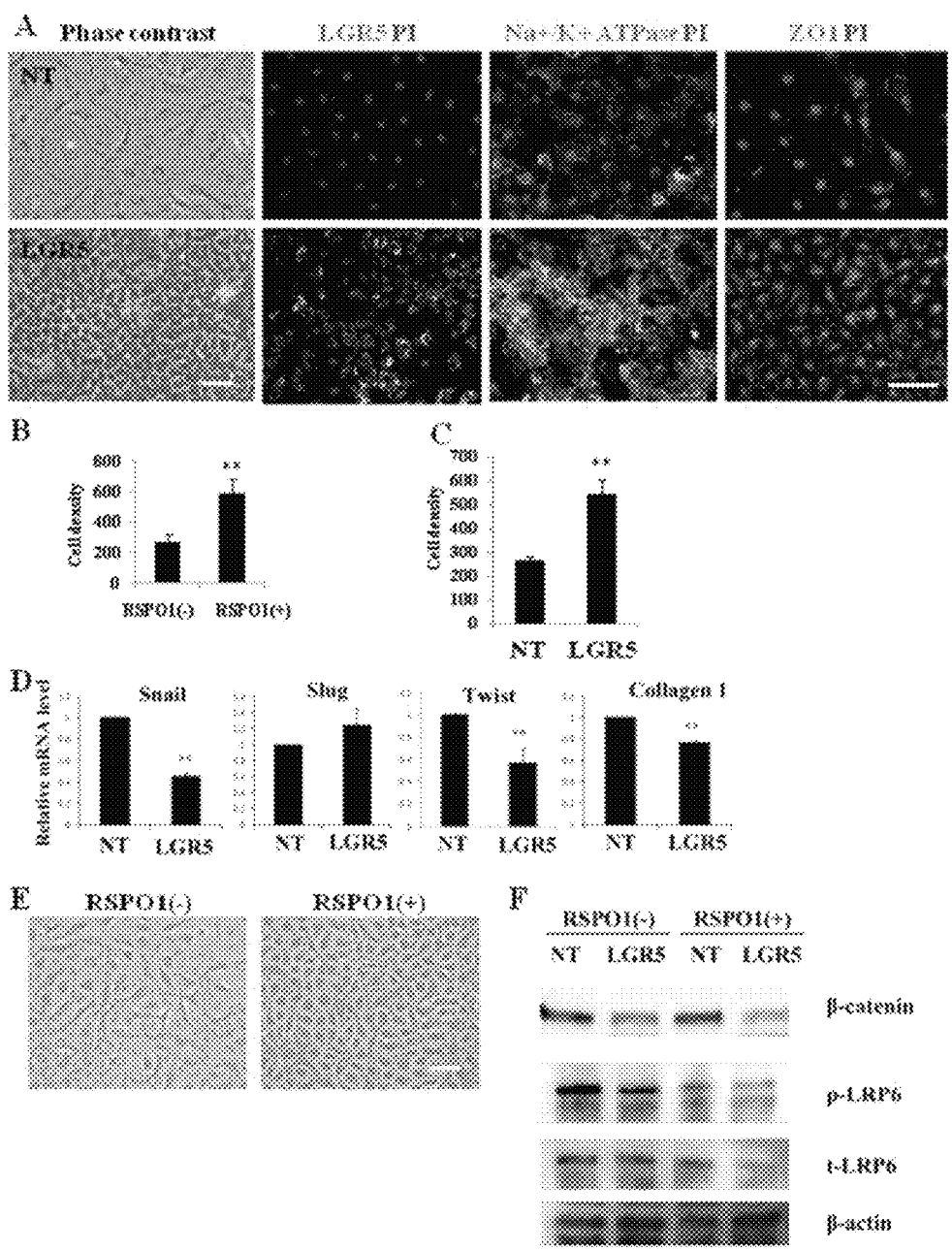
FIG. 6B shows the functions of GPR49/LGR5 and RSPO1 in a corneal endothelial cell (CEO). (A) shows a phase contrast microscope image (the leftmost), as well as the immunostaining of GPR49/LGR5 (second from the left side), $Na^+/K^+$ ATPase (second from the right side) and ZO1 (the rightmost) in NT (the upper row) and shLGR-transfected human CEC (the lower row). The scale bar=100 µm.

When the condition under which expression of GPR49/LGR5 mRNA was significantly decreased was first studied by real time PCR, it was confirmed that shGPR49/LGR5-589 can suppress the amount of expression of GPR49/LGR5 mRNA by about 60% as compared with a control (FIG. 6a). Then, in order to study the influence of suppression of expression of GPR49/LGR5 on a Hedgehog signal, the amounts of expression of mRNA of Hedgehog signal-associated molecules (Ptch1, Gli1, Gli2) were analyzed using a monkey corneal endothelial cell transfected with shGPR49/LGR5-589. As a result, no changes in the amounts of expression of Hedgehog signal-associated molecules could be confirmed (FIG. 6b). Without being bound to any theory, there is a possibility that suppression of expression of a PR49/LGR5 gene influenced proliferation ability.

Example 8A

Force Expression of GPR49/LGR5 Gene

In order to analyze the function of GPR49/LGR5 in a corneal endothelial cell, forced expression of GPR49/LGR5 by a gene introduction method was tried using a cultured human corneal endothelial cell in which GPR49/LGR5 expression was remarkably reduced under normal culture conditions.

Figure 6C:
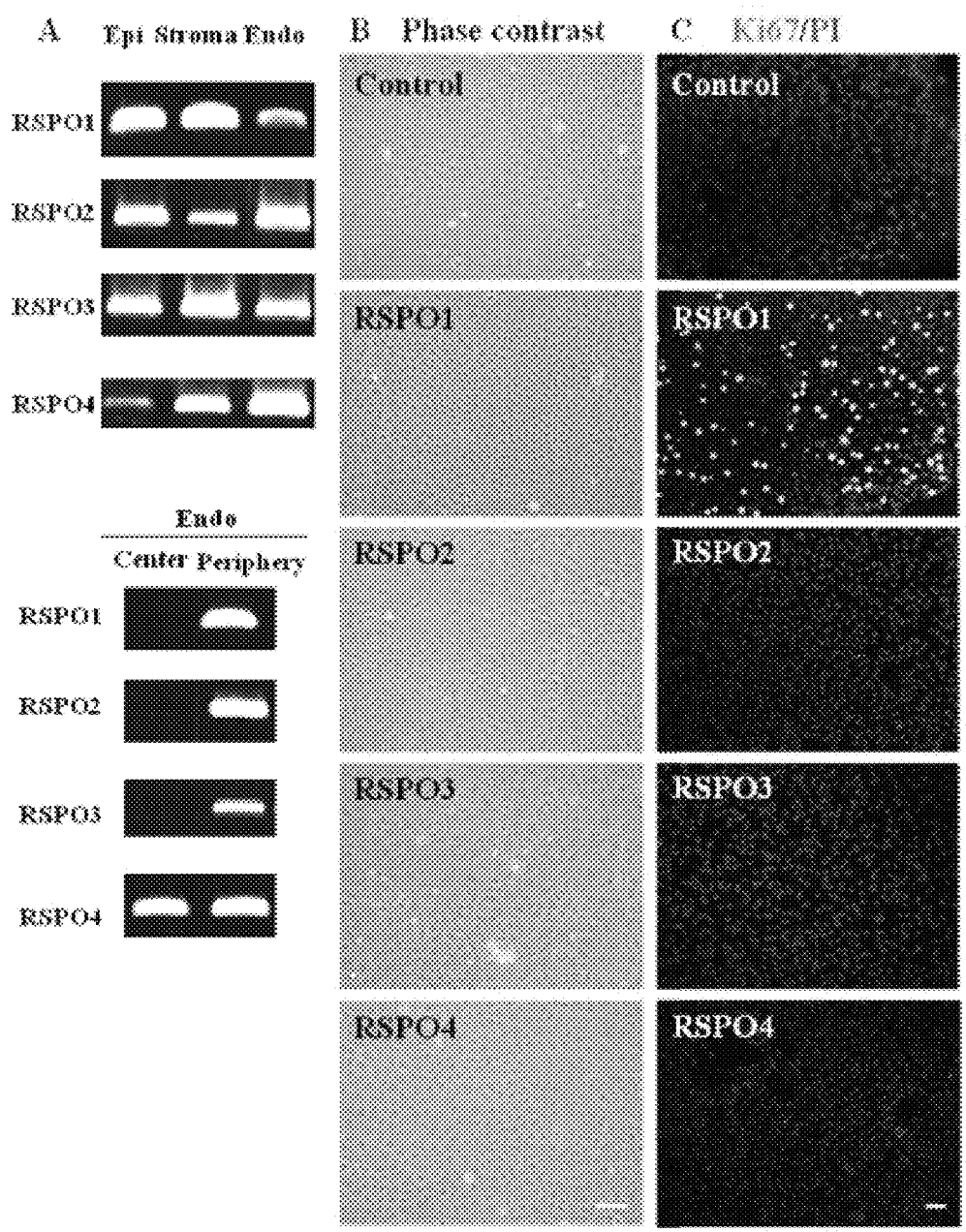
FIG. 6C shows expression and function of RSPO in a human corneal endothelial cell (CEC). (A) the upper panel shows the results of PCR concerning RSPO1 (the uppermost row), RSPO2 (second row from the upper side), RSPO3 (third row from the upper side) and RSPO4 (fourth row from the upper side) in a human corneal epithelial cell (Epi), a parenchymal cell (Stroma) and an endothelial cell (Endo). The lower panel shows the results of PCR concerning RSPO1 (the uppermost row), RSPO2 (second row from the upper side), RSPO3 (third row from the upper side) and RSPO4 (fourth row from the upper side) at a central part (Center) and a periphery part (Periphery), among endothelial cells (Endo) (B) shows a phase contrast microscope image of cultured human CEC in the presence or absence of RSPO1 (the uppermost row), RSPO2 (second row from the upper side), RSPO3 (third row from the upper side) and RSPO4 (fourth row from the upper side) (all are 50 ng/ml). The scale bar=100 (C) shows the immunostaining of Ki67 in human CEC in the presence or absence of RSPO1 (the uppermost row), RSPO2 (second row from the upper side), RSPO3 (third row from the upper side) and RSPO4 (fourth row from the upper side) (all are 50 ng/ml). The scale bar shows 100 µm.
Figure 6D:
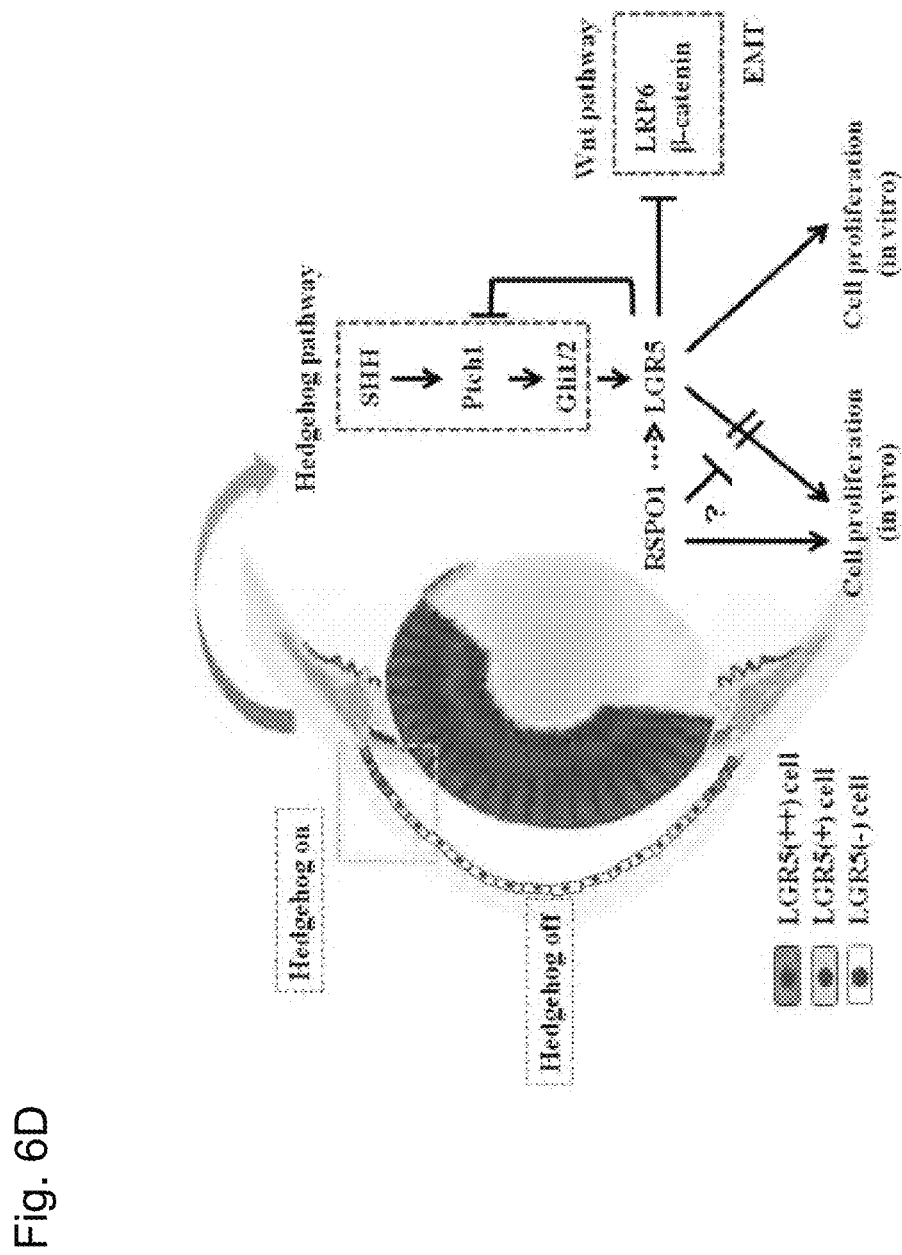
FIG. 6D shows a schematic view of the molecular mechanism of CEC maintenance. Human CEC shows regional diversity regarding GRP49/LGR5 expression. GRP49/LGR5 is expressed peculiarly at a peripheral region of CEC, and herein, HH signal transmission is clearly activated. GRP49/LGR5 is a target molecule in the HE pathway, and under in vitro conditions, the HH pathway could induce CEC proliferation. However, under in vivo circumstances, stimulation of only the HH pathway was insufficient for inducing CEC proliferation. The permanent expression of GRP49/LGR5 maintained a normal CEC phenotype by inhibition of the Wnt pathway. RSPO1 which is a GRP49/LGR5 ligand accelerated CEC proliferation in vivo, and inhibited MT via the Wnt pathway.

In a cultured human corneal endothelial cell transfected with a GPR49/LGR5 expression vector, about 60 times of expression elevation was recognized as compared with a control (FIG. 6d). In a cell with a gene of GPR49/LGR5 introduced therein, cell differentiation was suppressed, and expression of $Na^+/K^+$ ATPase used for evaluating the pumping function of a corneal endothelial cell was elevated (FIG. 6c). Using a cell under this condition, the amounts of expression of mRNA of Hedgehog signal-associated molecules (ptch1, gli1, gli2) were investigated. As a result, the amount of expression was suppressed (negative feedback) in all the associated molecules (FIG. 6d).
(Discussion)

From the above Example, it was made clear that GPR49/LGR5 is specifically expressed in a stem cell and a precursor cell of a corneal endothelial cell existing in a peripheral part of a corneal tissue. In addition, it was made clear that a Hedgehog signal has the function of promoting proliferation of a corneal endothelial cell, and GPR49/LGR5 being a downstream gene of a Hedgehog signal plays a particularly important role in maintaining undifferentiation property of a cell by suppressively functioning on a Hedgehog signal.

From the result of flow cytometry using a cultured monkey corneal endothelial cell, expression of a Ki-67-positive cell being a cell proliferation marker was observed only in a GPR49/LGR5-positive cell (FIG. 4c, d). In a cultured human corneal endothelial cell, expression of GPR49/LGR5 was elevated by activation of a Hedgehog signal (FIGS. 5d, e), and promotion of cell proliferation was confirmed (FIGS. 5f, g). Since the occurrence of cell proliferation by activation of a Hedgehog signal has been reported by promotion of proliferation of an adult neural stem cell by addition of rhShh (Lai et al., Nature neuroscience 6: 21-27, 2003), and promotion of proliferation and differentiation of a stromal stem cell by addition of purmorphamine (Wu et al., Chem. Biol. 11, 1,229-1,23B, 2004), it was considered that a corneal endothelial cell similarly has the cell proliferation promoting action by activation of a signal. Since a stable method for culture of a corneal endothelial cell is not currently established, it is understood that the present invention can be possibly applied to establishment of a novel culture method utilizing the cell proliferation promoting effect by Hedgehog signal activation. It is understood that, in the present Example, by activation of SHH, proliferation is elevated in a cultured endothelial cell. In addition, it is understood that SHH can be used as a marker of the degree of differentiation. In contrast, in a corneal endothelial tissue, by activation of a Hedgehog signal, expression of GPR49/LGR5 was elevated, but the effect of promoting cell proliferation was not obtained (FIG. 5b). It has been reported that human corneal endothelial cells in a living body are extremely close to each other, and unless adhesion between cells is alleviated using EDTA, the cell cycle does not work (Senoo et al., IOVS 41 2930-2935, 2000). Therefore, it was presumed that expression of a target gene is elevated by activation of a Hedgehog signal, but adhesion between cells in a living body is very intimate to not lead to cell proliferation. In addition, by an experiment of forced expression of GPR49/LGR5, the present inventors paid an attention to that expression of Ptch1, Gli1 and Gli2 which were each an associated molecule of a Hedgehog signal and also an index of signal activation was reduced (FIG. 6d). That is, there is a possibility that, although GPR49/LGR5 exists as a target gene of a Hedgehog signal, it has a role as a negative control factor which suppresses expression of associated molecules of a Hedgehog signal. Therefore, it is presumed that expression of a cell proliferation-associated gene such as Cyclin D/E or Myc which is other target gene is also suppressed by suppression of a Hedgehog signal. Further, GPR49/LGR5 forced-expressed cells tend to be in contact with each other at a high density, and the function of a corneal endothelial cell is high. It was presumed that controlling of progression into proliferation and differentiation due to Hedgehog signal activation by GPR49/LGR5 contributes to maintenance of undifferentiation property. There is a possibility that GPR49/LGR5 is associated with adhesion between cells, and it is considered that further research is necessary as a study theme in the future.
(Summary)

In summary, there is a possibility that cell proliferation of a corneal endothelial cell in a living body is controlled by a Hedgehog signal with Sonic hedgehog as a ligand. In addition, it is considered that GPR49/LGR5 being a target gene of a Hedgehog signal is involved in the undifferentiation property-maintaining mechanism of a corneal endothelial cell.

Example 8B

Further Analysis of GPR49/LGR5

(Downregulation of GPR49/LGR5 Decreased Proliferation of CEC)

The direct action of GPR49/LGR5 on CEC was revealed by knockdown of GPR49/LGR5 by shRNA. Due to the fact that cultured human CEC expresses GPR49/LGR5 rarely (FIGS. 3a, b), cultured CEC of a primate was employed in this experiment. Nine sets of shRNA were designed, and validity of the knocking down ability thereof was studied. It was found that shRNA-589 among them is most effective in knocking down GPR49/LGR5 mRNA expression (about 60% knockdown) (FIG. 6A-A). Real time PCR with respect to Ptch1, Gli1 and Gli2 showed that a significant difference is not seen between a shLGR5 group and a control (FIG. 6A-A). In order to verify influence of GPR49/LGR5 gene knockdown on GEC proliferation, immunocytochemical study with respect to Ki67 was conducted. As compared with a control, cell morphology of a shLGR5-treated cell did not change dramatically, but the number of Ki67(+) cells in the shLGR5-treated cell was greatly decreased (FIG. 6A-B). These findings showed that downregulation of GPR49/LGR5 has no influence on the HH pathway, but decreases in vitro CEC proliferation.

(Permanent GPR49/LGR5 Expression Inhibited Mesenchymal Transition (MT) via Wnt Pathway)

In order to investigate the direct action of permanent GPR49/LGR5 expression on CEC, the present inventors tried to allow GPR49/LGR5 to be overexpressed using a lentivirus containing CMV-LGR5-mRFP. In this experiment, human cultured CEC was employed. This is because it expresses GPR49/LGR5 rarely (FIG. 3a). Real time PCR showed that expression of GPR49/LGR5 in a cell transfected with GPR49/LGR5 is about 60 times higher than expression in a cell transfected with a NT vector (FIG. 6B-B). When an immunofluorescence method was used, it was confirmed that expression of GPR49/LGR5 in a cell transfected with GPR49/LGR5 is increased as compared with expression in a NT cell (FIG. 6B-A). Very interestingly, the relative mRNA level of a HH signaling molecule in a cell transfected with GPR49/LGR5 is downregulated as compared with that in a NT cell (FIG. 6B-B), and it is understood that GPR49/LGR5 functions as a negative feedback regulation factor of the HH pathway.

Human CEC easily undergoes fibroblast-like morphological change under normal culture conditions, according to a report [Peh G S et al., Transplantation., 2011; 91: 811-819]. After transfection with a lentivirus, NT cells showed an enlarged elongate form (fibroblast-like change), and the shape was not a uniform hexagonal shape (FIG. 6B-A). Very interestingly, it was shown that a cell transfected with GPR49/LGR5 is gradually changed in terms of its morphology and becomes a compact uniform hexagonal cell having a smaller size, and takes normal physiological morphology again (FIG. 6B-A). The cell density of a cell transfected with GPR49/LGR5 was greatly increased as compared with that of a NT cell (FIG. 6B-C). In order to investigate the function of cultured CEC transfected with NT and LGR5 vectors, an immunohistochemical method was performed with respect to $Na^+/K^+$ ATPase and ZO1. It was found that these two functional proteins are considerably highly expressed in a cell transfected with GPR49/LGR5 than in a NT cell (FIG. 6B-A). In consideration of these findings, it seems that GPR49/LGR5 can be an important molecule for maintaining a normal CEC phenotype.

From very interesting finding observed in a cell transfected with GPR49/LGR5, the present inventors further studied whether permanent expression of GPR49/LGR5 can block a MT process or not. The expression levels of epithelium NT (EMT)-associated molecules (Snail, Slug, Twist and collagen 1) [Lee J M et al., J Cell Biol., 2006; 172: 973-981] were investigated using real time PCR. Most importantly, the relative mRNA levels of EMT markers except for Slug were lower in a cell transfected with GPR49/LGR5 than in a NT cell (FIG. 6B-D), and it is understood that permanent GPR49/LGR5 expression blocked a MT process. The present inventors further investigated which pathway regulated endothelial MT observed in CEC. Recent research suggests that a Wnt/β-catenin signaling pathway plays an important role in EMT [Lee J M et al., J Cell Biol., 2006; 172: 973-981]. For this reason, using Western Blotting analysis, the expression level of a Wnt/β-catenin-associated molecule was investigated. It is worthy of special mentioning that the protein levels of cytosol (non-membrane-bound type) β-catenin and phosphorylation LDL receptor-associated protein 6 (p-LRP6) were greatly decreased in a cell transfected with GPR49/LGR5 (FIG. 6B-F). These findings showed that permanent GPR49/LGR5 expression inhibits corneal endothelial MT through a Wnt/β-catenin pathway.

(RSPO1 Accelerated CEC Proliferation and Inhibited MT Through Wnt Pathway.)

GPR49/LGR5 was an orphan receptor of a G protein-coupled receptor superfamily, and a ligand thereof was not known previously. However, some reports in recent years have demonstrated that RSPO functions as a ligand of GPR49/LGR5, and regulates Wnt/β-catenin signaling [Carmon K S et al., Proc Natl Acad Sci USA., 2011; 108: 11452-11457; de Lau W et al., Nature, 2011; 476: 293-297; Glinka A et al., EMBO Rep., 2011; 12: 1055-1061]. Interestingly, the present inventors found that RSPO1, 2, 3 and 4 are expressed in cells of an epithelium, a parenchyma and an endothelium of a cornea, and RSPO1, 2 and 3 are expressed only in CEC in a peripheral region (FIG. 6C-A). In order to determine the function of RSPO on CEC differentiation, the present inventors cultured primate CEC with human recombinant RSPO, or without human recombinant RSPO. It is worthy of special mention that only cultured human CEC treated with RSPO1 showed a compact and uniform hexagonal cell having a smaller size, and on the other hand, other RSPOs had no influence on in vitro CEC differentiation (FIG. 6C-B). In order to determine the function of RSPO on CEC proliferation, the present inventors performed immunohistochemical research on Ki67. Most surprisingly and very interestingly, CEC incubated with RSPO1 showed a dramatically increased level of the Ki67(+) cell ratio as compared with other RSPOs (FIG. 6C-C). In view of these findings, the present inventors considered that among a RSPO family, particularly, RSPO1 can play an important role in maintenance of CEC.

Finally, in order to further determine influence of RSPO1 on CEC, the present inventors maintained a secondary culture of human CEC in the presence or absence of RSPO1. Through culturing of CEC under both the conditions, the present inventors clearly observed that while a cell cultured with RSPO1 maintained its hexagonal form, a cell cultured without RSPO1 showed a fibroblast-like phenotype (FIG. 6B-E). The cell density of a RSPO1-treated cell increased as compared with that of a non-treated cell (FIG. 6B-E). In order to verify which pathway regulated this type of corneal endothelial MT, the present inventors investigated the expression level of a Wnt/β-catenin-associated molecule using Western blotting analysis. Surprisingly, the protein level of cytosol β-catenin and p-LRP6 in a cell transfected with GPR49/LGR5 and treated with RSPO1 clearly decreased as compared with that of a NT cell. Further, the protein level of a cell transfected with NT and GPR49/LGR5 and treated with RSPO1 decreased as compared with that of a cell group not treated with RSPO1 (FIG. 6B-F). These results suggested that stimulation of a cell overexpressing GPR49/LGR5 with RSPO1 accelerates degradation of pLRP and turnover of β-catenin.

(Discussion)

Since a majority of mammals gains a majority of external information through a cornea, a corneal tissue is extremely important. In recent years, from the fact that cornea transplant technique has undergone paradigm shift from keratoplasty to corneal endothelium transplantation, CEC has particularly attracted attention. For this reason, in order to scientifically and clinically establish novel therapy of the next generation for treating cornea-associated blindness in the world, it is considerably important to understand the molecular mechanism of a corneal endothelial stem cell/precursor cell. However, with respect to the molecular mechanism of them, only little is currently known.

It has been reported that the characteristics and the proliferation ability of CEC are different between CEC positioned in a central region of a cornea, and CEC positioned in a peripheral region of a cornea [Bednarz J et al., In vitro Cell Dev Biol Anim., 1998; 34: 149-153], and it has been shown by research that a cornea has a higher endothelial cell density in a peripheral region than in a central region [Schimmelpfennig B H, Invest Ophthalmol Vis Sci., 1984; 25: 223-229]. Further, CEC derived from a peripheral region maintains a higher replicating ability than that of CEC derived from a central region, according to a report [Mimura T et al., Invest Ophthalmol Vis Sci., 2006; 47: 1387-1396], and CEC in a peripheral region contains a large number of precursor cells, and has a stronger self-renewal ability than CEC in a central region [Mimura T et al., Invest Ophthalmol Vis Sci., 2005; 46: 3645-3648]. Therefore, there is a high possibility that a human corneal endothelial stem cell/precursor cell are distributed mainly in a peripheral region. In fact, a stem cell/precursor cell marker concerning CEC has not been previously revealed. The result of the present research first verified that CEC exhibits regional diversity regarding GPR49/LGR5 expression. When these findings and an especial expression pattern of GPR49/LGR5 are considered, there is a possibility that this serve as a first marker concerning a population including a corneal endothelial stem cell.

It has been reported that a keratin-producing cell stem cell can be identified from a temporarily proliferating cell or a differentiated cell [Barrandon Y et al., Proc Natl Acad Sci USA, 1985; 82: 5390-5394]. In an epidermis, a response to a phorbol ester of the minimum of keratin-producing cells is different from that of other cells. These keratin-producing cells also exhibited the highest colony forming ability. CEC was different from that of a keratin-producing cell derived from an ectoderm, and the average diameter of a GPR49/LGR5(+) cell by the present inventors was, in fact, smaller than that of a GPR49/LGR5(−) cell. Based on these findings, and the size of peripheral CEC reported, it seems that the size of a cell serves as a latent index of a cornea endothelial stem cell/precursor cell.

The present inventors have found that GPR49/LGR5 is an important molecule for maintenance of the undifferentiated state of CEC, and in vitro regulation of a normal cell phenotype. The present inventors have also found that an isolated cell fractionated based on the GPR49/LGR5 expression intensity can generate different cell populations having different properties. Only a cell in a GPR49/LGR5(+) population exhibited an exceptionally high proliferation ability which was the characteristic associated with a stem cell/precursor cell population. Based on these findings, a peculiar expression pattern and unavoidability under the in vitro condition, there is a possibility that there is some relationship between GPR49/LGR5 and the function of a corneal endothelial stem cell/precursor cell.

The previous research has shown that SSH in a high concentration results in a remarkable increase in retinal precursor cell population, and the total increase in accumulation of a differentiated cell [Stanton B Z et al., Mol Biosyst., 2010; 6: 44-54]. The finding of the present application shows that, under the in vitro situation, a HH pathway can induce proliferation of CEC, in agreement with the previous report. HH is a family of a secretory molecule which functions as a morphogen during a plurality of aspects of generation of a wide range of tissue types. HH regulates proliferation and living of a cell to be involved in determination of left and right asymmetry and determination of an antero-posterior axis in determination of a limb pattern. In CEC, there is regional variation in the HH signal activity, and based on the findings by the preset inventors, there is a possibility that HH signaling controls corneal endothelial morphosis.

RSPO is a family of a 4 cysteine-rich secretory protein, isolated as a strong enhancing substance of Wnt/β-catenin signaling. A large amount of information regarding the cell biological function of RSPO has been revealed, particularly regarding a role of an orphan receptor LGR4/5/6 as a ligand, over past several years. From these updated important findings, the present inventors further studied whether RSPO could influence the function of human CEC or not. Since human CEC is mitotically inactive, and has substantially no regeneration ability in vivo, compensating extension of a remaining endothelial cell is generated after loss of a corneal epithelium due to a disease or trauma. As far as the present inventors know, there is no report regarding a useful induction reagent or molecule which increases proliferation of human CEC and the level of the CEC density. The finding of the present research first showed that CEC incubated with RSPO1 exhibits a dramatically increased level of cell proliferation and the cell density, and it is suggested that there is a possibility that this molecule serves as a first candidate molecule for reconstituting a corneal which has received damage by local administration or a culture reagent.

Some research have suggested that a Wnt/β-catenin pathway plays an important role in EMT, and Wnt/β-catenin-dependent signaling regulates expression of an EMT-associated gene [Lee J M et al., J Cell Biol., 2006; 172: 973-981]. However, the previous reports have shown that RSPO, in fact, enhances Wnt/β-catenin signaling by functioning as a ligand of GPR49/LGR5 [Carmon K S et al, Proc Natl Acad Sci USA., 2011; 108: 11452-11457; de Lau W et al., Nature, 2011; 476: 293-297; Glinka A et al., EMBO Rep., 2011; 12: 1055-1061]. The actual mechanism regarding this activation has unknown yet, and there are some contradictory findings, concerning whether GPR49/LGR5 is a positive regulatory factor or a negative regulatory factor of the Wnt pathway [Garcia M I et al., DevBiol., 2009; 331: 58-67; Schuijers J et al., EMBOJ., 2012; Walker F et al., PLoSOne., 2011; 6: e22733]. One possible explanation is that the molecular mechanism depends on a tissue, an organ and a species thereof. A cornea is a peculiar blood vessel-free tissue which is maintained by tear and aqueous humor. To the contrary, a majority of other organs are maintained by supporting of a blood vessel structure, and it is suggested that the characteristics and the mechanism of a corneal cell are fundamentally different from those of an epithelial cell of other tissues. Therefore, based on the findings of the present research, RSPO1 dramatically accelerates proliferation of CEC, and inhibits corneal endothelial MT through the Wnt pathway.

(Conclusion)

As conclusion, the findings of the present research first verify the function of GPR49/LGR5 in human CEC (FIG. 6D). It was demonstrated that GPR49/LGR5 serves as a powerful tool upon identification of many stem cell/precursor cell populations. By regulation of GPR49/LGR5 through HH and Wnt pathways, completeness of CEC was sufficiently systemized, and maintained. In addition, it is understood that RSPO1 being a GPR49/LGR5 ligand can develop a novel sufficient protocol for providing an effective increase in CEC, and RSPO1-based three-dimensional culture or medical treatment promises the future regenerative medicine not only for treatment of corneal dysfunction, but also treatment of a variety of serious systemic diseases.

Example 9

Cell Proliferation Promoting Effect of R-Spondins

In the present Example, an experiment was performed for the purpose of studying the cell proliferation promoting effect of R-spondins, particularly R-spondin 1 in culture of a corneal endothelial cell.

(Method)

After addition of an R-spondin 1 protein to a cultured monkey corneal endothelial cell and culturing for 48 hours, a cell during proliferation was detected using the Click-iT Edu imaging Kit, and the positivity rates of EdU and the cell densities of a control cell and a cell to which R-spondin 1 was added were compared.

EdU (5-ethynyl-2'-deoxyuridine) is a modified nucleic acid taken into DNA at a DNA synthesis phase by a chemical reaction, and is widely used in place of a conventional BrdU for identifying a DNA synthesis phase cell. By measuring the positivity rate of EdU, the proliferative cell rate in a cultured cell is found.

(Reagents Used)
Click-iT EdU Imaging Kit (Invitrogen Cat. C10337)
Recombinant Human R-spondin 1 (R&D Cat. 4645-RS)
(Cell Used)
Cultured monkey corneal endothelial cell (Lot. 20111222-4 P2)
(Experiment: Study of Cell Proliferation Promoting Effect of R-Spondin 1 in Cultured Monkey Corneal Endothelial Cell Culture)
(Procedure)
(1) Seeding of Cultured Monkey Corneal Endothelial Cell and Addition of R-Spondin 1

A cultured monkey corneal endothelial cell (Lot. 20111222-4 P2) was treated with 0.05% trypsin at 37° C. for 10 minutes, peeled from a T-25 flask, and suspended in a culture medium (10% FBS+bFGF/DMEM). The number of cells was counted, and the suspension was adjusted with a culture medium to $3 \times 10^4$ cells/300 µl. Cells were seeded on a Lab-TekII chamber Slide (8 well) coated with FNS, in 300 µl/well.

(2) Detection of Proliferating Cell Using Click-iT EdU Imaging Kit

Figure 8:
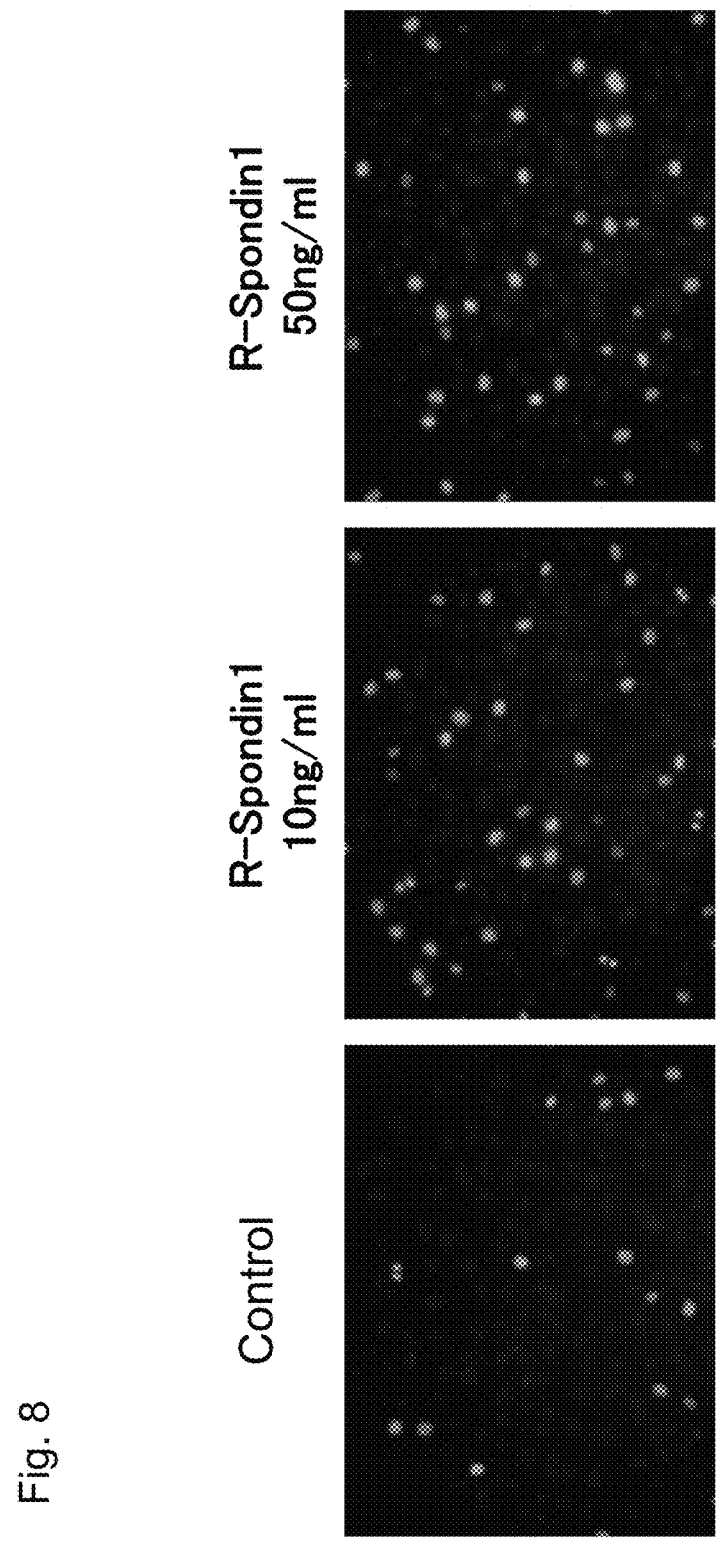
FIG. 8 shows the detection (magnification ×200) of a proliferating cell using a Click-iT EdU Imaging kit in Example 9. Monkey cultured corneal endothelial cells were seeded, the cells were exchanged with a medium containing R-spondin 1 (from the left side, 0, 10, 50 ng/ml) in the state where the cells were in the approximately confluent, and after 24 hours from the addition of R-spondin 1, EdU was stained with Click-iT EdU, and an EdU-positive cell rate was counted.
Figure 9:
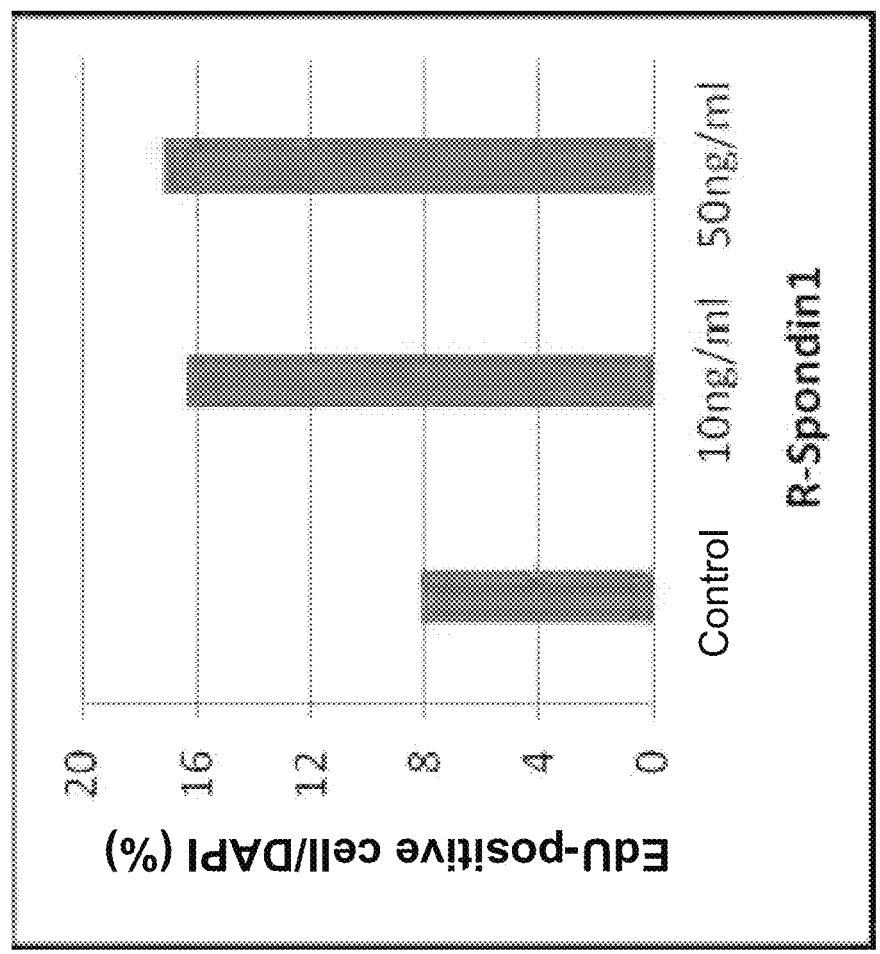
FIG. 9 shows an EdU-positive cell ratio in FIG. 8. As a result of counting of EdU-positive cell/DAPI, it was found that the EdU-positive cell was increased two times in a well to which R-spondin 1 was added at 10 ng/ml or 50 ng/ml, as compared with a control.

At 7 days after cell seeding, a medium was exchanged with a medium containing R-spondin 1 (0, 10, 50 ng/ml) in the state where cells were almost confluent, and at 24 hours after addition of R-spondin 1, Click-iT EdU was added so that the final concentration was 10 µM. (Although a manual of Kit recommended that a half of a medium was exchanged, a medium was not exchanged) After additional 24 hours (48 hours after addition of R-spondin 1), cells were fixed with 4% PFA/PBS, EdU was detected according to a manual of Kit, and the EdU-positive cell rate was counted (FIGS. 8 and 9).

(3) Measurement of Cell Density

Figure 10:
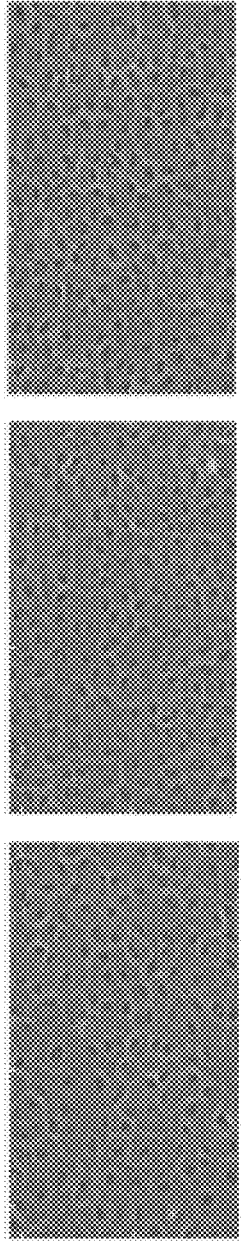
FIG. 10 shows the endothelial cell density of corneal endothelial cells which are cultured by the method shown in FIG. 8. A photograph was taken with a phase contrast microscope, and the cell density was measured using a corneal endothelial cell density calculating software Konan Storage system KSS-400EB. From the left side, addition of no medium, 10 ng/ml R-spondin 1, and 50 ng/ml R-spondin 1 are shown.
Figure 11:
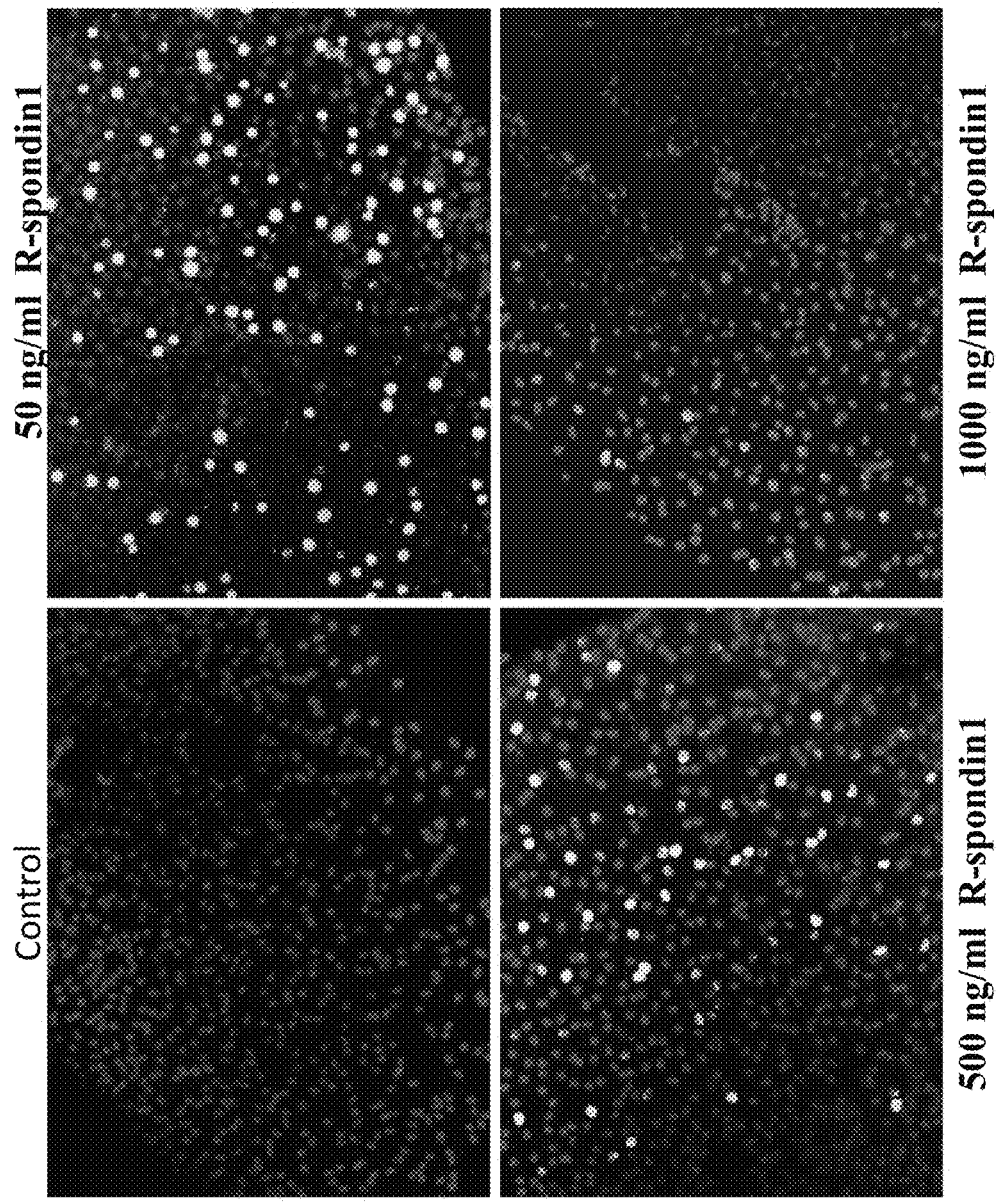
FIG. 11 shows the action of R-spondin 1 in a human cultured corneal endothelial cell. A Ki67-positive cell rate was increased in a corneal endothelial cell to which RSPO1 was added (50 ng/ml (the right upper side), 500 ng/ml (the left lower side)), as compared with a control. The left upper side shows a control, the right upper side shows an example of culturing with 50 ng/ml R-spondin 1, the left lower side shows an example of culturing with 500 ng/ml R-spondin 1, and the right lower side shows an example of culturing with 1000 ng/ml R-spondin 1. Ki67 is stained with green, a color is not seen in the control, Ki67 is remarkably stained at 50 ng/ml and 500 ng/ml, and staining is also observed at 1000 ng/ml. PI is stained with red, and all cells are stained.
Figure 12:
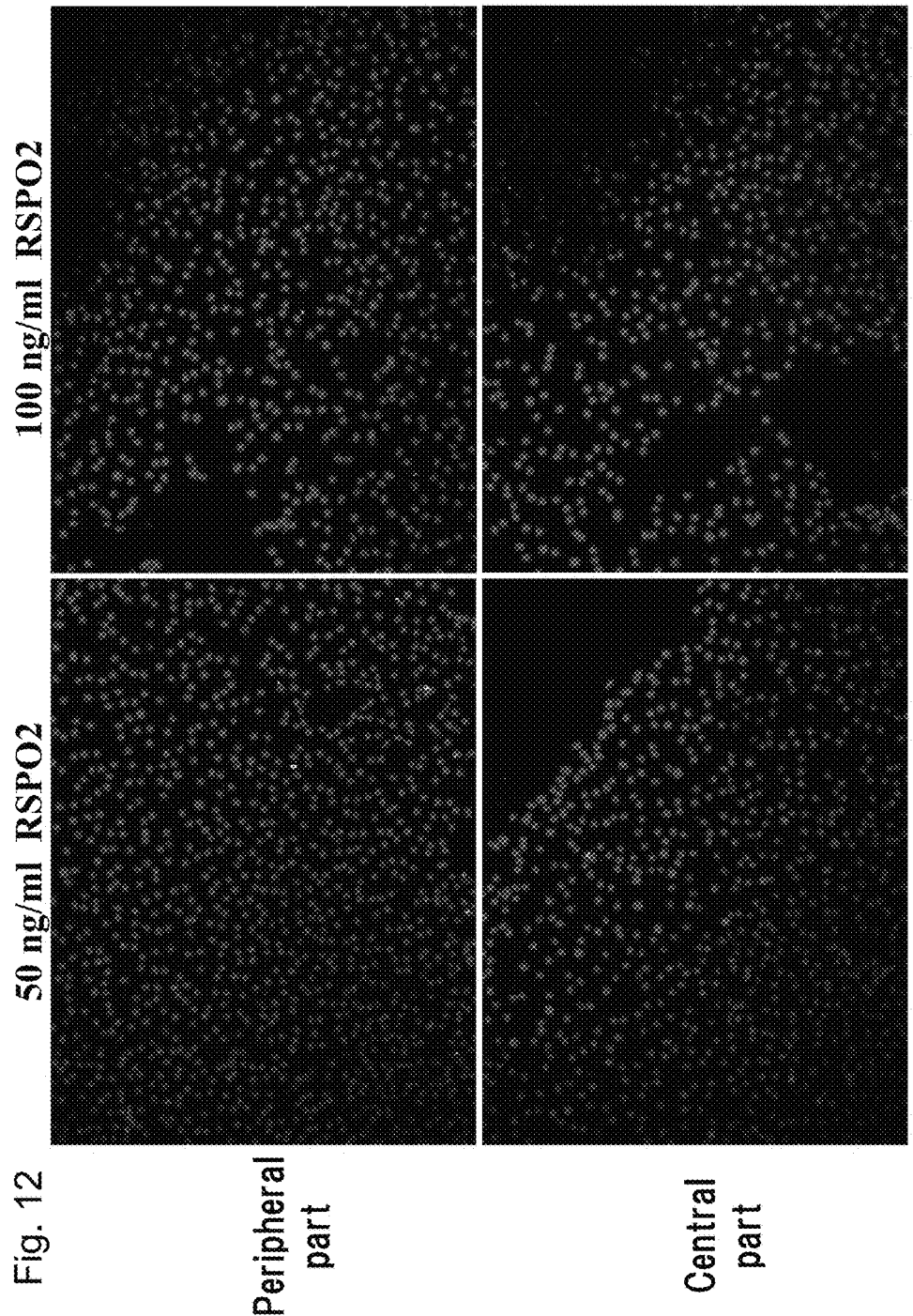
FIG. 12 shows the action of R-spondin 2 in a human cultured corneal endothelial cell. In a corneal endothelial cell to which RSPO2 was added, a Ki67-positive cell rate was slightly increased as compared with a control. The left side shows an example of culturing with 50 ng/ml R-spondin 2, the right side shows an example of culturing with 100 ng/ml R-spondin 2, the upper side shows limbus cornea and the lower side shows a central part.
Figure 13:
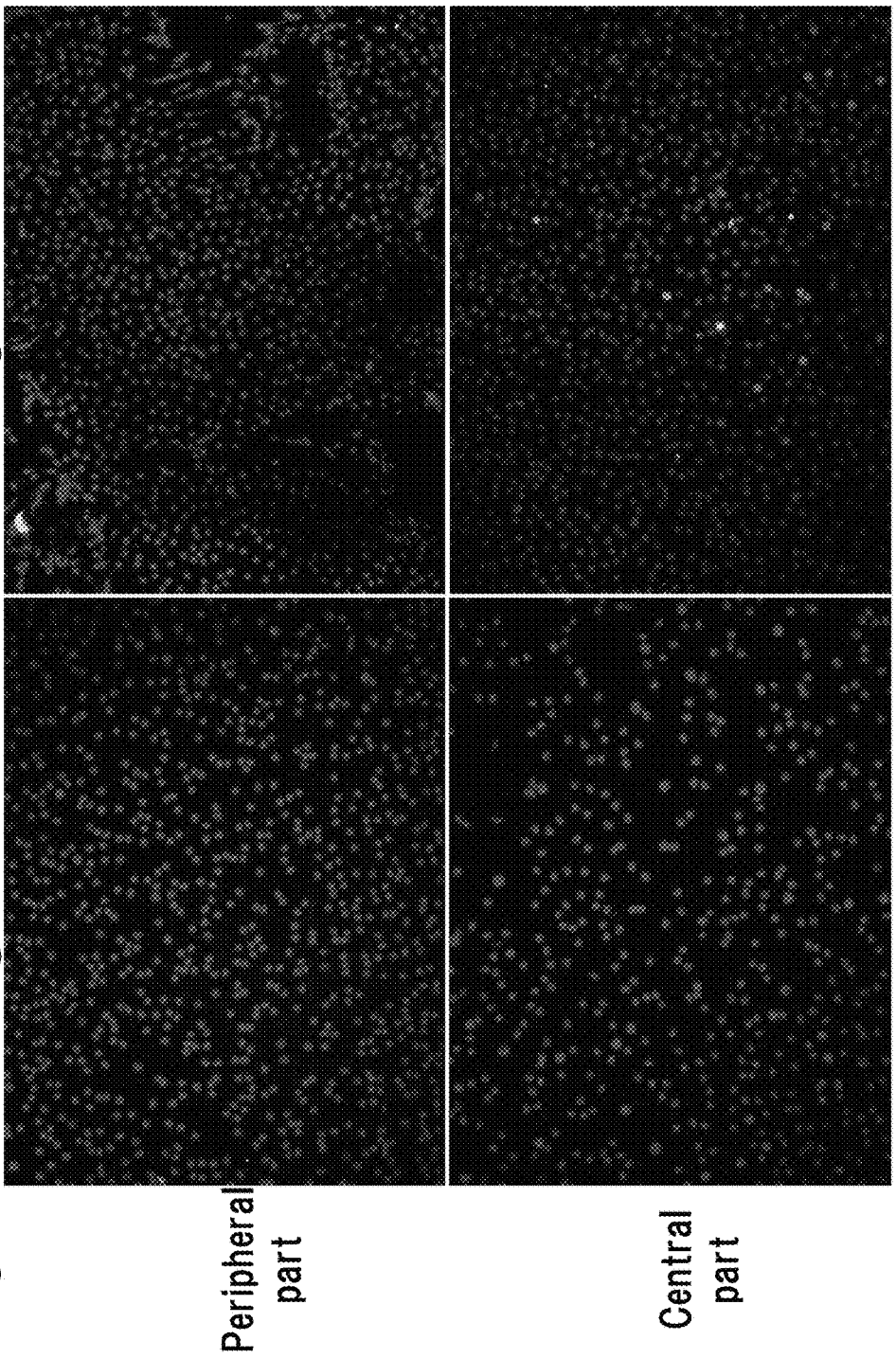
FIG. 13 shows the action of R-spondin 3 in a human cultured corneal endothelial cell. In a corneal endothelial cell to which RSPO3 was added, a Ki67-positive cell rate was slightly increased as compared with a control. The left side shows an example of culturing with 50 ng/ml R-spondin 3, the right side shows an example of culturing with 200 ng/ml R-spondin 3, the upper side shows limbus cornea, and the lower side shows a central part.
Figure 14:
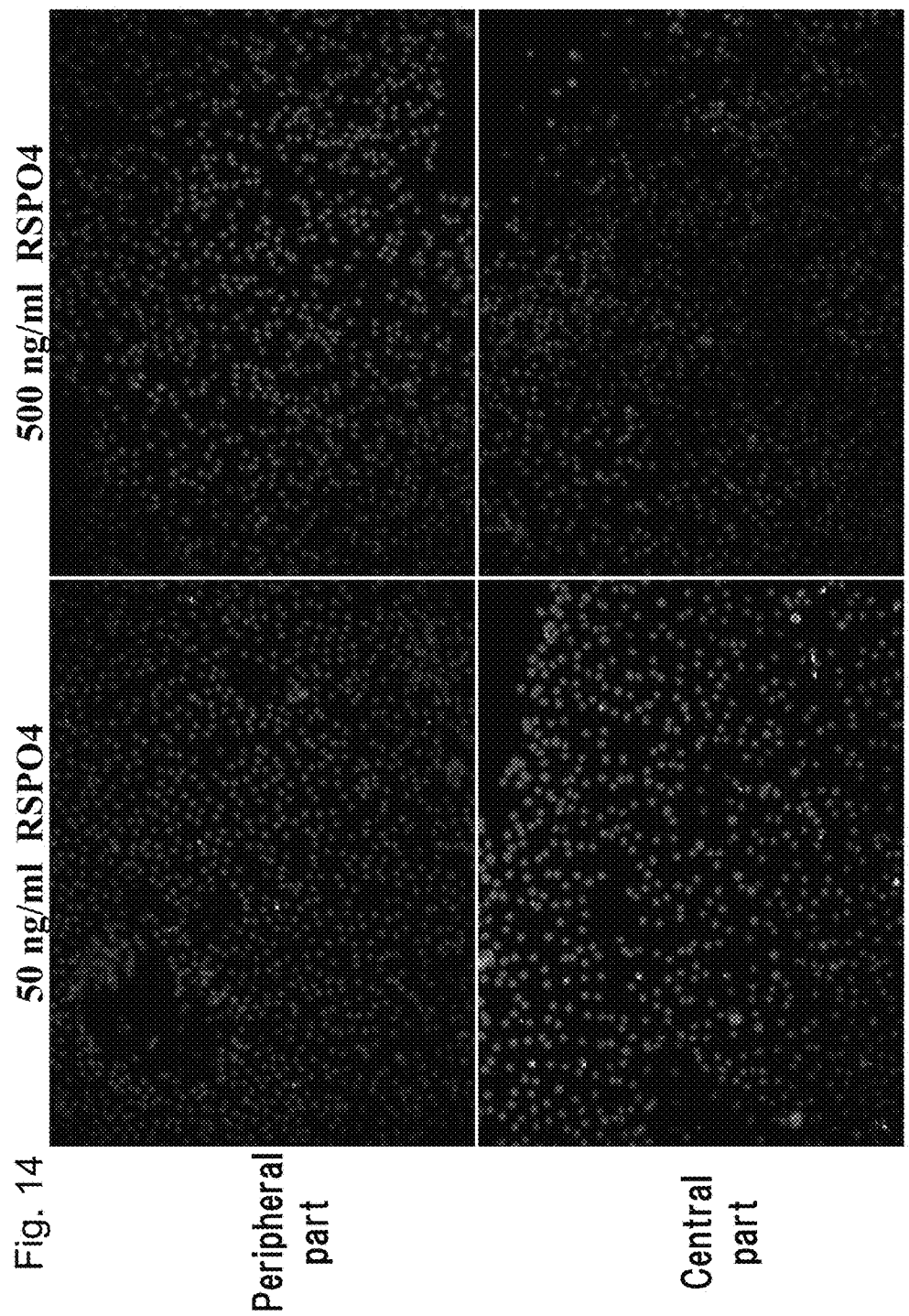
FIG. 14 shows the action of R-spondin 4 in a human cultured corneal endothelial cell. In a corneal endothelial cell to which RSPO4 was added, a Ki67-positive cell rate was slightly increased as compared with a control. The left side shows an example of culturing with 50 ng/ml R-spondin 4, the right side shows an example of culturing with 500 ng/ml R-spondin 4, the upper side shows limbus cornea, and the lower side shows a central part.

A chamber slide after staining was photographed with a phase contrast microscope, and the cell density was measured using the corneal endothelial cell density calculating software, Konan Storage System KSS-400EB (FIG. 10).

(Result)

As a result of counting of EdU-positive cell/DAPI, an EdU-positive cell was found to be increased twice in a well to which 10 ng/ml or 50 ng/ml R-spondin 1 was added, as compared with a control. In addition, as a result of measurement of the cell density, the cell density was found to be increased 1.3 times in a well to which 10 ng/ml or 50 ng/ml R-spondin 1 was added, as compared with a control.

(Discussion)

The cell proliferation promoting effect of R-spondin 1 was recognized in a cultured monkey corneal endothelial cell. In addition, the same effect is expected to be exerted in a cultured human corneal endothelial cell and a human corneal endothelial tissue.

Example 10

Cell Proliferation Promoting Effect of R-Sporadins in Cultured Human Corneal Endothelial Cell In order to investigate a relationship between R-sporadin 1 (RSPO1), R-spondin 2 (RSPO2), R-spondin 3 (RSPO3), or R-spondin 4 (RSPO4) and differentiation of a corneal endothelial cell, the relationship was studied using RSPO1. Reagents used are as follows.
RSPO1 R&D systems catalog No.: 4645-RS
RSPO2 R&D systems catalog No.: 3266-RS
RSPO3 R&D systems catalog No.: 3500-RS
RSPO4 R&D systems catalog No.: 4575-RS A cultured human corneal endothelial cell was cultured for 7 days under conditions of 37° C. and 5% $CO_2$, with being divided into a group of addition of RSPO1 (50 ng/ml) and a group of addition of no RSPO1. As a result, morphology of a cell was maintained in a cobblestone manner in the RSPO1 addition group, while a cell was differentiated into fibroblast-like cells in the non-addition group. From the above result, the effect of suppressing differentiation of a corneal endothelial cell was recognized in RSPO1.

Then, for the purpose of investigating the influence of RSPO on cell proliferation, RSPO1 to 4 were incubated into a human corneal endothelial cell under conditions of 37° C. and 5% $CO_2$ for 1 day. Thereafter, Ki-67 being a cell proliferation marker was immunostained. As a result, a proliferation tendency was seen in all RSPO1 to 4, but only RSPO1 statistically significantly promoted proliferation of a human corneal endothelial cell.

Example 11

Effect of R-Spondins on Confluent Cell

In the present Example, whether R-spondins had the proliferation effect on a corneal endothelial cell which reached the confluent state or not was confirmed.

(Method)
(Source and culture method): As a human corneal endothelial cell, a corneal endothelial cell was mechanically peeled together with a basal membrane from a cornea for research, purchased from Seattle Eye Bank, and the corneal endothelial cell was peeled and recovered from the basal membrane using collagenase (ROCHE catalog No.: 10 103 586 001), and was subjected to primary culturing. As a medium, for human, Opti-MEM I Reduced-Serum Medium, Liquid (INVITROGEN catalog No.: 31985-070), 8% fetal bovine serum (FES) (BIO-WEST, catalog No.: S1820-500), 200 mg/ml $CaCl_2.2H_2O$ (SIGMA catalog No.: C7902-500G), 0.08% chondroitin sulfate (SIGMA catalog No.: C9819-5G), 20 µg/ml ascorbic acid (SIGMA catalog No.: A4544-25G), 50 µg/ml gentamicin (INVITROGEN catalog No.: 15710-064) and 5 ng/ml EGF (INVITROGEN catalog No.: PHG0311), acclimated for a 3T3 feeder cell, were used.

After subculturing, at the time point where cells reached confluent and were cultured for 2 weeks or longer, and no clear change in the corneal endothelium density was recognized, R-spondin 1 was added into a medium in a concentration of 10 ng/ml, and culture was continued. Observation of cell morphology was performed with a phase contrast microscope, and the cell density was calculated.
(Result)

Figure 15:
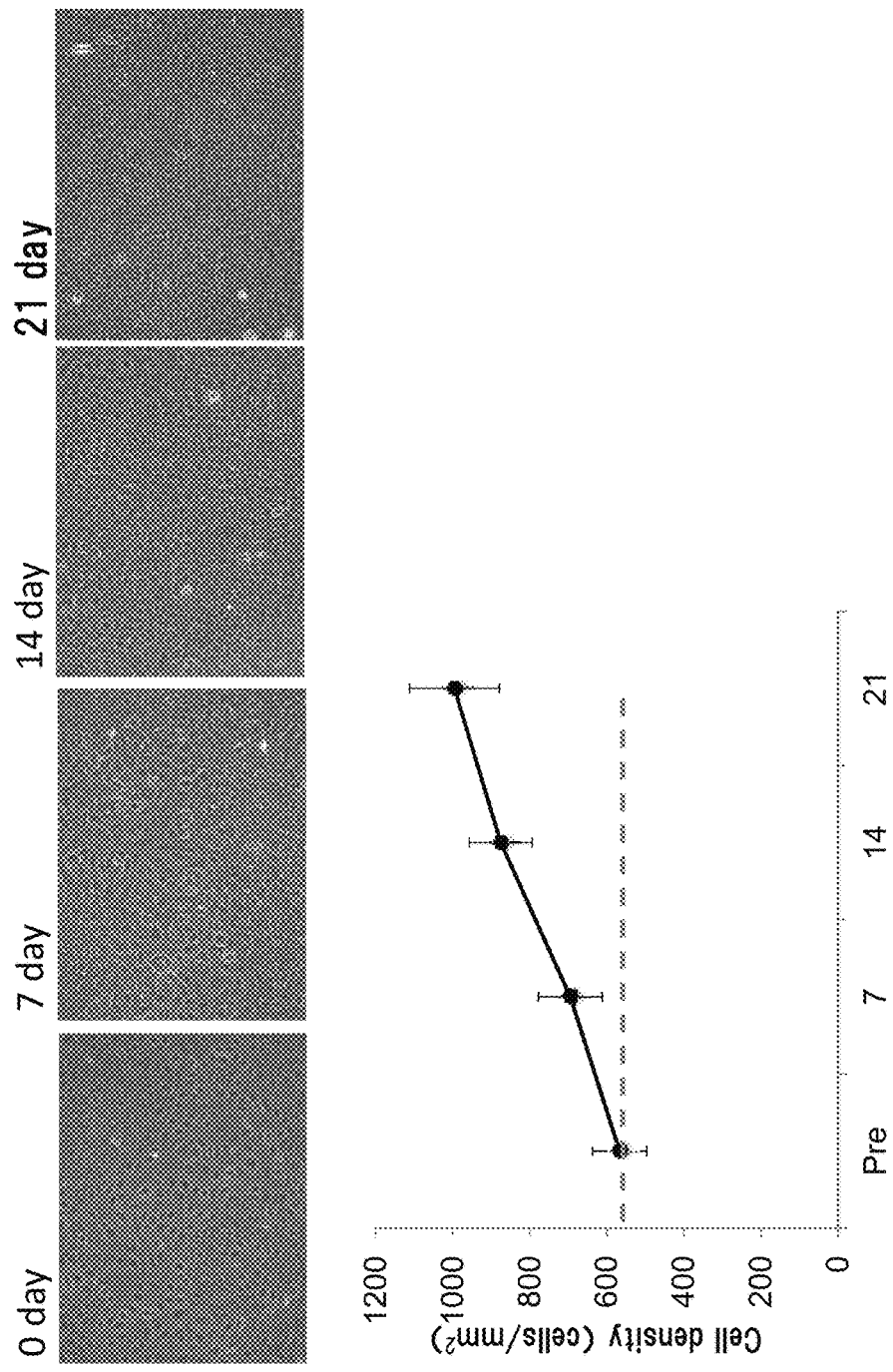
FIG. 15 shows the results obtained by adding R-spondin 1 to a medium at a concentration of 10 ng/ml at the time point when the subculture of human corneal endothelial cells was performed, thereafter, the cells reached confluent, and were cultured for 2 weeks or longer, and clear change was not recognized in the corneal endothelial density; continuing culturing; observing a cell form with a phase contrast microscope; and calculating the cell density. A photograph shows the number of days after addition (from the left side, 0 day, 7 day, 14 day and 21 day). The lower graph shows a change in the cell density of the group of R-spondin 1 addition on 0 day, 7 day, 14 day and 21 day, as compared with a non-addition group.

The results are shown in FIG. 15. The average corneal endothelial cell density at the time point where cells reached confluent and no clear change in the corneal endothelial density was recognized was 566.8 cells/mm$^2$, and the density was increased with time, reached about 695 cells/mm$^2$ on 7$^{th}$ day, reached about 875 cells/mm$^2$ after 14 days, and reached 995.8 cells/mm$^2$ after 21 days. On the other hand, when a cell in the same lot was cultured as a control in a medium not containing R-spondin 1 for 21 days being the same period, the density was 535.4 cells/mm$^2$.
(Discussion)

These results mean that, in a corneal endothelial cell, the density of which is easily decreased by culturing, the corneal endothelial cell density can be increased by culturing using R-spondin 1. This means that cells having a high corneal endothelium density being an important prognosis determinant after transplantation can be transplanted, towards clinical application of cultured corneal endothelial transplantation. In addition to usefulness for regenerative medicine of a corneal endothelium, it is understood that, also in other cells, use of R-spondin 1 allows for transplantation of cells having a higher function.

Example 12

Production of Tissue in Which Corneal Endothelium Density is Increased by R-Spondins In the present Example, it is demonstrated that a tissue having an increased corneal endothelium density can be prepared by treatment of a corneal tissue with R-spondins.
(Method)

Eyeballs of white rabbit (Nacalai) euthanized for another object were purchased, and a sclerocorneal section was prepared. The sclerocorneal section was cultured in an incubator at 37° C. for 1 week in DMEM (INVITROGEN, catalog No.: 12320) and 10% fetal bovine serum (FBS) (BIOWEST, catalog No.: 51820-500). After one week, the sclerocorneal section was fixed with 4% paraformaldehyde at room temperature for 10 minutes, and after fixing, Ki67 (Sigma-Aldrich Co., catalog No.: P6834) was used as a marker of cell proliferation to immunostaining a corneal endothelial cell, and this was observed with a fluorescent microscope. A corneal endothelial cell was subjected to nuclear staining with DAPI, and the Ki67-positive cell rate was calculated. In addition, a corneal endothelial cell was immunostained with ZO-1, and the cell density was calculated.
(Result)

The results are shown in FIG. 16. When the culturing was performed in a medium containing R-spondin 1, a Ki67-positive cell was recognized at a higher ratio as compared with a control, also in the sclerocorneal section. That is, while the rate of a Ki67-positive cell was about 1.0% in a control to which R-spondin 1 was not added, the rate was 4.49% in addition of 1 ng/ml R-spondin 1, was 10.58% in addition of 10 ng/ml R-spondin 1, and was 7.94% in addition of 100 ng/ml R-spondin 1.

Further, the corneal endothelial cell density showed a significantly high value by R-spondin 1. That is, the corneal endothelial cell density was 3674 cells/mm$^2$ in a control to which R-spondin 1 was not added, and was increased to 4314 cells/mm$^2$ in addition of 1 ng/ml R-spondin 1, increased to 4626 cells/mm$^2$ in addition of 10 ng/ml R-spondin 1, and increased to 5037 cells/mm$^2$ in addition of 100 ng/ml R-spondin 1.
(Discussion)

The result means that a tissue having an increased corneal endothelium density being an important prognosis determinant after transplantation can be transplanted by allowing R-spondin 1 to act on a corneal tissue, in corneal transplant medicine. In addition to usefulness in corneal transplant medicine, it is understood that, also in other tissues, use of R-spondin 1 allows for transplantation of a tissue having a higher function.

Example 13

Proliferation Effect in Cells of Corneal Parenchyma, Epithelium, Retinal Pigment Epithelium (RPE), Vitreous Body, and the Like In the present Example, the proliferation effects of R-spondins in cells of a corneal parenchyma, an epithelium, RPE, a vitreous body and the like are confirmed, respectively. Culturing methods are listed below. In each culturing method, by culturing in the presence or absence of R-spondins according to the above Example, it can be confirmed that the effect on proliferation is promoted.
(Corneal Parenchymal Cell Culture Method)

A corneal parenchymal cell is cultured based on the procedure of Yamamoto M, Quantock A J, Young R D, Okumura N, Ueno M, Sakamoto Y, Kinoshita S, Koizumi N. Mol Vis. 2012; 18: 1727-39. In brief, a rabbit cornea is incubated with 1.2 U/ml Dispose (Invitrogen) at 37° C. for 1 hour. Thereafter, a corneal epithelium and a corneal endothelium are removed by mechanical scraping. Then, a corneal parenchyma is cut into about 1 cm$^2$ sections, and these are incubated in DMEM/F12 containing 1 mg/ml collagenase A (Roche Diagnostics Japan) and 1% penicillin-streptomycin at 37° C. overnight. After centrifugation at 1500 rpm (440×g) for 3 minutes, cells are successively cultured in a cell-free medium (DMEM/F12 containing 10 μg/ml 1 mM ascorbic acid, and 1% penicillin-streptomycin) for 48 hours. Cells thus obtained can be used to perform an experiment.
(Retinal Pigment Epithelium (RPE) Cell Culture Method)

RPE cells are cultured based on the procedure of Hatanaka H, Koizumi N, et al., Investigative Ophthalmology & Visual Science. 2012; 53(11): 6955-6963. In brief, a monkey retinal pigment epithelial cell (MRPEC) is cultured from a rear region of eyeballs taken out from cynomolgus monkey (3 to 5 years old, corresponding to 5 to 20 years old in human; obtained from Nissei Bilis Co. Ltd., Otsu Japan). Then, a RPEC fragment of MRPEC (cell mass of MRPEC) is separated and prepared based on the procedure (Maminishkis A, Chen S, Jalickee S, et al. Confluent monolayers of cultured human fetal retinal pigment epithelium exhibit morphology and physiology of native tissue. Invest Ophthalmol Vis Sci. 2006; 47: 3612-3624) previously reported regarding a human fetal RPE. Then, MRPEC is cultured, in DMEM/F12 supplemented with 10% FBA, 50 U/ml penicillin and 50 μg/ml streptomycin, on a dish coated with FNC Coating Mix (registered trademark), and further expanded at 37° C. under a humidified environment in 5% CO$_2$. Then, a culture medium is exchanged every 2 days. When cells reach confluent in 5 to 7 days, cells are rinsed with the Dulbecco's phosphate buffered physiological saline (PBS) not containing Ca$^{2+}$ and Mg$^{2+}$, trypsin-treated with 0.05% trypsin- EDTA (Life Technologies) at 37° C. for 5 minutes, and subjected to subculture at a ratio of 1:2 to 4. Cultured MRPEC at 1 to 3 passages is used in all experiments.
(Corneal Epithelial Cell Culture Method)

An amnion was collected according to the method approved by Ethics Committee of Kyoto Prefectural University of medicine, and used for research. After written consent was obtained from a pregnant woman scheduled to receive Caesarean section, having neither an infectious disease nor complication, an amnion was sterilely collected in Caesarean section, washed, immersed in a 50% glycerol DMEM solution, and frozen and preserved at −80° C. Then, a corneal epithelial stem cell collected from a human sclerocorneal tissue for which authorization was gained to use for the research purpose from Northwest Lion Eye Bank (Seattle, Wash., USA) was cultured. In order to prepare a cultured corneal epithelial sheet containing a corneal epithelial stem cell, a corneal epithelial cell was recovered as a cell suspension by enzyme treatment using 1.2 U Dispase at 37° C. for 1 hour. Then, the cell suspension was seeded on an amnion, and cultured in an incubator at 37° C. in 5% $CO_2$ for about 2 weeks.
(Vitreous Body Cell (Hyalocyte) Culture Method)

A vitreous body cell is cultured in accordance with the method reported in Sommer F, Pollonger K, et al. Graefes Arch Clin Exp Ophthalmol, 2008. First, a vitreous body is collected from monkey eyeballs, and washed with DMEM with 1% penicillin/streptomycin added thereto three times. The sample is immersed in 1 mg/ml collagenase, and incubated overnight at 37° C. with rotations. After centrifugation, the supernatant is removed, and the resultant is washed with DMEM with 1% penicillin/streptomycin added thereto. DMEM, 10% FBS, and 1% P/S are added, and the resultant is seeded on a culture dish.

Example 14

Experiment Concerning Other Cells

In the present Example, concerning a nerve cell, a conjunctival epithelium, an amniotic epithelium, an oral mucosa epithelium, and a nose mucosa epithelium, the proliferation effect of R-spondins is confirmed, respectively. A culture method can be performed in accordance with a known method. In each culture method, by culturing in the presence or absence of R-spondins in accordance with the above Examples, it can be confirmed that the effect on proliferation is promoted.

Example 15

Preparation Example: Cornea Preservation Solution Containing Agent for Stimulating Proliferation or Controlling Differentiation In the present Example, as Preparation Example, the cornea preservation solution containing a culture-normalizing agent of the present invention is produced as follows.
According to a conventional method, the following preservation solution is prepared.
R-spondin 1 10-500 ng/ml (appropriately adjusted)
Optisol-GS (Bausch-Lomb) proper quantity
Total amount 100 mL
Each ingredient can be obtained from R&D Systems Inc. (Minneapolis, Minn.).

Example 16

Preparation Example of Infusion

Preparation Example of Eye Drops
The composition of each test substance in each concentration is shown below.

| | |
|---|---|
| R-spondin 1 | 10-500 ng/ml (appropriately adjusted) |
| Sodium chloride | 0.85 g |
| Sodium dihydrogen phosphate dihydrate | 0.1 g |
| Benzalkonium chloride | 0.005 g |
| Sodium hydroxide | proper quantity |
| Purified water | proper quantity |
| Total amount | 100 mg (pH 7.0) |

Eye drops can also be diluted with a base.
The composition of a base is as follows.

| | |
|---|---|
| Sodium chloride | 0.85 g |
| Sodium dihydrogen phosphate dihydrate | 0.1 g |
| Benzalkonium chloride | 0.005 g |
| Sodium hydroxide | proper quantity |
| Purified water | proper quantity |
| Total amount | 100 mg (pH 7.0) |

Each ingredient can be obtained from R&D Systems Inc. (Minneapolis, Minn.).

As described above, the present invention has been exemplified using preferable embodiments of the present invention, but it is understood that the scope of the present invention should be construed only by the scope of claims. It is understood that patents, patent applications and literatures cited herein are incorporated herein as reference, as if the contents thereof themselves are specifically described herein.

INDUSTRIAL APPLICABILITY

A differentiation marker and a differentiation controlling technique of an eye cell are provided, and a technique which can be utilized in industries involved in a technique associated with corneal transplant (cell culture industry, pharmacy, and the like) is provided.

SEQUENCE LISTING FREE TEXT

SEQ ID No.: 1: Gene sequence encoding human GPR49/LGR5 (OMIM: 606667; NM_003667.2)
SEQ ID No.: 2: Amino acid sequence of human GPR49/LGR5 (OMIM: 606667; NP 003658.1)
SEQ ID No.: 3: Gene sequence encoding R-spondin 1 (RSPO1) (OMIM: 609595; NM_001038633) (transcript variant 1)
SEQ ID No.: 4: Amino acid sequence of R-spondin 1 (RSPO1) (OMIM: 609595; NM_001038633) (transcript variant 1)
SEQ ID No.: 5: Gene sequence encoding R-spondin 2 (RSPO2) (OMIM: 610575; NM_178565)
SEQ ID No.: 6: Amino acid sequence of R-spondin 2 (RSPO2) (OMIM: 610575; NM_178565)
SEQ ID No.: 7: Gene sequence encoding R-spondin 3 (RSPO3) (OMIM: 610574; NM_032784)
SEQ ID No.: 8: Amino acid sequence of R-spondin 3 (RSPO3) (OMIM: 610574; NM_032784)

SEQ ID No.: 9: Gene sequence encoding R-spondin 4 (RSPO4) (OMIM: 610573; NM_001029871) (transcript variant 1)
SEQ ID No.: 10: Amino acid sequence of R-spondin 4 (RSPO4) (OMIM: 610573; NM_001029871) (transcript variant 1)
SEQ ID No.: 11: Gene sequence encoding SHH (SONIC HEDGEHOG) (OMIM: 600725; NM_000193)
SEQ ID No.: 12: Amino acid sequence of SHH (SONIC HEDGEHOG) (OMIM: 600725; NM_000193)
SEQ ID No.: 13: Forward primer of HumanGPR49 (Table 1)
SEQ ID No.: 14: Reverse primer of HumanGPR49 (Table 1)
SEQ ID No.: 15: Forward primer of HumanNestin (Table 1)
SEQ ID No.: 16: Reverse primer of HumanNestin (Table 1)
SEQ ID No.: 17: Forward primer of HumanABCG2 (Table 1)
SEQ ID No.: 18: Reverse primer of HumanABCG2 (Table 1)
SEQ ID No.: 19: Forward primer of HumanSHH (Table 1)
SEQ ID No.: 20: Reverse primer of HumanSHH (Table 1)
SEQ ID No.: 21: Forward primer of HumanPtch1 (Table 1)
SEQ ID No.: 22: Reverse primer of HumanPtch1 (Table 1)
SEQ ID No.: 23: Forward primer of HumanSmo (Table 1)
SEQ ID No.: 24: Reverse primer of HumanSmo (Table 1)
SEQ ID No.: 25: Forward primer of HumanGli1 (Table 1)
SEQ ID No.: 26: Reverse primer of HumanGli1 (Table 1)
SEQ ID No.: 27: Forward primer of HumanGli2 (Table 1)
SEQ ID No.: 28: Reverse primer of HumanGli2 (Table 1)
SEQ ID No.: 29: Forward primer of Humanbeta-actin (Table 1)
SEQ ID No.: 30: Reverse primer of Humanbeta-actin (Table 1)
SEQ ID No.: 31: Insertion sequence of shRNA shGPR40-587 (Table 2)
SEQ ID No.: 32: Insertion sequence of shRNA shGPR40-588 (Table 2)
SEQ ID No.: 33: Insertion sequence of shRNA shGPR40-589 (Table 2)
SEQ ID No.: 34: Insertion sequence of shRNA BNon-Target (NT) (Table 2)
SEQ ID No.: 35: Gene sequence encoding R-spondin 1 (RSPO1) (OMIM: 609595; NM_001242908) (transcript variant 2)
SEQ ID No.: 35: Gene sequence encoding R-spondin 1 (RSPO1) (OMIM: 609595; NM_001242908) (transcript variant 2)
SEQ ID No.: 36: Amino acid sequence of R-spondin 1 (RSPO1) (OMIM: 609595; NM_001242908) (transcript variant 2)
SEQ ID No.: 37: Gene sequence encoding R-spondin 1 (RSPO1) (OMIM: 609595; NM_001242909) (transcript variant 3)
SEQ ID No.: 38: Amino acid sequence of R-spondin 1 (RSPO1) (OMIM: 609595; NM_001242909) (transcript variant 3)
SEQ ID No.: 39: Gene sequence encoding R-spondin 1 (RSPO1) (OMIM: 609595; NM_001242910) (transcript variant 4)
SEQ ID No.: 40: Amino acid sequence of R-spondin 1 (RSPO1) (OMIM: 609595; NM_001242910) (transcript variant 4)
SEQ ID No.: 41: Gene acid sequence encoding R-spondin 4 (RSPO4) (OMIM: 610573; NM_001040007) (transcript variant 2)
SEQ ID No.: 42: Amino acid sequence of R-spondin 4 (RSPO4) (OMIM: 610573; NM_001040007) (transcript variant 2)
SEQ ID No.: 43: Nucleic acid sequence of ptch1 <NM_001083602.1>
SEQ ID No.: 44: Amino acid sequence of ptch1 <NM_001083602.1>
SEQ ID No.: 45: Nucleic acid sequence of gli1 <NM_001167609.1>
SEQ ID No.: 46: Amino acid sequence of gli1 <NM_001167609.1>
SEQ ID No.: 47: Nucleic acid sequence of gli2 <NM_005270.4>
SEQ ID No.: 48: Amino acid sequence of gli2 <NM_005270.4>
SEQ ID No.: 49: Nucleic acid sequence of lrp6 <NM_002336.2>
SEQ ID No.: 50: Amino acid sequence of lrp6 <NM_002336.2>
SEQ ID NO.: 51: Nucleic acid sequence of β-catenin <NM_131059.2>
SEQ ID No.: 52: Amino acid sequence of β-catenin <NM_131059.2>

The invention claimed is:

1. A method for suppressing morphological change of a cultured corneal endothelial cell, comprising contacting one or more R-spondins with the corneal endothelial cell, wherein the R-spondins comprise R-spondin 1.

2. The method according to claim 1, wherein the corneal endothelial cell is a cell which does not proliferate in the stationary state.

3. The method according to claim 1, wherein the corneal endothelial cell comprises a corneal endothelial cell of a primate.

4. The method according to claim 1, wherein the corneal endothelial cell comprises a human corneal endothelial cell.

5. The method according to claim 1, wherein the corneal endothelial cell is in the confluent state.

6. The method according to claim 1, wherein the corneal endothelial cell is provided in the form of a corneal tissue.

7. A method for suppressing morphological change and promoting proliferation of a cultured corneal endothelial cell, comprising contacting R-spondins with the corneal endothelial cell, wherein the R-spondins comprise R-spondin 1.

8. The method according to claim 7, wherein the R-spondins further comprise an R-spondin selected from R-spondin-2, R-spondin 3 and R-spondin 4.

9. The method according to claim 7, wherein the corneal endothelial cell is a cell which does not proliferate in the stationary state.

10. The method according to claim 7, wherein the corneal endothelial cell comprises a corneal endothelial cell of a primate.

11. The method according to claim 7, wherein the corneal endothelial cell comprises a human corneal endothelial cell.

12. The method according to claim 7, wherein the corneal endothelial cell is in the confluent state.

13. The method according to claim 7, wherein the corneal endothelial cell is provided in the form of a corneal tissue.

* * * * *

SEQUENCE LISTING

```
<160> NUMBER OF SEQ ID NOS: 52

<210> SEQ ID NO 1
<211> LENGTH: 2880
<212> TYPE: DNA
<213> ORGANISM: Homo sapiens
<220> FEATURE:
<221> NAME/KEY: CDS
<222> LOCATION: (49)..(2772)

<400> SEQUENCE: 1
tgctgctctc cgcccgcgtc cggctcgtgg ccccctactt cgggcacc atg gac acc      57
                                                    Met Asp Thr
                                                    1 tcc cgg ctc ggt gtg ctc ctg tcc ttg cct gtg ctg ctg cag ctg gcg     105
Ser Arg Leu Gly Val Leu Leu Ser Leu Pro Val Leu Leu Gln Leu Ala
        5                  10                  15 acc ggg ggc agc tct ccc agg tct ggt gtg ttg ctg agg ggc tgc ccc     153
Thr Gly Gly Ser Ser Pro Arg Ser Gly Val Leu Leu Arg Gly Cys Pro
20                  25                  30                  35
```

```
aca cac tgt cat tgc gag ccc gac ggc agg atg ttg ctc agg gtg gac      201
Thr His Cys His Cys Glu Pro Asp Gly Arg Met Leu Leu Arg Val Asp
             40                  45                  50 tgc tcc gac ctg ggg ctc tcg gag ctg cct tcc aac ctc agc gtc ttc      249
Cys Ser Asp Leu Gly Leu Ser Glu Leu Pro Ser Asn Leu Ser Val Phe
         55                  60                  65 acc tcc tac cta gac ctc agt atg aac aac atc agt cag ctg ctc ccg      297
Thr Ser Tyr Leu Asp Leu Ser Met Asn Asn Ile Ser Gln Leu Leu Pro
         70                  75                  80 aat ccc ctg ccc agt ctc cgc ttc ctg gag gag tta cgt ctt gcg gga      345
Asn Pro Leu Pro Ser Leu Arg Phe Leu Glu Glu Leu Arg Leu Ala Gly
85                  90                  95 aac gct ctg aca tac att ccc aag gga gca ttc act ggc ctt tac agt      393
Asn Ala Leu Thr Tyr Ile Pro Lys Gly Ala Phe Thr Gly Leu Tyr Ser
100                 105                 110                 115 ctt aaa gtt ctt atg ctg cag aat aat cag cta aga cac gta ccc aca      441
Leu Lys Val Leu Met Leu Gln Asn Asn Gln Leu Arg His Val Pro Thr
                120                 125                 130 gaa gct ctg cag aat ttg cga agc ctt caa tcc ctg cgt ctg gat gct      489
Glu Ala Leu Gln Asn Leu Arg Ser Leu Gln Ser Leu Arg Leu Asp Ala
                135                 140                 145 aac cac atc agc tat gtg ccc cca agc tgt ttc agt ggc ctg cat tcc      537
Asn His Ile Ser Tyr Val Pro Pro Ser Cys Phe Ser Gly Leu His Ser
            150                 155                 160 ctg agg cac ctg tgg ctg gat gac aat gcg tta aca gaa atc ccc gtc      585
Leu Arg His Leu Trp Leu Asp Asp Asn Ala Leu Thr Glu Ile Pro Val
        165                 170                 175 cag gct ttt aga agt tta tcg gca ttg caa gcc atg acc ttg gcc ctg      633
Gln Ala Phe Arg Ser Leu Ser Ala Leu Gln Ala Met Thr Leu Ala Leu
180                 185                 190                 195 aac aaa ata cac cac ata cca gac tat gcc ttt gga aac ctc tcc agc      681
Asn Lys Ile His His Ile Pro Asp Tyr Ala Phe Gly Asn Leu Ser Ser
                200                 205                 210 ttg gta gtt cta cat ctc cat aac aat aga atc cac tcc ctg gga aag      729
Leu Val Val Leu His Leu His Asn Asn Arg Ile His Ser Leu Gly Lys
                215                 220                 225 aaa tgc ttt gat ggg ctc cac agc cta gag act tta gat tta aat tac      777
Lys Cys Phe Asp Gly Leu His Ser Leu Glu Thr Leu Asp Leu Asn Tyr
            230                 235                 240 aat aac ctt gat gaa ttc ccc act gca att agg aca ctc tcc aac ctt      825
Asn Asn Leu Asp Glu Phe Pro Thr Ala Ile Arg Thr Leu Ser Asn Leu
        245                 250                 255 aaa gaa cta gga ttt cat agc aac aat atc agg tcg ata cct gag aaa      873
Lys Glu Leu Gly Phe His Ser Asn Asn Ile Arg Ser Ile Pro Glu Lys
260                 265                 270                 275 gca ttt gta ggc aac cct tct ctt att aca ata cat ttc tat gac aat      921
Ala Phe Val Gly Asn Pro Ser Leu Ile Thr Ile His Phe Tyr Asp Asn
                280                 285                 290 ccc atc caa ttt gtt ggg aga tct gct ttt caa cat tta cct gaa cta      969
Pro Ile Gln Phe Val Gly Arg Ser Ala Phe Gln His Leu Pro Glu Leu
                295                 300                 305 aga aca ctg act ctg aat ggt gcc tca caa ata act gaa ttt cct gat     1017
Arg Thr Leu Thr Leu Asn Gly Ala Ser Gln Ile Thr Glu Phe Pro Asp
            310                 315                 320 tta act gga act gca aac ctg gag agt ctg act tta act gga gca cag     1065
Leu Thr Gly Thr Ala Asn Leu Glu Ser Leu Thr Leu Thr Gly Ala Gln
        325                 330                 335 atc tca tct ctt cct caa acc gtc tgc aat cag tta cct aat ctc caa     1113
Ile Ser Ser Leu Pro Gln Thr Val Cys Asn Gln Leu Pro Asn Leu Gln
```

```
                                              -continued 340                   345                   350                   355 gtg cta gat ctg tct tac aac cta tta gaa gat tta ccc agt ttt tca       1161
Val Leu Asp Leu Ser Tyr Asn Leu Leu Glu Asp Leu Pro Ser Phe Ser
                360                   365                   370 gtc tgc caa aag ctt cag aaa att gac cta aga cat aat gaa atc tac       1209
Val Cys Gln Lys Leu Gln Lys Ile Asp Leu Arg His Asn Glu Ile Tyr
            375                   380                   385 gaa att aaa gtt gac act ttc cag cag ttg ctt agc ctc cga tcg ctg       1257
Glu Ile Lys Val Asp Thr Phe Gln Gln Leu Leu Ser Leu Arg Ser Leu
        390                   395                   400 aat ttg gct tgg aac aaa att gct att att cac ccc aat gca ttt tcc       1305
Asn Leu Ala Trp Asn Lys Ile Ala Ile Ile His Pro Asn Ala Phe Ser
405                   410                   415 act ttg cca tcc cta ata aag ctg gac cta tcg tcc aac ctc ctg tcg       1353
Thr Leu Pro Ser Leu Ile Lys Leu Asp Leu Ser Ser Asn Leu Leu Ser
420                   425                   430                   435 tct ttt cct ata act ggg tta cat ggt tta act cac tta aaa tta aca       1401
Ser Phe Pro Ile Thr Gly Leu His Gly Leu Thr His Leu Lys Leu Thr
                440                   445                   450 gga aat cat gcc tta cag agc ttg ata tca tct gaa aac ttt cca gaa       1449
Gly Asn His Ala Leu Gln Ser Leu Ile Ser Ser Glu Asn Phe Pro Glu
            455                   460                   465 ctc aag gtt ata gaa atg cct tat gct tac cag tgc tgt gca ttt gga       1497
Leu Lys Val Ile Glu Met Pro Tyr Ala Tyr Gln Cys Cys Ala Phe Gly
        470                   475                   480 gtg tgt gag aat gcc tat aag att tct aat caa tgg aat aaa ggt gac       1545
Val Cys Glu Asn Ala Tyr Lys Ile Ser Asn Gln Trp Asn Lys Gly Asp
485                   490                   495 aac agc agt atg gac gac ctt cat aag aaa gat gct gga atg ttt cag       1593
Asn Ser Ser Met Asp Asp Leu His Lys Lys Asp Ala Gly Met Phe Gln
500                   505                   510                   515 gct caa gat gaa cgt gac ctt gaa gat ttc ctg ctt gac ttt gag gaa       1641
Ala Gln Asp Glu Arg Asp Leu Glu Asp Phe Leu Leu Asp Phe Glu Glu
                520                   525                   530 gac ctg aaa gcc ctt cat tca gtg cag tgt tca cct tcc cca ggc ccc       1689
Asp Leu Lys Ala Leu His Ser Val Gln Cys Ser Pro Ser Pro Gly Pro
            535                   540                   545 ttc aaa ccc tgt gaa cac ctg ctt gat ggc tgg ctg atc aga att gga       1737
Phe Lys Pro Cys Glu His Leu Leu Asp Gly Trp Leu Ile Arg Ile Gly
        550                   555                   560 gtg tgg acc ata gca gtt ctg gca ctt act tgt aat gct ttg gtg act       1785
Val Trp Thr Ile Ala Val Leu Ala Leu Thr Cys Asn Ala Leu Val Thr
565                   570                   575 tca aca gtt ttc aga tcc cct ctg tac att tcc ccc att aaa ctg tta       1833
Ser Thr Val Phe Arg Ser Pro Leu Tyr Ile Ser Pro Ile Lys Leu Leu
580                   585                   590                   595 att ggg gtc atc gca gca gtg aac atg ctc acg gga gtc tcc agt gcc       1881
Ile Gly Val Ile Ala Ala Val Asn Met Leu Thr Gly Val Ser Ser Ala
                600                   605                   610 gtg ctg gct ggt gtg gat gcg ttc act ttt ggc agc ttt gca cga cat       1929
Val Leu Ala Gly Val Asp Ala Phe Thr Phe Gly Ser Phe Ala Arg His
            615                   620                   625 ggt gcc tgg tgg gag aat ggg gtt ggt tgc cat gtc att ggt ttt ttg       1977
Gly Ala Trp Trp Glu Asn Gly Val Gly Cys His Val Ile Gly Phe Leu
        630                   635                   640 tcc att ttt gct tca gaa tca tct gtt ttc ctg ctt act ctg gca gcc       2025
Ser Ile Phe Ala Ser Glu Ser Ser Val Phe Leu Leu Thr Leu Ala Ala
645                   650                   655 ctg gag cgt ggg ttc tct gtg aaa tat tct gca aaa ttt gaa acg aaa       2073
```

| | | | | | | | | | | | | | | |
|---|---|---|---|---|---|---|---|---|---|---|---|---|---|---|
|Leu|Glu|Arg|Gly|Phe|Ser|Val|Lys|Tyr|Ser|Ala|Lys|Phe|Glu|Thr|Lys|
|660| | | | |665| | | |670| | | | |675|

```
gct cca ttt tct agc ctg aaa gta atc att ttg ctc tgt gcc ctg ctg    2121
Ala Pro Phe Ser Ser Leu Lys Val Ile Ile Leu Leu Cys Ala Leu Leu
            680                 685                 690 gcc ttg acc atg gcc gca gtt ccc ctg ctg ggt ggc agc aag tat ggc    2169
Ala Leu Thr Met Ala Ala Val Pro Leu Leu Gly Gly Ser Lys Tyr Gly
            695                 700                 705 gcc tcc cct ctc tgc ctg cct ttg cct ttt ggg gag ccc agc acc atg    2217
Ala Ser Pro Leu Cys Leu Pro Leu Pro Phe Gly Glu Pro Ser Thr Met
        710                 715                 720 ggc tac atg gtc gct ctc atc ttg ctc aat tcc ctt tgc ttc ctc atg    2265
Gly Tyr Met Val Ala Leu Ile Leu Leu Asn Ser Leu Cys Phe Leu Met
    725                 730                 735 atg acc att gcc tac acc aag ctc tac tgc aat ttg gac aag gga gac    2313
Met Thr Ile Ala Tyr Thr Lys Leu Tyr Cys Asn Leu Asp Lys Gly Asp
740                 745                 750                 755 ctg gag aat att tgg gac tgc tct atg gta aaa cac att gcc ctg ttg    2361
Leu Glu Asn Ile Trp Asp Cys Ser Met Val Lys His Ile Ala Leu Leu
                760                 765                 770 ctc ttc acc aac tgc atc cta aac tgc cct gtg gct ttc ttg tcc ttc    2409
Leu Phe Thr Asn Cys Ile Leu Asn Cys Pro Val Ala Phe Leu Ser Phe
            775                 780                 785 tcc tct tta ata aac ctt aca ttt atc agt cct gaa gta att aag ttt    2457
Ser Ser Leu Ile Asn Leu Thr Phe Ile Ser Pro Glu Val Ile Lys Phe
        790                 795                 800 atc ctt ctg gtg gta gtc cca ctt cct gca tgt ctc aat ccc ctt ctc    2505
Ile Leu Leu Val Val Val Pro Leu Pro Ala Cys Leu Asn Pro Leu Leu
    805                 810                 815 tac atc ttg ttc aat cct cac ttt aag gag gat ctg gtg agc ctg aga    2553
Tyr Ile Leu Phe Asn Pro His Phe Lys Glu Asp Leu Val Ser Leu Arg
820                 825                 830                 835 aag caa acc tac gtc tgg aca aga tca aaa cac cca agc ttg atg tca    2601
Lys Gln Thr Tyr Val Trp Thr Arg Ser Lys His Pro Ser Leu Met Ser
                840                 845                 850 att aac tct gat gat gtc gaa aaa cag tcc tgt gac tca act caa gcc    2649
Ile Asn Ser Asp Asp Val Glu Lys Gln Ser Cys Asp Ser Thr Gln Ala
            855                 860                 865 ttg gta acc ttt acc agc tcc agc atc act tat gac ctg cct ccc agt    2697
Leu Val Thr Phe Thr Ser Ser Ser Ile Thr Tyr Asp Leu Pro Pro Ser
        870                 875                 880 tcc gtg cca tca cca gct tat cca gtg act gag agc tgc cat ctt tcc    2745
Ser Val Pro Ser Pro Ala Tyr Pro Val Thr Glu Ser Cys His Leu Ser
    885                 890                 895 tct gtg gca ttt gtc cca tgt ctc taa ttaatatgtg aaggaaaatg          2792
Ser Val Ala Phe Val Pro Cys Leu
900                 905 ttttcaaagg ttgagaacct gaaaatgtga gattgagtat atcagagcag taattaataa  2852
gaagagctga ggtgaaactc ggtttaaa                                     2880

<210> SEQ ID NO 2
<211> LENGTH: 907
<212> TYPE: PRT
<213> ORGANISM: Homo sapiens

<400> SEQUENCE: 2

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
```

```
              20                  25                  30
Gly Cys Pro Thr His Cys His Cys Glu Pro Asp Gly Arg Met Leu Leu
             35                  40                  45
Arg Val Asp Cys Ser Asp Leu Gly Leu Ser Glu Leu Pro Ser Asn Leu
             50                  55                  60
Ser Val Phe Thr Ser Tyr Leu Asp Leu Ser Met Asn Asn Ile Ser Gln
65                  70                  75                  80
Leu Leu Pro Asn Pro Leu Pro Ser Leu Arg Phe Leu Glu Glu Leu Arg
                 85                  90                  95
Leu Ala Gly Asn Ala Leu Thr Tyr Ile Pro Lys Gly Ala Phe Thr Gly
                100                 105                 110
Leu Tyr Ser Leu Lys Val Leu Met Leu Gln Asn Asn Gln Leu Arg His
                115                 120                 125
Val Pro Thr Glu Ala Leu Gln Asn Leu Arg Ser Leu Gln Ser Leu Arg
                130                 135                 140
Leu Asp Ala Asn His Ile Ser Tyr Val Pro Pro Ser Cys Phe Ser Gly
145                 150                 155                 160
Leu His Ser Leu Arg His Leu Trp Leu Asp Asp Asn Ala Leu Thr Glu
                165                 170                 175
Ile Pro Val Gln Ala Phe Arg Ser Leu Ser Ala Leu Gln Ala Met Thr
                180                 185                 190
Leu Ala Leu Asn Lys Ile His His Ile Pro Asp Tyr Ala Phe Gly Asn
                195                 200                 205
Leu Ser Ser Leu Val Val Leu His Leu His Asn Asn Arg Ile His Ser
                210                 215                 220
Leu Gly Lys Lys Cys Phe Asp Gly Leu His Ser Leu Glu Thr Leu Asp
225                 230                 235                 240
Leu Asn Tyr Asn Asn Leu Asp Glu Phe Pro Thr Ala Ile Arg Thr Leu
                245                 250                 255
Ser Asn Leu Lys Glu Leu Gly Phe His Ser Asn Asn Ile Arg Ser Ile
                260                 265                 270
Pro Glu Lys Ala Phe Val Gly Asn Pro Ser Leu Ile Thr Ile His Phe
                275                 280                 285
Tyr Asp Asn Pro Ile Gln Phe Val Gly Arg Ser Ala Phe Gln His Leu
                290                 295                 300
Pro Glu Leu Arg Thr Leu Thr Leu Asn Gly Ala Ser Gln Ile Thr Glu
305                 310                 315                 320
Phe Pro Asp Leu Thr Gly Thr Ala Asn Leu Glu Ser Leu Thr Leu Thr
                325                 330                 335
Gly Ala Gln Ile Ser Ser Leu Pro Gln Thr Val Cys Asn Gln Leu Pro
                340                 345                 350
Asn Leu Gln Val Leu Asp Leu Ser Tyr Asn Leu Leu Glu Asp Leu Pro
                355                 360                 365
Ser Phe Ser Val Cys Gln Lys Leu Gln Lys Ile Asp Leu Arg His Asn
                370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile Ile His Pro Asn
                405                 410                 415
Ala Phe Ser Thr Leu Pro Ser Leu Ile Lys Leu Asp Leu Ser Ser Asn
                420                 425                 430
Leu Leu Ser Ser Phe Pro Ile Thr Gly Leu His Gly Leu Thr His Leu
                435                 440                 445
```

-continued

```
Lys Leu Thr Gly Asn His Ala Leu Gln Ser Leu Ile Ser Ser Glu Asn
    450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
                500                 505                 510
Met Phe Gln Ala Gln Asp Glu Arg Asp Leu Glu Asp Phe Leu Leu Asp
            515                 520                 525
Phe Glu Glu Asp Leu Lys Ala Leu His Ser Val Gln Cys Ser Pro Ser
530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
                580                 585                 590
Lys Leu Leu Ile Gly Val Ile Ala Ala Val Asn Met Leu Thr Gly Val
            595                 600                 605
Ser Ser Ala Val Leu Ala Gly Val Asp Ala Phe Thr Phe Gly Ser Phe
        610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
                660                 665                 670
Glu Thr Lys Ala Pro Phe Ser Ser Leu Lys Val Ile Ile Leu Leu Cys
            675                 680                 685
Ala Leu Leu Ala Leu Thr Met Ala Ala Val Pro Leu Leu Gly Gly Ser
        690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
                740                 745                 750
Lys Gly Asp Leu Glu Asn Ile Trp Asp Cys Ser Met Val Lys His Ile
            755                 760                 765
Ala Leu Leu Leu Phe Thr Asn Cys Ile Leu Asn Cys Pro Val Ala Phe
        770                 775                 780
Leu Ser Phe Ser Ser Leu Ile Asn Leu Thr Phe Ile Ser Pro Glu Val
785                 790                 795                 800
Ile Lys Phe Ile Leu Leu Val Val Pro Leu Pro Ala Cys Leu Asn
                805                 810                 815
Pro Leu Leu Tyr Ile Leu Phe Asn Pro His Phe Lys Glu Asp Leu Val
                820                 825                 830
Ser Leu Arg Lys Gln Thr Tyr Val Trp Thr Arg Ser Lys His Pro Ser
            835                 840                 845
Leu Met Ser Ile Asn Ser Asp Asp Val Glu Lys Gln Ser Cys Asp Ser
        850                 855                 860
```

-continued

```
Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 3
<211> LENGTH: 3089
<212> TYPE: DNA
<213> ORGANISM: Homo sapiens
<220> FEATURE:
<221> NAME/KEY: CDS
<222> LOCATION: (893)..(1684)

<400> SEQUENCE: 3
attccctccc tggtgctcgc agaggactgg cccctctccg ggctgggagc tccggccgag      60
cggaggcgcg acggagagca ccagcgcagg gcagagagcc cggagcgacc ggccagagta     120
gggcatccgc tcgggtgctg cggagaacga gggcagctcc gagccgcccc ggaggaccga     180
tgcgccgggt ggggcgctgg ccccgagggc gtgagccgtc cgcagattga gcaacttggg     240
aacgggcggg cggagcgcag gcgagccggg cgcccaggac agtcccgcag cgggcgggtg     300
agcgggccgc gccctcgccc ctccggggcc tgccccgtc gcgactggca gcacgaagct      360
gagattgtgg tttcctggtg attcaggtgg gagtgggcca aagatcacc gctggcaagg      420 actggtgttt gtcaactgta aggactcatg aacagatct accagggatt ctcagacctt      480
agtttgagaa atgctgcaat taaaggcaaa tcctatcact ctgagtgatc gctttggtgt     540
cgaggcaatc aaccataaag ataaatgcaa atatggaaat tgcataacag tactcagtat     600
taaggttggt ttttggagta gtccctgctg acgtgacaaa aagatctctc atatgatatt     660
ccgaggtatc tttgaggaag tctctctttg aggacctccc tttgagctga tggagaactg     720
ggctccccac accctctctg tccccagctg agattatggt ggatttgggc tacggcccag     780
gcctgggcct cctgctgctg acccagcccc agaggtgtta gcaagagccg tgtgctatcc     840
accctccccg agaccacccc tccgaccagg ggcctggagc tggcgcgtga ct atg cgg      898
                                                            Met Arg
                                                              1 ctt ggg ctg tgt gtg gtg gcc ctg gtt ctg agc tgg acg cac ctc acc       946
Leu Gly Leu Cys Val Val Ala Leu Val Leu Ser Trp Thr His Leu Thr
        5                  10                  15 atc agc agc cgg ggg atc aag ggg aaa agg cag agg cgg atc agt gcc       994
Ile Ser Ser Arg Gly Ile Lys Gly Lys Arg Gln Arg Arg Ile Ser Ala
 20                  25                  30 gag ggg agc cag gcc tgt gcc aaa ggc tgt gag ctc tgc tct gaa gtc      1042
Glu Gly Ser Gln Ala Cys Ala Lys Gly Cys Glu Leu Cys Ser Glu Val
35                  40                  45                  50 aac ggc tgc ctc aag tgc tca ccc aag ctg ttc atc ctg ctg gag agg      1090
Asn Gly Cys Leu Lys Cys Ser Pro Lys Leu Phe Ile Leu Leu Glu Arg
                55                  60                  65 aac gac atc cgc cag gtg ggc gtc tgc ttg ccg tcc tgc cca cct gga      1138
Asn Asp Ile Arg Gln Val Gly Val Cys Leu Pro Ser Cys Pro Pro Gly
         70                  75                  80 tac ttc gac gcc cgc aac ccc gac atg aac aag tgc atc aaa tgc aag      1186
Tyr Phe Asp Ala Arg Asn Pro Asp Met Asn Lys Cys Ile Lys Cys Lys
             85                  90                  95 atc gag cac tgt gag gcc tgc ttc agc cat aac ttc tgc acc aag tgt      1234
Ile Glu His Cys Glu Ala Cys Phe Ser His Asn Phe Cys Thr Lys Cys
            100                 105                 110
```

-continued

```
aag gag ggc ttg tac ctg cac aag ggc cgc tgc tat cca gct tgt ccc         1282
Lys Glu Gly Leu Tyr Leu His Lys Gly Arg Cys Tyr Pro Ala Cys Pro
115                 120                 125                 130 gag ggc tcc tca gct gcc aat ggc acc atg gag tgc agt agt cct gcg         1330
Glu Gly Ser Ser Ala Ala Asn Gly Thr Met Glu Cys Ser Ser Pro Ala
                135                 140                 145 caa tgt gaa atg agc gag tgg tct ccg tgg ggg ccc tgc tcc aag aag         1378
Gln Cys Glu Met Ser Glu Trp Ser Pro Trp Gly Pro Cys Ser Lys Lys
            150                 155                 160 cag cag ctc tgt ggt ttc cgg agg ggc tcc gag gag cgg aca cgc agg         1426
Gln Gln Leu Cys Gly Phe Arg Arg Gly Ser Glu Glu Arg Thr Arg Arg
        165                 170                 175 gtg cta cat gcc cct gtg ggg gac cat gct gcc tgc tct gac acc aag         1474
Val Leu His Ala Pro Val Gly Asp His Ala Ala Cys Ser Asp Thr Lys
    180                 185                 190 gag acc cgg agg tgc aca gtg agg aga gtg ccg tgt cct gag ggg cag         1522
Glu Thr Arg Arg Cys Thr Val Arg Arg Val Pro Cys Pro Glu Gly Gln
195                 200                 205                 210 aag agg agg aag gga ggc cag ggc cgg cgg gag aat gcc aac agg aac         1570
Lys Arg Arg Lys Gly Gly Gln Gly Arg Arg Glu Asn Ala Asn Arg Asn
                215                 220                 225 ctg gcc agg aag gag agc aag gag gcg ggt gct ggc tct cga aga cgc         1618
Leu Ala Arg Lys Glu Ser Lys Glu Ala Gly Ala Gly Ser Arg Arg Arg
            230                 235                 240 aag ggg cag caa cag cag cag cag caa ggg aca gtg ggg cca ctc aca         1666
Lys Gly Gln Gln Gln Gln Gln Gln Gly Thr Val Gly Pro Leu Thr
        245                 250                 255 tct gca ggg cct gcc tag ggacactgtc cagcctccag gcccatgcag              1714
Ser Ala Gly Pro Ala
    260 aaagagttca gtgctactct gcgtgattca agctttcctg aactggaacg tcggggcaa       1774 agcatacaca cacactccaa tccatccatg catacataga cacaagacac acacgctcaa      1834 accccctgtcc acatatacaa ccatacatac ttgcacatgt gtgttcatgt acacacgcag    1894 acacagacac cacacacaca catacacaca cacacacaca cacacctgag gccaccagaa      1954 gacacttcca tccctcgggc ccagcagtac acacttggtt tccagagctc ccagtggaca     2014 tgtcagagac aacacttccc agcatctgag accaaactgc agaggggagc cttctggaga     2074 agctgctggg atcggaccag ccactgtggc agatgggagc caagcttgag gactgctggt    2134 gacctgggaa gaaaccttct tcccatcctg ttcagcactc ccagctgtgt gactttatcg    2194 ttggagagta ttgttaccct tccaggatac atatcagggt taacctgact ttgaaaactg    2254 cttaaaggtt tatttcaaat taaaacaaaa aaatcaacga cagcagtaga cacaggcacc    2314 acattccttt gcagggtgtg agggtttggc gaggtatgcg taggagcaag aagggacagg    2374 gaatttcaag agaccccaaa tagcctgctc agtagagggt catgcagaca aggaagaaaa    2434 cttaggggct gctctgacgg tggtaaacag gctgtctata tccttgttac tcagagcatg    2494 gcccggcagc agtgttgtca cagggcagct tgttaggaat gagaatctca ggtctcattc    2554 cagacctggt gagccagagt ctaaatttta agattcctga tgattggcat gttacccaaa   2614 tttgagaagt gctgctgtaa ttccccttaa aggacgggag aaagggcccc ggccatcttg    2674 cagcaggagg gattctggtc agctataaag gaggactttc catctgggag aggcagaatc    2734 tatatactga agggctagtg gcactgccag gggaagggag tgcgtaggct tccagtgatg    2794 gttggggaca atcctgccca aaggcagggc agtggatgga ataactcctt gtggcattct    2854
```

-continued

```
gaagtgtgtg ccaggctctg gactaggtgc taggttttcca gggaggagcc aaacacgggc      2914
cttgctcttg tggagcttag aggttggtgg ggaagaaaat aggcatgcac caaggaattg      2974
tacaaacaca tatataacta caaaaggatg gtgccaaggg caggtgacca ctggcatcta      3034
tgcttagcta tgaaagtgaa taaagcagaa taaaaataaa atactttctc tcagg           3089
```

<210> SEQ ID NO 4
<211> LENGTH: 263
<212> TYPE: PRT
<213> ORGANISM: Homo sapiens

<400> SEQUENCE: 4

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260
```

<210> SEQ ID NO 5
<211> LENGTH: 3149
<212> TYPE: DNA
<213> ORGANISM: Homo sapiens
<220> FEATURE:
<221> NAME/KEY: CDS
<222> LOCATION: (659)..(1390)

<400> SEQUENCE: 5

```
agcctagact tagatgcctt ggaccacagc accacctact tatagaagca tcccaagcct       60
```

-continued

```
cagccggtct gcatctccat cggaaagtgc gcttgccaca tcccttcgga tcacttcgtc      120
ctcccgagag cgttctgcct tctacagctc ggaaagaaag aaatcttagc tgtgaagtga      180
ccgtggagaa agcgcaggaa gcgacacaat tggttaggga ggcagagagt gtgagcgggc      240
gcaccccttg cctggggacc gcgctcgcgg gcggggacgg agcatcccag tggctgcacc      300
cgccgctccg cgctcctgcc tggcgtcgcc aaccccgcgg cggccgctgg aattccagag      360
ctgccaggcg ctcccagccg gtctcggcaa acttttcccc agcccacgtg ctaaccaagc      420
ggctcgcttc ccgagcccgg gatggagcac cgcgcctagg gaggccgcgc cgcccgagac      480
gtgcgcacgg ttcgtggcgg agagatgctg atcgcgctga actgaccggt gcggccgggg      540
ggtgagtggc gagtctccct ctgagtcctc cccagcagcg cggccggcgc cggctctttg      600
ggcgaaccct ccagttccta gactttgaga ggcgtctctc ccccgcccga ccgcccag       658
```

| | | | | | | | | | | | | | | | | |
|---|---|---|---|---|---|---|---|---|---|---|---|---|---|---|---|---|
| atg | cag | ttt | cgc | ctt | ttc | tcc | ttt | gcc | ctc | atc | att | ctg | aac | tgc | atg | 706 |
| Met | Gln | Phe | Arg | Leu | Phe | Ser | Phe | Ala | Leu | Ile | Ile | Leu | Asn | Cys | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gat | tac | agc | cac | tgc | caa | ggc | aac | cga | tgg | aga | cgc | agt | aag | cga | gct | 754 |
| Asp | Tyr | Ser | His | Cys | Gln | Gly | Asn | Arg | Trp | Arg | Arg | Ser | Lys | Arg | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| agt | tat | gta | tca | aat | ccc | att | tgc | aag | ggt | tgt | ttg | tct | tgt | tca | aag | 802 |
| Ser | Tyr | Val | Ser | Asn | Pro | Ile | Cys | Lys | Gly | Cys | Leu | Ser | Cys | Ser | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | aat | ggg | tgt | agc | cga | tgt | caa | cag | aag | ttg | ttc | ttc | ttc | ctt | cga | 850 |
| Asp | Asn | Gly | Cys | Ser | Arg | Cys | Gln | Gln | Lys | Leu | Phe | Phe | Phe | Leu | Arg | |
| 50 | | | | 55 | | | | | 60 | | | | | | | |

| | | | | | | | | | | | | | | | | |
|---|---|---|---|---|---|---|---|---|---|---|---|---|---|---|---|---|
| aga | gaa | ggg | atg | cgc | cag | tat | gga | gag | tgc | ctg | cat | tcc | tgc | cca | tcc | 898 |
| Arg | Glu | Gly | Met | Arg | Gln | Tyr | Gly | Glu | Cys | Leu | His | Ser | Cys | Pro | Ser | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggg | tac | tat | gga | cac | cga | gcc | cca | gat | atg | aac | aga | tgt | gca | aga | tgc | 946 |
| Gly | Tyr | Tyr | Gly | His | Arg | Ala | Pro | Asp | Met | Asn | Arg | Cys | Ala | Arg | Cys | |
| | | | 85 | | | | | 90 | | | | | 95 | | | |

| | | | | | | | | | | | | | | | | |
|---|---|---|---|---|---|---|---|---|---|---|---|---|---|---|---|---|
| aga | ata | gaa | aac | tgt | gat | tct | tgc | ttt | agc | aaa | gac | ttt | tgt | acc | aag | 994 |
| Arg | Ile | Glu | Asn | Cys | Asp | Ser | Cys | Phe | Ser | Lys | Asp | Phe | Cys | Thr | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| tgc | aaa | gta | ggc | ttt | tat | ttg | cat | aga | ggc | cgt | tgc | ttt | gat | gaa | tgt | 1042 |
| Cys | Lys | Val | Gly | Phe | Tyr | Leu | His | Arg | Gly | Arg | Cys | Phe | Asp | Glu | Cys | |
| | | | 115 | | | | | 120 | | | | | 125 | | | |

| | | | | | | | | | | | | | | | | |
|---|---|---|---|---|---|---|---|---|---|---|---|---|---|---|---|---|
| cca | gat | ggt | ttt | gca | cca | tta | gaa | gaa | acc | atg | gaa | tgt | gtg | gaa | gga | 1090 |
| Pro | Asp | Gly | Phe | Ala | Pro | Leu | Glu | Glu | Thr | Met | Glu | Cys | Val | Glu | Gly | |
| | | | 130 | | | | | 135 | | | | | 140 | | | |

| | | | | | | | | | | | | | | | | |
|---|---|---|---|---|---|---|---|---|---|---|---|---|---|---|---|---|
| tgt | gaa | gtt | ggt | cat | tgg | agc | gaa | tgg | gga | act | tgt | agc | aga | aat | aat | 1138 |
| Cys | Glu | Val | Gly | His | Trp | Ser | Glu | Trp | Gly | Thr | Cys | Ser | Arg | Asn | Asn | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| cgc | aca | tgt | gga | ttt | aaa | tgg | ggt | ctg | gaa | acc | aga | aca | cgg | caa | att | 1186 |
| Arg | Thr | Cys | Gly | Phe | Lys | Trp | Gly | Leu | Glu | Thr | Arg | Thr | Arg | Gln | Ile | |
| | | | 165 | | | | | 170 | | | | | 175 | | | |

| | | | | | | | | | | | | | | | | |
|---|---|---|---|---|---|---|---|---|---|---|---|---|---|---|---|---|
| gtt | aaa | aag | cca | gtg | aaa | gac | aca | ata | ctg | tgt | cca | acc | att | gct | gaa | 1234 |
| Val | Lys | Lys | Pro | Val | Lys | Asp | Thr | Ile | Leu | Cys | Pro | Thr | Ile | Ala | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| tcc | agg | aga | tgc | aag | atg | aca | atg | agg | cat | tgt | cca | gga | ggg | aag | aga | 1282 |
| Ser | Arg | Arg | Cys | Lys | Met | Thr | Met | Arg | His | Cys | Pro | Gly | Gly | Lys | Arg | |
| | | | 195 | | | | | 200 | | | | | 205 | | | |

| | | | | | | | | | | | | | | | | |
|---|---|---|---|---|---|---|---|---|---|---|---|---|---|---|---|---|
| aca | cca | aag | gcg | aag | gag | aag | agg | aac | aag | aaa | aag | agg | aag | ctg | | 1330 |
| Thr | Pro | Lys | Ala | Lys | Glu | Lys | Arg | Asn | Lys | Lys | Lys | Arg | Lys | Leu | | |
| | | 210 | | | | | 215 | | | | | 220 | | | | |

| | | | | | | | | | | | | | | | | |
|---|---|---|---|---|---|---|---|---|---|---|---|---|---|---|---|---|
| ata | gaa | agg | gcc | cag | gag | caa | cac | agc | gtc | ttc | cta | gct | aca | gac | aga | 1378 |
| Ile | Glu | Arg | Ala | Gln | Glu | Gln | His | Ser | Val | Phe | Leu | Ala | Thr | Asp | Arg | |

```
                 225                 230                 235                 240
gct aac caa taa aacaagagat ccggtagatt tttaggggtt tttgttttg           1430
Ala Asn Gln caaatgtgca caaagctact ctccactcct gcacactggt gtgcagcctt tgtgctgctc   1490
tgcccagtat ctgttcccag taacatggtg aaaggaagca ccaccagcat ggcccctgtg   1550
ttatttatgc tttgatttga atctggagac tgtgaaggca ggagtaagtg cacagcccgt   1610
gacttggctc agtgtgtgct gagagaatcc gtccccggca ccatggacat gctagaggtg   1670
tgaggctgca gaacaccgct ggaggacgga cttgtgccta tttatgtgaa agaagatgct   1730
tggcaggcaa tgcgctactc actcgtgacc tttatttctc acattgtgca ttttcaagga   1790
tatgtttgtg tggatatctg cttagtgtta ccacatggta ttctcagcat gttaccttca   1850
cactgttgtg cgatgaaact gcttttagct gaggatatgc tctggaaatt cctgctcagt   1910
ttcactgcag ccctaatatg tacatatact gcaggagcta catataaagc tcttatttac   1970
tgtatattta tgctttcttg tgggtaacaa gtcatacctg attaatatga tgccactttg   2030
tttctagtgg ttcctaaccc attgtctgat aaatgacttt tctagtttgg ggaattgaca   2090
cttgttttgt tgcctcttga aacttttttt ttttcccctc attgtgggct tatttctcat   2150
tgtaagggta ggataaacta gttttgtat atagagtcaa atgaccagtg tcaaagagtt    2210
tgcatattgg gtagaccttc tccactccac atgtcccaca catatagata aagcagcagg   2270
cggcatctgg caatcagaag cccaaactgc ctttgagtct aagatgtgat gactttgatg   2330
aaacacaact gaaacatga gggactatat ccagtcactt gtagccagtt tcacaggcca    2390
gctacagaat tgtccaaaca acattattt ctgactgcaa ttttttttccc ccaaatttaa   2450 agcaatccct ggctttaaat gacaaggcac ctaccaatgt tcttgggtca ctgaagaagc   2510
tactaccatg agcctgggca tagaatttta ggagataaaa ggatgaattt ctgtgactgc   2570
cagtcagatc ttaacaggtt tctgttgagc cagaatctgt ttcagatcca agatggagag   2630
gaacactatg gaaacttccc aggtgacttt cagagcagtt gtttcaaaca catcattgtc   2690
cttttagggg aaccagtttt tagaaggttg tgaattggct ttttcacaaa gcatgattat   2750
cttcctggct gatccaggag aaaattagaa cagaaaaata atggttgtgg attttgaaac   2810
aaagcaaggt aaagcctttt ttttttcacc ttgcattggc aaaactacct cttcagtgtt   2870
tttaactttt gattcaaaag catcttacca ataaggataa atatcatata catcgttatg   2930
aaaatattgc tatgagataa taagccacat atgaatgttg tatacaactt tagggtttac   2990
atttaatcct gaagtgttac ctcctttcat gtctatttac actattttcc catttactaa   3050
gtggggaggg ggtctcctta tatagtgctt catcgttaat aagtcaatac ctgttgttcc   3110
tgggatgttc ttttttgtgc attaaaaact tcaaaatta                          3149
```

<210> SEQ ID NO 6
<211> LENGTH: 243
<212> TYPE: PRT
<213> ORGANISM: Homo sapiens

<400> SEQUENCE: 6

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

```
Asp Asn Gly Cys Ser Arg Cys Gln Gln Lys Leu Phe Phe Leu Arg
     50                  55                  60

Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                 85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln

<210> SEQ ID NO 7
<211> LENGTH: 2165
<212> TYPE: DNA
<213> ORGANISM: Homo sapiens
<220> FEATURE:
<221> NAME/KEY: CDS
<222> LOCATION: (291)..(1109)

<400> SEQUENCE: 7
```

| | |
|---|---:|
| gcggccgccc cggcggctcc tggaaccccg gttcgcggcg atgccagcca ccccagcgaa | 60 |
| gccgccgcag ttcagtgctt ggataatttg aaagtacaat agttggtttc cctgtccacc | 120 |
| cgccccactt cgcttgccat cacagcacgc ctatcggatg tgagaggaga agtcccgctg | 180 |
| ctcgggcact gtctatatac gcctaacacc tacatatatt ttaaaaacat taaatataat | 240 |
| taacaatcaa agaaagagg agaaaggaag ggaagcatta ctgggttact atg cac<br>                                                                                                                          Met His<br>                                                                                                                           1 | 296 |

```
ttg cga ctg att tct tgg ctt ttt atc att ttg aac ttt atg gaa tac    344
Leu Arg Leu Ile Ser Trp Leu Phe Ile Ile Leu Asn Phe Met Glu Tyr
      5                  10                  15 atc ggc agc caa aac gcc tcc cgg gga agg cgc cag cga aga atg cat    392
Ile Gly Ser Gln Asn Ala Ser Arg Gly Arg Arg Gln Arg Arg Met His
         20                  25                  30 cct aac gtt agt caa ggc tgc caa gga ggc tgt gca aca tgc tca gat    440
Pro Asn Val Ser Gln Gly Cys Gln Gly Gly Cys Ala Thr Cys Ser Asp
 35                  40                  45                  50 tac aat gga tgt ttg tca tgt aag ccc aga cta ttt ttt gct ctg gaa    488
Tyr Asn Gly Cys Leu Ser Cys Lys Pro Arg Leu Phe Phe Ala Leu Glu
                 55                  60                  65 aga att ggc atg aag cag att gga gta tgt ctc tct tca tgt cca agt    536
```

```
                Arg Ile Gly Met Lys Gln Ile Gly Val Cys Leu Ser Ser Cys Pro Ser
                                 70                  75                  80 gga tat tat gga act cga tat cca gat ata aat aag tgt aca aaa tgc         584
Gly Tyr Tyr Gly Thr Arg Tyr Pro Asp Ile Asn Lys Cys Thr Lys Cys
             85                  90                  95 aaa gct gac tgt gat acc tgt ttc aac aaa aat ttc tgc aca aaa tgt         632
Lys Ala Asp Cys Asp Thr Cys Phe Asn Lys Asn Phe Cys Thr Lys Cys
100                 105                 110 aaa agt gga ttt tac tta cac ctt gga aag tgc ctt gac aat tgc cca         680
Lys Ser Gly Phe Tyr Leu His Leu Gly Lys Cys Leu Asp Asn Cys Pro
115                 120                 125                 130 gaa ggg ttg gaa gcc aac aac cat act atg gag tgt gtc agt att gtg         728
Glu Gly Leu Glu Ala Asn Asn His Thr Met Glu Cys Val Ser Ile Val
                135                 140                 145 cac tgt gag gtc agt gaa tgg aat cct tgg agt cca tgc acg aag aag         776
His Cys Glu Val Ser Glu Trp Asn Pro Trp Ser Pro Cys Thr Lys Lys
            150                 155                 160 gga aaa aca tgt ggc ttc aaa aga ggg act gaa aca cgg gtc cga gaa         824
Gly Lys Thr Cys Gly Phe Lys Arg Gly Thr Glu Thr Arg Val Arg Glu
        165                 170                 175 ata ata cag cat cct tca gca aag ggt aac ctg tgt ccc cca aca aat         872
Ile Ile Gln His Pro Ser Ala Lys Gly Asn Leu Cys Pro Pro Thr Asn
180                 185                 190 gag aca aga aag tgt aca gtg caa agg aag aag tgt cag aag gga gaa         920
Glu Thr Arg Lys Cys Thr Val Gln Arg Lys Lys Cys Gln Lys Gly Glu
195                 200                 205                 210 cga gga aaa aaa gga agg gag agg aaa aga aaa aaa cct aat aaa gga         968
Arg Gly Lys Lys Gly Arg Glu Arg Lys Arg Lys Lys Pro Asn Lys Gly
                215                 220                 225 gaa agt aaa gaa gca ata cct gac agc aaa agt ctg gaa tcc agc aaa        1016
Glu Ser Lys Glu Ala Ile Pro Asp Ser Lys Ser Leu Glu Ser Ser Lys
            230                 235                 240 gaa atc cca gag caa cga gaa aac aaa cag cag cag aag aag cga aaa        1064
Glu Ile Pro Glu Gln Arg Glu Asn Lys Gln Gln Gln Lys Lys Arg Lys
        245                 250                 255 gtc caa gat aaa cag aaa tcg gta tca gtc agc act gta cac tag            1109
Val Gln Asp Lys Gln Lys Ser Val Ser Val Ser Thr Val His
260                 265                 270 agggttccat gagattattg tagactcatg atgctgctat ctcaaccaga tgcccaggac      1169
aggtgctcta gccattagga ccacaaatgg acatgtcagt tattgctctg tctaaacaac      1229
attcccagta gttgctatat tcttcataca agcatagtta acaacaaaga gccaaaagat      1289
caaagaaggg atactttcag atggttgtct tgtgtgcttc tctgcatttt taaaagacaa      1349
gacattcttg tacatattat caataggcta taagatgtaa caacgaaatg atgacatctg      1409
gagaagaaac atcttttcct tataaaaatg tgttttcaag ctgttgtttt aagaagcaaa      1469
agatagttct gcaaattcaa agatacagta tcccttcaaa acaaatagga gttcagggaa      1529
gagaaacatc cttcaaagga cagtgttgtt ttgaccggga gatctagaga gtgctcagaa      1589
ttagggcctg gcatttggaa tcacaggatt tatcatcaca gaaacaactg ttttaagatt      1649
agttccatca ctctcatcct gtatttttat aagaaacaca agagtgcata ccagaattga      1709
atataccata tgggattgga gaaagacaaa tgtggaagaa atcatagagc tggagactac      1769
ttttgtgctt tacaaaactg tgaaggattg tggtcacctg aacaggtct ccaatctatg       1829 ttagcactat gtggctcagc ctctgttacc ccttggatta tatatcaacc tgtaaacatg      1889
tgcctgtaac ttacttccaa aaacaaaatc atacttatta gaagaaaatt ctgatttat       1949
```

```
agaaaaaaaa tagagcaagg agaatataac atgtttgcaa agtcatgtgt tttctttctc      2009
aatgagggaa aaacaatttt attacctgct taatggtcca cctggaacta aaagggatac      2069
tattttctaa caaggtatat ctagtagggg agaaagccac cacaataaat atatttgtta      2129
atagtttttc aaaaaaaaaa aaaaaaaaaa aaaaa                                 2165
```

<210> SEQ ID NO 8
<211> LENGTH: 272
<212> TYPE: PRT
<213> ORGANISM: Homo sapiens

<400> SEQUENCE: 8

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
            195                 200                 205

Gly Glu Arg Gly Lys Lys Gly Arg Glu Arg Lys Arg Lys Pro Asn
        210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
                245                 250                 255

Arg Lys Val Gln Asp Lys Gln Lys Ser Val Ser Val Ser Thr Val His
            260                 265                 270
```

<210> SEQ ID NO 9
<211> LENGTH: 2725
<212> TYPE: DNA
<213> ORGANISM: Homo sapiens
<220> FEATURE:
<221> NAME/KEY: CDS
<222> LOCATION: (101)..(805)

<400> SEQUENCE: 9

```
gcccacagca gcccccgcgc ccgccgtgcc gccgccggga cgtggggccc ttgggccgtc     60
```

```
gggccgcctg ggagcgcca gcccggatcc ggctgcccag atg cgg gcg cca ctc         115
                                            Met Arg Ala Pro Leu
                                            1               5 tgc ctg ctc ctg ctc gtc gcc cac gcc gtg gac atg ctc gcc ctg aac         163
Cys Leu Leu Leu Leu Val Ala His Ala Val Asp Met Leu Ala Leu Asn
            10              15                  20 cga agg aag aag caa gtg ggc act ggc ctg ggg ggc aac tgc aca ggc         211
Arg Arg Lys Lys Gln Val Gly Thr Gly Leu Gly Gly Asn Cys Thr Gly
        25              30                  35 tgt atc atc tgc tca gag gag aac ggc tgt tcc acc tgc cag cag agg         259
Cys Ile Ile Cys Ser Glu Glu Asn Gly Cys Ser Thr Cys Gln Gln Arg
        40              45                  50 ctc ttc ctg ttc atc cgc cgg gaa ggc atc cgc cag tac ggc aag tgc         307
Leu Phe Leu Phe Ile Arg Arg Glu Gly Ile Arg Gln Tyr Gly Lys Cys
    55              60              65 ctg cac gac tgt ccc cct ggg tac ttc ggc atc cgc ggc cag gag gtc         355
Leu His Asp Cys Pro Pro Gly Tyr Phe Gly Ile Arg Gly Gln Glu Val
70              75              80              85 aac agg tgc aaa aaa tgt ggg gcc act tgt gag agc tgc ttc agc cag         403
Asn Arg Cys Lys Lys Cys Gly Ala Thr Cys Glu Ser Cys Phe Ser Gln
            90              95              100 gac ttc tgc atc cgg tgc aag agg cag ttt tac ttg tac aag ggg aag         451
Asp Phe Cys Ile Arg Cys Lys Arg Gln Phe Tyr Leu Tyr Lys Gly Lys
            105             110             115 tgt ctg ccc acc tgc ccg ccg ggc act ttg gcc cac cag aac aca cgg         499
Cys Leu Pro Thr Cys Pro Pro Gly Thr Leu Ala His Gln Asn Thr Arg
        120             125             130 gag tgc cag ggg gag tgt gaa ctg ggt ccc tgg ggc ggc tgg agc ccc         547
Glu Cys Gln Gly Glu Cys Glu Leu Gly Pro Trp Gly Gly Trp Ser Pro
    135             140             145 tgc aca cac aat gga aag acc tgc ggc tcg gct tgg ggc ctg gag agc         595
Cys Thr His Asn Gly Lys Thr Cys Gly Ser Ala Trp Gly Leu Glu Ser
150             155             160             165 cgg gta cga gag gct ggc cgg gct ggg cat gag gag gca gcc acc tgc         643
Arg Val Arg Glu Ala Gly Arg Ala Gly His Glu Glu Ala Ala Thr Cys
            170             175             180 cag gtg ctt tct gag tca agg aaa tgt ccc atc cag agg ccc tgc cca         691
Gln Val Leu Ser Glu Ser Arg Lys Cys Pro Ile Gln Arg Pro Cys Pro
        185             190             195 gga gag agg agc ccc ggc cag aag aag ggc agg aag gac cgg cgc cca         739
Gly Glu Arg Ser Pro Gly Gln Lys Lys Gly Arg Lys Asp Arg Arg Pro
    200             205             210 cgc aag gac agg aag ctg gac cgc agg ctg gac gtg agg ccg cgc cag         787
Arg Lys Asp Arg Lys Leu Asp Arg Arg Leu Asp Val Arg Pro Arg Gln
    215             220             225 ccc ggc ctg cag ccc tga ccgccggctc tccgactct ctggtcctag                 835
Pro Gly Leu Gln Pro
230 tcctcggccc ctgcacacct cctcctgctc cttctcctcc tctcctctta ctctttctcc       895 tctgtcttct ccatttgtcc tctctttctt tccacccttc tatcattttt ctgtcagtct       955 accttccctt tcttttttctt ttttatttcc tttatttctt ccactccat tctcctctcc      1015 tttctccctc cctccttccc ttccttcctc ttctttctca cttatctttt atctttcctt      1075 ttctttcttc ctgtgtttct tcctgtcctt caccgcatcc ttctctctct ccctcctctt      1135 gtctccctct cacacacact ttaagaggga ccatgagcct gtgccctccc ctgcagcttt      1195 ctctatctac aacttaaaga aagcaaacat cttttcccag gcctttccct gaccccatct      1255
```

```
ttgcagagaa agggtttcca gagggcaaag ctgggacaca gcacaggtga atcctgaagg   1315
ccctgcttct gctctggggg aggctccagg accctgagct gtgagcacct ggttctctgg   1375
acagtcccca gaggccattt ccacagcctt cagccaccag ccaccccgag gagctggctg   1435
gacaaggctc cagggcttcc agaggcctgg cttggacacc tccccagct ggccgtggag    1495 ggtcacaacc tggcctctgg gtgggcagcc agccctggag ggcatcctct gcaagctgcc   1555
tgccaccctc atcggcactc ccccacaggc ctccctctca tgggttccat gccccttttt   1615
cccaagccgg atcaggtgag ctgtcactgc tgggggatcc acctgcccag cccagaagag   1675
gccactgaaa cggaaaggaa agctgagatt atccagcagc tctgttcccc acctcagcgc   1735
ttcctgccca tgtggggaaa caggtctgag aaggaagggg cttgcccagg tcacacagg    1795 aagccttcag gctctgcttc tgcctgatgg ctctgctcag cattcacg gtggagagga    1855 gaatttgggg gtcacttgag gggggaaatg tagggaattg tgggtgggga gcaagggaag   1915
atccgtgcac tcgtccacac ccaccaccac actcgctgac acccacccc acacgctgac    1975 acccaccccc acacttgccc acaccatca ccgcactcgc ccacacccac caccacactg    2035
ccccacaccc accaccacac tcccccacac ccaccaccac actcgcccac acccaccacc   2095
agtgacttga gcatctgtgc ttcgctgtga cgccctcgc cctaggcagg aacgacgctg    2155
ggaggagtct ccaggtcaga cccagcttgg aagcaagtct gtcctcactg cctatccttc    2215
tgccatcata acaccccctt cctgctctgc tccccggaat cctcagaaac gggatttgta    2275
tttgccgtga ctggttggcc tgaacacgta gggctccgtg actgggacag gaatgggcag   2335
gagaagcaag agtcggagct ccaaggggcc caggggtggc ctggggaagg aagatggtca   2395
gcaggctggg ggagaggctc taggtgatga aatattacat tcccgacccc aagagagcac   2455
ccaccctcag acctgccctc cacctggcag ctggggagcc ctggcctgaa ccccccctc    2515 ccagcaggcc caccctctct ctgacttccc tgctctcacc tccccgagaa cagctagagc   2575
cccctcctcc gcctggccag gccaccagct tctcttctgc aaacgtttgt gcctctgaaa   2635
tgctccgttg ttattgtttc aagaccctaa cttttttta aaactttctt aataaaggga    2695
aaagaaactt gtaaaaaaaa aaaaaaaaaa                                    2725
```

<210> SEQ ID NO 10
<211> LENGTH: 234
<212> TYPE: PRT
<213> ORGANISM: Homo sapiens

<400> SEQUENCE: 10

```
Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110
```

```
Leu Tyr Lys Gly Lys Cys Leu Pro Thr Cys Pro Pro Gly Thr Leu Ala
            115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230

<210> SEQ ID NO 11
<211> LENGTH: 1576
<212> TYPE: DNA
<213> ORGANISM: Homo sapiens
<220> FEATURE:
<221> NAME/KEY: CDS
<222> LOCATION: (152)..(1540)

<400> SEQUENCE: 11
gcgaggcagc cagcgaggga gagagcgagc gggcgagccg gagcgaggaa gggaaagcgc      60
aagagagagc gcacacgcac acacccgccg cgcgcactcg cgcacggacc cgcacgggga     120
cagctcggaa gtcatcagtt ccatgggcga g atg ctg ctg ctg gcg aga tgt       172
                                   Met Leu Leu Leu Ala Arg Cys
                                    1               5 ctg ctg cta gtc ctc gtc tcc tcg ctg ctg gta tgc tcg gga ctg gcg       220
Leu Leu Leu Val Leu Val Ser Ser Leu Leu Val Cys Ser Gly Leu Ala
            10                  15                  20 tgc gga ccg ggc agg ggg ttc ggg aag agg agg cac ccc aaa aag ctg       268
Cys Gly Pro Gly Arg Gly Phe Gly Lys Arg Arg His Pro Lys Lys Leu
 25                  30                  35 acc cct tta gcc tac aag cag ttt atc ccc aat gtg gcc gag aag acc       316
Thr Pro Leu Ala Tyr Lys Gln Phe Ile Pro Asn Val Ala Glu Lys Thr
 40                  45                  50                  55 cta ggc gcc agc gga agg tat gaa ggg aag atc tcc aga aac tcc gag       364
Leu Gly Ala Ser Gly Arg Tyr Glu Gly Lys Ile Ser Arg Asn Ser Glu
                 60                  65                  70 cga ttt aag gaa ctc acc ccc aat tac aac ccc gac atc ata ttt aag       412
Arg Phe Lys Glu Leu Thr Pro Asn Tyr Asn Pro Asp Ile Ile Phe Lys
             75                  80                  85 gat gaa gaa aac acc gga gcg gac agg ctg atg act cag agg tgt aag       460
Asp Glu Glu Asn Thr Gly Ala Asp Arg Leu Met Thr Gln Arg Cys Lys
         90                  95                 100 gac aag ttg aac gct ttg gcc atc tcg gtg atg aac cag tgg cca gga       508
Asp Lys Leu Asn Ala Leu Ala Ile Ser Val Met Asn Gln Trp Pro Gly
    105                 110                 115 gtg aaa ctg cgg gtg acc gag ggc tgg gac gaa gat ggc cac cac tca       556
Val Lys Leu Arg Val Thr Glu Gly Trp Asp Glu Asp Gly His His Ser
120                 125                 130                 135 gag gag tct ctg cac tac gag ggc cgc gca gtg gac atc acc acg tct       604
Glu Glu Ser Leu His Tyr Glu Gly Arg Ala Val Asp Ile Thr Thr Ser
                140                 145                 150
```

```
gac cgc gac cgc agc aag tac ggc atg ctg gcc cgc ctg gcg gtg gag      652
Asp Arg Asp Arg Ser Lys Tyr Gly Met Leu Ala Arg Leu Ala Val Glu
            155                 160                 165 gcc ggc ttc gac tgg gtg tac tac gag tcc aag gca cat atc cac tgc      700
Ala Gly Phe Asp Trp Val Tyr Tyr Glu Ser Lys Ala His Ile His Cys
            170                 175                 180 tcg gtg aaa gca gag aac tcg gtg gcg gcc aaa tcg gga ggc tgc ttc      748
Ser Val Lys Ala Glu Asn Ser Val Ala Ala Lys Ser Gly Gly Cys Phe
            185                 190                 195 ccg ggc tcg gcc acg gtg cac ctg gag cag ggc ggc acc aag ctg gtg      796
Pro Gly Ser Ala Thr Val His Leu Glu Gln Gly Gly Thr Lys Leu Val
200             205                 210                 215 aag gac ctg agc ccc ggg gac cgc gtg ctg gcg gcg gac gac cag ggc      844
Lys Asp Leu Ser Pro Gly Asp Arg Val Leu Ala Ala Asp Asp Gln Gly
                220                 225                 230 cgg ctg ctc tac agc gac ttc ctc act ttc ctg gac cgc gac gac ggc      892
Arg Leu Leu Tyr Ser Asp Phe Leu Thr Phe Leu Asp Arg Asp Asp Gly
            235                 240                 245 gcc aag aag gtc ttc tac gtg atc gag acg cgg gag ccg cgc gag cgc      940
Ala Lys Lys Val Phe Tyr Val Ile Glu Thr Arg Glu Pro Arg Glu Arg
            250                 255                 260 ctg ctg ctc acc gcc gcg cac ctg ctc ttt gtg gcg ccg cac aac gac      988
Leu Leu Leu Thr Ala Ala His Leu Leu Phe Val Ala Pro His Asn Asp
265                 270                 275 tcg gcc acc ggg gag ccc gag gcg tcc tcg ggc tcg ggg ccg cct tcc     1036
Ser Ala Thr Gly Glu Pro Glu Ala Ser Ser Gly Ser Gly Pro Pro Ser
280                 285                 290                 295 ggg ggc gca ctg ggg cct cgg gcg ctg ttc gcc agc cgc gtg cgc ccg     1084
Gly Gly Ala Leu Gly Pro Arg Ala Leu Phe Ala Ser Arg Val Arg Pro
                300                 305                 310 ggc cag cgc gtg tac gtg gtg gcc gag cgt gac ggg gac cgc cgg ctc     1132
Gly Gln Arg Val Tyr Val Val Ala Glu Arg Asp Gly Asp Arg Arg Leu
            315                 320                 325 ctg ccc gcc gct gtg cac agc gtg acc cta agc gag gag gcc gcg ggc     1180
Leu Pro Ala Ala Val His Ser Val Thr Leu Ser Glu Glu Ala Ala Gly
            330                 335                 340 gcc tac gcg ccg ctc acg gcc cag ggc acc att ctc atc aac cgg gtg     1228
Ala Tyr Ala Pro Leu Thr Ala Gln Gly Thr Ile Leu Ile Asn Arg Val
345                 350                 355 ctg gcc tcg tgc tac gcg gtc atc gag gag cac agc tgg gcg cac cgg     1276
Leu Ala Ser Cys Tyr Ala Val Ile Glu Glu His Ser Trp Ala His Arg
360                 365                 370                 375 gcc ttc gcg ccc ttc cgc ctg gcg cac gcg ctc ctg gct gca ctg gcg     1324
Ala Phe Ala Pro Phe Arg Leu Ala His Ala Leu Leu Ala Ala Leu Ala
            380                 385                 390 ccc gcg cgc acg gac cgc ggg ggg gac agc ggc ggc ggg gac cgc ggg     1372
Pro Ala Arg Thr Asp Arg Gly Gly Asp Ser Gly Gly Gly Asp Arg Gly
            395                 400                 405 ggc ggc ggc gga aga gta gcc cta acc gct cca ggt gct gcc gac gct     1420
Gly Gly Gly Gly Arg Val Ala Leu Thr Ala Pro Gly Ala Ala Asp Ala
        410                 415                 420 ccg ggt gcg ggg gcc acc gcg ggc atc cac tgg tac tcg cag ctg ctc     1468
Pro Gly Ala Gly Ala Thr Ala Gly Ile His Trp Tyr Ser Gln Leu Leu
            425                 430                 435 tac caa ata ggc acc tgg ctc ctg gac agc gag gcc ctg cac ccg ctg     1516
Tyr Gln Ile Gly Thr Trp Leu Leu Asp Ser Glu Ala Leu His Pro Leu
440                 445                 450                 455 ggc atg gcg gtc aag tcc agc tga agccgggggg ccgggggagg ggcgcgggag    1570
Gly Met Ala Val Lys Ser Ser
                460
```

```
gggcg                                                                    1576
```

<210> SEQ ID NO 12
<211> LENGTH: 462
<212> TYPE: PRT
<213> ORGANISM: Homo sapiens
<400> SEQUENCE: 12

```
Met Leu Leu Leu Ala Arg Cys Leu Leu Val Leu Val Ser Ser Leu
 1               5                  10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365
```

-continued

```
Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460

<210> SEQ ID NO 13
<211> LENGTH: 22
<212> TYPE: DNA
<213> ORGANISM: Artificial sequence
<220> FEATURE:
<223> OTHER INFORMATION: Human GPR49 Fw primer(Table 1)

<400> SEQUENCE: 13
gaggatctgg tgagcctgag aa                                              22

<210> SEQ ID NO 14
<211> LENGTH: 24
<212> TYPE: DNA
<213> ORGANISM: Artificial sequence
<220> FEATURE:
<223> OTHER INFORMATION: Human GPR49 Rv primer(Table 1)

<400> SEQUENCE: 14
cataagtgat gctggagctg gtaa                                            24

<210> SEQ ID NO 15
<211> LENGTH: 22
<212> TYPE: DNA
<213> ORGANISM: Artificial sequence
<220> FEATURE:
<223> OTHER INFORMATION: Human Nestin Fw primer(Table 1)

<400> SEQUENCE: 15
atgctcctct ctctctgctc ca                                              22

<210> SEQ ID NO 16
<211> LENGTH: 25
<212> TYPE: DNA
<213> ORGANISM: Artificial sequence
<220> FEATURE:
<223> OTHER INFORMATION: Human Nestin Rv primer(Table 1)

<400> SEQUENCE: 16
ctagtgtctc atggctctgg ttttc                                           25

<210> SEQ ID NO 17
<211> LENGTH: 20
<212> TYPE: DNA
<213> ORGANISM: Artificial sequence
<220> FEATURE:
<223> OTHER INFORMATION: Human ABCG2 Fw primer(Table 1)

<400> SEQUENCE: 17
agtggctttc taccttgtcg                                                 20
```

<210> SEQ ID NO 18
<211> LENGTH: 20
<212> TYPE: DNA
<213> ORGANISM: Artificial sequence
<220> FEATURE:
<223> OTHER INFORMATION: Human ABCG2 Rv primer(Table 1)

<400> SEQUENCE: 18
acagaaacca cactctgacc                                          20

<210> SEQ ID NO 19
<211> LENGTH: 20
<212> TYPE: DNA
<213> ORGANISM: Artificial sequence
<220> FEATURE:
<223> OTHER INFORMATION: Human SHH Fw primer(Table 1)

<400> SEQUENCE: 19
acggcccagg gcaccattct                                          20

<210> SEQ ID NO 20
<211> LENGTH: 20
<212> TYPE: DNA
<213> ORGANISM: Artificial sequence
<220> FEATURE:
<223> OTHER INFORMATION: Human SHH Rv primer(Table 1)

<400> SEQUENCE: 20
ggacttgacc gccatgccca                                          20

<210> SEQ ID NO 21
<211> LENGTH: 25
<212> TYPE: DNA
<213> ORGANISM: Artificial sequence
<220> FEATURE:
<223> OTHER INFORMATION: Human Ptch1 Fw primer(Table 1)

<400> SEQUENCE: 21
tcgctctgga gcagatttcc aaggg                                    25

<210> SEQ ID NO 22
<211> LENGTH: 22
<212> TYPE: DNA
<213> ORGANISM: Artificial sequence
<220> FEATURE:
<223> OTHER INFORMATION: Human Ptch1 Rv primer(Table 1)

<400> SEQUENCE: 22
gcagtctgga tcggccggat tg                                       22

<210> SEQ ID NO 23
<211> LENGTH: 24
<212> TYPE: DNA
<213> ORGANISM: Artificial sequence
<220> FEATURE:
<223> OTHER INFORMATION: Human Smo Fw primer(Table 1)

<400> SEQUENCE: 23
gtgagtggca tttgttttgt gggc                                     24

<210> SEQ ID NO 24
<211> LENGTH: 20
<212> TYPE: DNA
<213> ORGANISM: Artificial sequence
<220> FEATURE:
<223> OTHER INFORMATION: Human Smo Rv primer(Table 1)

```
<400> SEQUENCE: 24
caggcatttc tgccggggca                                            20

<210> SEQ ID NO 25
<211> LENGTH: 20
<212> TYPE: DNA
<213> ORGANISM: Artificial sequence
<220> FEATURE:
<223> OTHER INFORMATION: Human Gli1 Fw primer(Table 1)

<400> SEQUENCE: 25
gcccccattg cccacttgct                                            20

<210> SEQ ID NO 26
<211> LENGTH: 19
<212> TYPE: DNA
<213> ORGANISM: Artificial sequence
<220> FEATURE:
<223> OTHER INFORMATION: Human Gli1 Rv primer(Table 1)

<400> SEQUENCE: 26
tgcaggggac tgcagctcc                                             19

<210> SEQ ID NO 27
<211> LENGTH: 20
<212> TYPE: DNA
<213> ORGANISM: Artificial sequence
<220> FEATURE:
<223> OTHER INFORMATION: Human Gli2 Fw primer(Table 1)

<400> SEQUENCE: 27
ggccgcctag catcagcgag                                            20

<210> SEQ ID NO 28
<211> LENGTH: 20
<212> TYPE: DNA
<213> ORGANISM: Artificial sequence
<220> FEATURE:
<223> OTHER INFORMATION: Human Gli2 Rv primer(Table 1)

<400> SEQUENCE: 28
caccgccagg ttgccctgag                                            20

<210> SEQ ID NO 29
<211> LENGTH: 20
<212> TYPE: DNA
<213> ORGANISM: Artificial sequence
<220> FEATURE:
<223> OTHER INFORMATION: Human beta-actin Fw primer(Table 1)

<400> SEQUENCE: 29
ggacttcgag caagagatgg                                            20

<210> SEQ ID NO 30
<211> LENGTH: 20
<212> TYPE: DNA
<213> ORGANISM: Artificial sequence
<220> FEATURE:
<223> OTHER INFORMATION: Human beta-actin Rv primer(Table 1)

<400> SEQUENCE: 30
atctgctgga aggtggacag                                            20

<210> SEQ ID NO 31
```

```
<211> LENGTH: 57
<212> TYPE: DNA
<213> ORGANISM: Artificial sequence
<220> FEATURE:
<223> OTHER INFORMATION: Insert sequence of shRNA shGPR40-587(Table 2)

<400> SEQUENCE: 31
ccggccgtct gcaatcagtt acctactcga gtaggtaact gattgcagac ggtttttt      57

<210> SEQ ID NO 32
<211> LENGTH: 57
<212> TYPE: DNA
<213> ORGANISM: Artificial sequence
<220> FEATURE:
<223> OTHER INFORMATION: Insert sequence of shRNA shGPR40-588(Table 2)

<400> SEQUENCE: 32
ccggcttaca tttatcagtc ctgaactcga gttcaggact gataaatgta agtttttt      57

<210> SEQ ID NO 33
<211> LENGTH: 57
<212> TYPE: DNA
<213> ORGANISM: Artificial sequence
<220> FEATURE:
<223> OTHER INFORMATION: Insert sequence of shRNA shGPR40-589(Table 2)

<400> SEQUENCE: 33
ccgggctcta ctgcaatttg gacaactcga gttgtccaaa ttgcagtaga gcttttt      57

<210> SEQ ID NO 34
<211> LENGTH: 57
<212> TYPE: DNA
<213> ORGANISM: Artificial sequence
<220> FEATURE:
<223> OTHER INFORMATION: Insert sequence of shRNA Non-Target(NT)
      (Table 2)

<400> SEQUENCE: 34
ccggcaacaa gatgaagagc accaactcga gttggtgctc ttcatcttgt tgttttt       57

<210> SEQ ID NO 35
<211> LENGTH: 2910
<212> TYPE: DNA
<213> ORGANISM: Homo sapiens
<220> FEATURE:
<221> NAME/KEY: CDS
<222> LOCATION: (714)..(1505)

<400> SEQUENCE: 35
attccctccc tggtgctcgc agaggactgg cccctctccg ggctgggagc tccggccgag      60
cggaggcgcg acggagagca ccagcgcagg gcagagagcc cggagcgacc ggccagagta     120
gggcatccgc tcgggtgctg cggagaacga gggcagctcc gagccgcccc ggaggaccga     180
tgcgccgggt ggggcgctgg ccccgagggc gtgagccgtc cgcagattga gcaacttggg     240
aacgggcggg cggagcgcag gcgagccggg cgcccaggac agtcccgcag cgggcgggtg     300
agcgggccgc gccctcgccc ctcccggggcc tgccccgtc gcgactggca gcacgaagct     360
gagattgtgg tttcctggtg attcaggtgg gagtgggcca gaagatcacc gctggcaagg     420
actgggttgg ttttttggagt agtccctgct gacgtgacaa aaagatctct catatgatat     480
tccgaggtat ctttgaggaa gtctctcttt gaggacctcc ctttgagctg atggagaact     540
gggctcccca caccctctct gtccccagct gagattatgg tggatttggg ctacggccca     600
ggcctgggcc tcctgctgct gacccagccc cagaggtgtt agcaagagcc gtgtgctatc     660
```

```
caccctcccc gagaccaccc ctccgaccag gggcctggag ctggcgcgtg act atg    716
                                                          Met
                                                          1 cgg ctt ggg ctg tgt gtg gtg gcc ctg gtt ctg agc tgg acg cac ctc    764
Arg Leu Gly Leu Cys Val Val Ala Leu Val Leu Ser Trp Thr His Leu
        5               10              15 acc atc agc agc cgg ggg atc aag ggg aaa agg cag agg cgg atc agt    812
Thr Ile Ser Ser Arg Gly Ile Lys Gly Lys Arg Gln Arg Arg Ile Ser
        20              25              30 gcc gag ggg agc cag gcc tgt gcc aaa ggc tgt gag ctc tgc tct gaa    860
Ala Glu Gly Ser Gln Ala Cys Ala Lys Gly Cys Glu Leu Cys Ser Glu
    35              40              45 gtc aac ggc tgc ctc aag tgc tca ccc aag ctg ttc atc ctg ctg gag    908
Val Asn Gly Cys Leu Lys Cys Ser Pro Lys Leu Phe Ile Leu Leu Glu
50              55              60              65 agg aac gac atc cgc cag gtg ggc gtc tgc ttg ccg tcc tgc cca cct    956
Arg Asn Asp Ile Arg Gln Val Gly Val Cys Leu Pro Ser Cys Pro Pro
                70              75              80 gga tac ttc gac gcc cgc aac ccc gac atg aac aag tgc atc aaa tgc   1004
Gly Tyr Phe Asp Ala Arg Asn Pro Asp Met Asn Lys Cys Ile Lys Cys
            85              90              95 aag atc gag cac tgt gag gcc tgc ttc agc cat aac ttc tgc acc aag   1052
Lys Ile Glu His Cys Glu Ala Cys Phe Ser His Asn Phe Cys Thr Lys
        100             105             110 tgt aag gag ggc ttg tac ctg cac aag ggc cgc tgc tat cca gct tgt   1100
Cys Lys Glu Gly Leu Tyr Leu His Lys Gly Arg Cys Tyr Pro Ala Cys
    115             120             125 ccc gag ggc tcc tca gct gcc aat ggc acc atg gag tgc agt agt cct   1148
Pro Glu Gly Ser Ser Ala Ala Asn Gly Thr Met Glu Cys Ser Ser Pro
130             135             140             145 gcg caa tgt gaa atg agc gag tgg tct ccg tgg ggg ccc tgc tcc aag   1196
Ala Gln Cys Glu Met Ser Glu Trp Ser Pro Trp Gly Pro Cys Ser Lys
                150             155             160 aag cag cag ctc tgt ggt ttc cgg agg ggc tcc gag gag cgg aca cgc   1244
Lys Gln Gln Leu Cys Gly Phe Arg Arg Gly Ser Glu Glu Arg Thr Arg
            165             170             175 agg gtg cta cat gcc cct gtg ggg gac cat gct gcc tgc tct gac acc   1292
Arg Val Leu His Ala Pro Val Gly Asp His Ala Ala Cys Ser Asp Thr
        180             185             190 aag gag acc cgg agg tgc aca gtg agg aga gtg ccg tgt cct gag ggg   1340
Lys Glu Thr Arg Arg Cys Thr Val Arg Arg Val Pro Cys Pro Glu Gly
    195             200             205 cag aag agg agg aag gga ggc cag ggc cgg cgg gag aat gcc aac agg   1388
Gln Lys Arg Arg Lys Gly Gly Gln Gly Arg Arg Glu Asn Ala Asn Arg
210             215             220             225 aac ctg gcc agg aag gag agc aag gag gcg ggt gct ggc tct cga aga   1436
Asn Leu Ala Arg Lys Glu Ser Lys Glu Ala Gly Ala Gly Ser Arg Arg
                230             235             240 cgc aag ggg cag caa cag cag cag cag caa ggg aca gtg ggg cca ctc   1484
Arg Lys Gly Gln Gln Gln Gln Gln Gln Gly Thr Val Gly Pro Leu
            245             250             255 aca tct gca ggg cct gcc tag ggacactgtc cagcctccag gcccatgcag      1535
Thr Ser Ala Gly Pro Ala
        260 aaagagttca gtgctactct gcgtgattca agctttcctg aactggaacg tcggggggcaa  1595 agcatacaca cacactccaa tccatccatg catatcataga cacaagacac acacgctcaa  1655 accccctgtcc acatatacaa ccatacatac ttgcacatgt gtgttcatgt acacacgcag  1715
```

```
acacagacac cacacacaca catacacaca cacacacaca cacacctgag gccaccagaa    1775
gacacttcca tccctcgggc ccagcagtac acacttggtt tccagagctc ccagtggaca    1835
tgtcagagac aacacttccc agcatctgag accaaactgc agaggggagc cttctggaga    1895
agctgctggg atcggaccag ccactgtggc agatgggagc caagcttgag gactgctggt    1955
gacctgggaa gaaaccttct tcccatcctg ttcagcactc ccagctgtgt gactttatcg    2015
ttggagagta ttgttaccct tccaggatac atatcagggt taacctgact ttgaaaactg    2075
cttaaaggtt tatttcaaat taaaacaaaa aaatcaacga cagcagtaga cacaggcacc    2135
acattccttt gcagggtgtg agggtttggc gaggtatgcg taggagcaag aagggacagg    2195
gaatttcaag agaccccaaa tagcctgctc agtagagggt catgcagaca aggaagaaaa    2255
cttaggggct gctctgacgg tggtaaacag gctgtctata tccttgttac tcagagcatg    2315
gcccggcagc agtgttgtca cagggcagct tgttaggaat gagaatctca ggtctcattc    2375
cagacctggt gagccagagt ctaaatttta agattcctga tgattggcat gttacccaaa    2435
tttgagaagt gctgctgtaa ttccccttaa aggacgggag aaagggcccc ggccatcttg    2495
cagcaggagg gattctggtc agctataaag gaggactttc catctgggag aggcagaatc    2555
tatatactga agggctagtg gcactgccag gggaagggag tgcgtaggct tccagtgatg    2615
gttggggaca atcctgccca aaggcagggc agtggatgga ataactcctt gtggcattct    2675
gaagtgtgtg ccaggctctg gactaggtgc taggtttcca gggaggagcc aaacacgggc    2735
cttgctcttg tggagcttag aggttggtgg ggaagaaaat aggcatgcac caaggaattg    2795
tacaaacaca tatataacta caaaaggatg gtgccaaggg caggtgacca ctggcatcta    2855
tgcttagcta tgaaagtgaa taaagcagaa taaaaataaa atactttctc tcagg         2910
```

<210> SEQ ID NO 36
<211> LENGTH: 263
<212> TYPE: PRT
<213> ORGANISM: Homo sapiens

<400> SEQUENCE: 36

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr

```
                    165                 170                 175
Arg Arg Val Leu His Ala Pro Val Gly Asp His Ala Ala Cys Ser Asp
            180                 185                 190

Thr Lys Glu Thr Arg Arg Cys Thr Val Arg Val Pro Cys Pro Glu
            195                 200             205

Gly Gln Lys Arg Lys Gly Gln Gly Arg Arg Glu Asn Ala Asn
            210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 37
<211> LENGTH: 2589
<212> TYPE: DNA
<213> ORGANISM: Homo sapiens
<220> FEATURE:
<221> NAME/KEY: CDS
<222> LOCATION: (474)..(1184)

<400> SEQUENCE: 37
attccctccc tggtgctcgc agaggactgg cccctctccg ggctgggagc tccggccgag      60
cggaggcgcg acggagagca ccagcgcagg gcagagagcc cggagcgacc ggccagagta     120
gggcatccgc tcgggtgctg cggagaacga gggcagctcc gagccgcccc ggaggaccga     180
tgcgccgggt ggggcgctgg ccccgagggc gtgagccgtc cgcagattga gcaacttggg     240
aacgggcggg cggagcgcag gcgagccggg cgcccaggac agtcccgcag cgggcgggtg     300
agcgggccgc gccctcgccc ctcccgggcc tgccccgtc gcgactggca gcacgaagct      360
gagattgtgg tttcctggtg attcaggtgg gagtgggcca gaagatcacc gctggcaagg     420
actgggttgg ttttggagt agtccctgct gacgtgacaa aagatctct cat atg          476
                                                          Met
                                                          1 ata ttc cga gtc agt gcc gag ggg agc cag gcc tgt gcc aaa ggc tgt       524
Ile Phe Arg Val Ser Ala Glu Gly Ser Gln Ala Cys Ala Lys Gly Cys
        5                  10                  15 gag ctc tgc tct gaa gtc aac ggc tgc ctc aag tgc tca ccc aag ctg       572
Glu Leu Cys Ser Glu Val Asn Gly Cys Leu Lys Cys Ser Pro Lys Leu
         20                  25                  30 ttc atc ctg ctg gag agg aac gac atc cgc cag gtg ggc gtc tgc ttg       620
Phe Ile Leu Leu Glu Arg Asn Asp Ile Arg Gln Val Gly Val Cys Leu
 35                  40                  45 ccg tcc tgc cca cct gga tac ttc gac gcc cgc aac ccc gac atg aac       668
Pro Ser Cys Pro Pro Gly Tyr Phe Asp Ala Arg Asn Pro Asp Met Asn
 50                  55                  60                  65 aag tgc atc aaa tgc aag atc gag cac tgt gag gcc tgc ttc agc cat       716
Lys Cys Ile Lys Cys Lys Ile Glu His Cys Glu Ala Cys Phe Ser His
             70                  75                  80 aac ttc tgc acc aag tgt aag gag ggc ttg tac ctg cac aag ggc cgc       764
Asn Phe Cys Thr Lys Cys Lys Glu Gly Leu Tyr Leu His Lys Gly Arg
             85                  90                  95 tgc tat cca gct tgt ccc gag ggc tcc tca gct gcc aat ggc acc atg       812
Cys Tyr Pro Ala Cys Pro Glu Gly Ser Ser Ala Ala Asn Gly Thr Met
             100                 105                 110 gag tgc agt agt cct gcg caa tgt gaa atg agc gag tgg tct ccg tgg       860
Glu Cys Ser Ser Pro Ala Gln Cys Glu Met Ser Glu Trp Ser Pro Trp
```

```
            115                 120                 125
ggg ccc tgc tcc aag aag cag cag ctc tgt ggt ttc cgg agg ggc tcc      908
Gly Pro Cys Ser Lys Lys Gln Gln Leu Cys Gly Phe Arg Arg Gly Ser
130                 135                 140                 145 gag gag cgg aca cgc agg gtg cta cat gcc cct gtg ggg gac cat gct      956
Glu Glu Arg Thr Arg Arg Val Leu His Ala Pro Val Gly Asp His Ala
                150                 155                 160 gcc tgc tct gac acc aag gag acc cgg agg tgc aca gtg agg aga gtg     1004
Ala Cys Ser Asp Thr Lys Glu Thr Arg Arg Cys Thr Val Arg Arg Val
            165                 170                 175 ccg tgt cct gag ggg cag aag agg agg aag gga ggc cag ggc cgg cgg     1052
Pro Cys Pro Glu Gly Gln Lys Arg Arg Lys Gly Gly Gln Gly Arg Arg
        180                 185                 190 gag aat gcc aac agg aac ctg gcc agg aag gag agc aag gag gcg ggt     1100
Glu Asn Ala Asn Arg Asn Leu Ala Arg Lys Glu Ser Lys Glu Ala Gly
    195                 200                 205 gct ggc tct cga aga cgc aag ggg cag caa cag cag cag cag caa ggg     1148
Ala Gly Ser Arg Arg Arg Lys Gly Gln Gln Gln Gln Gln Gln Gln Gly
210                 215                 220                 225 aca gtg ggg cca ctc aca tct gca ggg cct gcc tag ggacactgtc          1194
Thr Val Gly Pro Leu Thr Ser Ala Gly Pro Ala
                230                 235 cagcctccag gcccatgcag aaagagttca gtgctactct gcgtgattca agctttcctg   1254
aactggaacg tcgggggcaa agcatacaca cacactccaa tccatccatg catacataga   1314
cacaagacac acacgctcaa acccctgtcc acatatacaa ccatacatac ttgcacatgt   1374
gtgttcatgt acacacgcag acacagacac cacacacaca catacacaca cacacacaca   1434
cacacctgag gccaccagaa gacacttcca tccctcgggc ccagcagtac acacttggtt   1494
tccagagctc ccagtggaca tgtcagagac aacacttccc agcatctgag accaaactgc   1554
agaggggagc cttctggaga agctgctggg atcggaccag ccactgtggc agatgggagc   1614
caagcttgag gactgctggt gacctgggaa gaaaccttct tcccatcctg ttcagcactc   1674
ccagctgtgt gactttatcg ttggagagta ttgttaccct tccaggatac atatcagggt   1734
taacctgact ttgaaaactg cttaaaggtt tatttcaaat taaaacaaaa aaatcaacga   1794
cagcagtaga cacaggcacc acattccttt gcagggtgtg agggtttggc gaggtatgcg   1854
taggagcaag aagggacagg gaatttcaag agacccccaaa tagcctgctc agtagagggt   1914
catgcagaca aggaagaaaa cttaggggct gctctgacgg tggtaaacag gctgtctata   1974
tccttgttac tcagagcatg gcccggcagc agtgttgtca cagggcagct tgttaggaat   2034
gagaatctca ggtctcattc cagacctggt gagccagagt ctaaattta agattcctga    2094 tgattggcat gttacccaaa tttgagaagt gctgctgtaa ttccccttaa aggacgggag   2154
aaagggcccc ggccatcttg cagcaggagg gattctggtc agctataaag gaggactttc   2214
catctgggag aggcagaatc tatatactga agggctagtg gcactgccag gggaagggag   2274
tgcgtaggct tccagtgatg gttggggaca atcctgccca aaggcagggc agtggatgga   2334
ataactcctt gtggcattct gaagtgtgtg ccaggctctg gactaggtgc taggtttcca   2394
gggaggagcc aaaacacggg cttgctcttg tggagcttag aggttggtgg ggaagaaaat   2454
aggcatgcac caaggaattg tacaaacaca tatataacta caaaaggatg gtgccaaggg   2514
caggtgacca ctggcatcta tgcttagcta tgaaagtgaa taaagcagaa taaaaataaa   2574
atactttctc tcagg                                                    2589
```

```
<210> SEQ ID NO 38
<211> LENGTH: 236
<212> TYPE: PRT
<213> ORGANISM: Homo sapiens

<400> SEQUENCE: 38

Met Ile Phe Arg Val Ser Ala Glu Gly Ser Gln Ala Cys Ala Lys Gly
1               5                   10                  15

Cys Glu Leu Cys Ser Glu Val Asn Gly Cys Leu Lys Cys Ser Pro Lys
            20                  25                  30

Leu Phe Ile Leu Leu Glu Arg Asn Asp Ile Arg Gln Val Gly Val Cys
        35                  40                  45

Leu Pro Ser Cys Pro Pro Gly Tyr Phe Asp Ala Arg Asn Pro Asp Met
    50                  55                  60

Asn Lys Cys Ile Lys Cys Lys Ile Glu His Cys Glu Ala Cys Phe Ser
65                  70                  75                  80

His Asn Phe Cys Thr Lys Cys Lys Glu Gly Leu Tyr Leu His Lys Gly
                85                  90                  95

Arg Cys Tyr Pro Ala Cys Pro Glu Gly Ser Ser Ala Ala Asn Gly Thr
            100                 105                 110

Met Glu Cys Ser Ser Pro Ala Gln Cys Glu Met Ser Glu Trp Ser Pro
        115                 120                 125

Trp Gly Pro Cys Ser Lys Lys Gln Gln Leu Cys Gly Phe Arg Arg Gly
    130                 135                 140

Ser Glu Glu Arg Thr Arg Arg Val Leu His Ala Pro Val Gly Asp His
145                 150                 155                 160

Ala Ala Cys Ser Asp Thr Lys Glu Thr Arg Arg Cys Thr Val Arg Arg
                165                 170                 175

Val Pro Cys Pro Glu Gly Gln Lys Arg Arg Lys Gly Gly Gln Gly Arg
            180                 185                 190

Arg Glu Asn Ala Asn Arg Asn Leu Ala Arg Lys Glu Ser Lys Glu Ala
        195                 200                 205

Gly Ala Gly Ser Arg Arg Lys Gly Gln Gln Gln Gln Gln Gln Gln Gln
    210                 215                 220

Gly Thr Val Gly Pro Leu Thr Ser Ala Gly Pro Ala
225                 230                 235

<210> SEQ ID NO 39
<211> LENGTH: 2721
<212> TYPE: DNA
<213> ORGANISM: Homo sapiens
<220> FEATURE:
<221> NAME/KEY: CDS
<222> LOCATION: (714)..(1316)

<400> SEQUENCE: 39
attccctccc tggtgctcgc agaggactgg cccctctccg gctgggagc tccggccgag      60 cggaggcgcg acggagagca ccagcgcagg gcagagagcc cggagcgacc ggccagagta    120
gggcatccgc tcgggtgctg cggagaacga gggcagctcc gagccgcccc ggaggaccga    180
tgcgccgggt ggggcgctgg ccccgagggc gtgagccgtc cgcagattga gcaacttggg    240
aacgggcggg cggagcgcag gcgagccggg cgccccaggac agtcccgcag cgggcgggtg    300
agcgggccgc gccctcgccc ctcccgggcc tgccccgtc gcgactggca gcacgaagct    360
gagattgtgg tttcctggtg attcaggtgg gagtgggcca gaagatcacc gctggcaagg    420
actgggttgg ttttttggagt agtccctgct gacgtgacaa aaagatctct catatgatat    480
```

```
tccgaggtat ctttgaggaa gtctctcttt gaggacctcc ctttgagctg atggagaact    540
gggctcccca caccctctct gtccccagct gagattatgg tggatttggg ctacggccca    600
ggcctgggcc tcctgctgct gacccagccc cagaggtgtt agcaagagcc gtgtgctatc    660
caccctcccc gagaccaccc ctccgaccag gggcctggag ctggcgcgtg act atg      716
                                                          Met
                                                           1 cgg ctt ggg ctg tgt gtg gtg gcc ctg gtt ctg agc tgg acg cac ctc     764
Arg Leu Gly Leu Cys Val Val Ala Leu Val Leu Ser Trp Thr His Leu
         5                  10                  15 acc atc agc agc cgg ggg atc aag ggg aaa agg cag agg cgg atc agt     812
Thr Ile Ser Ser Arg Gly Ile Lys Gly Lys Arg Gln Arg Arg Ile Ser
         20                  25                  30 gcc gag ggg agc cag gcc tgt gcc aaa ggc tgt gag ctc tgc tct gaa     860
Ala Glu Gly Ser Gln Ala Cys Ala Lys Gly Cys Glu Leu Cys Ser Glu
 35                  40                  45 gtc aac ggc tgc ctc aag tgc tca ccc aag ctg ttc atc ctg ctg gag     908
Val Asn Gly Cys Leu Lys Cys Ser Pro Lys Leu Phe Ile Leu Leu Glu
 50                  55                  60                  65 agg aac gac atc cgc cag gtg ggc gtc tgc ttg ccg tcc tgc cca cct     956
Arg Asn Asp Ile Arg Gln Val Gly Val Cys Leu Pro Ser Cys Pro Pro
                 70                  75                  80 gga tac ttc gac gcc cgc aac ccc gac atg aac aag tgc atc aaa tgc    1004
Gly Tyr Phe Asp Ala Arg Asn Pro Asp Met Asn Lys Cys Ile Lys Cys
                 85                  90                  95 aag atc gag cac tgt gag gcc tgc ttc agc cat aac ttc tgc acc aag    1052
Lys Ile Glu His Cys Glu Ala Cys Phe Ser His Asn Phe Cys Thr Lys
                100                 105                 110 tgt aag gag ggc ttg tac ctg cac aag ggc cgc tgc tat cca gct tgt    1100
Cys Lys Glu Gly Leu Tyr Leu His Lys Gly Arg Cys Tyr Pro Ala Cys
115                 120                 125 ccc gag ggc tcc tca gct gcc aat ggc acc atg gag tgc agt agt cct    1148
Pro Glu Gly Ser Ser Ala Ala Asn Gly Thr Met Glu Cys Ser Ser Pro
130                 135                 140                 145 ggg cag aag agg agg aag gga ggc cag ggc cgg cgg gag aat gcc aac    1196
Gly Gln Lys Arg Arg Lys Gly Gly Gln Gly Arg Arg Glu Asn Ala Asn
                150                 155                 160 agg aac ctg gcc agg aag gag agc aag gag gcg ggt gct ggc tct cga    1244
Arg Asn Leu Ala Arg Lys Glu Ser Lys Glu Ala Gly Ala Gly Ser Arg
                165                 170                 175 aga cgc aag ggg cag caa cag cag cag cag caa ggg aca gtg ggg cca    1292
Arg Arg Lys Gly Gln Gln Gln Gln Gln Gln Gly Thr Val Gly Pro
                180                 185                 190 ctc aca tct gca ggg cct gcc tag ggacactgtc cagcctccag gcccatgcag    1346
Leu Thr Ser Ala Gly Pro Ala
195                 200 aaagagttca gtgctactct gcgtgattca agctttcctg aactggaacg tcggggggcaa  1406 agcatacaca cacactccaa tccatccatg catacataga cacaagacac acacgctcaa    1466 accccctgtcc acatatacaa ccatacatac ttgcacatgt gtgttcatgt acacacgcag   1526
acacagacac cacacacaca catacacaca cacacacaca cacacctgag gccaccagaa    1586
gacacttcca tccctcgggc ccagcagtac acacttggtt tccagagctc ccagtggaca    1646
tgtcagagac aacacttccc agcatctgag accaaactgc agaggggagc cttctggaga    1706
agctgctggg atcggaccag ccactgtggc agatgggagc caagcttgag gactgctggt    1766
gacctgggaa gaaaccttct tcccatcctg ttcagcactc ccagctgtgt gactttatcg    1826
ttggagagta ttgttaccct tccaggatac atatcagggt taacctgact ttgaaaactg    1886
```

```
cttaaaggtt tatttcaaat taaaacaaaa aaatcaacga cagcagtaga cacaggcacc   1946
acattccttt gcagggtgtg agggtttggc gaggtatgcg taggagcaag aagggacagg   2006
gaatttcaag accccaaa tagcctgctc agtagagggt catgcagaca aggaagaaaa    2066
cttaggggct gctctgacgg tggtaaacag gctgtctata tccttgttac tcagagcatg   2126
gcccggcagc agtgttgtca cagggcagct tgttaggaat gagaatctca ggtctcattc   2186
cagacctggt gagccagagt ctaaatttta agattcctga tgattggcat gttacccaaa   2246
tttgagaagt gctgctgtaa ttccccttaa aggacgggag aaagggcccc ggccatcttg   2306
cagcaggagg gattctggtc agctataaag gaggactttc catctgggag aggcagaatc   2366
tatatactga agggctagtg gcactgccag gggaagggag tgcgtaggct tccagtgatg   2426
gttggggaca atcctgccca aaggcagggc agtggatgga ataactcctt gtggcattct   2486
gaagtgtgtg ccaggctctg gactaggtgc taggtttcca gggaggagcc aaacacgggc   2546
cttgctcttg tggagcttag aggttggtgg ggaagaaaat aggcatgcac caaggaattg   2606
tacaaacaca tataacta caaaaggatg gtgccaaggg caggtgacca ctggcatcta    2666
tgcttagcta tgaaagtgaa taaagcagaa taaaaataaa atactttctc tcagg        2721
```

<210> SEQ ID NO 40
<211> LENGTH: 200
<212> TYPE: PRT
<213> ORGANISM: Homo sapiens

<400> SEQUENCE: 40

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Gly Gln Lys Arg Arg Lys Gly Gly Gln Gly Arg Glu Asn Ala
145                 150                 155                 160

Asn Arg Asn Leu Ala Arg Lys Glu Ser Lys Glu Ala Gly Ala Gly Ser
                165                 170                 175

Arg Arg Arg Lys Gly Gln Gln Gln Gln Gln Gln Gly Thr Val Gly
            180                 185                 190

Pro Leu Thr Ser Ala Gly Pro Ala
        195                 200
```

<210> SEQ ID NO 41
<211> LENGTH: 2539

```
<212> TYPE: DNA
<213> ORGANISM: Homo sapiens
<220> FEATURE:
<221> NAME/KEY: CDS
<222> LOCATION: (101)..(619)

<400> SEQUENCE: 41
```

| | | |
|---|---|---|
| gcccacagca gccccgcgc cgccgtgcc gccgcggga cgtggggccc ttgggccgtc | 60 |
| gggccgcctg gggagcgcca gcccggatcc ggctgcccag atg cgg gcg cca ctc<br>                                                                     Met Arg Ala Pro Leu<br>                                                                     1             5 | 115 |
| tgc ctg ctc ctg ctc gtc gcc cac gcc gtg gac atg ctc gcc ctg aac<br>Cys Leu Leu Leu Leu Val Ala His Ala Val Asp Met Leu Ala Leu Asn<br>              10                    15                    20 | 163 |
| cga agg aag aag caa gtg ggc act ggc ctg ggg ggc aac tgc aca ggc<br>Arg Arg Lys Lys Gln Val Gly Thr Gly Leu Gly Gly Asn Cys Thr Gly<br>          25                    30                      35 | 211 |
| tgt atc atc tgc tca gag gag aac ggc tgt tcc acc tgc cag cag agg<br>Cys Ile Ile Cys Ser Glu Glu Asn Gly Cys Ser Thr Cys Gln Gln Arg<br>      40                    45                    50 | 259 |
| ctc ttc ctg ttc atc cgc cgg gaa ggc atc cgc cag tac ggc aag tgc<br>Leu Phe Leu Phe Ile Arg Arg Glu Gly Ile Arg Gln Tyr Gly Lys Cys<br>55                    60                      65 | 307 |
| ctg cac gac tgt ccc cct ggg tac ttc ggc atc cgc ggc cag gag gtc<br>Leu His Asp Cys Pro Pro Gly Tyr Phe Gly Ile Arg Gly Gln Glu Val<br>70                    75                    80                    85 | 355 |
| aac agg tgc aaa aaa tgt ggg gcc act tgt gag agc tgc ttc agc cag<br>Asn Arg Cys Lys Lys Cys Gly Ala Thr Cys Glu Ser Cys Phe Ser Gln<br>              90                    95                   100 | 403 |
| gac ttc tgc atc cgg tgc aag agg cag ttt tac ttg tac aag ggg aag<br>Asp Phe Cys Ile Arg Cys Lys Arg Gln Phe Tyr Leu Tyr Lys Gly Lys<br>                 105                   110                   115 | 451 |
| tgt ctg ccc acc tgc ccg ccg ggc act ttg gcc cac cag aac aca cgg<br>Cys Leu Pro Thr Cys Pro Pro Gly Thr Leu Ala His Gln Asn Thr Arg<br>          120                    125                   130 | 499 |
| gag tgc cag gag agg agc ccc ggc cag aag aag ggc agg aag gac cgg<br>Glu Cys Gln Glu Arg Ser Pro Gly Gln Lys Lys Gly Arg Lys Asp Arg<br>135                   140                   145 | 547 |
| cgc cca cgc aag gac agg aag ctg gac cgc agg ctg gac gtg agg ccg<br>Arg Pro Arg Lys Asp Arg Lys Leu Asp Arg Arg Leu Asp Val Arg Pro<br>150                   155                   160                   165 | 595 |
| cgc cag ccc ggc ctg cag ccc tga ccgccggctc tcccgactct ctggtcctag<br>Arg Gln Pro Gly Leu Gln Pro<br>                 170 | 649 |
| tcctcggccc ctgcacacct cctcctgctc cttctcctcc tctcctctta ctctttctcc | 709 |
| tctgtcttct ccatttgtcc tctctttctt tccacccttc tatcattttt ctgtcagtct | 769 |
| accttccctt tcttttttctt ttttatttcc tttatttctt ccacctccat tctcctctcc | 829 |
| tttctccctc cctccttccc ttccttcctc tctttctca cttatctttt atctttcctt | 889 |
| ttctttcttc ctgtgtttct tcctgtcctt caccgcatcc ttctctctct ccctcctctt | 949 |
| gtctccctct cacacacact ttaagaggga ccatgagcct gtgccctccc ctgcagcttt | 1009 |
| ctctatctac aacttaaaga aagcaaacat cttttcccag gcctttccct gaccccatct | 1069 |
| ttgcagagaa agggtttcca gagggcaaag ctgggacaca gcacaggtga atcctgaagg | 1129 |
| ccctgcttct gctctggggg aggctccagg accctgagct gtgagcacct ggttctctgg | 1189 |
| acagtccccca gaggccattt ccacagcctt cagccaccag ccaccccgag gagctggctg | 1249 |
| gacaaggctc cagggcttcc agaggcctgg cttggacacc tcccccagct ggccgtggag | 1309 |

-continued

```
ggtcacaacc tggcctctgg gtgggcagcc agccctggag ggcatcctct gcaagctgcc    1369
tgccaccctc atcggcactc ccccacaggc ctccctctca tgggttccat gcccttttt     1429
cccaagccgg atcaggtgag ctgtcactgc tgggggatcc acctgcccag cccagaagag    1489
gccactgaaa cggaaggaa agctgagatt atccagcagc tctgttcccc acctcagcgc     1549
ttcctgccca tgtggggaaa caggtctgag aaggaagggg cttgcccagg gtcacacagg    1609
aagccttcag gctctgcttc tgcctgatgg ctctgctcag cacattcacg gtggagagga    1669
gaatttgggg gtcacttgag gggggaaatg tagggaattg tgggtgggga gcaagggaag    1729
atccgtgcac tcgtccacac ccaccaccac actcgctgac acccaccccc acacgctgac    1789
acccacccc acacttgccc acacccatca ccgcactcgc ccacacccac caccacactg     1849
ccccacaccc accaccacac tccccacac ccaccaccac actcgcccac acccaccacc    1909
agtgacttga gcatctgtgc ttcgctgtga cgccctcgc cctaggcagg aacgacgctg     1969
ggaggagtct ccaggtcaga cccagcttgg aagcaagtct gtcctcactg cctatccttc    2029
tgccatcata cacccccctt cctgctctgc tccccggaat cctcagaaac gggatttgta    2089
tttgccgtga ctggttggcc tgaacacgta gggctccgtg actgggacag gaatgggcag    2149
gagaagcaag agtcggagct ccaaggggcc caggggtggc ctggggaagg aagatggtca    2209
gcaggctggg ggagaggctc taggtgatga aatattacat tcccgacccc aagagagcac    2269
ccaccctcag acctgccctc cacctggcag ctggggagcc ctggcctgaa ccccccctc    2329
ccagcaggcc caccctctct ctgacttccc tgctctcacc tccccgagaa cagctagagc    2389
cccctcctcc gcctggccag gccaccagct tctcttctgc aaacgtttgt gcctctgaaa    2449
tgctccgttg ttattgtttc aagaccctaa cttttttta aaactttctt aataaaggga    2509
aaagaaactt gtaaaaaaaa aaaaaaaaa                                      2539
```

<210> SEQ ID NO 42
<211> LENGTH: 172
<212> TYPE: PRT
<213> ORGANISM: Homo sapiens

<400> SEQUENCE: 42

```
Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Gly Thr Leu Ala
            115                 120                 125

His Gln Asn Thr Arg Glu Cys Gln Glu Arg Ser Pro Gly Gln Lys Lys
    130                 135                 140

Gly Arg Lys Asp Arg Arg Pro Arg Lys Asp Arg Lys Leu Asp Arg Arg
```

```
145             150             155             160
Leu Asp Val Arg Pro Arg Gln Pro Gly Leu Gln Pro
                    165             170

<210> SEQ ID NO 43
<211> LENGTH: 8065
<212> TYPE: DNA
<213> ORGANISM: Homo sapiens
<220> FEATURE:
<221> NAME/KEY: CDS
<222> LOCATION: (495)..(4640)

<400> SEQUENCE: 43
acccaggagg gctgtgctga tagcacgttc ctcgagttta ctttgctttc cttgagttta      60
ttgtaaaggg gtaaagtttt cggatccgtc acgtgaccct gacaggtcct gcctatggcg     120
cggcagacca cccacgccga gggccatgga actgcttaat agaaacaggc ttgtaattgt     180
gagtccgcgc tgcactccgc cgaaagcctc cggcggccca gcgcgccggg gtttttacac     240
tttccgttcc ttttgtaaag acggaggagg aggagaagaa gaagaagaaa acggaggaga     300 agaaaagac gacaggggag acaaagagac ccgcagcgac aaggcaaggg ggagacgagg     360
gaagactggg agaagacgga ggagcggagg acgaggaaag gggggccagg gaaaaaaaag     420
gaattgatgt gaaatccaag cccagcgtcc gcgccatcgg cacccgcgct ccgagcaggg     480
gttgacggcc ggct atg ggg aag gct act ggc cgg aaa gcg ccg ctg tgg        530
         Met Gly Lys Ala Thr Gly Arg Lys Ala Pro Leu Trp
          1               5                   10 ctg aga gcg aag ttt cag aga ctc tta ttt aaa ctg ggt tgt tac att        578
Leu Arg Ala Lys Phe Gln Arg Leu Leu Phe Lys Leu Gly Cys Tyr Ile
         15                  20                  25 caa aaa aac tgc ggc aag ttc ttg gtt gtg ggc ctc ctc ata ttt ggg        626
Gln Lys Asn Cys Gly Lys Phe Leu Val Val Gly Leu Leu Ile Phe Gly
     30                  35                  40 gcc ttc gcg gtg gga tta aaa gca gcg aac ctc gag acc aac gtg gag        674
Ala Phe Ala Val Gly Leu Lys Ala Ala Asn Leu Glu Thr Asn Val Glu
 45                  50                  55                  60 gag ctg tgg gtg gaa gtt gga gga cga gta agt cgt gaa tta aat tat        722
Glu Leu Trp Val Glu Val Gly Gly Arg Val Ser Arg Glu Leu Asn Tyr
                 65                  70                  75 act cgc cag aag att gga gaa gag gct atg ttt aat cct caa ctc atg        770
Thr Arg Gln Lys Ile Gly Glu Glu Ala Met Phe Asn Pro Gln Leu Met
             80                  85                  90 ata cag acc cct aaa gaa gaa ggt gct aat gtc ctg acc aca gaa gcg        818
Ile Gln Thr Pro Lys Glu Glu Gly Ala Asn Val Leu Thr Thr Glu Ala
         95                  100                 105 ctc cta caa cac ctg gac tcg gca ctc cag gcc agc cgt gtc cat gta        866
Leu Leu Gln His Leu Asp Ser Ala Leu Gln Ala Ser Arg Val His Val
     110                 115                 120 tac atg tac aac agg cag tgg aaa ttg gaa cat ttg tgt tac aaa tca        914
Tyr Met Tyr Asn Arg Gln Trp Lys Leu Glu His Leu Cys Tyr Lys Ser
125                 130                 135                 140 gga gag ctt atc aca gaa aca ggt tac atg gat cag ata ata gaa tat        962
Gly Glu Leu Ile Thr Glu Thr Gly Tyr Met Asp Gln Ile Ile Glu Tyr
                145                 150                 155 ctt tac cct tgt ttg att att aca cct ttg gac tgc ttc tgg gaa ggg       1010
Leu Tyr Pro Cys Leu Ile Ile Thr Pro Leu Asp Cys Phe Trp Glu Gly
            160                 165                 170 gcg aaa tta cag tct ggg aca gca tac ctc cta ggt aaa cct cct ttg       1058
Ala Lys Leu Gln Ser Gly Thr Ala Tyr Leu Leu Gly Lys Pro Pro Leu
        175                 180                 185
```

| | | |
|---|---|---|
| cgg tgg aca aac ttc gac cct ttg gaa ttc ctg gaa gag tta aag aaa<br>Arg Trp Thr Asn Phe Asp Pro Leu Glu Phe Leu Glu Glu Leu Lys Lys<br>190                              195                        200 | | 1106 |
| ata aac tat caa gtg gac agc tgg gag gaa atg ctg aat aag gct gag<br>Ile Asn Tyr Gln Val Asp Ser Trp Glu Glu Met Leu Asn Lys Ala Glu<br>205                      210                        215                        220 | | 1154 |
| gtt ggt cat ggt tac atg gac cgc ccc tgc ctc aat ccg gcc gat cca<br>Val Gly His Gly Tyr Met Asp Arg Pro Cys Leu Asn Pro Ala Asp Pro<br>                      225                        230                        235 | | 1202 |
| gac tgc ccc gcc aca gcc ccc aac aaa aat tca acc aaa cct ctt gat<br>Asp Cys Pro Ala Thr Ala Pro Asn Lys Asn Ser Thr Lys Pro Leu Asp<br>                240                        245                        250 | | 1250 |
| atg gcc ctt gtt ttg aat ggt gga tgt cat ggc tta tcc aga aag tat<br>Met Ala Leu Val Leu Asn Gly Gly Cys His Gly Leu Ser Arg Lys Tyr<br>                      255                        260                        265 | | 1298 |
| atg cac tgg cag gag gag ttg att gtg ggt ggc aca gtc aag aac agc<br>Met His Trp Gln Glu Glu Leu Ile Val Gly Gly Thr Val Lys Asn Ser<br>270                              275                        280 | | 1346 |
| act gga aaa ctc gtc agc gcc cat gcc ctg cag acc atg ttc cag tta<br>Thr Gly Lys Leu Val Ser Ala His Ala Leu Gln Thr Met Phe Gln Leu<br>285                              290                        295                        300 | | 1394 |
| atg act ccc aag caa atg tac gag cac ttc aag ggg tac gag tat gtc<br>Met Thr Pro Lys Gln Met Tyr Glu His Phe Lys Gly Tyr Glu Tyr Val<br>                              305                        310                        315 | | 1442 |
| tca cac atc aac tgg aac gag gac aaa gcg gca gcc atc ctg gag gcc<br>Ser His Ile Asn Trp Asn Glu Asp Lys Ala Ala Ala Ile Leu Glu Ala<br>                      320                        325                        330 | | 1490 |
| tgg cag agg aca tat gtg gag gtg gtt cat cag agt gtc gca cag aac<br>Trp Gln Arg Thr Tyr Val Glu Val Val His Gln Ser Val Ala Gln Asn<br>                335                        340                        345 | | 1538 |
| tcc act caa aag gtg ctt tcc ttc acc acc acg acc ctg gac gac atc<br>Ser Thr Gln Lys Val Leu Ser Phe Thr Thr Thr Thr Leu Asp Asp Ile<br>350                              355                        360 | | 1586 |
| ctg aaa tcc ttc tct gac gtc agt gtc atc cgc gtg gcc agc ggc tac<br>Leu Lys Ser Phe Ser Asp Val Ser Val Ile Arg Val Ala Ser Gly Tyr<br>365                              370                        375                        380 | | 1634 |
| tta ctc atg ctc gcc tat gcc tgt cta acc atg ctg cgc tgg gac tgc<br>Leu Leu Met Leu Ala Tyr Ala Cys Leu Thr Met Leu Arg Trp Asp Cys<br>                              385                        390                        395 | | 1682 |
| tcc aag tcc cag ggt gcc gtg ggg ctg gct ggc gtc ctg ctg gtt gca<br>Ser Lys Ser Gln Gly Ala Val Gly Leu Ala Gly Val Leu Leu Val Ala<br>                      400                        405                        410 | | 1730 |
| ctg tca gtg gct gca gga ctg ggc ctg tgc tca ttg atc gga att tcc<br>Leu Ser Val Ala Ala Gly Leu Gly Leu Cys Ser Leu Ile Gly Ile Ser<br>                              415                        420                        425 | | 1778 |
| ttt aac gct gca aca act cag gtt ttg cca ttt ctc gct ctt ggt gtt<br>Phe Asn Ala Ala Thr Thr Gln Val Leu Pro Phe Leu Ala Leu Gly Val<br>430                              435                        440 | | 1826 |
| ggt gtg gat gat gtt ttt ctt ctg gcc cac gcc ttc agt gaa aca gga<br>Gly Val Asp Asp Val Phe Leu Leu Ala His Ala Phe Ser Glu Thr Gly<br>445                              450                        455                        460 | | 1874 |
| cag aat aaa aga atc cct ttt gag gac agg acc ggg gag tgc ctg aag<br>Gln Asn Lys Arg Ile Pro Phe Glu Asp Arg Thr Gly Glu Cys Leu Lys<br>                              465                        470                        475 | | 1922 |
| cgc aca gga gcc agc gtg gcc ctc acg tcc atc agc aat gtc aca gcc<br>Arg Thr Gly Ala Ser Val Ala Leu Thr Ser Ile Ser Asn Val Thr Ala<br>                      480                        485                        490 | | 1970 |
| ttc ttc atg gcc gcg tta atc cca att ccc gct ctg cgg gcg ttc tcc<br>Phe Phe Met Ala Ala Leu Ile Pro Ile Pro Ala Leu Arg Ala Phe Ser | | 2018 |

```
                495                 500                 505
ctc cag gca gcg gta gta gtg ttc aat ttt gcc atg gtt ctg ctc    2066
Leu Gln Ala Ala Val Val Val Phe Asn Phe Ala Met Val Leu Leu
        510                 515                 520 att ttt cct gca att ctc agc atg gat tta tat cga cgc gag gac agg    2114
Ile Phe Pro Ala Ile Leu Ser Met Asp Leu Tyr Arg Arg Glu Asp Arg
525                 530                 535                 540 aga ctg gat att ttc tgc tgt ttt aca agc ccc tgc gtc agc aga gtg    2162
Arg Leu Asp Ile Phe Cys Cys Phe Thr Ser Pro Cys Val Ser Arg Val
            545                 550                 555 att cag gtt gaa cct cag gcc tac acc gac aca cac gac aat acc cgc    2210
Ile Gln Val Glu Pro Gln Ala Tyr Thr Asp Thr His Asp Asn Thr Arg
        560                 565                 570 tac agc ccc cca cct ccc tac agc agc cac agc ttt gcc cat gaa acg    2258
Tyr Ser Pro Pro Pro Pro Tyr Ser Ser His Ser Phe Ala His Glu Thr
575                 580                 585 cag att acc atg cag tcc act gtc cag ctc cgc acg gag tac gac ccc    2306
Gln Ile Thr Met Gln Ser Thr Val Gln Leu Arg Thr Glu Tyr Asp Pro
590                 595                 600 cac acg cac gtg tac tac acc acc gct gag ccg cgc tcc gag atc tct    2354
His Thr His Val Tyr Tyr Thr Thr Ala Glu Pro Arg Ser Glu Ile Ser
605                 610                 615                 620 gtg cag ccc gtc acc gtg aca cag gac acc ctc agc tgc cag agc cca    2402
Val Gln Pro Val Thr Val Thr Gln Asp Thr Leu Ser Cys Gln Ser Pro
                625                 630                 635 gag agc acc agc tcc aca agg gac ctg ctc tcc cag ttc tcc gac tcc    2450
Glu Ser Thr Ser Ser Thr Arg Asp Leu Leu Ser Gln Phe Ser Asp Ser
            640                 645                 650 agc ctc cac tgc ctc gag ccc ccc tgt acg aag tgg aca ctc tca tct    2498
Ser Leu His Cys Leu Glu Pro Pro Cys Thr Lys Trp Thr Leu Ser Ser
        655                 660                 665 ttt gct gag aag cac tat gct cct ttc ctc ttg aaa cca aaa gcc aag    2546
Phe Ala Glu Lys His Tyr Ala Pro Phe Leu Leu Lys Pro Lys Ala Lys
670                 675                 680 gta gtg gtg atc ttc ctt ttt ctg ggc ttg ctg ggg gtc agc ctt tat    2594
Val Val Val Ile Phe Leu Phe Leu Gly Leu Leu Gly Val Ser Leu Tyr
685                 690                 695                 700 ggc acc acc cga gtg aga gac ggg ctg gac ctt acg gac att gta cct    2642
Gly Thr Thr Arg Val Arg Asp Gly Leu Asp Leu Thr Asp Ile Val Pro
                705                 710                 715 cgg gaa acc aga gaa tat gac ttt att gct gca caa ttc aaa tac ttt    2690
Arg Glu Thr Arg Glu Tyr Asp Phe Ile Ala Ala Gln Phe Lys Tyr Phe
            720                 725                 730 tct ttc tac aac atg tat ata gtc acc cag aaa gca gac tac ccg aat    2738
Ser Phe Tyr Asn Met Tyr Ile Val Thr Gln Lys Ala Asp Tyr Pro Asn
        735                 740                 745 atc cag cac tta ctt tac gac cta cac agg agt ttc agt aac gtg aag    2786
Ile Gln His Leu Leu Tyr Asp Leu His Arg Ser Phe Ser Asn Val Lys
750                 755                 760 tat gtc atg ttg gaa gaa aac aaa cag ctt ccc aaa atg tgg ctg cac    2834
Tyr Val Met Leu Glu Glu Asn Lys Gln Leu Pro Lys Met Trp Leu His
765                 770                 775                 780 tac ttc aga gac tgg ctt cag gga ctt cag gat gca ttt gac agt gac    2882
Tyr Phe Arg Asp Trp Leu Gln Gly Leu Gln Asp Ala Phe Asp Ser Asp
                785                 790                 795 tgg gaa acc ggg aaa atc atg cca aac aat tac aag aat gga tca gac    2930
Trp Glu Thr Gly Lys Ile Met Pro Asn Asn Tyr Lys Asn Gly Ser Asp
            800                 805                 810 gat gga gtc ctt gcc tac aaa ctc ctg gtg caa acc ggc agc cgc gat    2978
```

```
                                         -continued

Asp Gly Val Leu Ala Tyr Lys Leu Leu Val Gln Thr Gly Ser Arg Asp
            815                 820                 825 aag ccc atc gac atc agc cag ttg act aaa cag cgt ctg gtg gat gca      3026
Lys Pro Ile Asp Ile Ser Gln Leu Thr Lys Gln Arg Leu Val Asp Ala
        830                 835                 840 gat ggc atc att aat ccc agc gct ttc tac atc tac ctg acg gct tgg      3074
Asp Gly Ile Ile Asn Pro Ser Ala Phe Tyr Ile Tyr Leu Thr Ala Trp
845                 850                 855                 860 gtc agc aac gac ccc gtc gcg tat gct gcc tcc cag gcc aac atc cgg      3122
Val Ser Asn Asp Pro Val Ala Tyr Ala Ala Ser Gln Ala Asn Ile Arg
                865                 870                 875 cca cac cga cca gaa tgg gtc cac gac aaa gcc gac tac atg cct gaa      3170
Pro His Arg Pro Glu Trp Val His Asp Lys Ala Asp Tyr Met Pro Glu
        880                 885                 890 aca agg ctg aga atc ccg gca gca gag ccc atc gag tat gcc cag ttc      3218
Thr Arg Leu Arg Ile Pro Ala Ala Glu Pro Ile Glu Tyr Ala Gln Phe
    895                 900                 905 cct ttc tac ctc aac ggc ttg cgg gac acc tca gac ttt gtg gag gca      3266
Pro Phe Tyr Leu Asn Gly Leu Arg Asp Thr Ser Asp Phe Val Glu Ala
        910                 915                 920 att gaa aaa gta agg acc atc tgc agc aac tat acg agc ctg ggg ctg      3314
Ile Glu Lys Val Arg Thr Ile Cys Ser Asn Tyr Thr Ser Leu Gly Leu
925                 930                 935                 940 tcc agt tac ccc aac ggc tac ccc ttc ctc ttc tgg gag cag tac atc      3362
Ser Ser Tyr Pro Asn Gly Tyr Pro Phe Leu Phe Trp Glu Gln Tyr Ile
                945                 950                 955 ggc ctc cgc cac tgg ctg ctg ctg ttc atc agc gtg gtg ttg gcc tgc      3410
Gly Leu Arg His Trp Leu Leu Leu Phe Ile Ser Val Val Leu Ala Cys
        960                 965                 970 aca ttc ctc gtg tgc gct gtc ttc ctt ctg aac ccc tgg acg gcc ggg      3458
Thr Phe Leu Val Cys Ala Val Phe Leu Leu Asn Pro Trp Thr Ala Gly
    975                 980                 985 atc att gtg atg gtc ctg gcg ctg atg acg gtc gag ctg ttc ggc atg      3506
Ile Ile Val Met Val Leu Ala Leu Met Thr Val Glu Leu Phe Gly Met
        990                 995                 1000 atg   ggc ctc atc gga atc   aag ctc agt gcc gtg   ccc gtg gtc atc    3551
Met   Gly Leu Ile Gly Ile   Lys Leu Ser Ala Val   Pro Val Val Ile
1005                  1010                    1015 ctg   atc gct tct gtt ggc   ata gga gtg gag ttc   acc gtt cac gtt    3596
Leu   Ile Ala Ser Val Gly   Ile Gly Val Glu Phe   Thr Val His Val
1020                  1025                    1030 gct   ttg gcc ttt ctg acg   gcc atc ggc gac aag   aac cgc agg gct    3641
Ala   Leu Ala Phe Leu Thr   Ala Ile Gly Asp Lys   Asn Arg Arg Ala
1035                  1040                    1045 gtg   ctt gcc ctg gag cac   atg ttt gca ccc gtc   ctg gat ggc gcc    3686
Val   Leu Ala Leu Glu His   Met Phe Ala Pro Val   Leu Asp Gly Ala
1050                  1055                    1060 gtg   tcc act ctg ctg gga   gtg ctg atg ctg gcg   gga tct gag ttc    3731
Val   Ser Thr Leu Leu Gly   Val Leu Met Leu Ala   Gly Ser Glu Phe
1065                  1070                    1075 gac   ttc att gtc agg tat   ttc ttt gct gtg ctg   gcg atc ctc acc    3776
Asp   Phe Ile Val Arg Tyr   Phe Phe Ala Val Leu   Ala Ile Leu Thr
1080                  1085                    1090 atc   ctc ggc gtt ctc aat   ggg ctg gtt ttg ctt   ccc gtg ctt ttg    3821
Ile   Leu Gly Val Leu Asn   Gly Leu Val Leu Leu   Pro Val Leu Leu
1095                  1100                    1105 tct   ttc ttt gga cca tat   cct gag gtg tct cca   gcc aac ggc ttg    3866
Ser   Phe Phe Gly Pro Tyr   Pro Glu Val Ser Pro   Ala Asn Gly Leu
1110                  1115                    1120
```

| | | |
|---|---|---|
| aac cgc ctg ccc aca ccc tcc cct gag cca ccc ccc agc gtg gtc<br>Asn Arg Leu Pro Thr Pro Ser Pro Glu Pro Pro Pro Ser Val Val<br>1125                                        1130                                    1135 | | 3911 |
| cgc ttc gcc atg ccg ccc ggc cac acg cac agc ggg tct gat tcc<br>Arg Phe Ala Met Pro Pro Gly His Thr His Ser Gly Ser Asp Ser<br>1140                                        1145                                    1150 | | 3956 |
| tcc gac tcg gag tat agt tcc cag acg aca gtg tca ggc ctc agc<br>Ser Asp Ser Glu Tyr Ser Ser Gln Thr Thr Val Ser Gly Leu Ser<br>1155                                        1160                                    1165 | | 4001 |
| gag gag ctt cgg cac tac gag gcc cag cag ggc gcg gga ggc cct<br>Glu Glu Leu Arg His Tyr Glu Ala Gln Gln Gly Ala Gly Gly Pro<br>1170                                        1175                                    1180 | | 4046 |
| gcc cac caa gtg atc gtg gaa gcc aca gaa aac ccc gtc ttc gcc<br>Ala His Gln Val Ile Val Glu Ala Thr Glu Asn Pro Val Phe Ala<br>1185                                        1190                                    1195 | | 4091 |
| cac tcc act gtg gtc cat ccc gaa tcc agg cat cac cca ccc tcg<br>His Ser Thr Val Val His Pro Glu Ser Arg His His Pro Pro Ser<br>1200                                        1205                                    1210 | | 4136 |
| aac ccg aga cag cag ccc cac ctg gac tca ggg tcc ctg cct ccc<br>Asn Pro Arg Gln Gln Pro His Leu Asp Ser Gly Ser Leu Pro Pro<br>1215                                        1220                                    1225 | | 4181 |
| gga cgg caa ggc cag cag ccc cgc agg gac ccc ccc aga gaa ggc<br>Gly Arg Gln Gly Gln Gln Pro Arg Arg Asp Pro Pro Arg Glu Gly<br>1230                                        1235                                    1240 | | 4226 |
| ttg tgg cca ccc ccc tac aga ccg cgc aga gac gct ttt gaa att<br>Leu Trp Pro Pro Pro Tyr Arg Pro Arg Arg Asp Ala Phe Glu Ile<br>1245                                        1250                                    1255 | | 4271 |
| tct act gaa ggg cat tct ggc cct agc aat agg gcc cgc tgg ggc<br>Ser Thr Glu Gly His Ser Gly Pro Ser Asn Arg Ala Arg Trp Gly<br>1260                                        1265                                    1270 | | 4316 |
| cct cgc ggg gcc cgt tct cac aac cct cgg aac cca gcg tcc act<br>Pro Arg Gly Ala Arg Ser His Asn Pro Arg Asn Pro Ala Ser Thr<br>1275                                        1280                                    1285 | | 4361 |
| gcc atg ggc agc tcc gtg ccc ggc tac tgc cag ccc atc acc act<br>Ala Met Gly Ser Ser Val Pro Gly Tyr Cys Gln Pro Ile Thr Thr<br>1290                                        1295                                    1300 | | 4406 |
| gtg acg gct tct gcc tcc gtg act gtc gcc gtg cac ccg ccg cct<br>Val Thr Ala Ser Ala Ser Val Thr Val Ala Val His Pro Pro Pro<br>1305                                        1310                                    1315 | | 4451 |
| gtc cct ggg cct ggg cgg aac ccc cga ggg gga ctc tgc cca ggc<br>Val Pro Gly Pro Gly Arg Asn Pro Arg Gly Gly Leu Cys Pro Gly<br>1320                                        1325                                    1330 | | 4496 |
| tac cct gag act gac cac ggc ctg ttt gag gac ccc cac gtg cct<br>Tyr Pro Glu Thr Asp His Gly Leu Phe Glu Asp Pro His Val Pro<br>1335                                        1340                                    1345 | | 4541 |
| ttc cac gtc cgg tgt gag agg agg gat tcg aag gtg gaa gtc att<br>Phe His Val Arg Cys Glu Arg Arg Asp Ser Lys Val Glu Val Ile<br>1350                                        1355                                    1360 | | 4586 |
| gag ctg cag gac gtg gaa tgc gag gag agg ccc cgg gga agc agc<br>Glu Leu Gln Asp Val Glu Cys Glu Glu Arg Pro Arg Gly Ser Ser<br>1365                                        1370                                    1375 | | 4631 |
| tcc aac tga gggtgattaa aatctgaagc aaagaggcca aagattggaa<br>Ser Asn<br>1380 | | 4680 |
| accccccacc cccacctctt tccagaactg cttgaagaga actggttgga gttatggaaa | | 4740 |
| agatgccctg tgccaggaca gcagttcatt gttactgtaa ccgattgtat tattttgtta | | 4800 |
| aatatttcta taaatattta agatgtac acatgtgtaa tataggaagg aaggatgtaa | | 4860 |
| agtggtatga tctggggctt ctccactcct gccccagagt gtggaggcca cagtggggcc | | 4920 |

```
tctccgtatt tgtgcattgg gctccgtgcc acaaccaagc ttcattagtc ttaaatttca    4980
gcatatgttg ctgctgctta aatattgtat aatttacttg tataattcta tgcaaatatt    5040
gcttatgtaa taggattatt ttgtaaaggt ttctgtttaa aatattttaa atttgcatat    5100
cacaaccctg tggtagtatg aaatgttact gttaactttc aaacacgcta tgcgtgataa    5160 ttttttgtt taatgagcag atatgaagaa agcacgttaa tcctggtggc ttctctaggt    5220
gtcgttgtgt gcggtcctct tgtttggctg tgcgtgtgaa cacgtgtgtg agttcaccat    5280
gtactgtact gtgattttt ttttgtcttg ttttgtttct ctacactgtc tgtaacctgt    5340
agtaggctct gacctagtca ggctggaagc gtcaggatat cttttcttcg tgctggtgag    5400
ggctggccct aaacatccac ctaatccttt caaatcagcc cggcaaaagc tagactctcc    5460
tcgtgtctac ggcatctctt atgatcattg gctgccatcc aggacccaa tttgtgcttc     5520 aggggataa tctccttctc tcggatcatt gtgatggatg ctggaacctc agggtatgga    5580
gctcacatca gttcatcatg gtgggtgtta gagaattcgg tgacatgcct agtgctgagc    5640
cttggctggg ccatgagagt ctgtatactc taaaaagcat gcagcatggt gcccctcttc    5700
tgaccaacac acacgacc cctccccaa cacccccaaa ttcaagagtg gatgtggccc        5760
tgtcacaggt agaaaaacct atttagttaa ttctttcttg gcccacagtc tcccagaaat    5820
gatgttttga gtccctatag tttaaactcc ctctcttaaa tggagcagct ggttgaggct    5880
ttctagatct gttgtcatct tctttaaaac taagtggtga gcatgcattg tggtgtagag    5940
gcaggcatta tgtaggataa gagctccggg gggattcttc atgcaccagt gtttagggta    6000
cgtgcttcct aagtaaatcc aaacattgtc tccatcctcc ccgtcattag tgctctttca    6060
atgtgatgtg ggaaagcagg aggatggaca caccccactg aaagatgtag gcaggggcag    6120
gtctctcaac caggcatatt tttaaaagtt gcttctgtac tggttctctt cttttgctct    6180
gaggtgtggg ctccctcatc tcgtaaccag agaccagcac atgtcaggga agcacccagt    6240
gtcggctccc catccaaatc cacaccagca ccttgttaca gacaagaagt cagaggaaag    6300
ggcggggtcc ctgcagggct gaagcctaag ctactgtgag gcgctcacga gtggcagctc    6360
ctgttactcc cttttaaatt acctgggaaa tcttaacaga aaggtaatgg gccccagaa     6420 atacccacag catagtgacc tcagaccctg atactcacca caaaactttt aagatgctga    6480
ttgggagccg cttgtggctg ctgggtgtgt gtgtgtgtgt gtgcgtgcgt gcgtgtgtgt    6540
gtgtctctgc tggggaccct ggccaccccc ctgctgctgt cttggtgcct gtcacccaca    6600
tggtctgcca tcctaacacc cagctctgct cagaaaacgt cctgcgtgga ggagggatga    6660
tgcagaattc tgaagtcgac ttccctctgg ctcctggcgt gccctcgctc ccttcctgag    6720
cccagctcgt gttgcgccgg aggctgcgcg gcccctgatt tctgcatggt gtagaacttt    6780
ctccaatagt cacattggca aagggagaac tggggtgggc ggggggtggg gctggcaggg    6840
aattagaatt tctctctctc ttttaatagt tttattttgt ctgtcctgtt tgttcatttg    6900
gatgttttaa tttttaaaaa aaaaaaaact ttgctgatat ttataatttt gtatcataag    6960
aatgttttcc tctacagtat ttgtcatgcc agtttataac aaaaaaaaat gcagggattt    7020
tatttctatt ggaaacatta cagctatgtt ttacttttgg acagaatttt tatttgtata    7080
gagtgcttac taatgttaaa tagttcagag tatataacat ttacattaag gactcatggt    7140
aggttttagg gtaaggagtt taaaggaaat aaatattcaa actgggtctc attgccaatt    7200
ttggtggaaa tgagtttgtg tcatttcaat tacaaagata aagtatgcc atataattta     7260
```

```
tttatatgaa gatttatttt tgtagtgtac atagtagtca tcaagtcttt tgacagaagt    7320 atattttaa agaatttata tgtgatgaat ccataatgtc tggaactttg ctgagacatg     7380
agtgggcaca gttttcattg taaattacag caaggaaaga aaatgtttaa cagtgttaag    7440
agagtcagag cagagtggat attcatgcga ttatgaagtg tttattagtt accattggcg    7500
acctagcatg cttctcattt caaaccttgg aaggtgaaaa tgtacaaact ctctaaataa    7560
ttaatgttca aacactgata gaaattctaa catgaataaa aataatata acttgttggt     7620 tatatctttg tttgtagaat gctttttttc tttaaaatac ttgggagaga cagttagtgt    7680
tggagccatc agaaactgtt gtttcatctt gctgaccttg tgacactctt cttttttgct    7740
ctatctgatg gagagagttt taggttttcc tccttttgt tttgtataaa tagtgggtat     7800
aagcatagct ctgttacatg gatgtattac aaagtggggg ctgagctttt agtgtgatca    7860
tcacccaaat agtgtacatt gtacccatta attaatttct tatcacctga ccctattttt    7920
gttttctcat accaagaaac ttcctaagtt aaccatcaaa attagtcctt ctgtcatctc    7980
tcttagcata cttatttccc ttatgtgatg cctaataatg agggaacata aataaagcca    8040
aattcaaaga taaaaaaaaa aaaaa                                           8065

<210> SEQ ID NO 44
<211> LENGTH: 1381
<212> TYPE: PRT
<213> ORGANISM: Homo sapiens

<400> SEQUENCE: 44

Met Gly Lys Ala Thr Gly Arg Lys Ala Pro Leu Trp Leu Arg Ala Lys
1               5                   10                  15

Phe Gln Arg Leu Leu Phe Lys Leu Gly Cys Tyr Ile Gln Lys Asn Cys
            20                  25                  30

Gly Lys Phe Leu Val Val Gly Leu Leu Ile Phe Gly Ala Phe Ala Val
        35                  40                  45

Gly Leu Lys Ala Ala Asn Leu Glu Thr Asn Val Glu Glu Leu Trp Val
    50                  55                  60

Glu Val Gly Gly Arg Val Ser Arg Glu Leu Asn Tyr Thr Arg Gln Lys
65                  70                  75                  80

Ile Gly Glu Glu Ala Met Phe Asn Pro Gln Leu Met Ile Gln Thr Pro
                85                  90                  95

Lys Glu Glu Gly Ala Asn Val Leu Thr Thr Glu Ala Leu Leu Gln His
            100                 105                 110

Leu Asp Ser Ala Leu Gln Ala Ser Arg Val His Val Tyr Met Tyr Asn
        115                 120                 125

Arg Gln Trp Lys Leu Glu His Leu Cys Tyr Lys Ser Gly Glu Leu Ile
    130                 135                 140

Thr Glu Thr Gly Tyr Met Asp Gln Ile Ile Glu Tyr Leu Tyr Pro Cys
145                 150                 155                 160

Leu Ile Ile Thr Pro Leu Asp Cys Phe Trp Glu Gly Ala Lys Leu Gln
                165                 170                 175

Ser Gly Thr Ala Tyr Leu Leu Gly Lys Pro Pro Leu Arg Trp Thr Asn
            180                 185                 190

Phe Asp Pro Leu Glu Phe Leu Glu Glu Leu Lys Lys Ile Asn Tyr Gln
        195                 200                 205

Val Asp Ser Trp Glu Glu Met Leu Asn Lys Ala Glu Val Gly His Gly
    210                 215                 220

Tyr Met Asp Arg Pro Cys Leu Asn Pro Ala Asp Pro Asp Cys Pro Ala
```

-continued

```
                225                 230                 235                 240
Thr Ala Pro Asn Lys Asn Ser Thr Lys Pro Leu Asp Met Ala Leu Val
                245                 250                 255

Leu Asn Gly Gly Cys His Gly Leu Ser Arg Lys Tyr Met His Trp Gln
                260                 265                 270

Glu Glu Leu Ile Val Gly Gly Thr Val Lys Asn Ser Thr Gly Lys Leu
                275                 280                 285

Val Ser Ala His Ala Leu Gln Thr Met Phe Gln Leu Met Thr Pro Lys
            290                 295                 300

Gln Met Tyr Glu His Phe Lys Gly Tyr Glu Tyr Val Ser His Ile Asn
305                 310                 315                 320

Trp Asn Glu Asp Lys Ala Ala Ile Leu Glu Ala Trp Gln Arg Thr
                325                 330                 335

Tyr Val Glu Val Val His Gln Ser Val Ala Gln Asn Ser Thr Gln Lys
                340                 345                 350

Val Leu Ser Phe Thr Thr Thr Leu Asp Asp Ile Leu Lys Ser Phe
                355                 360                 365

Ser Asp Val Ser Val Ile Arg Val Ala Ser Gly Tyr Leu Leu Met Leu
    370                 375                 380

Ala Tyr Ala Cys Leu Thr Met Leu Arg Trp Asp Cys Ser Lys Ser Gln
385                 390                 395                 400

Gly Ala Val Gly Leu Ala Gly Val Leu Val Ala Leu Ser Val Ala
                405                 410                 415

Ala Gly Leu Gly Leu Cys Ser Leu Ile Gly Ile Ser Phe Asn Ala Ala
                420                 425                 430

Thr Thr Gln Val Leu Pro Phe Leu Ala Leu Gly Val Gly Val Asp Asp
                435                 440                 445

Val Phe Leu Leu Ala His Ala Phe Ser Glu Thr Gly Gln Asn Lys Arg
    450                 455                 460

Ile Pro Phe Glu Asp Arg Thr Gly Glu Cys Leu Lys Arg Thr Gly Ala
465                 470                 475                 480

Ser Val Ala Leu Thr Ser Ile Ser Asn Val Thr Ala Phe Phe Met Ala
                485                 490                 495

Ala Leu Ile Pro Ile Pro Ala Leu Arg Ala Phe Ser Leu Gln Ala Ala
                500                 505                 510

Val Val Val Val Phe Asn Phe Ala Met Val Leu Leu Ile Phe Pro Ala
                515                 520                 525

Ile Leu Ser Met Asp Leu Tyr Arg Arg Glu Asp Arg Leu Asp Ile
    530                 535                 540

Phe Cys Cys Phe Thr Ser Pro Cys Val Ser Arg Val Ile Gln Val Glu
545                 550                 555                 560

Pro Gln Ala Tyr Thr Asp Thr His Asp Asn Thr Arg Tyr Ser Pro Pro
                565                 570                 575

Pro Pro Tyr Ser Ser His Ser Phe Ala His Glu Thr Gln Ile Thr Met
                580                 585                 590

Gln Ser Thr Val Gln Leu Arg Thr Glu Tyr Asp Pro His Thr His Val
            595                 600                 605

Tyr Tyr Thr Thr Ala Glu Pro Arg Ser Glu Ile Ser Val Gln Pro Val
                610                 615                 620

Thr Val Thr Gln Asp Thr Leu Ser Cys Gln Ser Pro Glu Ser Thr Ser
625                 630                 635                 640

Ser Thr Arg Asp Leu Leu Ser Gln Phe Ser Asp Ser Ser Leu His Cys
                645                 650                 655
```

-continued

Leu Glu Pro Pro Cys Thr Lys Trp Thr Leu Ser Ser Phe Ala Glu Lys
                660                 665                 670

His Tyr Ala Pro Phe Leu Leu Lys Pro Lys Ala Lys Val Val Val Ile
            675                 680                 685

Phe Leu Phe Leu Gly Leu Leu Gly Val Ser Leu Tyr Gly Thr Thr Arg
690                 695                 700

Val Arg Asp Gly Leu Asp Leu Thr Asp Ile Val Pro Arg Glu Thr Arg
705                 710                 715                 720

Glu Tyr Asp Phe Ile Ala Ala Gln Phe Lys Tyr Phe Ser Phe Tyr Asn
                725                 730                 735

Met Tyr Ile Val Thr Gln Lys Ala Asp Tyr Pro Asn Ile Gln His Leu
            740                 745                 750

Leu Tyr Asp Leu His Arg Ser Phe Ser Asn Val Lys Tyr Val Met Leu
        755                 760                 765

Glu Glu Asn Lys Gln Leu Pro Lys Met Trp Leu His Tyr Phe Arg Asp
770                 775                 780

Trp Leu Gln Gly Leu Gln Asp Ala Phe Asp Ser Asp Trp Glu Thr Gly
785                 790                 795                 800

Lys Ile Met Pro Asn Asn Tyr Lys Asn Gly Ser Asp Asp Gly Val Leu
                805                 810                 815

Ala Tyr Lys Leu Leu Val Gln Thr Gly Ser Arg Asp Lys Pro Ile Asp
            820                 825                 830

Ile Ser Gln Leu Thr Lys Gln Arg Leu Val Asp Ala Asp Gly Ile Ile
        835                 840                 845

Asn Pro Ser Ala Phe Tyr Ile Tyr Leu Thr Ala Trp Val Ser Asn Asp
850                 855                 860

Pro Val Ala Tyr Ala Ala Ser Gln Ala Asn Ile Arg Pro His Arg Pro
865                 870                 875                 880

Glu Trp Val His Asp Lys Ala Asp Tyr Met Pro Glu Thr Arg Leu Arg
                885                 890                 895

Ile Pro Ala Ala Glu Pro Ile Glu Tyr Ala Gln Phe Pro Phe Tyr Leu
            900                 905                 910

Asn Gly Leu Arg Asp Thr Ser Asp Phe Val Glu Ala Ile Glu Lys Val
        915                 920                 925

Arg Thr Ile Cys Ser Asn Tyr Thr Ser Leu Gly Leu Ser Ser Tyr Pro
930                 935                 940

Asn Gly Tyr Pro Phe Leu Phe Trp Glu Gln Tyr Ile Gly Leu Arg His
945                 950                 955                 960

Trp Leu Leu Leu Phe Ile Ser Val Val Leu Ala Cys Thr Phe Leu Val
                965                 970                 975

Cys Ala Val Phe Leu Leu Asn Pro Trp Thr Ala Gly Ile Ile Val Met
            980                 985                 990

Val Leu Ala Leu Met Thr Val Glu Leu Phe Gly Met Met Gly Leu Ile
        995                 1000                1005

Gly Ile Lys Leu Ser Ala Val  Pro Val Val Ile Leu  Ile Ala Ser
    1010                1015                1020

Val Gly Ile Gly Val Glu Phe  Thr Val His Val Ala  Leu Ala Phe
    1025                1030                1035

Leu Thr Ala Ile Gly Asp Lys  Asn Arg Arg Ala Val  Leu Ala Leu
    1040                1045                1050

Glu His Met Phe Ala Pro Val  Leu Asp Gly Ala Val  Ser Thr Leu
    1055                1060                1065

| Leu | Gly | Val | Leu | Met | Leu | Ala | Gly | Ser | Glu | Phe | Asp | Phe | Ile | Val |
|---|---|---|---|---|---|---|---|---|---|---|---|---|---|---|
| 1070 | | | | 1075 | | | | | 1080 | | | | | |

| Arg | Tyr | Phe | Phe | Ala | Val | Leu | Ala | Ile | Leu | Thr | Ile | Leu | Gly | Val |
|---|---|---|---|---|---|---|---|---|---|---|---|---|---|---|
| 1085 | | | | | 1090 | | | | | 1095 | | | | |

| Leu | Asn | Gly | Leu | Val | Leu | Leu | Pro | Val | Leu | Leu | Ser | Phe | Phe | Gly |
|---|---|---|---|---|---|---|---|---|---|---|---|---|---|---|
| 1100 | | | | | 1105 | | | | | 1110 | | | | |

| Pro | Tyr | Pro | Glu | Val | Ser | Pro | Ala | Asn | Gly | Leu | Asn | Arg | Leu | Pro |
|---|---|---|---|---|---|---|---|---|---|---|---|---|---|---|
| 1115 | | | | | 1120 | | | | | 1125 | | | | |

| Thr | Pro | Ser | Pro | Glu | Pro | Pro | Ser | Val | Val | Arg | Phe | Ala | Met |
|---|---|---|---|---|---|---|---|---|---|---|---|---|---|
| 1130 | | | | | 1135 | | | | | 1140 | | | | |

| Pro | Pro | Gly | His | Thr | His | Ser | Gly | Ser | Asp | Ser | Ser | Asp | Ser | Glu |
|---|---|---|---|---|---|---|---|---|---|---|---|---|---|---|
| 1145 | | | | | 1150 | | | | | 1155 | | | | |

| Tyr | Ser | Ser | Gln | Thr | Thr | Val | Ser | Gly | Leu | Ser | Glu | Glu | Leu | Arg |
|---|---|---|---|---|---|---|---|---|---|---|---|---|---|---|
| 1160 | | | | | 1165 | | | | | 1170 | | | | |

| His | Tyr | Glu | Ala | Gln | Gln | Gly | Ala | Gly | Gly | Pro | Ala | His | Gln | Val |
|---|---|---|---|---|---|---|---|---|---|---|---|---|---|---|
| 1175 | | | | | 1180 | | | | | 1185 | | | | |

| Ile | Val | Glu | Ala | Thr | Glu | Asn | Pro | Val | Phe | Ala | His | Ser | Thr | Val |
|---|---|---|---|---|---|---|---|---|---|---|---|---|---|---|
| 1190 | | | | | 1195 | | | | | 1200 | | | | |

| Val | His | Pro | Glu | Ser | Arg | His | His | Pro | Pro | Ser | Asn | Pro | Arg | Gln |
|---|---|---|---|---|---|---|---|---|---|---|---|---|---|---|
| 1205 | | | | | 1210 | | | | | 1215 | | | | |

| Gln | Pro | His | Leu | Asp | Ser | Gly | Ser | Leu | Pro | Pro | Gly | Arg | Gln | Gly |
|---|---|---|---|---|---|---|---|---|---|---|---|---|---|---|
| 1220 | | | | | 1225 | | | | | 1230 | | | | |

| Gln | Gln | Pro | Arg | Arg | Asp | Pro | Arg | Glu | Gly | Leu | Trp | Pro | Pro |
|---|---|---|---|---|---|---|---|---|---|---|---|---|---|
| 1235 | | | | | 1240 | | | | | 1245 | | | | |

| Pro | Tyr | Arg | Pro | Arg | Arg | Asp | Ala | Phe | Glu | Ile | Ser | Thr | Glu | Gly |
|---|---|---|---|---|---|---|---|---|---|---|---|---|---|---|
| 1250 | | | | | 1255 | | | | | 1260 | | | | |

| His | Ser | Gly | Pro | Ser | Asn | Arg | Ala | Arg | Trp | Gly | Pro | Arg | Gly | Ala |
|---|---|---|---|---|---|---|---|---|---|---|---|---|---|---|
| 1265 | | | | | 1270 | | | | | 1275 | | | | |

| Arg | Ser | His | Asn | Pro | Arg | Asn | Pro | Ala | Ser | Thr | Ala | Met | Gly | Ser |
|---|---|---|---|---|---|---|---|---|---|---|---|---|---|---|
| 1280 | | | | | 1285 | | | | | 1290 | | | | |

| Ser | Val | Pro | Gly | Tyr | Cys | Gln | Pro | Ile | Thr | Thr | Val | Thr | Ala | Ser |
|---|---|---|---|---|---|---|---|---|---|---|---|---|---|---|
| 1295 | | | | | 1300 | | | | | 1305 | | | | |

| Ala | Ser | Val | Thr | Val | Ala | Val | His | Pro | Pro | Val | Pro | Gly | Pro |
|---|---|---|---|---|---|---|---|---|---|---|---|---|---|
| 1310 | | | | | 1315 | | | | | 1320 | | | | |

| Gly | Arg | Asn | Pro | Arg | Gly | Gly | Leu | Cys | Pro | Gly | Tyr | Pro | Glu | Thr |
|---|---|---|---|---|---|---|---|---|---|---|---|---|---|---|
| 1325 | | | | | 1330 | | | | | 1335 | | | | |

| Asp | His | Gly | Leu | Phe | Glu | Asp | Pro | His | Val | Pro | Phe | His | Val | Arg |
|---|---|---|---|---|---|---|---|---|---|---|---|---|---|---|
| 1340 | | | | | 1345 | | | | | 1350 | | | | |

| Cys | Glu | Arg | Arg | Asp | Ser | Lys | Val | Glu | Val | Ile | Glu | Leu | Gln | Asp |
|---|---|---|---|---|---|---|---|---|---|---|---|---|---|---|
| 1355 | | | | | 1360 | | | | | 1365 | | | | |

| Val | Glu | Cys | Glu | Glu | Arg | Pro | Arg | Gly | Ser | Ser | Ser | Asn |
|---|---|---|---|---|---|---|---|---|---|---|---|---|
| 1370 | | | | | 1375 | | | | | 1380 | | | |

<210> SEQ ID NO 45
<211> LENGTH: 3483
<212> TYPE: DNA
<213> ORGANISM: Homo sapiens
<220> FEATURE:
<221> NAME/KEY: CDS
<222> LOCATION: (79)..(3276)

<400> SEQUENCE: 45

```
cccagactcc agccctggac cgcgcatccc gagcccagcg cccagacaga gtgtccccac    60
accctcctct gagacgcc atg ttc aac tcg atg acc cca cca cca atc agt   111
                    Met Phe Asn Ser Met Thr Pro Pro Pro Ile Ser
                      1               5                  10
```

```
agc tat ggc gag ccc tgc tgt ctc cgg ccc ctc ccc agt cag ggg gcc      159
Ser Tyr Gly Glu Pro Cys Cys Leu Arg Pro Leu Pro Ser Gln Gly Ala
        15                  20                  25 ccc agt gtg ggg aca gaa gtc aag ttg acc aag aag cgg gca ctg tcc      207
Pro Ser Val Gly Thr Glu Val Lys Leu Thr Lys Lys Arg Ala Leu Ser
    30                  35                  40 atc tca cct ctg tcg gat gcc agc ctg gac ctg cag acg gtt atc cgc      255
Ile Ser Pro Leu Ser Asp Ala Ser Leu Asp Leu Gln Thr Val Ile Arg
45                  50                  55 acc tca ccc agc tcc ctc gta gct ttc atc aac tcg cga tgc aca tct      303
Thr Ser Pro Ser Ser Leu Val Ala Phe Ile Asn Ser Arg Cys Thr Ser
60                  65                  70                  75 cca gga ggc tcc tac ggt cat ctc tcc att ggc acc atg agc cca tct      351
Pro Gly Gly Ser Tyr Gly His Leu Ser Ile Gly Thr Met Ser Pro Ser
                80                  85                  90 ctg gga ttc cca gcc cag atg aat cac caa aaa ggg ccc tcg cct tcc      399
Leu Gly Phe Pro Ala Gln Met Asn His Gln Lys Gly Pro Ser Pro Ser
            95                  100                 105 ttt ggg gtc cag cct tgt ggt ccc cat gac tct gcc cgg ggt ggg atg      447
Phe Gly Val Gln Pro Cys Gly Pro His Asp Ser Ala Arg Gly Gly Met
        110                 115                 120 atc cca cat cct cag tcc cgg gga ccc ttc cca act tgc cag ctg aag      495
Ile Pro His Pro Gln Ser Arg Gly Pro Phe Pro Thr Cys Gln Leu Lys
125                 130                 135 tct gag ctg gac atg ctg gtt ggc aag tgc cgg gag gaa ccc ttg gaa      543
Ser Glu Leu Asp Met Leu Val Gly Lys Cys Arg Glu Glu Pro Leu Glu
140                 145                 150                 155 ggt gat atg tcc agc ccc aac tcc aca ggc ata cag gat ccc ctg ttg      591
Gly Asp Met Ser Ser Pro Asn Ser Thr Gly Ile Gln Asp Pro Leu Leu
                160                 165                 170 ggg atg ctg gat ggg cgg gag gac ctc gag aga gag gag aag cgt gag      639
Gly Met Leu Asp Gly Arg Glu Asp Leu Glu Arg Glu Glu Lys Arg Glu
            175                 180                 185 cct gaa tct gtg tat gaa act gac tgc cgt tgg gat ggc tgc agc cag      687
Pro Glu Ser Val Tyr Glu Thr Asp Cys Arg Trp Asp Gly Cys Ser Gln
        190                 195                 200 gaa ttt gac tcc caa gag cag ctg gtg cac cac atc aac agc gag cac      735
Glu Phe Asp Ser Gln Glu Gln Leu Val His His Ile Asn Ser Glu His
205                 210                 215 atc cac ggg gag cgg aag gag ttc gtg tgc cac tgg ggg ggc tgc tcc      783
Ile His Gly Glu Arg Lys Glu Phe Val Cys His Trp Gly Gly Cys Ser
220                 225                 230                 235 agg gag ctg agg ccc ttc aaa gcc cag tac atg ctg gtg gtt cac atg      831
Arg Glu Leu Arg Pro Phe Lys Ala Gln Tyr Met Leu Val Val His Met
                240                 245                 250 cgc aga cac act ggc gag aag cca cac aag tgc acg ttt gaa ggg tgc      879
Arg Arg His Thr Gly Glu Lys Pro His Lys Cys Thr Phe Glu Gly Cys
            255                 260                 265 cgg aag tca tac tca cgc ctc gaa aac ctg aag acg cac ctg cgg tca      927
Arg Lys Ser Tyr Ser Arg Leu Glu Asn Leu Lys Thr His Leu Arg Ser
        270                 275                 280 cac acg ggt gag aag cca tac atg tgt gag cac gag ggc tgc agt aaa      975
His Thr Gly Glu Lys Pro Tyr Met Cys Glu His Glu Gly Cys Ser Lys
285                 290                 295 gcc ttc agc aat gcc agt gac cga gcc aag cac cag aat cgg acc cat     1023
Ala Phe Ser Asn Ala Ser Asp Arg Ala Lys His Gln Asn Arg Thr His
300                 305                 310                 315 tcc aat gag aag ccg tat gta tgt aag ctc cct ggc tgc acc aaa cgc     1071
Ser Asn Glu Lys Pro Tyr Val Cys Lys Leu Pro Gly Cys Thr Lys Arg
```

-continued

```
                   320                 325                 330
tat aca gat cct agc tcg ctg cga aaa cat gtc aag aca gtg cat ggt    1119
Tyr Thr Asp Pro Ser Ser Leu Arg Lys His Val Lys Thr Val His Gly
                335                 340                 345 cct gac gcc cat gtg acc aaa cgg cac cgt ggg gat ggc ccc ctg cct    1167
Pro Asp Ala His Val Thr Lys Arg His Arg Gly Asp Gly Pro Leu Pro
            350                 355                 360 cgg gca cca tcc att tct aca gtg gag ccc aag agg gag cgg gaa gga    1215
Arg Ala Pro Ser Ile Ser Thr Val Glu Pro Lys Arg Glu Arg Glu Gly
        365                 370                 375 ggt ccc atc agg gag gaa agc aga ctg act gtg cca gag ggt gcc atg    1263
Gly Pro Ile Arg Glu Glu Ser Arg Leu Thr Val Pro Glu Gly Ala Met
380                 385                 390                 395 aag cca cag cca agc cct ggg gcc cag tca tcc tgc agc agt gac cac    1311
Lys Pro Gln Pro Ser Pro Gly Ala Gln Ser Ser Cys Ser Ser Asp His
                400                 405                 410 tcc ccg gca ggg agt gca gcc aat aca gac agt ggt gtg gaa atg act    1359
Ser Pro Ala Gly Ser Ala Ala Asn Thr Asp Ser Gly Val Glu Met Thr
            415                 420                 425 ggc aat gca ggg ggc agc act gaa gac ctc tcc agc ttg gac gag gga    1407
Gly Asn Ala Gly Gly Ser Thr Glu Asp Leu Ser Ser Leu Asp Glu Gly
        430                 435                 440 cct tgc att gct ggc act ggt ctg tcc act ctt cgc cgc ctt gag aac    1455
Pro Cys Ile Ala Gly Thr Gly Leu Ser Thr Leu Arg Arg Leu Glu Asn
    445                 450                 455 ctc agg ctg gac cag cta cat caa ctc cgg cca ata ggg acc cgg ggt    1503
Leu Arg Leu Asp Gln Leu His Gln Leu Arg Pro Ile Gly Thr Arg Gly
460                 465                 470                 475 ctc aaa ctg ccc agc ttg tcc cac acc ggt acc act gtg tcc cgc cgc    1551
Leu Lys Leu Pro Ser Leu Ser His Thr Gly Thr Thr Val Ser Arg Arg
                480                 485                 490 gtg ggc ccc cca gtc tct ctt gaa cgc cgc agc agc agc tcc agc agc    1599
Val Gly Pro Pro Val Ser Leu Glu Arg Arg Ser Ser Ser Ser Ser Ser
            495                 500                 505 atc agc tct gcc tat act gtc agc cgc cgc tcc tcc ctg gcc tct cct    1647
Ile Ser Ser Ala Tyr Thr Val Ser Arg Arg Ser Ser Leu Ala Ser Pro
        510                 515                 520 ttc ccc cct ggc tcc cca cca gag aat gga gca tcc tcc ctg cct ggc    1695
Phe Pro Pro Gly Ser Pro Pro Glu Asn Gly Ala Ser Ser Leu Pro Gly
    525                 530                 535 ctt atg cct gcc cag cac tac ctg ctt cgg gca aga tat gct tca gcc    1743
Leu Met Pro Ala Gln His Tyr Leu Leu Arg Ala Arg Tyr Ala Ser Ala
540                 545                 550                 555 aga ggg ggt ggt act tcg ccc act gca gca tcc agc ctg gat cgg ata    1791
Arg Gly Gly Gly Thr Ser Pro Thr Ala Ala Ser Ser Leu Asp Arg Ile
                560                 565                 570 ggt ggt ctt ccc atg cct cct tgg aga agc cga gcc gag tat cca gga    1839
Gly Gly Leu Pro Met Pro Pro Trp Arg Ser Arg Ala Glu Tyr Pro Gly
            575                 580                 585 tac aac ccc aat gca ggg gtc acc cgg agg gcc agt gac cca gcc cag    1887
Tyr Asn Pro Asn Ala Gly Val Thr Arg Arg Ala Ser Asp Pro Ala Gln
        590                 595                 600 gct gct gac cgt cct gct cca gct aga gtc cag agg ttc aag agc ctg    1935
Ala Ala Asp Arg Pro Ala Pro Ala Arg Val Gln Arg Phe Lys Ser Leu
    605                 610                 615 ggc tgt gtc cat acc cca ccc act gtg gca ggg gga gga cag aac ttt    1983
Gly Cys Val His Thr Pro Pro Thr Val Ala Gly Gly Gly Gln Asn Phe
620                 625                 630                 635 gat cct tac ctc cca acc tct gtc tac tca cca cag ccc ccc agc atc    2031
```

```
                                                          -continued

Asp Pro Tyr Leu Pro Thr Ser Val Tyr Ser Pro Gln Pro Ser Ile
                640             645             650 act gag aat gct gcc atg gat gct aga ggg cta cag gaa gag cca gaa      2079
Thr Glu Asn Ala Ala Met Asp Ala Arg Gly Leu Gln Glu Glu Pro Glu
                655             660             665 gtt ggg acc tcc atg gtg ggc agt ggt ctg aac ccc tat atg gac ttc      2127
Val Gly Thr Ser Met Val Gly Ser Gly Leu Asn Pro Tyr Met Asp Phe
                670             675             680 cca cct act gat act ctg gga tat ggg gga cct gaa ggg gca gca gct      2175
Pro Pro Thr Asp Thr Leu Gly Tyr Gly Gly Pro Glu Gly Ala Ala Ala
            685             690             695 gag cct tat gga gcg agg ggt cca ggc tct ctg cct ctt ggg cct ggt      2223
Glu Pro Tyr Gly Ala Arg Gly Pro Gly Ser Leu Pro Leu Gly Pro Gly
700             705             710             715 cca ccc acc aac tat ggc ccc aac ccc tgt ccc cag cag gcc tca tat      2271
Pro Pro Thr Asn Tyr Gly Pro Asn Pro Cys Pro Gln Gln Ala Ser Tyr
                720             725             730 cct gac ccc acc caa gaa aca tgg ggt gag ttc cct tcc cac tct ggg      2319
Pro Asp Pro Thr Gln Glu Thr Trp Gly Glu Phe Pro Ser His Ser Gly
                735             740             745 ctg tac cca ggc ccc aag gct cta ggt gga acc tac agc cag tgt cct      2367
Leu Tyr Pro Gly Pro Lys Ala Leu Gly Gly Thr Tyr Ser Gln Cys Pro
            750             755             760 cga ctt gaa cat tat gga caa gtg caa gtc aag cca gaa cag ggg tgc      2415
Arg Leu Glu His Tyr Gly Gln Val Gln Val Lys Pro Glu Gln Gly Cys
765             770             775 cca gtg ggg tct gac tcc aca gga ctg gca ccc tgc ctc aat gcc cac      2463
Pro Val Gly Ser Asp Ser Thr Gly Leu Ala Pro Cys Leu Asn Ala His
780             785             790             795 ccc agt gag ggg ccc cca cat cca cag cct ctc ttt tcc cat tac ccc      2511
Pro Ser Glu Gly Pro Pro His Pro Gln Pro Leu Phe Ser His Tyr Pro
                800             805             810 cag ccc tct cct ccc caa tat ctc cag tca ggc ccc tat acc cag cca      2559
Gln Pro Ser Pro Pro Gln Tyr Leu Gln Ser Gly Pro Tyr Thr Gln Pro
            815             820             825 ccc cct gat tat ctt cct tca gaa ccc agg cct tgc ctg gac ttt gat      2607
Pro Pro Asp Tyr Leu Pro Ser Glu Pro Arg Pro Cys Leu Asp Phe Asp
            830             835             840 tcc ccc acc cat tcc aca ggg cag ctc aag gct cag ctt gtg tgt aat      2655
Ser Pro Thr His Ser Thr Gly Gln Leu Lys Ala Gln Leu Val Cys Asn
845             850             855 tat gtt caa tct caa cag gag cta ctg tgg gag ggt ggc agg gaa          2703
Tyr Val Gln Ser Gln Gln Glu Leu Leu Trp Glu Gly Gly Gly Arg Glu
860             865             870             875 gat gcc ccc gcc cag gaa cct tcc tac cag agt ccc aag ttt ctg ggg      2751
Asp Ala Pro Ala Gln Glu Pro Ser Tyr Gln Ser Pro Lys Phe Leu Gly
                880             885             890 ggt tcc cag gtt agc cca agc cgt gct aaa gct cca gtg aac aca tat      2799
Gly Ser Gln Val Ser Pro Ser Arg Ala Lys Ala Pro Val Asn Thr Tyr
            895             900             905 gga cct ggc ttt gga ccc aac ttg ccc aat cac aag tca ggt tcc tat      2847
Gly Pro Gly Phe Gly Pro Asn Leu Pro Asn His Lys Ser Gly Ser Tyr
        910             915             920 ccc acc cct tca cca tgc cat gaa aat ttt gta gtg ggg gca aat agg      2895
Pro Thr Pro Ser Pro Cys His Glu Asn Phe Val Val Gly Ala Asn Arg
        925             930             935 gct tca cat agg gca gca gca cca cct cga ctt ctg ccc cca ttg ccc      2943
Ala Ser His Arg Ala Ala Ala Pro Pro Arg Leu Leu Pro Pro Leu Pro
940             945             950             955
```

| | | | | | | | | | | | | | | |
|---|---|---|---|---|---|---|---|---|---|---|---|---|---|---|
| act | tgc | tat | ggg | cct | ctc | aaa | gtg | gga | ggc | aca | aac | ccc | agc | tgt | ggt | 2991 |
| Thr | Cys | Tyr | Gly | Pro | Leu | Lys | Val | Gly | Gly | Thr | Asn | Pro | Ser | Cys | Gly | |
| | | | 960 | | | | | 965 | | | | | 970 | | |

```
act tgc tat ggg cct ctc aaa gtg gga ggc aca aac ccc agc tgt ggt    2991
Thr Cys Tyr Gly Pro Leu Lys Val Gly Gly Thr Asn Pro Ser Cys Gly
            960                 965                 970 cat cct gag gtg ggc agg cta gga ggg ggt cct gcc ttg tac cct cct    3039
His Pro Glu Val Gly Arg Leu Gly Gly Gly Pro Ala Leu Tyr Pro Pro
            975                 980                 985 ccc gaa gga cag gta tgt aac ccc ctg gac tct ctt gat ctt gac aac    3087
Pro Glu Gly Gln Val Cys Asn Pro Leu Asp Ser Leu Asp Leu Asp Asn
            990                 995                 1000 act cag ctg gac ttt gtg gct att ctg gat gag ccc cag ggg ctg        3132
Thr Gln Leu Asp Phe Val Ala Ile Leu Asp Glu Pro Gln Gly Leu
            1005                1010                1015 agt cct cct cct tcc cat gat cag cgg ggc agc tct gga cat acc        3177
Ser Pro Pro Pro Ser His Asp Gln Arg Gly Ser Ser Gly His Thr
            1020                1025                1030 cca cct ccc tct ggg ccc ccc aac atg gct gtg ggc aac atg agt        3222
Pro Pro Pro Ser Gly Pro Pro Asn Met Ala Val Gly Asn Met Ser
            1035                1040                1045 gtc tta ctg aga tcc cta cct ggg gaa aca gaa ttc ctc aac tct        3267
Val Leu Leu Arg Ser Leu Pro Gly Glu Thr Glu Phe Leu Asn Ser
            1050                1055                1060 agt gcc taa agagtaggga atctcatcca tcacagatcg catttcctaa            3316
Ser Ala
    1065 ggggtttcta tccttccaga aaaattgggg gagctgcagt cccatgcaca agatgcccca  3376 gggatgggag gtatgggctg ggggctatgt atagtctgta tacgttttga ggagaaattt  3436 gataatgaca ctgtttcctg ataataaagg aactgcatca gaaaaaa                3483
```

<210> SEQ ID NO 46
<211> LENGTH: 1065
<212> TYPE: PRT
<213> ORGANISM: Homo sapiens

<400> SEQUENCE: 46

```
Met Phe Asn Ser Met Thr Pro Pro Ile Ser Ser Tyr Gly Glu Pro
1               5                   10                  15

Cys Cys Leu Arg Pro Leu Pro Ser Gln Gly Ala Pro Ser Val Gly Thr
                20                  25                  30

Glu Val Lys Leu Thr Lys Lys Arg Ala Leu Ser Ile Ser Pro Leu Ser
            35                  40                  45

Asp Ala Ser Leu Asp Leu Gln Thr Val Ile Arg Thr Ser Pro Ser Ser
        50                  55                  60

Leu Val Ala Phe Ile Asn Ser Arg Cys Thr Ser Pro Gly Gly Ser Tyr
65                  70                  75                  80

Gly His Leu Ser Ile Gly Thr Met Ser Pro Ser Leu Gly Phe Pro Ala
                85                  90                  95

Gln Met Asn His Gln Lys Gly Pro Ser Pro Ser Phe Gly Val Gln Pro
            100                 105                 110

Cys Gly Pro His Asp Ser Ala Arg Gly Gly Met Ile Pro His Pro Gln
        115                 120                 125

Ser Arg Gly Pro Phe Pro Thr Cys Gln Leu Lys Ser Glu Leu Asp Met
    130                 135                 140

Leu Val Gly Lys Cys Arg Glu Glu Pro Leu Glu Gly Asp Met Ser Ser
145                 150                 155                 160

Pro Asn Ser Thr Gly Ile Gln Asp Pro Leu Leu Gly Met Leu Asp Gly
                165                 170                 175
```

-continued

Arg Glu Asp Leu Glu Arg Glu Glu Lys Arg Glu Pro Glu Ser Val Tyr
            180                 185                 190

Glu Thr Asp Cys Arg Trp Asp Gly Cys Ser Gln Glu Phe Asp Ser Gln
            195                 200                 205

Glu Gln Leu Val His His Ile Asn Ser Glu His Ile His Gly Glu Arg
            210                 215                 220

Lys Glu Phe Val Cys His Trp Gly Gly Cys Ser Arg Glu Leu Arg Pro
225                 230                 235                 240

Phe Lys Ala Gln Tyr Met Leu Val Val His Met Arg Arg His Thr Gly
            245                 250                 255

Glu Lys Pro His Lys Cys Thr Phe Glu Gly Cys Arg Lys Ser Tyr Ser
            260                 265                 270

Arg Leu Glu Asn Leu Lys Thr His Leu Arg Ser His Thr Gly Glu Lys
            275                 280                 285

Pro Tyr Met Cys Glu His Glu Gly Cys Ser Lys Ala Phe Ser Asn Ala
            290                 295                 300

Ser Asp Arg Ala Lys His Gln Asn Arg Thr His Ser Asn Glu Lys Pro
305                 310                 315                 320

Tyr Val Cys Lys Leu Pro Gly Cys Thr Lys Arg Tyr Thr Asp Pro Ser
            325                 330                 335

Ser Leu Arg Lys His Val Lys Thr Val His Gly Pro Asp Ala His Val
            340                 345                 350

Thr Lys Arg His Arg Gly Asp Gly Pro Leu Pro Arg Ala Pro Ser Ile
            355                 360                 365

Ser Thr Val Glu Pro Lys Arg Glu Arg Glu Gly Pro Ile Arg Glu
            370                 375                 380

Glu Ser Arg Leu Thr Val Pro Glu Gly Ala Met Lys Pro Gln Pro Ser
385                 390                 395                 400

Pro Gly Ala Gln Ser Ser Cys Ser Ser Asp His Ser Pro Ala Gly Ser
            405                 410                 415

Ala Ala Asn Thr Asp Ser Gly Val Glu Met Thr Gly Asn Ala Gly Gly
            420                 425                 430

Ser Thr Glu Asp Leu Ser Ser Leu Asp Glu Gly Pro Cys Ile Ala Gly
            435                 440                 445

Thr Gly Leu Ser Thr Leu Arg Arg Leu Glu Asn Leu Arg Leu Asp Gln
450                 455                 460

Leu His Gln Leu Arg Pro Ile Gly Thr Arg Gly Leu Lys Leu Pro Ser
465                 470                 475                 480

Leu Ser His Thr Gly Thr Thr Val Ser Arg Arg Val Gly Pro Pro Val
            485                 490                 495

Ser Leu Glu Arg Arg Ser Ser Ser Ser Ser Ile Ser Ser Ala Tyr
            500                 505                 510

Thr Val Ser Arg Arg Ser Ser Leu Ala Ser Pro Phe Pro Pro Gly Ser
            515                 520                 525

Pro Pro Glu Asn Gly Ala Ser Ser Leu Pro Gly Leu Met Pro Ala Gln
            530                 535                 540

His Tyr Leu Leu Arg Ala Arg Tyr Ala Ser Ala Arg Gly Gly Gly Thr
545                 550                 555                 560

Ser Pro Thr Ala Ala Ser Ser Leu Asp Arg Ile Gly Gly Leu Pro Met
            565                 570                 575

Pro Pro Trp Arg Ser Arg Ala Glu Tyr Pro Gly Tyr Asn Pro Asn Ala
            580                 585                 590

Gly Val Thr Arg Arg Ala Ser Asp Pro Ala Gln Ala Ala Asp Arg Pro

```
                595                 600                 605
Ala Pro Ala Arg Val Gln Arg Phe Lys Ser Leu Gly Cys Val His Thr
610                 615                 620

Pro Pro Thr Val Ala Gly Gly Gln Asn Phe Asp Pro Tyr Leu Pro
625                 630                 635                 640

Thr Ser Val Tyr Ser Pro Gln Pro Pro Ser Ile Thr Glu Asn Ala Ala
                645                 650                 655

Met Asp Ala Arg Gly Leu Gln Glu Glu Pro Glu Val Gly Thr Ser Met
                660                 665                 670

Val Gly Ser Gly Leu Asn Pro Tyr Met Asp Phe Pro Pro Thr Asp Thr
                675                 680                 685

Leu Gly Tyr Gly Gly Pro Glu Gly Ala Ala Ala Glu Pro Tyr Gly Ala
690                 695                 700

Arg Gly Pro Gly Ser Leu Pro Leu Gly Pro Gly Pro Pro Thr Asn Tyr
705                 710                 715                 720

Gly Pro Asn Pro Cys Pro Gln Gln Ala Ser Tyr Pro Asp Pro Thr Gln
                725                 730                 735

Glu Thr Trp Gly Glu Phe Pro Ser His Ser Gly Leu Tyr Pro Gly Pro
                740                 745                 750

Lys Ala Leu Gly Gly Thr Tyr Ser Gln Cys Pro Arg Leu Glu His Tyr
                755                 760                 765

Gly Gln Val Gln Val Lys Pro Glu Gln Gly Cys Pro Val Gly Ser Asp
770                 775                 780

Ser Thr Gly Leu Ala Pro Cys Leu Asn Ala His Pro Ser Glu Gly Pro
785                 790                 795                 800

Pro His Pro Gln Pro Leu Phe Ser His Tyr Pro Gln Pro Ser Pro Pro
                805                 810                 815

Gln Tyr Leu Gln Ser Gly Pro Tyr Thr Gln Pro Pro Asp Tyr Leu
                820                 825                 830

Pro Ser Glu Pro Arg Pro Cys Leu Asp Phe Asp Ser Pro Thr His Ser
                835                 840                 845

Thr Gly Gln Leu Lys Ala Gln Leu Val Cys Asn Tyr Val Gln Ser Gln
850                 855                 860

Gln Glu Leu Leu Trp Glu Gly Gly Gly Arg Glu Asp Ala Pro Ala Gln
865                 870                 875                 880

Glu Pro Ser Tyr Gln Ser Pro Lys Phe Leu Gly Gly Ser Gln Val Ser
                885                 890                 895

Pro Ser Arg Ala Lys Ala Pro Val Asn Thr Tyr Gly Pro Gly Phe Gly
                900                 905                 910

Pro Asn Leu Pro Asn His Lys Ser Gly Ser Tyr Pro Thr Pro Ser Pro
                915                 920                 925

Cys His Glu Asn Phe Val Gly Ala Asn Arg Ala Ser His Arg Ala
                930                 935                 940

Ala Ala Pro Pro Arg Leu Leu Pro Pro Leu Pro Thr Cys Tyr Gly Pro
945                 950                 955                 960

Leu Lys Val Gly Gly Thr Asn Pro Ser Cys Gly His Pro Glu Val Gly
                965                 970                 975

Arg Leu Gly Gly Gly Pro Ala Leu Tyr Pro Pro Glu Gly Gln Val
                980                 985                 990

Cys Asn Pro Leu Asp Ser Leu Asp  Leu Asp Asn Thr Gln  Leu Asp Phe
                995                 1000                1005

Val Ala  Ile Leu Asp Glu Pro  Gln Gly Leu Ser Pro  Pro Pro Ser
    1010                1015                1020
```

| His | Asp | Gln | Arg | Gly | Ser | Ser | Gly | His | Thr | Pro | Pro | Pro | Ser | Gly |
|  | 1025 |  |  |  | 1030 |  |  |  | 1035 |  |  |  |  |  |

| Pro | Pro | Asn | Met | Ala | Val | Gly | Asn | Met | Ser | Val | Leu | Leu | Arg | Ser |
| 1040 |  |  |  |  | 1045 |  |  |  |  | 1050 |  |  |  |  |

| Leu | Pro | Gly | Glu | Thr | Glu | Phe | Leu | Asn | Ser | Ser | Ala |
|  | 1055 |  |  |  |  | 1060 |  |  |  | 1065 |  |

```
<210> SEQ ID NO 47
<211> LENGTH: 6780
<212> TYPE: DNA
<213> ORGANISM: Homo sapiens
<220> FEATURE:
<221> NAME/KEY: CDS
<222> LOCATION: (31)..(4791)

<400> SEQUENCE: 47
gattgccacc caggacgatg agcggctgag atg gag acg tct gcc tca gcc act        54
                                Met Glu Thr Ser Ala Ser Ala Thr
                                  1               5 gcc tcc gag aag caa gaa gcc aaa agt ggg atc ctg gag gcc gct ggc       102
Ala Ser Glu Lys Gln Glu Ala Lys Ser Gly Ile Leu Glu Ala Ala Gly
     10                  15                  20 ttc ccc gac ccg ggt aaa aag gcc tct cct ttg gtg gtg gct gca gcg       150
Phe Pro Asp Pro Gly Lys Lys Ala Ser Pro Leu Val Val Ala Ala Ala
 25                  30                  35                  40 gca gca gca gcg gta gct gcc caa gga gtg ccg cag cat ctc ttg cca       198
Ala Ala Ala Ala Val Ala Ala Gln Gly Val Pro Gln His Leu Leu Pro
                 45                  50                  55 cca ttc cat gcg ccc cta ccg att gac atg cga cac cag gaa gga agg       246
Pro Phe His Ala Pro Leu Pro Ile Asp Met Arg His Gln Glu Gly Arg
             60                  65                  70 tac cat tac gag cct cat tct gtc cac ggt gtg cac ggg ccc cct gcc       294
Tyr His Tyr Glu Pro His Ser Val His Gly Val His Gly Pro Pro Ala
         75                  80                  85 ctc agc ggc agc cct gtc atc tct gac atc tcc ttg atc cgg ctt tcc       342
Leu Ser Gly Ser Pro Val Ile Ser Asp Ile Ser Leu Ile Arg Leu Ser
     90                  95                 100 ccg cac ccg gct ggc cct ggg gag tcc ccc ttc aac gcc ccc cac ccg       390
Pro His Pro Ala Gly Pro Gly Glu Ser Pro Phe Asn Ala Pro His Pro
105                 110                 115                 120 tac gtg aac ccc cac atg gag cac tac ctc cgt tct gtg cac agc agc       438
Tyr Val Asn Pro His Met Glu His Tyr Leu Arg Ser Val His Ser Ser
                125                 130                 135 ccc acg ctc tcc atg atc tct gca gcc agg ggc ctc agc ccc gct gat       486
Pro Thr Leu Ser Met Ile Ser Ala Ala Arg Gly Leu Ser Pro Ala Asp
            140                 145                 150 gtg gcc cag gag cac ctt aag gag agg gga ctg ttt ggc ctt cct gct       534
Val Ala Gln Glu His Leu Lys Glu Arg Gly Leu Phe Gly Leu Pro Ala
        155                 160                 165 cca ggc acc acc ccc tca gac tat tac cac cag atg acc ctc gtg gca       582
Pro Gly Thr Thr Pro Ser Asp Tyr Tyr His Gln Met Thr Leu Val Ala
    170                 175                 180 ggc cac ccc gcg ccc tac ggg gac ctg ctg atg cag agc ggg ggc gct       630
Gly His Pro Ala Pro Tyr Gly Asp Leu Leu Met Gln Ser Gly Gly Ala
185                 190                 195                 200 gcc agc gca ccc cat ctc cac gac tac ctc aac ccc gtg gac gtg tcc       678
Ala Ser Ala Pro His Leu His Asp Tyr Leu Asn Pro Val Asp Val Ser
                205                 210                 215 cgt ttc tcc agc ccg cgg gtg acg ccc cgc ctg agc cgc aag cgg gcg       726
Arg Phe Ser Ser Pro Arg Val Thr Pro Arg Leu Ser Arg Lys Arg Ala
```

-continued

```
                      220                 225                 230
ctg tcc atc tcc cca ctc tca gac gcc agc ctg gac ctg cag cgg atg       774
Leu Ser Ile Ser Pro Leu Ser Asp Ala Ser Leu Asp Leu Gln Arg Met
            235                 240                 245 atc cgc acc tca ccc aac tcg cta gtg gcc tac atc aac aac tcc cga       822
Ile Arg Thr Ser Pro Asn Ser Leu Val Ala Tyr Ile Asn Asn Ser Arg
    250                 255                 260 agc agc tcg gcg gcc agc ggt tcc tac ggg cat ctg tca gcg ggt gcc       870
Ser Ser Ser Ala Ala Ser Gly Ser Tyr Gly His Leu Ser Ala Gly Ala
265                 270                 275                 280 ctc agc cca gcc ttc acc ttc ccc cac ccc atc aac ccc gtg gcc tac       918
Leu Ser Pro Ala Phe Thr Phe Pro His Pro Ile Asn Pro Val Ala Tyr
                285                 290                 295 cag cag att ctg agc cag cag agg ggt ctg ggg tca gcc ttt gga cac       966
Gln Gln Ile Leu Ser Gln Gln Arg Gly Leu Gly Ser Ala Phe Gly His
            300                 305                 310 aca cca ccc ctg atc cag ccc tca ccc acc ttc ctg gcc cag cag ccc      1014
Thr Pro Pro Leu Ile Gln Pro Ser Pro Thr Phe Leu Ala Gln Gln Pro
    315                 320                 325 atg gcc ctc acc tcc atc aat gcc acg ccc acc cag ctc agc agc agc      1062
Met Ala Leu Thr Ser Ile Asn Ala Thr Pro Thr Gln Leu Ser Ser Ser
330                 335                 340 agc aac tgt ctg agt gac acc aac cag aac aag cag agc agt gag tcg      1110
Ser Asn Cys Leu Ser Asp Thr Asn Gln Asn Lys Gln Ser Ser Glu Ser
345                 350                 355                 360 gcc gtc agc agc acc gtc aac cct gtc gcc att cac aag cgc agc aag      1158
Ala Val Ser Ser Thr Val Asn Pro Val Ala Ile His Lys Arg Ser Lys
                365                 370                 375 gtc aag acc gag cct gag ggc ctg cgg ccg gcc tcc cct ctg gcg ctg      1206
Val Lys Thr Glu Pro Glu Gly Leu Arg Pro Ala Ser Pro Leu Ala Leu
            380                 385                 390 acg cag ggc cag gtg tct gga cac ggc tca tgt ggg tgt gcc ctt ccc      1254
Thr Gln Gly Gln Val Ser Gly His Gly Ser Cys Gly Cys Ala Leu Pro
    395                 400                 405 ctc tcc cag gag cag ctg gct gac ctc aag gaa gat ctg gac agg gat      1302
Leu Ser Gln Glu Gln Leu Ala Asp Leu Lys Glu Asp Leu Asp Arg Asp
410                 415                 420 gac tgt aag cag gag gct gag gtg gtc atc tat gag acc aac tgc cac      1350
Asp Cys Lys Gln Glu Ala Glu Val Val Ile Tyr Glu Thr Asn Cys His
425                 430                 435                 440 tgg gaa gac tgc acc aag gag tac gac acc cag gag cag ctg gtg cat      1398
Trp Glu Asp Cys Thr Lys Glu Tyr Asp Thr Gln Glu Gln Leu Val His
                445                 450                 455 cac atc aac aac gag cac atc cac ggg gag aag aag gag ttt gtg tgc      1446
His Ile Asn Asn Glu His Ile His Gly Glu Lys Lys Glu Phe Val Cys
            460                 465                 470 cgc tgg cag gcc tgc acg cgg gag cag aag ccc ttc aag gcg cag tac      1494
Arg Trp Gln Ala Cys Thr Arg Glu Gln Lys Pro Phe Lys Ala Gln Tyr
    475                 480                 485 atg ctg gtg gtg cac atg cgg cga cac acg ggc gag aag ccc cac aag      1542
Met Leu Val Val His Met Arg Arg His Thr Gly Glu Lys Pro His Lys
490                 495                 500 tgc acg ttc gag ggc tgc tcg aag gcc tac tcc cgc ctg gag aac ctg      1590
Cys Thr Phe Glu Gly Cys Ser Lys Ala Tyr Ser Arg Leu Glu Asn Leu
505                 510                 515                 520 aag aca cac ctg cgg tcc cac acc ggg gag aag cca tat gtg tgt gag      1638
Lys Thr His Leu Arg Ser His Thr Gly Glu Lys Pro Tyr Val Cys Glu
                525                 530                 535 cac gag ggc tgc aac aaa gcc ttc tcc aac gcc tcg gac cgc gcc aag      1686
His Glu Gly Cys Asn Lys Ala Phe Ser Asn Ala Ser Asp Arg Ala Lys
```

```
         His Glu Gly Cys Asn Lys Ala Phe Ser Asn Ala Ser Asp Arg Ala Lys
                         540                 545                 550 cac cag aat cgc acc cac tcc aac gag aaa ccc tac atc tgc aag atc       1734
His Gln Asn Arg Thr His Ser Asn Glu Lys Pro Tyr Ile Cys Lys Ile
                555                 560                 565 cca ggc tgc acc aag aga tac aca gac ccc agc tct ctc cgg aag cat       1782
Pro Gly Cys Thr Lys Arg Tyr Thr Asp Pro Ser Ser Leu Arg Lys His
        570                 575                 580 gtg aaa acg gtc cac ggc cca gat gcc cac gtc acc aag aag cag cgc       1830
Val Lys Thr Val His Gly Pro Asp Ala His Val Thr Lys Lys Gln Arg
585                 590                 595                 600 aat gac gtg cac ctc cgc aca ccg ctg ctc aaa gag aat ggg gac agt       1878
Asn Asp Val His Leu Arg Thr Pro Leu Leu Lys Glu Asn Gly Asp Ser
                605                 610                 615 gag gcc ggc acg gag cct ggc ggc cca gag agc acc gag gcc agc agc       1926
Glu Ala Gly Thr Glu Pro Gly Gly Pro Glu Ser Thr Glu Ala Ser Ser
                620                 625                 630 acc agc cag gcc gtg gag gac tgc ctg cac gtc aga gcc atc aag acc       1974
Thr Ser Gln Ala Val Glu Asp Cys Leu His Val Arg Ala Ile Lys Thr
                635                 640                 645 gag agc tcc ggg ctg tgt cag tcc agc ccc ggg gcc cag tcg tcc tgc       2022
Glu Ser Ser Gly Leu Cys Gln Ser Ser Pro Gly Ala Gln Ser Ser Cys
        650                 655                 660 agc agc gag ccc tct cct ctg ggc agt gcc ccc aac aat gac agt ggc       2070
Ser Ser Glu Pro Ser Pro Leu Gly Ser Ala Pro Asn Asn Asp Ser Gly
665                 670                 675                 680 gtg gag atg ccg ggg acg ggg ccc ggg agc ctg gga gac ctg acg gca       2118
Val Glu Met Pro Gly Thr Gly Pro Gly Ser Leu Gly Asp Leu Thr Ala
                685                 690                 695 ctg gat gac aca ccc cca ggg gcc gac acc tca gcc ctg gct gcc ccc       2166
Leu Asp Asp Thr Pro Pro Gly Ala Asp Thr Ser Ala Leu Ala Ala Pro
                700                 705                 710 tcc gct ggt ggc ctc cag ctg cgc aaa cac atg acc acc atg cac cgg       2214
Ser Ala Gly Gly Leu Gln Leu Arg Lys His Met Thr Thr Met His Arg
        715                 720                 725 ttc gag cag ctc aag aag gag aag ctc aag tca ctc aag gat tcc tgc       2262
Phe Glu Gln Leu Lys Lys Glu Lys Leu Lys Ser Leu Lys Asp Ser Cys
        730                 735                 740 tca tgg gcc ggg ccg act cca cac acg cgg aac acc aag ctg cct ccc       2310
Ser Trp Ala Gly Pro Thr Pro His Thr Arg Asn Thr Lys Leu Pro Pro
745                 750                 755                 760 ctc ccg gga agt ggc tcc atc ctg gaa aac ttc agt ggc agt ggg ggc       2358
Leu Pro Gly Ser Gly Ser Ile Leu Glu Asn Phe Ser Gly Ser Gly Gly
                765                 770                 775 ggc ggg ccc gcg ggg ctg ctg ccg aac ccg cgg ctg tcg gag ctg tcc       2406
Gly Gly Pro Ala Gly Leu Leu Pro Asn Pro Arg Leu Ser Glu Leu Ser
            780                 785                 790 gcg agc gag gtg acc atg ctg agc cag ctg cag gag cgc cgc gac agc       2454
Ala Ser Glu Val Thr Met Leu Ser Gln Leu Gln Glu Arg Arg Asp Ser
        795                 800                 805 tcc acc agc acg gtc agc tcg gcc tac acc gtg agc cgc cgc tcc tcc       2502
Ser Thr Ser Thr Val Ser Ser Ala Tyr Thr Val Ser Arg Arg Ser Ser
        810                 815                 820 ggc atc tcc ccc tac ttc tcc agc cgc cgc tcc agc gag gcc tcg ccc       2550
Gly Ile Ser Pro Tyr Phe Ser Ser Arg Arg Ser Ser Glu Ala Ser Pro
825                 830                 835                 840 ctg ggc gcc ggc cgc ccg cac aac gcg agc tcc gct gac tcc tac gac       2598
Leu Gly Ala Gly Arg Pro His Asn Ala Ser Ser Ala Asp Ser Tyr Asp
                845                 850                 855
```

```
                                             -continued ccc atc tcc acg gac gcg tcg cgg cgc tcg agc gag gcc agc cag tgc    2646
Pro Ile Ser Thr Asp Ala Ser Arg Arg Ser Ser Glu Ala Ser Gln Cys
            860                 865                 870 agc ggc ggc tcc ggg ctg ctc aac ctc acg ccg gcg cag cag tac agc    2694
Ser Gly Gly Ser Gly Leu Leu Asn Leu Thr Pro Ala Gln Gln Tyr Ser
    875                 880                 885 ctg cgg gcc aag tac gcg gca gcc act ggc ggc ccc ccg ccc act ccg    2742
Leu Arg Ala Lys Tyr Ala Ala Ala Thr Gly Gly Pro Pro Pro Thr Pro
890                 895                 900 ctg ccg ggc ctg gag cgc atg agc ctg cgg acc agg ctg gcg ctg ctg    2790
Leu Pro Gly Leu Glu Arg Met Ser Leu Arg Thr Arg Leu Ala Leu Leu
905                 910                 915                 920 gac gcg ccc gag cgc acg ctg ccc gcc ggc tgc cca cgc cca ctg ggg    2838
Asp Ala Pro Glu Arg Thr Leu Pro Ala Gly Cys Pro Arg Pro Leu Gly
                925                 930                 935 ccg cgg cgt ggc agc gac ggg ccg acc tat ggc cac ggc cac gcg ggg    2886
Pro Arg Arg Gly Ser Asp Gly Pro Thr Tyr Gly His Gly His Ala Gly
            940                 945                 950 gct gcg ccc gcc ttc ccc cac gag gct cca ggc ggc gga gcc agg cgg    2934
Ala Ala Pro Ala Phe Pro His Glu Ala Pro Gly Gly Gly Ala Arg Arg
        955                 960                 965 gcc agc gac cct gtg cgg cgg ccc gat gcc ctg tcc ctg ccg cgg gtg    2982
Ala Ser Asp Pro Val Arg Arg Pro Asp Ala Leu Ser Leu Pro Arg Val
970                 975                 980 cag cgc ttc cac agc acc cac aac gtg aac ccc ggc ccg ctg ccg ccc    3030
Gln Arg Phe His Ser Thr His Asn Val Asn Pro Gly Pro Leu Pro Pro
985                 990                 995                 1000 tgt gcc gac agg cga ggc ctc cgc ctg cag agc cac ccg agc acc       3075
Cys Ala Asp Arg Arg Gly Leu Arg Leu Gln Ser His Pro Ser Thr
                1005                1010                1015 gac ggc ggc ctg gcc cgc ggc gcc tac tcg ccc cgg ccg cct agc       3120
Asp Gly Gly Leu Ala Arg Gly Ala Tyr Ser Pro Arg Pro Pro Ser
            1020                1025                1030 atc agc gag aac gtg gcg atg gag gcc gtg gcg gca gga gtg gac       3165
Ile Ser Glu Asn Val Ala Met Glu Ala Val Ala Ala Gly Val Asp
        1035                1040                1045 ggc gcg ggg ccc gag gcc gac ctg ggg ctg ccg gag gac gac ctg       3210
Gly Ala Gly Pro Glu Ala Asp Leu Gly Leu Pro Glu Asp Asp Leu
    1050                1055                1060 gtg ctt cca gac gac gtg gtg cag tac atc aag gcg cac gcc agt       3255
Val Leu Pro Asp Asp Val Val Gln Tyr Ile Lys Ala His Ala Ser
1065                1070                1075 ggc gct ctg gac gag ggc acc ggg cag gtg tat ccc acg gaa agc       3300
Gly Ala Leu Asp Glu Gly Thr Gly Gln Val Tyr Pro Thr Glu Ser
                1080                1085                1090 act ggc ttc tct gac aac ccc aga cta ccc agc ccg ggg ctg cac       3345
Thr Gly Phe Ser Asp Asn Pro Arg Leu Pro Ser Pro Gly Leu His
            1095                1100                1105 ggc cag cgc agg atg gtg gct gcg gac tcc aac gtg ggc ccc tcc       3390
Gly Gln Arg Arg Met Val Ala Ala Asp Ser Asn Val Gly Pro Ser
        1110                1115                1120 gcc cct atg ctg gga gga tgc cag tta ggc ttt ggg gcg ccc tcc       3435
Ala Pro Met Leu Gly Gly Cys Gln Leu Gly Phe Gly Ala Pro Ser
    1125                1130                1135 agc ctg aac aaa aat aac atg cct gtg cag tgg aat gag gtg agc       3480
Ser Leu Asn Lys Asn Asn Met Pro Val Gln Trp Asn Glu Val Ser
1140                1145                1150 tcc ggc acc gta gac gcc ctg gcc agc cag gtg aag cct cca ccc       3525
Ser Gly Thr Val Asp Ala Leu Ala Ser Gln Val Lys Pro Pro Pro
                1155                1160                1165
```

| | | |
|---|---|---|
| ttt cct cag ggc aac ctg gcg gtg gtg cag cag aag cct gcc ttt | | 3570 |
| Phe Pro Gln Gly Asn Leu Ala Val Val Gln Gln Lys Pro Ala Phe | | |
| 1170 1175 1180 | | |
| ggc cag tac ccg ggc tac agt ccg caa ggc cta cag gct agc cct | | 3615 |
| Gly Gln Tyr Pro Gly Tyr Ser Pro Gln Gly Leu Gln Ala Ser Pro | | |
| 1185 1190 1195 | | |
| ggg ggc ctg gac agc acg cag cca cac ctg cag ccc cgc agc gga | | 3660 |
| Gly Gly Leu Asp Ser Thr Gln Pro His Leu Gln Pro Arg Ser Gly | | |
| 1200 1205 1210 | | |
| gcc ccc tcc cag ggc atc ccc agg gta aac tac atg cag cag ctg | | 3705 |
| Ala Pro Ser Gln Gly Ile Pro Arg Val Asn Tyr Met Gln Gln Leu | | |
| 1215 1220 1225 | | |
| cga cag cca gtg gca ggc agc cag tgt cct ggc atg act acc act | | 3750 |
| Arg Gln Pro Val Ala Gly Ser Gln Cys Pro Gly Met Thr Thr Thr | | |
| 1230 1235 1240 | | |
| atg agc ccc cat gcc tgc tat ggc caa gtc cac ccc cag ctg agc | | 3795 |
| Met Ser Pro His Ala Cys Tyr Gly Gln Val His Pro Gln Leu Ser | | |
| 1245 1250 1255 | | |
| ccc agc acc atc agt ggg gcc ctc aac cag ttc ccc caa tcc tgc | | 3840 |
| Pro Ser Thr Ile Ser Gly Ala Leu Asn Gln Phe Pro Gln Ser Cys | | |
| 1260 1265 1270 | | |
| agc aac atg cca gcc aag cca ggg cat ctg ggg cac cct cag cag | | 3885 |
| Ser Asn Met Pro Ala Lys Pro Gly His Leu Gly His Pro Gln Gln | | |
| 1275 1280 1285 | | |
| aca gaa gtg gca cct gac ccc acc acg atg ggc aat cgc cac agg | | 3930 |
| Thr Glu Val Ala Pro Asp Pro Thr Thr Met Gly Asn Arg His Arg | | |
| 1290 1295 1300 | | |
| gaa ctt ggg gtc ccc gat tca gcc ctg gct gga gtg cca cca cct | | 3975 |
| Glu Leu Gly Val Pro Asp Ser Ala Leu Ala Gly Val Pro Pro Pro | | |
| 1305 1310 1315 | | |
| cac cca gtc cag agc tac cca cag cag agc cat cac ctg gca gcc | | 4020 |
| His Pro Val Gln Ser Tyr Pro Gln Gln Ser His His Leu Ala Ala | | |
| 1320 1325 1330 | | |
| tcc atg agc cag gag ggc tac cac cag gtc ccc agc ctt ctg cct | | 4065 |
| Ser Met Ser Gln Glu Gly Tyr His Gln Val Pro Ser Leu Leu Pro | | |
| 1335 1340 1345 | | |
| gcc cgc cag cct ggc ttc atg gag ccc caa aca ggc ccg atg ggg | | 4110 |
| Ala Arg Gln Pro Gly Phe Met Glu Pro Gln Thr Gly Pro Met Gly | | |
| 1350 1355 1360 | | |
| gtg gct aca gca ggc ttt ggc cta gtg cag ccc cgg cct ccc ctc | | 4155 |
| Val Ala Thr Ala Gly Phe Gly Leu Val Gln Pro Arg Pro Pro Leu | | |
| 1365 1370 1375 | | |
| gag ccc agc ccc act ggc cgc cac cgt ggg gta cgt gct gtg cag | | 4200 |
| Glu Pro Ser Pro Thr Gly Arg His Arg Gly Val Arg Ala Val Gln | | |
| 1380 1385 1390 | | |
| cag cag ctg gcc tac gcc agg gcc aca ggc cat gcc atg gct gcc | | 4245 |
| Gln Gln Leu Ala Tyr Ala Arg Ala Thr Gly His Ala Met Ala Ala | | |
| 1395 1400 1405 | | |
| atg ccg tcc agt cag gaa aca gca gag gct gtg ccc aag gga gcg | | 4290 |
| Met Pro Ser Ser Gln Glu Thr Ala Glu Ala Val Pro Lys Gly Ala | | |
| 1410 1415 1420 | | |
| atg ggc aac atg ggg tcg gtg cct ccc cag ccg cct ccg cag gac | | 4335 |
| Met Gly Asn Met Gly Ser Val Pro Pro Gln Pro Pro Pro Gln Asp | | |
| 1425 1430 1435 | | |
| gca ggt ggg gcc ccg gac cac agc atg ctc tac tac tac ggc cag | | 4380 |
| Ala Gly Gly Ala Pro Asp His Ser Met Leu Tyr Tyr Tyr Gly Gln | | |
| 1440 1445 1450 | | |
| atc cac atg tac gaa cag gat gga ggc ctg gag aac ctc ggg agc | | 4425 |
| Ile His Met Tyr Glu Gln Asp Gly Gly Leu Glu Asn Leu Gly Ser | | |

|  |  |  |  | 1455 |  |  |  | 1460 |  |  |  | 1465 |  |  |
|---|---|---|---|---|---|---|---|---|---|---|---|---|---|---|
| tgc | cag | gtc | atg | cgg | tcc | cag | cca | cca | cag | cca | cag | gcc | tgt | cag |
| Cys | Gln | Val | Met | Arg | Ser | Gln | Pro | Pro | Gln | Pro | Gln | Ala | Cys | Gln |
|  |  |  | 1470 |  |  |  | 1475 |  |  |  | 1480 |  |  |  |

4470

| gac | agc | atc | cag | ccc | cag | ccc | ttg | ccc | tca | cca | ggg | gtc | aac | cag |
|---|---|---|---|---|---|---|---|---|---|---|---|---|---|---|
| Asp | Ser | Ile | Gln | Pro | Gln | Pro | Leu | Pro | Ser | Pro | Gly | Val | Asn | Gln |
|  | 1485 |  |  |  | 1490 |  |  |  | 1495 |  |  |  |  |  |

4515

| gtg | tcc | agc | act | gtg | gac | tcc | cag | ctc | ctg | gag | gcc | ccc | cag | att |
|---|---|---|---|---|---|---|---|---|---|---|---|---|---|---|
| Val | Ser | Ser | Thr | Val | Asp | Ser | Gln | Leu | Leu | Glu | Ala | Pro | Gln | Ile |
| 1500 |  |  |  |  | 1505 |  |  |  | 1510 |  |  |  |  |  |

4560

| gac | ttc | gat | gcc | atc | atg | gat | gat | ggc | gat | cac | tcg | agt | ttg | ttc |
|---|---|---|---|---|---|---|---|---|---|---|---|---|---|---|
| Asp | Phe | Asp | Ala | Ile | Met | Asp | Asp | Gly | Asp | His | Ser | Ser | Leu | Phe |
|  |  |  | 1515 |  |  |  | 1520 |  |  |  | 1525 |  |  |  |

4605

| tcg | ggt | gct | ctg | agc | ccc | agc | ctc | ctc | cac | agc | ctc | tcc | cag | aac |
|---|---|---|---|---|---|---|---|---|---|---|---|---|---|---|
| Ser | Gly | Ala | Leu | Ser | Pro | Ser | Leu | Leu | His | Ser | Leu | Ser | Gln | Asn |
|  |  | 1530 |  |  |  | 1535 |  |  |  | 1540 |  |  |  |  |

4650

| tcc | tcc | cgc | ctc | acc | acc | ccc | cga | aac | tcc | ttg | acc | ctg | ccc | tcc |
|---|---|---|---|---|---|---|---|---|---|---|---|---|---|---|
| Ser | Ser | Arg | Leu | Thr | Thr | Pro | Arg | Asn | Ser | Leu | Thr | Leu | Pro | Ser |
|  |  |  | 1545 |  |  |  | 1550 |  |  |  | 1555 |  |  |  |

4695

| atc | ccc | gca | ggc | atc | agc | aac | atg | gct | gtc | ggg | gac | atg | agc | tcc |
|---|---|---|---|---|---|---|---|---|---|---|---|---|---|---|
| Ile | Pro | Ala | Gly | Ile | Ser | Asn | Met | Ala | Val | Gly | Asp | Met | Ser | Ser |
|  |  | 1560 |  |  |  | 1565 |  |  |  | 1570 |  |  |  |  |

4740

| atg | ctc | acc | agc | ctc | gcc | gag | gag | agc | aag | ttc | ctg | aac | atg | atg |
|---|---|---|---|---|---|---|---|---|---|---|---|---|---|---|
| Met | Leu | Thr | Ser | Leu | Ala | Glu | Glu | Ser | Lys | Phe | Leu | Asn | Met | Met |
|  | 1575 |  |  |  | 1580 |  |  |  | 1585 |  |  |  |  |  |

4785

| acc | tag | aggcccgagc | gcctggtgct | gagtgcaccc | ggaggggtca | tcgctgccca | 4841 |
|---|---|---|---|---|---|---|---|
| Thr |  |  |  |  |  |  |  | gagcctgggg attccagctg tcttgtcttt ttccaaaaaa gtgttaaata ggcttgaggg    4901 gttgttcgc aatggccgct tcagatgaca gatgttgtaa gagaaggttt atgggcatcc    4961 tctctggtct tttggattat tcctcagaac aatgaaaaaa gtctccatag gacaggaagg    5021 aatgcaaaac tcatttacac agtgctttcc agcctttggt gcttacagga ccgcgctgtt    5081 ccggcttctt cacggctgac attcggctaa cgagggatta ctttggccaa aacctttcaa    5141 aggatatgca gaaagatggt agggagcatt tgggtttgaa tctgaatgct atactggata    5201 ctctgctccg gaaagatgag cttttttattc tactacttgg aaggaaaagg aattcctggt    5261 ccacctgaat tcctctatga agcctaactc ttgaggtctc taacatacct tgtcatagag    5321 gaaaagcaca gattatacct ggatgattca ggagcacatt ctgattccag gtttggtaga    5381 gctggctctt ctactccgta aagccgagtc tgggactggc agccatcca agtgtatatg    5441 aatgaataaa gcatccaagt atatgtgaat gaataaagta tgtaagtatc accagaaaaa    5501 ggaaagaaaa aatgtactcc ttggggcaag cccagaagct gccctggcct ctccagaccg    5561 tgtttacagt gtttgcatgt agaatgtagc ccttcctgaa aagaagactt gtttctaaat    5621 acctcggggc tgctggagcc gctgtgggtt agggatggac tgaggcctcg aggagtgagg    5681 gtgcacccgg ggcccagcct caggctgccc tagggatctc tcagtaggaa gaggaagttg    5741 cgtgtttacc caatcctgtt tctccaatgc aacgtccacc cactttacca ccaaaaactc    5801 cagggcctga cggcagcccg gtcccccagc actcaccagc agcccagtgt tctccaccaa    5861 gccacagtgt gcatgcctgg tatcctccgg attcccttcc ttctgcccgc tgagtcactg    5921 ggcagagaat gatgacatgt gtaggtggtg tggttggggg tggaaggggg aagggggttga    5981 tcctcaggac tctgagggag catcgttgaa ttttcctgtt cagtgtgacc aagacccacc    6041 tggaaatgga atttggaact ggcttcagga gacatcattc ctgaacacac tgtagggtga    6101

-continued

```
attggtgcat cttccccacc atacacacac acacacacac acacacacac acacacacac    6161
acacacccca aacctttca tggggaatgt gtggcaacct tgccaaacag caccactcag    6221
agtgtgactc tgactgtgac cttggcctta atgaggaact tcttaggaga gtttgaggac    6281
aaggccaaca tcgtcatctg ggctcgctgc gtcccagcac atcaaactct gtccagagac    6341
aaggccaact gcaaatgaaa gccagggaac attgctaagg gtctgtggct ctgtggtggt    6401
gttcatcgcc ttcctgagat aggatttccc ttgccagtcc caacctgtat atattctgta    6461
cagaagacat ccctgaatat actgtaggtg agtcgtccag ccaaatttat atctccaaaa    6521
cattttagc ttttctaca tgctatgaat tgagatgaca tgctcaactt gtaaataagt    6581
ctttttgtac attaaaaaag taattttttc ataatttatc ttgtctatct gcttccccct    6641
tgacagtagt taatgagaac ctgggcagta aatttggtgc attcgagcag aaattaggct    6701
gtatttttc ttaacagtgt caaaattgac tatcccgcct tgccaagaa atgtttaatg    6761
ctgaggcaaa aaaaaaaaa                                               6780
```

<210> SEQ ID NO 48
<211> LENGTH: 1586
<212> TYPE: PRT
<213> ORGANISM: Homo sapiens

<400> SEQUENCE: 48

```
Met Glu Thr Ser Ala Ser Ala Thr Ala Ser Glu Lys Gln Glu Ala Lys
1               5                   10                  15

Ser Gly Ile Leu Glu Ala Ala Gly Phe Pro Asp Pro Gly Lys Lys Ala
            20                  25                  30

Ser Pro Leu Val Val Ala Ala Ala Ala Ala Val Ala Ala Gln
        35                  40                  45

Gly Val Pro Gln His Leu Leu Pro Pro Phe His Ala Pro Leu Pro Ile
    50                  55                  60

Asp Met Arg His Gln Glu Gly Arg Tyr His Tyr Glu Pro His Ser Val
65                  70                  75                  80

His Gly Val His Gly Pro Pro Ala Leu Ser Gly Ser Pro Val Ile Ser
                85                  90                  95

Asp Ile Ser Leu Ile Arg Leu Ser Pro His Pro Ala Gly Pro Gly Glu
            100                 105                 110

Ser Pro Phe Asn Ala Pro His Pro Tyr Val Asn Pro His Met Glu His
        115                 120                 125

Tyr Leu Arg Ser Val His Ser Ser Pro Thr Leu Ser Met Ile Ser Ala
    130                 135                 140

Ala Arg Gly Leu Ser Pro Ala Asp Val Ala Gln Glu His Leu Lys Glu
145                 150                 155                 160

Arg Gly Leu Phe Gly Leu Pro Ala Pro Gly Thr Thr Pro Ser Asp Tyr
                165                 170                 175

Tyr His Gln Met Thr Leu Val Ala Gly His Pro Ala Pro Tyr Gly Asp
            180                 185                 190

Leu Leu Met Gln Ser Gly Gly Ala Ala Ser Ala Pro His Leu His Asp
        195                 200                 205

Tyr Leu Asn Pro Val Asp Val Ser Arg Phe Ser Pro Arg Val Thr
    210                 215                 220

Pro Arg Leu Ser Arg Lys Arg Ala Leu Ser Ile Ser Pro Leu Ser Asp
225                 230                 235                 240

Ala Ser Leu Asp Leu Gln Arg Met Ile Arg Thr Ser Pro Asn Ser Leu
                245                 250                 255
```

Val Ala Tyr Ile Asn Asn Ser Arg Ser Ser Ala Ala Ser Gly Ser
            260                 265                 270

Tyr Gly His Leu Ser Ala Gly Ala Leu Ser Pro Ala Phe Thr Phe Pro
            275                 280                 285

His Pro Ile Asn Pro Val Ala Tyr Gln Gln Ile Leu Ser Gln Gln Arg
290                 295                 300

Gly Leu Gly Ser Ala Phe Gly His Thr Pro Leu Ile Gln Pro Ser
305                 310                 315                 320

Pro Thr Phe Leu Ala Gln Gln Pro Met Ala Leu Thr Ser Ile Asn Ala
                325                 330                 335

Thr Pro Thr Gln Leu Ser Ser Ser Asn Cys Leu Ser Asp Thr Asn
                340                 345                 350

Gln Asn Lys Gln Ser Ser Glu Ser Ala Val Ser Ser Thr Val Asn Pro
                355                 360                 365

Val Ala Ile His Lys Arg Ser Lys Val Lys Thr Glu Pro Glu Gly Leu
            370                 375                 380

Arg Pro Ala Ser Pro Leu Ala Leu Thr Gln Gly Gln Val Ser Gly His
385                 390                 395                 400

Gly Ser Cys Gly Cys Ala Leu Pro Leu Ser Gln Glu Gln Leu Ala Asp
                405                 410                 415

Leu Lys Glu Asp Leu Asp Arg Asp Asp Cys Lys Gln Glu Ala Glu Val
                420                 425                 430

Val Ile Tyr Glu Thr Asn Cys His Trp Glu Asp Cys Thr Lys Glu Tyr
            435                 440                 445

Asp Thr Gln Glu Gln Leu Val His His Ile Asn Asn Glu His Ile His
                450                 455                 460

Gly Glu Lys Lys Glu Phe Val Cys Arg Trp Gln Ala Cys Thr Arg Glu
465                 470                 475                 480

Gln Lys Pro Phe Lys Ala Gln Tyr Met Leu Val Val His Met Arg Arg
                485                 490                 495

His Thr Gly Glu Lys Pro His Lys Cys Thr Phe Glu Gly Cys Ser Lys
            500                 505                 510

Ala Tyr Ser Arg Leu Glu Asn Leu Lys Thr His Leu Arg Ser His Thr
            515                 520                 525

Gly Glu Lys Pro Tyr Val Cys Glu His Glu Gly Cys Asn Lys Ala Phe
            530                 535                 540

Ser Asn Ala Ser Asp Arg Ala Lys His Gln Asn Arg Thr His Ser Asn
545                 550                 555                 560

Glu Lys Pro Tyr Ile Cys Lys Ile Pro Gly Cys Thr Lys Arg Tyr Thr
                565                 570                 575

Asp Pro Ser Ser Leu Arg Lys His Val Lys Thr Val His Gly Pro Asp
                580                 585                 590

Ala His Val Thr Lys Lys Gln Arg Asn Asp Val His Leu Arg Thr Pro
            595                 600                 605

Leu Leu Lys Glu Asn Gly Asp Ser Glu Ala Gly Thr Glu Pro Gly Gly
            610                 615                 620

Pro Glu Ser Thr Glu Ala Ser Ser Thr Ser Gln Ala Val Glu Asp Cys
625                 630                 635                 640

Leu His Val Arg Ala Ile Lys Thr Glu Ser Ser Gly Leu Cys Gln Ser
                645                 650                 655

Ser Pro Gly Ala Gln Ser Ser Cys Ser Ser Glu Pro Ser Pro Leu Gly
            660                 665                 670

```
Ser Ala Pro Asn Asn Asp Ser Gly Val Glu Met Pro Gly Thr Gly Pro
            675                 680                 685
Gly Ser Leu Gly Asp Leu Thr Ala Leu Asp Asp Thr Pro Pro Gly Ala
    690                 695                 700
Asp Thr Ser Ala Leu Ala Ala Pro Ser Ala Gly Gly Leu Gln Leu Arg
705                 710                 715                 720
Lys His Met Thr Thr Met His Arg Phe Glu Gln Leu Lys Lys Glu Lys
                725                 730                 735
Leu Lys Ser Leu Lys Asp Ser Cys Ser Trp Ala Gly Pro Thr Pro His
            740                 745                 750
Thr Arg Asn Thr Lys Leu Pro Pro Leu Pro Gly Ser Gly Ser Ile Leu
        755                 760                 765
Glu Asn Phe Ser Gly Ser Gly Gly Gly Pro Ala Gly Leu Leu Pro
    770                 775                 780
Asn Pro Arg Leu Ser Glu Leu Ser Ala Ser Glu Val Thr Met Leu Ser
785                 790                 795                 800
Gln Leu Gln Glu Arg Arg Asp Ser Ser Thr Ser Thr Val Ser Ser Ala
                805                 810                 815
Tyr Thr Val Ser Arg Arg Ser Ser Gly Ile Ser Pro Tyr Phe Ser Ser
            820                 825                 830
Arg Arg Ser Ser Glu Ala Ser Pro Leu Gly Ala Gly Arg Pro His Asn
835                 840                 845
Ala Ser Ser Ala Asp Ser Tyr Asp Pro Ile Ser Thr Asp Ala Ser Arg
        850                 855                 860
Arg Ser Ser Glu Ala Ser Gln Cys Ser Gly Gly Ser Gly Leu Leu Asn
865                 870                 875                 880
Leu Thr Pro Ala Gln Gln Tyr Ser Leu Arg Ala Lys Tyr Ala Ala Ala
                885                 890                 895
Thr Gly Gly Pro Pro Thr Pro Leu Pro Gly Leu Glu Arg Met Ser
            900                 905                 910
Leu Arg Thr Arg Leu Ala Leu Leu Asp Ala Pro Glu Arg Thr Leu Pro
        915                 920                 925
Ala Gly Cys Pro Arg Pro Leu Gly Pro Arg Arg Gly Ser Asp Gly Pro
    930                 935                 940
Thr Tyr Gly His Gly His Ala Gly Ala Ala Pro Ala Phe Pro His Glu
945                 950                 955                 960
Ala Pro Gly Gly Gly Ala Arg Arg Ala Ser Asp Pro Val Arg Arg Pro
                965                 970                 975
Asp Ala Leu Ser Leu Pro Arg Val Gln Arg Phe His Ser Thr His Asn
            980                 985                 990
Val Asn Pro Gly Pro Leu Pro Pro Cys Ala Asp Arg Arg Gly Leu Arg
        995                 1000                1005
Leu Gln Ser His Pro Ser Thr Asp Gly Gly Leu Ala Arg Gly Ala
    1010                1015                1020
Tyr Ser Pro Arg Pro Pro Ser Ile Ser Glu Asn Val Ala Met Glu
    1025                1030                1035
Ala Val Ala Ala Gly Val Asp Gly Ala Gly Pro Glu Ala Asp Leu
    1040                1045                1050
Gly Leu Pro Glu Asp Asp Leu Val Leu Pro Asp Asp Val Val Gln
    1055                1060                1065
Tyr Ile Lys Ala His Ala Ser Gly Ala Leu Asp Glu Gly Thr Gly
    1070                1075                1080
Gln Val Tyr Pro Thr Glu Ser Thr Gly Phe Ser Asp Asn Pro Arg
```

-continued

```
           1085                1090                1095
Leu Pro Ser Pro Gly Leu His Gly Gln Arg Arg Met Val Ala Ala
       1100                1105                1110
Asp Ser Asn Val Gly Pro Ser Ala Pro Met Leu Gly Gly Cys Gln
       1115                1120                1125
Leu Gly Phe Gly Ala Pro Ser Ser Leu Asn Lys Asn Asn Met Pro
       1130                1135                1140
Val Gln Trp Asn Glu Val Ser Ser Gly Thr Val Asp Ala Leu Ala
       1145                1150                1155
Ser Gln Val Lys Pro Pro Phe Pro Gln Gly Asn Leu Ala Val
       1160                1165                1170
Val Gln Gln Lys Pro Ala Phe Gly Gln Tyr Pro Gly Tyr Ser Pro
       1175                1180                1185
Gln Gly Leu Gln Ala Ser Pro Gly Gly Leu Asp Ser Thr Gln Pro
       1190                1195                1200
His Leu Gln Pro Arg Ser Gly Ala Pro Ser Gln Gly Ile Pro Arg
       1205                1210                1215
Val Asn Tyr Met Gln Gln Leu Arg Gln Pro Val Ala Gly Ser Gln
       1220                1225                1230
Cys Pro Gly Met Thr Thr Thr Met Ser Pro His Ala Cys Tyr Gly
       1235                1240                1245
Gln Val His Pro Gln Leu Ser Pro Ser Thr Ile Ser Gly Ala Leu
       1250                1255                1260
Asn Gln Phe Pro Gln Ser Cys Ser Asn Met Pro Ala Lys Pro Gly
       1265                1270                1275
His Leu Gly His Pro Gln Gln Thr Glu Val Ala Pro Asp Pro Thr
       1280                1285                1290
Thr Met Gly Asn Arg His Arg Glu Leu Gly Val Pro Asp Ser Ala
       1295                1300                1305
Leu Ala Gly Val Pro Pro Pro His Pro Val Gln Ser Tyr Pro Gln
       1310                1315                1320
Gln Ser His His Leu Ala Ala Ser Met Ser Gln Glu Gly Tyr His
       1325                1330                1335
Gln Val Pro Ser Leu Leu Pro Ala Arg Gln Pro Gly Phe Met Glu
       1340                1345                1350
Pro Gln Thr Gly Pro Met Gly Val Ala Thr Ala Gly Phe Gly Leu
       1355                1360                1365
Val Gln Pro Arg Pro Pro Leu Glu Pro Ser Pro Thr Gly Arg His
       1370                1375                1380
Arg Gly Val Arg Ala Val Gln Gln Leu Ala Tyr Ala Arg Ala
       1385                1390                1395
Thr Gly His Ala Met Ala Ala Met Pro Ser Ser Gln Glu Thr Ala
       1400                1405                1410
Glu Ala Val Pro Lys Gly Ala Met Gly Asn Met Gly Ser Val Pro
       1415                1420                1425
Pro Gln Pro Pro Pro Gln Asp Ala Gly Gly Ala Pro Asp His Ser
       1430                1435                1440
Met Leu Tyr Tyr Tyr Gly Gln Ile His Met Tyr Glu Gln Asp Gly
       1445                1450                1455
Gly Leu Glu Asn Leu Gly Ser Cys Gln Val Met Arg Ser Gln Pro
       1460                1465                1470
Pro Gln Pro Gln Ala Cys Gln Asp Ser Ile Gln Pro Gln Pro Leu
       1475                1480                1485
```

```
Pro Ser Pro Gly Val Asn Gln Val Ser Ser Thr Val Asp Ser Gln
    1490                1495                1500

Leu Leu Glu Ala Pro Gln Ile Asp Phe Asp Ala Ile Met Asp Asp
    1505                1510                1515

Gly Asp His Ser Ser Leu Phe Ser Gly Ala Leu Ser Pro Ser Leu
    1520                1525                1530

Leu His Ser Leu Ser Gln Asn Ser Ser Arg Leu Thr Thr Pro Arg
    1535                1540                1545

Asn Ser Leu Thr Leu Pro Ser Ile Pro Ala Gly Ile Ser Asn Met
    1550                1555                1560

Ala Val Gly Asp Met Ser Ser Met Leu Thr Ser Leu Ala Glu Glu
    1565                1570                1575

Ser Lys Phe Leu Asn Met Met Thr
    1580                1585

<210> SEQ ID NO 49
<211> LENGTH: 10088
<212> TYPE: DNA
<213> ORGANISM: Homo sapiens
<220> FEATURE:
<221> NAME/KEY: CDS
<222> LOCATION: (143)..(4984)

<400> SEQUENCE: 49
gtgccccttt ctttcttctc tcgctgggaa gctgggaagt atgagcgtgc agccctgccg      60
ctgcggcggc cgccccggct cctcgcctcc cccacttctg gccacccctc gccggtgaga    120
gaagagaacg cgagaaggga ag atg ggg gcc gtc ctg agg agc ctc ctg gcc    172
                        Met Gly Ala Val Leu Arg Ser Leu Leu Ala
                          1               5                  10 tgc agc ttc tgt gtg ctc ctg aga gcg gcc cct ttg ttg ctt tat gca    220
Cys Ser Phe Cys Val Leu Leu Arg Ala Ala Pro Leu Leu Leu Tyr Ala
            15                  20                  25 aac aga cgg gac ttg cga ttg gtt gat gct aca aat ggc aaa gag aat    268
Asn Arg Arg Asp Leu Arg Leu Val Asp Ala Thr Asn Gly Lys Glu Asn
        30                  35                  40 gct acg att gta gtt gga ggc ttg gag gat gca gct gcg gtg gac ttt    316
Ala Thr Ile Val Val Gly Gly Leu Glu Asp Ala Ala Ala Val Asp Phe
    45                  50                  55 gtg ttt agt cat ggc ttg ata tac tgg agt gat gtc agc gaa gaa gcc    364
Val Phe Ser His Gly Leu Ile Tyr Trp Ser Asp Val Ser Glu Glu Ala
60                  65                  70 att aaa cga aca gaa ttt aac aaa act gag agt gtg cag aat gtt gtt    412
Ile Lys Arg Thr Glu Phe Asn Lys Thr Glu Ser Val Gln Asn Val Val
75                  80                  85                  90 gtt tct gga tta ttg tcc ccc gat ggg ctg gca tgt gat tgg ctt gga    460
Val Ser Gly Leu Leu Ser Pro Asp Gly Leu Ala Cys Asp Trp Leu Gly
                95                  100                 105 gaa aaa ttg tac tgg aca gat tct gaa act aat cgg att gaa gtt tct    508
Glu Lys Leu Tyr Trp Thr Asp Ser Glu Thr Asn Arg Ile Glu Val Ser
            110                 115                 120 aat tta gat gga tct tta cga aaa gtt tta ttt tgg caa gag ttg gat    556
Asn Leu Asp Gly Ser Leu Arg Lys Val Leu Phe Trp Gln Glu Leu Asp
        125                 130                 135 caa ccc aga gct att gcc tta gat cct tca agt ggg ttc atg tac tgg    604
Gln Pro Arg Ala Ile Ala Leu Asp Pro Ser Ser Gly Phe Met Tyr Trp
    140                 145                 150 aca gac tgg gga gaa gtg cca aag ata gaa cgt gct gga atg gat ggt    652
Thr Asp Trp Gly Glu Val Pro Lys Ile Glu Arg Ala Gly Met Asp Gly
```

-continued

| | | | | | | | | | | | | | | | | |
|---|---|---|---|---|---|---|---|---|---|---|---|---|---|---|---|---|
| 155 | | | | | 160 | | | | | 165 | | | | | 170 | |

```
            155                 160                 165                 170
    tca agt cgc ttc att ata ata aac agt gaa att tac tgg cca aat gga              700
    Ser Ser Arg Phe Ile Ile Ile Asn Ser Glu Ile Tyr Trp Pro Asn Gly
                175                 180                 185 ctg act ttg gat tat gaa gaa caa aag ctt tat tgg gca gat gca aaa              748
    Leu Thr Leu Asp Tyr Glu Glu Gln Lys Leu Tyr Trp Ala Asp Ala Lys
                190                 195                 200 ctt aat ttc atc cac aaa tca aat ctg gat gga aca aat cgg cag gca              796
    Leu Asn Phe Ile His Lys Ser Asn Leu Asp Gly Thr Asn Arg Gln Ala
            205                 210                 215 gtg gtt aaa ggt tcc ctt cca cat cct ttt gcc ttg acg tta ttt gag              844
    Val Val Lys Gly Ser Leu Pro His Pro Phe Ala Leu Thr Leu Phe Glu
        220                 225                 230 gac ata ttg tac tgg act gac tgg agc aca cac tcc att ttg gct tgc              892
    Asp Ile Leu Tyr Trp Thr Asp Trp Ser Thr His Ser Ile Leu Ala Cys
    235                 240                 245                 250 aac aag tat act ggt gag ggt ctg cgt gaa atc cat tct gac atc ttc              940
    Asn Lys Tyr Thr Gly Glu Gly Leu Arg Glu Ile His Ser Asp Ile Phe
                255                 260                 265 tct ccc atg gat ata cat gcc ttc agc caa cag agg cag cca aat gcc              988
    Ser Pro Met Asp Ile His Ala Phe Ser Gln Gln Arg Gln Pro Asn Ala
                270                 275                 280 aca aat cca tgt gga att gac aat ggg ggt tgt tcc cat ttg tgt ttg             1036
    Thr Asn Pro Cys Gly Ile Asp Asn Gly Gly Cys Ser His Leu Cys Leu
            285                 290                 295 atg tct cca gtc aag cct ttt tat cag tgt gct tgc ccc act ggg gtc             1084
    Met Ser Pro Val Lys Pro Phe Tyr Gln Cys Ala Cys Pro Thr Gly Val
        300                 305                 310 aaa ctc ctg gag aat gga aaa acc tgc aaa gat ggt gcc aca gaa tta             1132
    Lys Leu Leu Glu Asn Gly Lys Thr Cys Lys Asp Gly Ala Thr Glu Leu
    315                 320                 325                 330 ttg ctt tta gct cga agg aca gac ttg aga cgc att tct ttg gat aca             1180
    Leu Leu Leu Ala Arg Arg Thr Asp Leu Arg Arg Ile Ser Leu Asp Thr
                335                 340                 345 cca gat ttt aca gac att gtt ctg cag tta gaa gac atc cgt cat gcc             1228
    Pro Asp Phe Thr Asp Ile Val Leu Gln Leu Glu Asp Ile Arg His Ala
                350                 355                 360 att gcc ata gat tac gat cct gtg gaa ggc tac atc tac tgg act gat             1276
    Ile Ala Ile Asp Tyr Asp Pro Val Glu Gly Tyr Ile Tyr Trp Thr Asp
            365                 370                 375 gat gaa gtg agg gcc ata cgc cgt tca ttt ata gat gga tct ggc agt             1324
    Asp Glu Val Arg Ala Ile Arg Arg Ser Phe Ile Asp Gly Ser Gly Ser
        380                 385                 390 cag ttt gtg gtc act gct caa att gcc cat cct gat ggt att gct gtg             1372
    Gln Phe Val Val Thr Ala Gln Ile Ala His Pro Asp Gly Ile Ala Val
    395                 400                 405                 410 gac tgg gtt gca cga aat ctt tat tgg aca gac act ggc act gat cga             1420
    Asp Trp Val Ala Arg Asn Leu Tyr Trp Thr Asp Thr Gly Thr Asp Arg
                415                 420                 425 ata gaa gtg aca agg ctc aat ggg acc atg agg aag atc ttg att tca             1468
    Ile Glu Val Thr Arg Leu Asn Gly Thr Met Arg Lys Ile Leu Ile Ser
                430                 435                 440 gag gac tta gag gaa ccc cgg gct att gtg tta gat ccc atg gtt ggg             1516
    Glu Asp Leu Glu Glu Pro Arg Ala Ile Val Leu Asp Pro Met Val Gly
            445                 450                 455 tac atg tat tgg act gac tgg gga gaa att ccg aaa att gag cga gca             1564
    Tyr Met Tyr Trp Thr Asp Trp Gly Glu Ile Pro Lys Ile Glu Arg Ala
        460                 465                 470 gct ctg gat ggt tct gac cgt gta gta ttg gtt aac act tct ctt ggt             1612
    Ala Leu Asp Gly Ser Asp Arg Val Val Leu Val Asn Thr Ser Leu Gly
```

```
                                                    -continued

Ala Leu Asp Gly Ser Asp Arg Val Val Leu Val Asn Thr Ser Leu Gly
475                 480                 485                 490 tgg cca aat ggt tta gcc ttg gat tat gat gaa ggc aaa ata tac tgg      1660
Trp Pro Asn Gly Leu Ala Leu Asp Tyr Asp Glu Gly Lys Ile Tyr Trp
            495                 500                 505 gga gat gcc aaa aca gac aag att gag gtt atg aat act gat ggc act      1708
Gly Asp Ala Lys Thr Asp Lys Ile Glu Val Met Asn Thr Asp Gly Thr
        510                 515                 520 ggg aga cga gta cta gtg gaa gac aaa att cct cac ata ttt gga ttt      1756
Gly Arg Arg Val Leu Val Glu Asp Lys Ile Pro His Ile Phe Gly Phe
    525                 530                 535 act ttg ttg ggt gac tat gtt tac tgg act gac tgg cag agg cgt agc      1804
Thr Leu Leu Gly Asp Tyr Val Tyr Trp Thr Asp Trp Gln Arg Arg Ser
540                 545                 550 att gaa aga gtt cat aaa cga agt gca gag agg gaa gtg atc ata gat      1852
Ile Glu Arg Val His Lys Arg Ser Ala Glu Arg Glu Val Ile Ile Asp
555                 560                 565                 570 cag ctg cct gac ctc atg ggc cta aag gct aca aat gtt cat cga gtg      1900
Gln Leu Pro Asp Leu Met Gly Leu Lys Ala Thr Asn Val His Arg Val
            575                 580                 585 att ggt tcc aac ccc tgt gct gag gaa aac ggg gga tgt agc cat ctc      1948
Ile Gly Ser Asn Pro Cys Ala Glu Glu Asn Gly Gly Cys Ser His Leu
        590                 595                 600 tgc ctc tat aga cct cag ggc ctt cgc tgt gct tgc cct att ggc ttt      1996
Cys Leu Tyr Arg Pro Gln Gly Leu Arg Cys Ala Cys Pro Ile Gly Phe
    605                 610                 615 gaa ctc atc agt gac atg aag acc tgc att gtc cca gag gct ttc ctt      2044
Glu Leu Ile Ser Asp Met Lys Thr Cys Ile Val Pro Glu Ala Phe Leu
620                 625                 630 ttg ttt tca cgg aga gca gat atc aga cga att tct ctg gaa aca aac      2092
Leu Phe Ser Arg Arg Ala Asp Ile Arg Arg Ile Ser Leu Glu Thr Asn
635                 640                 645                 650 aat aat aat gtg gct att cca ctc act ggt gtc aaa gaa gct tct gct      2140
Asn Asn Asn Val Ala Ile Pro Leu Thr Gly Val Lys Glu Ala Ser Ala
            655                 660                 665 ttg gat ttt gat gtg aca gac aac cga att tat tgg act gat ata tca      2188
Leu Asp Phe Asp Val Thr Asp Asn Arg Ile Tyr Trp Thr Asp Ile Ser
        670                 675                 680 ctc aag acc atc agc aga gcc ttt atg aat ggc agt gca ctg gaa cat      2236
Leu Lys Thr Ile Ser Arg Ala Phe Met Asn Gly Ser Ala Leu Glu His
    685                 690                 695 gtg gta gaa ttc ggc tta gat tat cca gaa ggc atg gca gta gac tgg      2284
Val Val Glu Phe Gly Leu Asp Tyr Pro Glu Gly Met Ala Val Asp Trp
700                 705                 710 ctt ggg aag aac ttg tac tgg gca gac aca gga acg aat cga att gag      2332
Leu Gly Lys Asn Leu Tyr Trp Ala Asp Thr Gly Thr Asn Arg Ile Glu
715                 720                 725                 730 gtg tca aag ttg gat ggg cag cac cga caa gtt ttg gtg tgg aaa gac      2380
Val Ser Lys Leu Asp Gly Gln His Arg Gln Val Leu Val Trp Lys Asp
            735                 740                 745 cta gat agt ccc aga gct ctc gcg ttg gac cct gcc gaa gga ttt atg      2428
Leu Asp Ser Pro Arg Ala Leu Ala Leu Asp Pro Ala Glu Gly Phe Met
        750                 755                 760 tat tgg act gaa tgg ggt gga aaa cct aag ata gac aga gct gca atg      2476
Tyr Trp Thr Glu Trp Gly Gly Lys Pro Lys Ile Asp Arg Ala Ala Met
    765                 770                 775 gat gga agt gaa cgt act acc tta gtt cca aat gtg ggg cgg gca aac      2524
Asp Gly Ser Glu Arg Thr Thr Leu Val Pro Asn Val Gly Arg Ala Asn
780                 785                 790
```

```
                                                       -continued ggc cta act att gat tat gct aaa agg agg ctt tat tgg aca gac ctg    2572
Gly Leu Thr Ile Asp Tyr Ala Lys Arg Arg Leu Tyr Trp Thr Asp Leu
795             800                 805                 810 gac acc aac tta ata gaa tct tca aat atg ctt ggg ctc aac cgt gaa    2620
Asp Thr Asn Leu Ile Glu Ser Ser Asn Met Leu Gly Leu Asn Arg Glu
                815                 820                 825 gtt ata gca gat gac ttg cct cat cct ttt ggc tta act cag tac caa    2668
Val Ile Ala Asp Asp Leu Pro His Pro Phe Gly Leu Thr Gln Tyr Gln
830             835                 840 gat tat atc tac tgg acg gac tgg agc cga cgc agc att gag cgt gcc    2716
Asp Tyr Ile Tyr Trp Thr Asp Trp Ser Arg Arg Ser Ile Glu Arg Ala
        845                 850                 855 aac aaa acc agt ggc caa aac cgc acc atc att cag ggc cat ttg gat    2764
Asn Lys Thr Ser Gly Gln Asn Arg Thr Ile Ile Gln Gly His Leu Asp
    860                 865                 870 tat gtg atg gac atc ctc gtc ttt cac tca tct cga cag tca ggg tgg    2812
Tyr Val Met Asp Ile Leu Val Phe His Ser Ser Arg Gln Ser Gly Trp
875             880                 885                 890 aat gaa tgt gct tcc agc aat ggg cac tgc tcc cac ctc tgc ttg gct    2860
Asn Glu Cys Ala Ser Ser Asn Gly His Cys Ser His Leu Cys Leu Ala
                895                 900                 905 gtg cca gtt ggg ggt ttt gtt tgt gga tgc cct gcc cac tac tct ctt    2908
Val Pro Val Gly Gly Phe Val Cys Gly Cys Pro Ala His Tyr Ser Leu
910             915                 920 aat gct gac aac agg act tgt agt gct cct acg act ttc ctg ctc ttc    2956
Asn Ala Asp Asn Arg Thr Cys Ser Ala Pro Thr Thr Phe Leu Leu Phe
    925                 930                 935 agt caa aag agt gcc atc aac cgc atg gtg att gat gaa caa cag agc    3004
Ser Gln Lys Ser Ala Ile Asn Arg Met Val Ile Asp Glu Gln Gln Ser
    940                 945                 950 ccc gac atc atc ctt ccc atc cac agc ctt cgg aat gtc cgg gcc att    3052
Pro Asp Ile Ile Leu Pro Ile His Ser Leu Arg Asn Val Arg Ala Ile
955             960                 965                 970 gac tat gac cca ctg gac aag caa ctc tat tgg att gac tca cga caa    3100
Asp Tyr Asp Pro Leu Asp Lys Gln Leu Tyr Trp Ile Asp Ser Arg Gln
                975                 980                 985 aac atg atc cga aag gca caa gaa gat ggc agc cag ggc ttt  act gtg   3148
Asn Met Ile Arg Lys Ala Gln Glu Asp Gly Ser Gln Gly Phe  Thr Val
                990                 995                 1000 gtt gtg agc  tca gtt ccg agt cag  aac ctg gaa ata caa  ccc tat     3193
Val Val Ser  Ser Val Pro Ser Gln  Asn Leu Glu Ile Gln  Pro Tyr
             1005                 1010                 1015 gac ctc agc  att gat att tac agc  cgc tac atc tac tgg  act tgt     3238
Asp Leu Ser  Ile Asp Ile Tyr Ser  Arg Tyr Ile Tyr Trp  Thr Cys
             1020                 1025                 1030 gag gct acc  aat gtc att aat gtg  aca aga tta gat ggg  aga tca     3283
Glu Ala Thr  Asn Val Ile Asn Val  Thr Arg Leu Asp Gly  Arg Ser
             1035                 1040                 1045 gtt gga gtg  gtg ctg aaa ggc gag  cag gac aga cct cga  gcc gtt     3328
Val Gly Val  Val Leu Lys Gly Glu  Gln Asp Arg Pro Arg  Ala Val
             1050                 1055                 1060 gtg gta aac  cca gag aaa ggg tat  atg tat ttt acc aat  ctt cag     3373
Val Val Asn  Pro Glu Lys Gly Tyr  Met Tyr Phe Thr Asn  Leu Gln
             1065                 1070                 1075 gaa agg tct  cct aaa att gaa cgg  gct gct ttg gat ggg  aca gaa     3418
Glu Arg Ser  Pro Lys Ile Glu Arg  Ala Ala Leu Asp Gly  Thr Glu
             1080                 1085                 1090 cgg gag gtc  ctc ttt ttc agt ggc  tta agt aaa cca att  gct tta     3463
Arg Glu Val  Leu Phe Phe Ser Gly  Leu Ser Lys Pro Ile  Ala Leu
             1095                 1100                 1105
```

```
gcc ctt gat agc agg ctg ggc aag ctc ttt tgg gct gat tca gat    3508
Ala Leu Asp Ser Arg Leu Gly Lys Leu Phe Trp Ala Asp Ser Asp
        1110                1115                1120 ctc cgg cga att gaa agc agt gat ctc tca ggt gct aac cgg ata    3553
Leu Arg Arg Ile Glu Ser Ser Asp Leu Ser Gly Ala Asn Arg Ile
        1125                1130                1135 gta tta gaa gac tcc aat atc ttg cag cct gtg gga ctt act gtg    3598
Val Leu Glu Asp Ser Asn Ile Leu Gln Pro Val Gly Leu Thr Val
        1140                1145                1150 ttt gaa aac tgg ctc tat tgg att gat aaa cag cag caa atg att    3643
Phe Glu Asn Trp Leu Tyr Trp Ile Asp Lys Gln Gln Gln Met Ile
        1155                1160                1165 gaa aaa att gac atg aca ggt cga gag ggt aga acc aaa gtc caa    3688
Glu Lys Ile Asp Met Thr Gly Arg Glu Gly Arg Thr Lys Val Gln
        1170                1175                1180 gct cga att gcc cag ctt agt gac att cat gca gta aag gag ctg    3733
Ala Arg Ile Ala Gln Leu Ser Asp Ile His Ala Val Lys Glu Leu
        1185                1190                1195 aac ctt caa gaa tac aga cag cac cct tgt gct cag gat aat ggt    3778
Asn Leu Gln Glu Tyr Arg Gln His Pro Cys Ala Gln Asp Asn Gly
        1200                1205                1210 ggc tgt tca cat att tgt ctt gta aag ggg gat ggt act aca agg    3823
Gly Cys Ser His Ile Cys Leu Val Lys Gly Asp Gly Thr Thr Arg
        1215                1220                1225 tgt tct tgc ccc atg cac ctg gtt cta ctt caa gat gag cta tca    3868
Cys Ser Cys Pro Met His Leu Val Leu Leu Gln Asp Glu Leu Ser
        1230                1235                1240 tgt gga gaa cct cca aca tgt tct cct cag cag ttt act tgt ttc    3913
Cys Gly Glu Pro Pro Thr Cys Ser Pro Gln Gln Phe Thr Cys Phe
        1245                1250                1255 acg ggg gaa att gac tgt atc cct gtg gct tgg cgg tgc gat ggg    3958
Thr Gly Glu Ile Asp Cys Ile Pro Val Ala Trp Arg Cys Asp Gly
        1260                1265                1270 ttt act gaa tgt gaa gac cac agt gat gaa ctc aat tgt cct gta    4003
Phe Thr Glu Cys Glu Asp His Ser Asp Glu Leu Asn Cys Pro Val
        1275                1280                1285 tgc tca gag tcc cag ttc cag tgt gcc agt ggg cag tgt att gat    4048
Cys Ser Glu Ser Gln Phe Gln Cys Ala Ser Gly Gln Cys Ile Asp
        1290                1295                1300 ggt gcc ctc cga tgc aat gga gat gca aac tgc cag gac aaa tca    4093
Gly Ala Leu Arg Cys Asn Gly Asp Ala Asn Cys Gln Asp Lys Ser
        1305                1310                1315 gat gag aag aac tgt gaa gtg ctt tgt tta att gat cag ttc cgc    4138
Asp Glu Lys Asn Cys Glu Val Leu Cys Leu Ile Asp Gln Phe Arg
        1320                1325                1330 tgt gcc aat ggt cag tgc att gga aag cac aag aag tgt gat cat    4183
Cys Ala Asn Gly Gln Cys Ile Gly Lys His Lys Lys Cys Asp His
        1335                1340                1345 aat gtg gat tgc agt gac aag tca gat gaa ctg gat tgt tat ccg    4228
Asn Val Asp Cys Ser Asp Lys Ser Asp Glu Leu Asp Cys Tyr Pro
        1350                1355                1360 act gaa gaa cca gca cca cag gcc acc aat aca gtt ggt tct gtt    4273
Thr Glu Glu Pro Ala Pro Gln Ala Thr Asn Thr Val Gly Ser Val
        1365                1370                1375 att ggc gta att gtc acc att ttt gtg tct gga act gta tac ttt    4318
Ile Gly Val Ile Val Thr Ile Phe Val Ser Gly Thr Val Tyr Phe
        1380                1385                1390 atc tgc cag agg atg ttg tgt cca cgt atg aag gga gat ggg gaa    4363
Ile Cys Gln Arg Met Leu Cys Pro Arg Met Lys Gly Asp Gly Glu
```

```
            1395                1400                1405
act atg act aat gac tat gta gtt cat gga cca gct tct gtg cct      4408
Thr Met Thr Asn Asp Tyr Val Val His Gly Pro Ala Ser Val Pro
        1410                1415                1420 ctt ggt tat gtg cca cac cca agt tct ttg tca gga tct ctt cca      4453
Leu Gly Tyr Val Pro His Pro Ser Ser Leu Ser Gly Ser Leu Pro
        1425                1430                1435 gga atg tct cga ggt aaa tca atg atc agc tcc ctc agt atc atg      4498
Gly Met Ser Arg Gly Lys Ser Met Ile Ser Ser Leu Ser Ile Met
        1440                1445                1450 ggg gga agc agt gga ccc ccc tat gac cga gcc cat gtt aca gga      4543
Gly Gly Ser Ser Gly Pro Pro Tyr Asp Arg Ala His Val Thr Gly
        1455                1460                1465 gca tca tca agt agt tct tca agc acc aaa ggc act tac ttc cct      4588
Ala Ser Ser Ser Ser Ser Ser Thr Lys Gly Thr Tyr Phe Pro
        1470                1475                1480 gca att ttg aac cct cca cca tcc cca gcc aca gag cga tca cat      4633
Ala Ile Leu Asn Pro Pro Pro Ser Pro Ala Thr Glu Arg Ser His
        1485                1490                1495 tac act atg gaa ttt gga tat tct tca aac agt cct tcc act cat      4678
Tyr Thr Met Glu Phe Gly Tyr Ser Ser Asn Ser Pro Ser Thr His
        1500                1505                1510 agg tca tac agc tac agg cca tat agc tac cgg cac ttt gca ccc      4723
Arg Ser Tyr Ser Tyr Arg Pro Tyr Ser Tyr Arg His Phe Ala Pro
        1515                1520                1525 ccc aca ccc tgc agc aca gat gtt tgt gac agt gac tat gct          4768
Pro Thr Thr Pro Cys Ser Thr Asp Val Cys Asp Ser Asp Tyr Ala
        1530                1535                1540 cct agt cgg aga atg acc tca gtg gca aca gcc aag ggc tat acc      4813
Pro Ser Arg Arg Met Thr Ser Val Ala Thr Ala Lys Gly Tyr Thr
        1545                1550                1555 agt gac ttg aac tat gat tca gaa cct gtg ccc cca cct ccc aca      4858
Ser Asp Leu Asn Tyr Asp Ser Glu Pro Val Pro Pro Pro Pro Thr
        1560                1565                1570 ccc cga agc caa tac ttg tca gca gag gag aac tat gaa agc tgc      4903
Pro Arg Ser Gln Tyr Leu Ser Ala Glu Glu Asn Tyr Glu Ser Cys
        1575                1580                1585 cca cct tct cca tac aca gag agg agc tat tct cat cac ctc tac      4948
Pro Pro Ser Pro Tyr Thr Glu Arg Ser Tyr Ser His His Leu Tyr
        1590                1595                1600 cca ccg cca ccc tct ccc tgt aca gac tcc tcc tga gggggcc          4994
Pro Pro Pro Pro Ser Pro Cys Thr Asp Ser Ser
        1605                1610 tcctcctctg actgcctcca acgtaaaaat gtaaatataa atttggttga gatctggagg  5054
gggggaggga gctattagag aaggatgagg cagaccatgt acagttaaaa ttataaaatg  5114
gggtagggaa tactggagat atttgtacag aagaaaagga tatttatata ttttcttaaa  5174
acagcagatt tgctgcttgt gccataaaag tttgtataaa aaaatttgt actaaaagtt   5234 ttattttgc aaactaaata cacaaagcat gccttaaacc cagtgaagca actgagtaca   5294
aaggaaacag gaataataaa ggcatcactg accaggaata tctgggcttt attgatacca  5354
aaaataaaaa agaggaagaa gaaaaattaa gtccatctca gagcagcaaa ccatagatac  5414
atggatgtag ccagatagcc ttcagttaac taacatttga gggccaacaa gtaagaaatg  5474
atgaaaggaa aaaaatgcaa ttaatactaa ccttggacga agggctttgt tttctctagg  5534
aatccaacag tgctagtgag gaaagtagat atttctaaaa acccattctg ggtgttgctg  5594
ttgtaggaga gatcagccct ctggtaagat gccatgaagc tgtgtgtgtg tgcaagtctc  5654
```

```
tgtccctacc tttagaatcc atacctctgt caaaatgaat ttttttctct aggtatgttt      5714
accttgctgc ctcctccagc aacttggtaa gtcattttgc taagatacca tgattttttt      5774
aagctgaagc attgactaaa tggaattttc taaattaaac ttgattttaa tatttcttct      5834
agctccattc cccagtaggc ttagctcttc aatttgactg ctgttttttgc ataatgatca     5894 aaagttagac atattatttc tcttcttcca agattgtttt aatgctcatt aaaatgtctt      5954
tttacaacac atatagacaa tgtttaagaa ttaaaaattt aaccattatg tttttgttgt      6014
aaatctcata tccttgcact actttcagca tatatcacag tacgaaatca tttatatata      6074
tatatatata tatatatata tatatatata tatatatata tatattttgt ttgtttgttt      6134
gttttctgag taaaacattt aaatatgttc tggttagaga caatctattt aaaaagattt      6194
ttttcttatt aggattttcc ctatattaac agtttgtgat gttttcatgt tctttagacc      6254 ggttttttctc agaataatgt ctacatacat acctcttcta atgtgtgaca tgaatttaat     6314
atctttctgt tacccactgt gaatgttagg ctgttttcaa attatccaca aattattctt      6374
gtaatcaccc aatattttta tgtgggtcct ctcttaccca ttatggatta agatagttta      6434
acaaatttaa caatgaggat taaatgagaa ggcaaactgt taacttctca gctgtcagaa      6494
tttgggtgga agggaataat ggaagcctct tttgtgatct gcctgacctg ctgtcatgta      6554
tggtactggg gctgctacat cttgagctat cagggctgac ctgtggaatg attctagcac      6614
ttgctctgcc accttgccag aagttcgttt cctgcttttt acacatgtgt agcacttctc      6674
tgctaaaatt gaatggtttt aaactaatgt attttttagct taagaggtgt tggtcagtta     6734
attattgaat tttttttttt tctttttttaa ttctgtcttg ccaaggcctc tctgggtttc     6794
agggcccaag agaaaacagt ggaagaaagg attcagaatt tgggcaaggg tgaagtaact      6854
gttcatgcaa gttaaaaata cctaagtaaa gttttgaag ataaaattgt ggtttcagaa       6914
taatgctgat tgttggagac tgtaagaatc aggtgcactt gattttgcat ataagcaaat      6974
ggtaaatcta tcagaatcct aaaacagaca agcatgaact cttcccattg ctggaactaa      7034
gtgcccacag tgtcagacaa aatggacatt gaacttggat tctgtgatac acagggcact      7094
tgatgcttaa atgaagatgg aaaggttagc aatacctggg tgtcagttag aatttgagaa      7154
ttctatatgt ttacatattt aaatgtgcat cttgatctgg tgggcttccc atgtggagac      7214
ttgcactcta attaactaag aagaatattg ccttgttgga tctcagtcca cgtgcttgca     7274
ctgcgatggc aatggcctct tcttcaaaat actaatttgt gtgccaattt gtttaaaatt     7334
atttgaaggc agttcagcct aatctcagtg ttctctttct ggggtagatg agatggattc     7394
ttaatatttc tgggagtact ttttaatgag agaattgtca aatttggaaa gatttattga     7454
gccttaggtt acatggacag ttaagcttaa gtaaactgta tattgattat caaacacaag     7514
ctgtaattgg aaaagttgag aggaaaagca tgagatcaca aattaggggg aaaaaagaaa     7574
agggattttt aaatttggtg tattaaattc attgtccaag ggggaaaatg aataatgttt     7634
cattagattc cttatatgca aaagtattta ttttgaacat gtgtcctaaa atatatgcac     7694
taactgatgt gattaaaaatt gtccaagaaa taaacttgag cataacatac tttgtgtgca    7754
ccacagtaag ctattctgca ttgaagtggt cttttataac taaggcctgg actttgctcc    7814
aacagagtcg tggtcttctg aatagtgact taaggagttt tgtttgctta agtcagataa    7874
tagcacattc acagggaaac aaagagagtt ggtggataga attttctgac tattaatttt    7934
tcttccatga aatttttatta tgcctttggc actttctgcc actcttacag catatcacaa   7994
```

```
gatatctgtt tagcagaaga ttatgtagtt actttaattt taatataaaa gtagcttgtg    8054
atacattacc aagagatctc tgattctttta gtaagtttga gaacacctat tctacagaga    8114
tgataggtac ttagaaatga agactttaaa gtacatttta atctaatata ggccagtaat    8174
tgggggaagg ggctttgagc agtacaattt taagatgatt ttgagggttg tatttcttta    8234
tcatttaaaa atatcctaaa gtcagtaatt tatatgaagg aaactcattc attattgaag    8294
gtattaaaaa tagccatcat ctgtattagg tagcagtttt ggaggatcat ctttttcttt    8354
tgctataaag ccctattaat gaagaatact tccagtagag ttaatagctg tagcttacct    8414
agtgtgttaa tgaagtgtgt ttatttatgt gacttgatac cagtagtcat aatagagact    8474
gaagaggtat gcgttaagca cgcctacttc tatgcagtaa acaggctgca gctgcctaga    8534
ttagattctt agaaatgtca tattttgaat tgttttattt cttgtagggg aagctttgtc    8594
ccacttcatt catttgcatg ccataggaat tacatattgg ttatcattac gtatctaaca    8654
agattcagaa acaaaaatct tggacttttc acatccgaaa tatgtcagct cttaataaat    8714
gtgtggtgct taagtctaca tatggcatcc atagttgatt tagagtatgg atatgagtgt    8774
gttgaccagt tatcagtagg tggacaaata tttgggcatc tacagatgag actatgcact    8834
aagtgtggac tgagtcctaa agaagcttat agtcaggtgt tgtttaaaac attatcagaa    8894
ttcttaaacc caaggaattt aatttttattt ggtatttctt aagcctaaaa tgaaccaaga    8954
gaaagatgat tttagaaagt acttgtagtg aagatgatt ttagaaagta cttgtagtgc    9014
atgtgtggct tctgactttt gggatggcac cattttataa tagtttcaaa atttagcttt    9074
tgaaattctc aacattttat ggtagaagac tttggacctc aagtataaaa ttatacgttt    9134
ataattttt taaaatttaa attataagta ttgtgaattc acactctcag gctattgtct    9194
gacttgatct acgtctcata aagcctgtac ctgagtggag tggaaggtgg agtcttaggt    9254
taatcagtta ctgactctac cctcacccctc tttcaattga ggtaaacttt gctgtttttc    9314
tttttcataa agcattctca aattgttgag tttattgctg aaaaaaatct ccatgactttt    9374
acagatagaa ttacaaacta aatgatgtct tgtatttaga agcagagtac agacctaacg    9434
aactgttaga ttctccacca tcacttaggg tttgcccaga agcaacacca gagaattaca    9494
gacaacgcgc ttttgctgaa ctgtccattt tggtggttgt gtttttcagt caaatataag    9554
caggatgggc gatagagata tatttatata tagatacata ttctatatat ctaatgccta    9614
aatatgggta ttaaagggaa aatttttaaa gtctgattaa atccaatatg acatgaaatt    9674
aaatatatgg attagtaagg aaaaatgtta aaaagtagag aggataccaa gaagattaaa    9734
ctggactagc cttatttgca agtgaaggat ctggtgctgc tttcagatgt ttatcttta    9794
ttttttccc ttaagcttta atcttcgtca ttgtcttaaa gtcaactggt gtttcttgtt    9854
cattgacttt ggtacgatgg tgctttgcaa ggatgtattt atgttataat ggccaacatt    9914
tggtcagccc ttgtccactt attcacttcc ctccttttgt aaaataagtg ctttaattat    9974
aaactgtata aaaataacctt gtataaaccc cttttttgat tattacaata aataagctga   10034
attgtaacaa atgaaatttg attttttgtaa taaaacagtg gaaaagtaaa aaaa           10088
```

<210> SEQ ID NO 50
<211> LENGTH: 1613
<212> TYPE: PRT
<213> ORGANISM: Homo sapiens

<400> SEQUENCE: 50

Met Gly Ala Val Leu Arg Ser Leu Leu Ala Cys Ser Phe Cys Val Leu

-continued

```
  1               5                  10                 15
Leu Arg Ala Ala Pro Leu Leu Tyr Ala Asn Arg Arg Asp Leu Arg
                20                  25                 30
Leu Val Asp Ala Thr Asn Gly Lys Glu Asn Ala Thr Ile Val Val Gly
                35                  40                 45
Gly Leu Glu Asp Ala Ala Val Asp Phe Val Phe Ser His Gly Leu
                50                  55                 60
Ile Tyr Trp Ser Asp Val Ser Glu Glu Ala Ile Lys Arg Thr Glu Phe
 65                 70                 75                 80
Asn Lys Thr Glu Ser Val Gln Asn Val Val Ser Gly Leu Leu Ser
                85                  90                 95
Pro Asp Gly Leu Ala Cys Asp Trp Leu Gly Glu Lys Leu Tyr Trp Thr
                100                 105                110
Asp Ser Glu Thr Asn Arg Ile Glu Val Ser Asn Leu Asp Gly Ser Leu
                115                 120                125
Arg Lys Val Leu Phe Trp Gln Glu Leu Asp Gln Pro Arg Ala Ile Ala
                130                 135                140
Leu Asp Pro Ser Ser Gly Phe Met Tyr Trp Thr Asp Trp Gly Glu Val
145                 150                 155                160
Pro Lys Ile Glu Arg Ala Gly Met Asp Gly Ser Ser Arg Phe Ile Ile
                165                 170                175
Ile Asn Ser Glu Ile Tyr Trp Pro Asn Gly Leu Thr Leu Asp Tyr Glu
                180                 185                190
Glu Gln Lys Leu Tyr Trp Ala Asp Ala Lys Leu Asn Phe Ile His Lys
                195                 200                205
Ser Asn Leu Asp Gly Thr Asn Arg Gln Ala Val Val Lys Gly Ser Leu
                210                 215                220
Pro His Pro Phe Ala Leu Thr Leu Phe Glu Asp Ile Leu Tyr Trp Thr
225                 230                 235                240
Asp Trp Ser Thr His Ser Ile Leu Ala Cys Asn Lys Tyr Thr Gly Glu
                245                 250                255
Gly Leu Arg Glu Ile His Ser Asp Ile Phe Ser Pro Met Asp Ile His
                260                 265                270
Ala Phe Ser Gln Gln Arg Gln Pro Asn Ala Thr Asn Pro Cys Gly Ile
                275                 280                285
Asp Asn Gly Gly Cys Ser His Leu Cys Leu Met Ser Pro Val Lys Pro
                290                 295                300
Phe Tyr Gln Cys Ala Cys Pro Thr Gly Val Lys Leu Leu Glu Asn Gly
305                 310                 315                320
Lys Thr Cys Lys Asp Gly Ala Thr Glu Leu Leu Leu Ala Arg Arg
                325                 330                335
Thr Asp Leu Arg Arg Ile Ser Leu Asp Thr Pro Asp Phe Thr Asp Ile
                340                 345                350
Val Leu Gln Leu Glu Asp Ile Arg His Ala Ile Ala Ile Asp Tyr Asp
                355                 360                365
Pro Val Glu Gly Tyr Ile Tyr Trp Thr Asp Asp Glu Val Arg Ala Ile
                370                 375                380
Arg Arg Ser Phe Ile Asp Gly Ser Gly Ser Gln Phe Val Thr Ala
385                 390                 395                400
Gln Ile Ala His Pro Asp Gly Ile Ala Val Asp Trp Val Ala Arg Asn
                405                 410                415
Leu Tyr Trp Thr Asp Thr Gly Thr Asp Arg Ile Glu Val Thr Arg Leu
                420                 425                430
```

```
Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
        450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
        530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
        610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
        675                 680                 685

Ala Phe Met Asn Gly Ser Ala Leu Glu His Val Val Glu Phe Gly Leu
        690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
        770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845
```

```
Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
                980                 985                 990

Gln Glu Asp Gly Ser Gln Gly Phe  Thr Val Val Ser  Ser Val Pro
                995                 1000                1005

Ser Gln  Asn Leu Glu Ile Gln  Pro Tyr Asp Leu Ser  Ile Asp Ile
    1010                1015                1020

Tyr Ser  Arg Tyr Ile Tyr Trp  Thr Cys Glu Ala Thr  Asn Val Ile
    1025                1030                1035

Asn Val  Thr Arg Leu Asp Gly  Arg Ser Val Gly Val  Val Leu Lys
    1040                1045                1050

Gly Glu  Gln Asp Arg Pro Arg  Ala Val Val Val Asn  Pro Glu Lys
    1055                1060                1065

Gly Tyr  Met Tyr Phe Thr Asn  Leu Gln Glu Arg Ser  Pro Lys Ile
    1070                1075                1080

Glu Arg  Ala Ala Leu Asp Gly  Thr Glu Arg Glu Val  Leu Phe Phe
    1085                1090                1095

Ser Gly  Leu Ser Lys Pro Ile  Ala Leu Ala Leu Asp  Ser Arg Leu
    1100                1105                1110

Gly Lys  Leu Phe Trp Ala Asp  Ser Asp Leu Arg Arg  Ile Glu Ser
    1115                1120                1125

Ser Asp  Leu Ser Gly Ala Asn  Arg Ile Val Leu Glu  Asp Ser Asn
    1130                1135                1140

Ile Leu  Gln Pro Val Gly Leu  Thr Val Phe Glu Asn  Trp Leu Tyr
    1145                1150                1155

Trp Ile  Asp Lys Gln Gln Gln  Met Ile Glu Lys Ile  Asp Met Thr
    1160                1165                1170

Gly Arg  Glu Gly Arg Thr Lys  Val Gln Ala Arg Ile  Ala Gln Leu
    1175                1180                1185

Ser Asp  Ile His Ala Val Lys  Glu Leu Asn Leu Gln  Glu Tyr Arg
    1190                1195                1200

Gln His  Pro Cys Ala Gln Asp  Asn Gly Gly Cys Ser  His Ile Cys
    1205                1210                1215

Leu Val  Lys Gly Asp Gly Thr  Thr Arg Cys Ser Cys  Pro Met His
    1220                1225                1230

Leu Val  Leu Leu Gln Asp Glu  Leu Ser Cys Gly Glu  Pro Pro Thr
    1235                1240                1245

Cys Ser  Pro Gln Gln Phe Thr  Cys Phe Thr Gly Glu  Ile Asp Cys
```

-continued

```
            1250                1255                1260
Ile Pro Val Ala Trp Arg Cys Asp Gly Phe Thr Glu Cys Glu Asp
    1265                1270                1275
His Ser Asp Glu Leu Asn Cys Pro Val Cys Ser Glu Ser Gln Phe
    1280                1285                1290
Gln Cys Ala Ser Gly Gln Cys Ile Asp Gly Ala Leu Arg Cys Asn
    1295                1300                1305
Gly Asp Ala Asn Cys Gln Asp Lys Ser Asp Glu Lys Asn Cys Glu
    1310                1315                1320
Val Leu Cys Leu Ile Asp Gln Phe Arg Cys Ala Asn Gly Gln Cys
    1325                1330                1335
Ile Gly Lys His Lys Lys Cys Asp His Asn Val Asp Cys Ser Asp
    1340                1345                1350
Lys Ser Asp Glu Leu Asp Cys Tyr Pro Thr Glu Glu Pro Ala Pro
    1355                1360                1365
Gln Ala Thr Asn Thr Val Gly Ser Val Ile Gly Val Ile Val Thr
    1370                1375                1380
Ile Phe Val Ser Gly Thr Val Tyr Phe Ile Cys Gln Arg Met Leu
    1385                1390                1395
Cys Pro Arg Met Lys Gly Asp Gly Glu Thr Met Thr Asn Asp Tyr
    1400                1405                1410
Val Val His Gly Pro Ala Ser Val Pro Leu Gly Tyr Val Pro His
    1415                1420                1425
Pro Ser Ser Leu Ser Gly Ser Leu Pro Gly Met Ser Arg Gly Lys
    1430                1435                1440
Ser Met Ile Ser Ser Leu Ser Ile Met Gly Gly Ser Ser Gly Pro
    1445                1450                1455
Pro Tyr Asp Arg Ala His Val Thr Gly Ala Ser Ser Ser Ser Ser
    1460                1465                1470
Ser Ser Thr Lys Gly Thr Tyr Phe Pro Ala Ile Leu Asn Pro Pro
    1475                1480                1485
Pro Ser Pro Ala Thr Glu Arg Ser His Tyr Thr Met Glu Phe Gly
    1490                1495                1500
Tyr Ser Ser Asn Ser Pro Ser Thr His Arg Ser Tyr Ser Tyr Arg
    1505                1510                1515
Pro Tyr Ser Tyr Arg His Phe Ala Pro Pro Thr Thr Pro Cys Ser
    1520                1525                1530
Thr Asp Val Cys Asp Ser Asp Tyr Ala Pro Ser Arg Arg Met Thr
    1535                1540                1545
Ser Val Ala Thr Ala Lys Gly Tyr Thr Ser Asp Leu Asn Tyr Asp
    1550                1555                1560
Ser Glu Pro Val Pro Pro Pro Thr Pro Arg Ser Gln Tyr Leu
    1565                1570                1575
Ser Ala Glu Glu Asn Tyr Glu Ser Cys Pro Pro Ser Pro Tyr Thr
    1580                1585                1590
Glu Arg Ser Tyr Ser His His Leu Tyr Pro Pro Pro Ser Pro
    1595                1600                1605
Cys Thr Asp Ser Ser
    1610

<210> SEQ ID NO 51
<211> LENGTH: 3375
<212> TYPE: DNA
<213> ORGANISM: Danio rerio
```

```
<220> FEATURE:
<221> NAME/KEY: CDS
<222> LOCATION: (196)..(2538)

<400> SEQUENCE: 51
gtgctgctgc tgcgcgagcg cggagttctc gcgcacacat tcactctcag caggagctgc      60
cgcgcgctgc gggttgttct ctcacatttt ctcaacggat tgtcgccatt attcgcgttt     120
tacgtgctga aaaccgaaac aggaatatac agcttttgac acagattagt agctgtgccc     180
ggctgtgaga aaatc atg gct acc cag tct gac ttg atg gag ctg gaa atg      231
                Met Ala Thr Gln Ser Asp Leu Met Glu Leu Glu Met
                  1               5                  10 gcc atg gat ccg gat cgc aag gct gca gtc agc cat tgg cag caa cag       279
Ala Met Asp Pro Asp Arg Lys Ala Ala Val Ser His Trp Gln Gln Gln
             15                  20                  25 tct tac ctg gac tca gga ata cac tct ggg gcc aca act act gcc ccg       327
Ser Tyr Leu Asp Ser Gly Ile His Ser Gly Ala Thr Thr Thr Ala Pro
 30                  35                  40 tcc ctg agt ggc aaa ggc aac ccg gag gat gac gat gtg gat aat cag       375
Ser Leu Ser Gly Lys Gly Asn Pro Glu Asp Asp Asp Val Asp Asn Gln
 45                  50                  55                  60 gtg ctt tat gag tgg gag cag ggc ttc aac cag tcc ttc aac caa gag       423
Val Leu Tyr Glu Trp Glu Gln Gly Phe Asn Gln Ser Phe Asn Gln Glu
                 65                  70                  75 caa gta gca gac atc gat ggt caa tac gcc atg acc aga gcc cag aga       471
Gln Val Ala Asp Ile Asp Gly Gln Tyr Ala Met Thr Arg Ala Gln Arg
             80                  85                  90 gtc cgg gcg gcc atg ttc ccg gag act ctc gat gag ggc atg cag ata       519
Val Arg Ala Ala Met Phe Pro Glu Thr Leu Asp Glu Gly Met Gln Ile
         95                 100                 105 cct tcc aca cag ttc gac tct gcg cat ccc acc aat gtc cag cgc ctg       567
Pro Ser Thr Gln Phe Asp Ser Ala His Pro Thr Asn Val Gln Arg Leu
    110                 115                 120 gct gag ccc tcg cag atg ctc aaa cat gcc gtg gtc aac ctc atc aac       615
Ala Glu Pro Ser Gln Met Leu Lys His Ala Val Val Asn Leu Ile Asn
125                 130                 135                 140 tac cag gac gac gca gag ctg gcc act cgt gcc att cca gag ctc acc       663
Tyr Gln Asp Asp Ala Glu Leu Ala Thr Arg Ala Ile Pro Glu Leu Thr
                145                 150                 155 aaa cta ctg aac gac gag gat cag gtg gtg gtt aat aag gca gct gtg       711
Lys Leu Leu Asn Asp Glu Asp Gln Val Val Val Asn Lys Ala Ala Val
            160                 165                 170 atg gtg cac cag ctc tcc aag aaa gag gcc tct cgt cac gcc atc atg       759
Met Val His Gln Leu Ser Lys Lys Glu Ala Ser Arg His Ala Ile Met
        175                 180                 185 cgc tcc cca cag atg gta tcg gcc att gtg agg acc atg cag aac act       807
Arg Ser Pro Gln Met Val Ser Ala Ile Val Arg Thr Met Gln Asn Thr
    190                 195                 200 aat gat gta gaa aca gcc cgt tgc acc tct ggc acc cta cac aat ctt       855
Asn Asp Val Glu Thr Ala Arg Cys Thr Ser Gly Thr Leu His Asn Leu
205                 210                 215                 220 tcc cac cac aga gaa gga ctg ctt gcc atc ttt aaa tca gga ggc atc       903
Ser His His Arg Glu Gly Leu Leu Ala Ile Phe Lys Ser Gly Gly Ile
                225                 230                 235 cct gcc ctc gtc aaa gtg ctc ggc tcc cct gtg gac tct gtg ctg ttt       951
Pro Ala Leu Val Lys Val Leu Gly Ser Pro Val Asp Ser Val Leu Phe
            240                 245                 250 tac gct att aca act cta cac aac ctg cta ctg cac caa gaa gga gcc       999
Tyr Ala Ile Thr Thr Leu His Asn Leu Leu Leu His Gln Glu Gly Ala
        255                 260                 265
```

| | | | | | | | | | | | | | | | | |
|---|---|---|---|---|---|---|---|---|---|---|---|---|---|---|---|---|
| aag | atg | gct | gtt | cga | ctg | gcc | gga | ggc | ctg | cag | aaa | atg | gtg | gcc | ttg | 1047 |
| Lys | Met | Ala | Val | Arg | Leu | Ala | Gly | Gly | Leu | Gln | Lys | Met | Val | Ala | Leu | |
| | 270 | | | | 275 | | | | | 280 | | | | | | |

| | | | | | | | | | | | | | | | | |
|---|---|---|---|---|---|---|---|---|---|---|---|---|---|---|---|---|
| tta | aac | aaa | aca | aac | gtc | aaa | ttc | ctc | gcc | atc | acg | aca | gac | tgc | ctt | 1095 |
| Leu | Asn | Lys | Thr | Asn | Val | Lys | Phe | Leu | Ala | Ile | Thr | Thr | Asp | Cys | Leu | |
| 285 | | | | | 290 | | | | | 295 | | | | | 300 | |

| | | | | | | | | | | | | | | | | |
|---|---|---|---|---|---|---|---|---|---|---|---|---|---|---|---|---|
| cag | att | ctg | gca | tac | ggc | aat | cag | gaa | agc | aaa | ctt | atc | att | ctg | gcc | 1143 |
| Gln | Ile | Leu | Ala | Tyr | Gly | Asn | Gln | Glu | Ser | Lys | Leu | Ile | Ile | Leu | Ala | |
| | | | | | 305 | | | | | 310 | | | | | 315 | |

| | | | | | | | | | | | | | | | | |
|---|---|---|---|---|---|---|---|---|---|---|---|---|---|---|---|---|
| agc | gga | ggc | cca | cag | gct | ttg | gtc | aac | atc | atg | agg | aca | tac | acc | tat | 1191 |
| Ser | Gly | Gly | Pro | Gln | Ala | Leu | Val | Asn | Ile | Met | Arg | Thr | Tyr | Thr | Tyr | |
| | | | 320 | | | | | 325 | | | | | 330 | | | |

| | | | | | | | | | | | | | | | | |
|---|---|---|---|---|---|---|---|---|---|---|---|---|---|---|---|---|
| gag | aag | ctg | tta | tgg | acg | acc | agt | cga | gtg | ctc | aag | gtg | ttg | tca | gtg | 1239 |
| Glu | Lys | Leu | Leu | Trp | Thr | Thr | Ser | Arg | Val | Leu | Lys | Val | Leu | Ser | Val | |
| | | | 335 | | | | | 340 | | | | | 345 | | | |

| | | | | | | | | | | | | | | | | |
|---|---|---|---|---|---|---|---|---|---|---|---|---|---|---|---|---|
| tgc | tcc | agt | aac | aaa | cct | gcc | att | gtg | gag | gct | ggt | ggc | atg | caa | gcc | 1287 |
| Cys | Ser | Ser | Asn | Lys | Pro | Ala | Ile | Val | Glu | Ala | Gly | Gly | Met | Gln | Ala | |
| 350 | | | | | 355 | | | | | 360 | | | | | | |

| | | | | | | | | | | | | | | | | |
|---|---|---|---|---|---|---|---|---|---|---|---|---|---|---|---|---|
| ctc | ggc | ctt | cat | ctc | aca | gac | ccc | agc | cag | cga | ctg | gta | cag | aac | tgc | 1335 |
| Leu | Gly | Leu | His | Leu | Thr | Asp | Pro | Ser | Gln | Arg | Leu | Val | Gln | Asn | Cys | |
| 365 | | | | | 370 | | | | | 375 | | | | | 380 | |

| | | | | | | | | | | | | | | | | |
|---|---|---|---|---|---|---|---|---|---|---|---|---|---|---|---|---|
| ttg | tgg | act | ttg | agg | aat | ctg | tca | gac | gcc | gcc | acc | aaa | cag | gag | ggc | 1383 |
| Leu | Trp | Thr | Leu | Arg | Asn | Leu | Ser | Asp | Ala | Ala | Thr | Lys | Gln | Glu | Gly | |
| | | | | 385 | | | | | 390 | | | | | 395 | | |

| | | | | | | | | | | | | | | | | |
|---|---|---|---|---|---|---|---|---|---|---|---|---|---|---|---|---|
| atg | gag | ggg | ctc | ttg | ggc | acc | ctg | gtg | cag | ttg | ctc | ggg | tca | gat | gac | 1431 |
| Met | Glu | Gly | Leu | Leu | Gly | Thr | Leu | Val | Gln | Leu | Leu | Gly | Ser | Asp | Asp | |
| | | | 400 | | | | | 405 | | | | | 410 | | | |

| | | | | | | | | | | | | | | | | |
|---|---|---|---|---|---|---|---|---|---|---|---|---|---|---|---|---|
| atc | aac | gtg | gtg | acg | tgt | gct | gct | gga | atc | ctg | tcc | aac | ctg | acc | tgc | 1479 |
| Ile | Asn | Val | Val | Thr | Cys | Ala | Ala | Gly | Ile | Leu | Ser | Asn | Leu | Thr | Cys | |
| | | | 415 | | | | | 420 | | | | | 425 | | | |

| | | | | | | | | | | | | | | | | |
|---|---|---|---|---|---|---|---|---|---|---|---|---|---|---|---|---|
| aac | aac | tac | aaa | aac | aag | atg | atg | gtg | tgc | caa | gtg | ggt | ggc | atc | gag | 1527 |
| Asn | Asn | Tyr | Lys | Asn | Lys | Met | Met | Val | Cys | Gln | Val | Gly | Gly | Ile | Glu | |
| | | | 430 | | | | | 435 | | | | | 440 | | | |

| | | | | | | | | | | | | | | | | |
|---|---|---|---|---|---|---|---|---|---|---|---|---|---|---|---|---|
| gcc | ccc | gtg | cgc | acc | gtt | ctt | cgt | gcc | gga | gac | aga | gag | gat | atc | aca | 1575 |
| Ala | Pro | Val | Arg | Thr | Val | Leu | Arg | Ala | Gly | Asp | Arg | Glu | Asp | Ile | Thr | |
| 445 | | | | | 450 | | | | | 455 | | | | | 460 | |

| | | | | | | | | | | | | | | | | |
|---|---|---|---|---|---|---|---|---|---|---|---|---|---|---|---|---|
| gag | ccg | gct | atc | tgc | gct | ctc | cgt | cac | ctc | aca | tcc | aga | cac | cag | gat | 1623 |
| Glu | Pro | Ala | Ile | Cys | Ala | Leu | Arg | His | Leu | Thr | Ser | Arg | His | Gln | Asp | |
| | | | | 465 | | | | | 470 | | | | | 475 | | |

| | | | | | | | | | | | | | | | | |
|---|---|---|---|---|---|---|---|---|---|---|---|---|---|---|---|---|
| gca | gag | atg | gcc | cag | aat | gca | gtg | cgg | ctg | cac | tat | gga | ctg | cct | gta | 1671 |
| Ala | Glu | Met | Ala | Gln | Asn | Ala | Val | Arg | Leu | His | Tyr | Gly | Leu | Pro | Val | |
| | | | 480 | | | | | 485 | | | | | 490 | | | |

| | | | | | | | | | | | | | | | | |
|---|---|---|---|---|---|---|---|---|---|---|---|---|---|---|---|---|
| gta | gtc | aaa | ctg | ctc | cac | cct | cct | tca | cat | tgg | cct | ctc | att | aag | gct | 1719 |
| Val | Val | Lys | Leu | Leu | His | Pro | Pro | Ser | His | Trp | Pro | Leu | Ile | Lys | Ala | |
| | | | 495 | | | | | 500 | | | | | 505 | | | |

| | | | | | | | | | | | | | | | | |
|---|---|---|---|---|---|---|---|---|---|---|---|---|---|---|---|---|
| aca | gtt | ggg | ctg | atc | cgc | aac | ctg | gca | ctg | tgc | ccc | gcc | aac | cat | gcc | 1767 |
| Thr | Val | Gly | Leu | Ile | Arg | Asn | Leu | Ala | Leu | Cys | Pro | Ala | Asn | His | Ala | |
| | 510 | | | | | 515 | | | | | 520 | | | | | |

| | | | | | | | | | | | | | | | | |
|---|---|---|---|---|---|---|---|---|---|---|---|---|---|---|---|---|
| ccg | ctc | cga | gag | cag | ggt | gcc | att | ccc | cgc | ctg | gtg | cag | ctt | cta | gtc | 1815 |
| Pro | Leu | Arg | Glu | Gln | Gly | Ala | Ile | Pro | Arg | Leu | Val | Gln | Leu | Leu | Val | |
| 525 | | | | | 530 | | | | | 535 | | | | | 540 | |

| | | | | | | | | | | | | | | | | |
|---|---|---|---|---|---|---|---|---|---|---|---|---|---|---|---|---|
| cgg | gcc | cat | cag | gat | act | cag | aga | cgc | acc | tcc | atg | ggt | gga | aca | cag | 1863 |
| Arg | Ala | His | Gln | Asp | Thr | Gln | Arg | Arg | Thr | Ser | Met | Gly | Gly | Thr | Gln | |
| | | | | 545 | | | | | 550 | | | | | 555 | | |

| | | | | | | | | | | | | | | | | |
|---|---|---|---|---|---|---|---|---|---|---|---|---|---|---|---|---|
| cag | cag | ttt | gtg | gag | ggt | gtg | cgt | atg | gag | gag | att | gtg | gag | ggc | tgc | 1911 |
| Gln | Gln | Phe | Val | Glu | Gly | Val | Arg | Met | Glu | Glu | Ile | Val | Glu | Gly | Cys | |
| | | | | 560 | | | | | 565 | | | | | 570 | | |

| | | | | | | | | | | | | | | | | |
|---|---|---|---|---|---|---|---|---|---|---|---|---|---|---|---|---|
| act | gga | gct | ctg | cac | att | cta | gcc | aga | gac | att | cac | aac | aga | att | gtc | 1959 |
| Thr | Gly | Ala | Leu | His | Ile | Leu | Ala | Arg | Asp | Ile | His | Asn | Arg | Ile | Val | |

-continued

|  |  | 575 |  |  |  | 580 |  |  |  | 585 |  |  |  |  |
|---|---|---|---|---|---|---|---|---|---|---|---|---|---|---|
| atc | aga | gga | ctc | aac | act | att | cca | ctc | ttt | gtt | cag | ttg | ctg | tat | tct | 2007 |
| Ile | Arg | Gly | Leu | Asn | Thr | Ile | Pro | Leu | Phe | Val | Gln | Leu | Leu | Tyr | Ser |
| 590 |  |  |  |  | 595 |  |  |  |  | 600 |  |  |  |  |

```
atc aga gga ctc aac act att cca ctc ttt gtt cag ttg ctg tat tct    2007
Ile Arg Gly Leu Asn Thr Ile Pro Leu Phe Val Gln Leu Leu Tyr Ser
590                 595                 600 cct atc gag aac atc cag cgt gtg gct gca gga gtg ctg tgt gaa ctg    2055
Pro Ile Glu Asn Ile Gln Arg Val Ala Ala Gly Val Leu Cys Glu Leu
605                 610                 615                 620 gct cag gat aag gag gcg gca gaa gcc atc gag gca gaa gga gcc act    2103
Ala Gln Asp Lys Glu Ala Ala Glu Ala Ile Glu Ala Glu Gly Ala Thr
            625                 630                 635 gct cca ctc aca gag ctc ctg cac tcc aga aac gag gga gtc gcc acg    2151
Ala Pro Leu Thr Glu Leu Leu His Ser Arg Asn Glu Gly Val Ala Thr
        640                 645                 650 tac gct gct gca gtt ctg ttc cgc atg tct gag gat aag ccc cag gac    2199
Tyr Ala Ala Ala Val Leu Phe Arg Met Ser Glu Asp Lys Pro Gln Asp
    655                 660                 665 tac aag aag cga ctg tct gtg gag ctc acc agc tct ctg ttc aga act    2247
Tyr Lys Lys Arg Leu Ser Val Glu Leu Thr Ser Ser Leu Phe Arg Thr
670                 675                 680 gag ccc atg acc tgg aac gag act gga gat cta ggg ctg gat atc ggt    2295
Glu Pro Met Thr Trp Asn Glu Thr Gly Asp Leu Gly Leu Asp Ile Gly
685                 690                 695                 700 gca cag gga gag cct ctg ggc tac aga cag gac gac cca agc tac cgc    2343
Ala Gln Gly Glu Pro Leu Gly Tyr Arg Gln Asp Asp Pro Ser Tyr Arg
            705                 710                 715 tcc ttc cat tcc gga ggt tat ggg cag gac gcc atg ggc atg gac ccc    2391
Ser Phe His Ser Gly Gly Tyr Gly Gln Asp Ala Met Gly Met Asp Pro
        720                 725                 730 atg atg gag cac gag atg gcc ggg cac cac ccg ggc cct gat tac ccc    2439
Met Met Glu His Glu Met Ala Gly His His Pro Gly Pro Asp Tyr Pro
    735                 740                 745 gta gac ggc ctg cct gac ctc ggc cac acc cag gac ctg atc gac ggc    2487
Val Asp Gly Leu Pro Asp Leu Gly His Thr Gln Asp Leu Ile Asp Gly
750                 755                 760 ctc ccg cca ggc gac agc aat cag ctg gcc tgg ttt gac acc gat ctg    2535
Leu Pro Pro Gly Asp Ser Asn Gln Leu Ala Trp Phe Asp Thr Asp Leu
765                 770                 775                 780 taa atacaatgac tttttagctg tatcgtctga tctgaatgaa cctgcattgt         2588
gattttggcc tgtagagttg ctgagcgggc tcaagagaga gtgggctagt ttctctgaaa  2648
gtgcctgaca cactaataca agctgagttt cctatgggaa cacgtggaag taaaacgttt  2708
ggttctgatc ctagccggtc agaattttg  gtgtgattga cagaagaaag aaagccccaa  2768
aaaaaaaaga agcaaatcct aagatggagt tttcaacctt agccttgcct gtacttttat  2828 ttgattttt  cttacttttt attttttcaaa ggatatctgg gtctgtaatg gtacttatct  2888
agcttgcttt atgatactcg tcttttttatt ttgctgaact ttgtattcct ttcgactgtc  2948
tctctttctc tctcatagtg ttgagttcta gtggtaatga tccatcaaga ttttatcgac  3008
tttatggtgt agaacactaa ttaatcagtt gaattgtatt cttatcaaat gtaacattgt  3068
gtagcttttg tataaaacca agaattggag aagtccaaat atcagctctc ttgctttaat  3128
gaaatcacaa atgttccaaa gggttttgcaa tcagttgggg ccagttttgc tttcattttt  3188
tttttacttt tcagctctcg tttgatttta ctttactgtc ttgatctatt atgattattt  3248
tttttttttg atggtagctt tagaaaggtt tttgaaaaga accctaatt attgtagcct    3308 gcgatttgtt ggttggagac ttggctaaat aaaatggact ttaaatttaa aaaaaaaaa    3368 aaaaaaa                                                             3375
```

<210> SEQ ID NO 52
<211> LENGTH: 780
<212> TYPE: PRT
<213> ORGANISM: Danio rerio

<400> SEQUENCE: 52

```
Met Ala Thr Gln Ser Asp Leu Met Glu Leu Glu Met Ala Met Asp Pro
1               5                   10                  15

Asp Arg Lys Ala Ala Val Ser His Trp Gln Gln Ser Tyr Leu Asp
            20                  25                  30

Ser Gly Ile His Ser Gly Ala Thr Thr Thr Ala Pro Ser Leu Ser Gly
            35                  40                  45

Lys Gly Asn Pro Glu Asp Asp Val Asp Asn Gln Val Leu Tyr Glu
    50                  55                  60

Trp Glu Gln Gly Phe Asn Gln Ser Phe Asn Gln Gln Val Ala Asp
65                  70                  75                  80

Ile Asp Gly Gln Tyr Ala Met Thr Arg Ala Gln Arg Val Arg Ala Ala
                85                  90                  95

Met Phe Pro Glu Thr Leu Asp Glu Gly Met Gln Ile Pro Ser Thr Gln
            100                 105                 110

Phe Asp Ser Ala His Pro Thr Asn Val Gln Arg Leu Ala Glu Pro Ser
        115                 120                 125

Gln Met Leu Lys His Ala Val Val Asn Leu Ile Asn Tyr Gln Asp Asp
    130                 135                 140

Ala Glu Leu Ala Thr Arg Ala Ile Pro Glu Leu Thr Lys Leu Leu Asn
145                 150                 155                 160

Asp Glu Asp Gln Val Val Asn Lys Ala Val Met Val His Gln
                165                 170                 175

Leu Ser Lys Lys Glu Ala Ser Arg His Ala Ile Met Arg Ser Pro Gln
            180                 185                 190

Met Val Ser Ala Ile Val Arg Thr Met Gln Asn Thr Asn Asp Val Glu
        195                 200                 205

Thr Ala Arg Cys Thr Ser Gly Thr Leu His Asn Leu Ser His His Arg
    210                 215                 220

Glu Gly Leu Leu Ala Ile Phe Lys Ser Gly Gly Ile Pro Ala Leu Val
225                 230                 235                 240

Lys Val Leu Gly Ser Pro Val Asp Ser Val Leu Phe Tyr Ala Ile Thr
                245                 250                 255

Thr Leu His Asn Leu Leu Leu His Gln Glu Gly Ala Lys Met Ala Val
            260                 265                 270

Arg Leu Ala Gly Gly Leu Gln Lys Met Val Ala Leu Leu Asn Lys Thr
        275                 280                 285

Asn Val Lys Phe Leu Ala Ile Thr Thr Asp Cys Leu Gln Ile Leu Ala
    290                 295                 300

Tyr Gly Asn Gln Glu Ser Lys Leu Ile Ile Leu Ala Ser Gly Gly Pro
305                 310                 315                 320

Gln Ala Leu Val Asn Ile Met Arg Thr Tyr Thr Tyr Glu Lys Leu Leu
                325                 330                 335

Trp Thr Thr Ser Arg Val Leu Lys Val Leu Ser Val Cys Ser Ser Asn
            340                 345                 350

Lys Pro Ala Ile Val Glu Ala Gly Gly Met Gln Ala Leu Gly Leu His
        355                 360                 365
```

Leu Thr Asp Pro Ser Gln Arg Leu Val Gln Asn Cys Leu Trp Thr Leu
        370                 375                 380

Arg Asn Leu Ser Asp Ala Ala Thr Lys Gln Glu Gly Met Glu Gly Leu
385                 390                 395                 400

Leu Gly Thr Leu Val Gln Leu Leu Gly Ser Asp Asp Ile Asn Val Val
                405                 410                 415

Thr Cys Ala Ala Gly Ile Leu Ser Asn Leu Thr Cys Asn Asn Tyr Lys
            420                 425                 430

Asn Lys Met Met Val Cys Gln Val Gly Gly Ile Glu Ala Pro Val Arg
        435                 440                 445

Thr Val Leu Arg Ala Gly Asp Arg Glu Asp Ile Thr Glu Pro Ala Ile
    450                 455                 460

Cys Ala Leu Arg His Leu Thr Ser Arg His Gln Asp Ala Glu Met Ala
465                 470                 475                 480

Gln Asn Ala Val Arg Leu His Tyr Gly Leu Pro Val Val Lys Leu
                485                 490                 495

Leu His Pro Pro Ser His Trp Pro Leu Ile Lys Ala Thr Val Gly Leu
            500                 505                 510

Ile Arg Asn Leu Ala Leu Cys Pro Ala Asn His Ala Pro Leu Arg Glu
        515                 520                 525

Gln Gly Ala Ile Pro Arg Leu Val Gln Leu Leu Val Arg Ala His Gln
    530                 535                 540

Asp Thr Gln Arg Arg Thr Ser Met Gly Gly Thr Gln Gln Gln Phe Val
545                 550                 555                 560

Glu Gly Val Arg Met Glu Glu Ile Val Glu Gly Cys Thr Gly Ala Leu
                565                 570                 575

His Ile Leu Ala Arg Asp Ile His Asn Arg Ile Val Ile Arg Gly Leu
            580                 585                 590

Asn Thr Ile Pro Leu Phe Val Gln Leu Leu Tyr Ser Pro Ile Glu Asn
        595                 600                 605

Ile Gln Arg Val Ala Ala Gly Val Leu Cys Glu Leu Ala Gln Asp Lys
    610                 615                 620

Glu Ala Ala Glu Ala Ile Glu Ala Glu Gly Ala Thr Ala Pro Leu Thr
625                 630                 635                 640

Glu Leu Leu His Ser Arg Asn Glu Gly Val Ala Thr Tyr Ala Ala Ala
                645                 650                 655

Val Leu Phe Arg Met Ser Glu Asp Lys Pro Gln Asp Tyr Lys Lys Arg
            660                 665                 670

Leu Ser Val Glu Leu Thr Ser Ser Leu Phe Arg Thr Glu Pro Met Thr
        675                 680                 685

Trp Asn Glu Thr Gly Asp Leu Gly Leu Asp Ile Gly Ala Gln Gly Glu
    690                 695                 700

Pro Leu Gly Tyr Arg Gln Asp Asp Pro Ser Tyr Arg Ser Phe His Ser
705                 710                 715                 720

Gly Gly Tyr Gly Gln Asp Ala Met Gly Met Asp Pro Met Met Glu His
                725                 730                 735

Glu Met Ala Gly His His Pro Gly Pro Asp Tyr Pro Val Asp Gly Leu
            740                 745                 750

Pro Asp Leu Gly His Thr Gln Asp Leu Ile Asp Gly Leu Pro Pro Gly
        755                 760                 765

Asp Ser Asn Gln Leu Ala Trp Phe Asp Thr Asp Leu
770                 775                 780